(12) United States Patent
Glassberg Csete et al.

(10) Patent No.: US 11,607,428 B2
(45) Date of Patent: Mar. 21, 2023

(54) MESENCHYMAL STEM CELL-DERIVED EXTRACELLULAR VESICLES AND USES THEREOF FOR TREATING AND DIAGNOSING FIBROTIC DISEASES

(71) Applicant: Spiritus Therapeutics, Inc., New York, NY (US)

(72) Inventors: Marilyn Glassberg Csete, Miami, FL (US); Sharon Elliot, Miami, FL (US); Robin Smith, New York, NY (US)

(73) Assignee: SPIRITUS THERAPEUTICS, INC., New York, NY (US)

( * ) Notice: Subject to any disclaimer, the term of this patent is extended or adjusted under 35 U.S.C. 154(b) by 285 days.

(21) Appl. No.: 16/893,271

(22) Filed: Jun. 4, 2020

(65) Prior Publication Data
US 2021/0052657 A1 Feb. 25, 2021

Related U.S. Application Data

(60) Provisional application No. 63/023,365, filed on May 12, 2020, provisional application No. 62/945,917, filed on Dec. 10, 2019, provisional application No. 62/858,154, filed on Jun. 6, 2019.

(51) Int. Cl.
*A61K 35/28* (2015.01)
*A61P 11/00* (2006.01)
*A61K 9/00* (2006.01)
*C12Q 1/6883* (2018.01)

(52) U.S. Cl.
CPC ............ *A61K 35/28* (2013.01); *A61K 9/0082* (2013.01); *A61P 11/00* (2018.01); *C12Q 1/6883* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 9,128,101 B2 * | 9/2015 | Halbert | A61P 25/28 |
| 2007/0092882 A1 | 4/2007 | Wang et al. | |
| 2011/0003704 A1 | 1/2011 | Skog et al. | |
| 2012/0283167 A1 | 11/2012 | Weston-Davies | |
| 2013/0287772 A1 | 10/2013 | Halbert et al. | |
| 2014/0234263 A1 | 8/2014 | Shiels | |
| 2016/0024319 A1 | 1/2016 | Blanchard et al. | |
| 2016/0041153 A1 | 2/2016 | Brown et al. | |
| 2016/0243192 A1 | 8/2016 | Seeger et al. | |
| 2018/0338997 A1 | 11/2018 | Shiels et al. | |
| 2019/0099471 A1 | 4/2019 | Liang et al. | |
| 2019/0127734 A1 | 5/2019 | Montgomery et al. | |
| 2020/0384034 A1 * | 12/2020 | Glassberg Csete | A61K 35/12 |

FOREIGN PATENT DOCUMENTS

| | | |
|---|---|---|
| WO | 2010053350 A1 | 5/2010 |
| WO | 2019/051355 A1 | 3/2019 |

OTHER PUBLICATIONS

Chen, J. et al. The Role of microRNAs in the Pathogenesis of Autoimmune Diseases. Autoimmunity Reviews 15:1171-1180, 2016. (Year: 2016).*
Salimian J. et al. Chronic Obstructive Pulmonary Disease . . . J of Research in Medical Sciences 23(27)1-12, 2018. (Year: 2018).*
Lv, L. et al. MicroRNA-29c in Urinary Exosome/Microvesicle as a Biomarker of Renal Fibrosis. American J Physiology Renal 305: 1220-1227, 2013. (Year: 2013).*
A. Ngu, M. Carlson, Q. Sheng, "Semantic-Based Mashup of Composite Applications," IEEE Transactions on Services Computing, vol. 3, No. 1, 2010.
Abbott et al.,Eelectrolytic processing of super-alloy aerospace castings using choline chloride-based ionic liquids, TT~NS IMF, 2012, 90(1), 9.
Abreu MT, et al. TLR Signaling in the Gut in Health and Disease. J Immunol. 2005; 174: 4453-4460.
Adesina SE, Kang BY, Bijli KM, Ma J, Cheng J, Murphy TC, Hart C Michael, Sutliff RL. Targeting mitochondrial reactive oxygen species to modulate hypoxia-induced pulmonary hypertension. Free Radic Biol Med. 2015:87:36-47.
Agrawal A, Mabalirajan U. Rejuvenating cellular respiration for optimizing respiratory function: targeting mitochondria. Am J Physiol— Lung Cell Mol Physiol. 2016;310(2):L103-L113.
Aguilar S, et al. Bone marrow stem cells expressing keratinocyte growth factor via an inducible lentivirus protects against bleomycin-induced pulmonary fibrosis. PLoS One 2009; 4: e8013.
Akram KM, et al., Mesenchymal stem cells promote alveolar epithelial cell wound repair in vitro through distinct migratory and paracrine mechanisms. Respir. Res. (2013) 14: 9.
Al-Tawfiq, IA, et al., Ribavirin and interferon therapy in patients infected with the Middle East respiratory syndrome coronavirus: an observational study, Int. J. Infect. Dis. (2014) 20: 42-6.
Alarid, E. T., Bakopoulos, N., and Solodin, N., Proteasome-mediated proteolysis of estrogen receptor: a novel component in autologous down-regulation. (1999) Mol. Endocrinol. 13, 1522-1534.
Alessi, DR et al., "Characterization of a 3-phosphoinositide-dependent protein kinase which phosphorylates and activates protein kinase B?," Curr Biol (1997) 7: 261-269.
Alexakis C, et al., Implication of the satellite cell in dystrophic muscle fibrosis: a self-perpetuating mechanism of collagen over-production. Am J Physiol Cell Physiol: C661-C669, 2007.
Alfarano C, et al., Intraparenchymal injection of bone marrow mesenchymal stem cells reduces kidney fibrosis after ischemia-reperfusion in cyclosporine-immunosuppressed rats. Cell Transplant. 2012; 21:2009-2019.
Alipoor, SD et al., Exosomes and Exosomal miRNA in Respiratory Diseases, Mediators of Inflammation (2016) 5628404.

(Continued)

*Primary Examiner* — Christopher M Babic
(74) *Attorney, Agent, or Firm* — McCarter & English, LLP; Beverly W. Lubit

(57) ABSTRACT

The described invention provides compositions and methods for treating a fibrotic condition in a subject. The methods include administering a therapeutic amount of a pharmaceutical composition comprising synthetic extracellular vesicles (EVs) and a pharmaceutically acceptable carrier.

7 Claims, 41 Drawing Sheets
(17 of 41 Drawing Sheet(s) Filed in Color)
Specification includes a Sequence Listing.

(56) References Cited

OTHER PUBLICATIONS

Almekhlafi, G.A., et al., Presentation and outcome of Middle East respiratory syndrome in Saudi intensive care unit patients, Crit. Care (2016) 20: 123.

Altschul, Gapped BLAST and PSI-BLAST: a new generation of protein database search programs, Nucl. Acids Res. 25 (1977), 3389-3402.

Alvarez et al., Lung microvascular endothelium is enriched with progenitor cells that exhibit vasculogenic capacity, Am J Physiol Lung Cell Mol Physiol. 2008; 294: L419-30.

Alviano, F. et al., Term Amniotic membrane is a high throughput source for multipotent Mesenchymal Stem Cells with the ability to differentiate into endothelial cells in vitro, BMC Dev Biol, 2007, 7: 11.

Amarnath A, et al., Bone Marrow-Derived Mesenchymal Stromal Cells Harness Purinergenic Signaling to Tolerize Human T h1 Cells In Vivo. Stem Cells (2015) 33: 1200-1212.

Amin MA, et al., Short-term evaluation of autologous transplantation of bone marrow-derived mesenchymal stem cells in patients with cirrhosis: Egyptian study. Clin Transplant. 2013; 27: 607-612.

Anderson JD, et al., Comprehensive Proteomic Analysis of Mesenchymal Stem Cell Exosomes Reveals Modulation of Angiogenesis via Nuclear Factor-KappaB Signaling. Stem Cells. Mar. 2016; 34(3): 601-13.

Anderson, RM et al., Epidemiology, transmission dynamics and control of SARS: the 2002-2203 epidemic, Philos. Trans. R. Soc. Lond. B.Biol. Sci. (2004) 359: 1091-105.

Andjelkovic , M et al., Activation and phosphorylation of a pleckstrin homology domain containing protein kinase (RAC-PK/PKB) promoted by serum and protein phosphatase inhibitors, Proc Natl Acad Sci (1996) 93: 5699-5704.

Aqil, M. et al., The HIV Nef protein modulates cellular and exosomaal miRNA profies in human monocytic cells, J. Extracell. Vesicles (2014) 3. doi: 10342/jev.v3.23129.

Arima N, et al., Single intra-arterial injection of mesenchymal stromal cells for treatment of steroid-refractory acute graft-versus-host disease: a pilot study, Cytotherapy 2010; 12: 265-268.

Arlan, F. et al., Mesenchymal stem cell-derived exosomes increase ATP levels, decrease oxidative stress and activate PI3K/Akt pathway to enhance myocardial viability and prevent adverse remodeling after myocardial ischemia/reperfusion injury, Stem Cell Res. (2013) 10: 301-12.

Asanuma H, et al., Arterially delivered mesenchymal stem cells prevent obstruction-induced renal fibrosis. J Surg Res 168: e51-e59, 2011.

Ashcroft T, Simpson JM, Timbrell V. Simple method of estimating severity of pulmonary fibrosis on a numerical scale. J Clin Pathol 1988; 41: 467-470.

Askar SF, et al., Engraftment patterns of human adult mesenchymal stem cells expose electrotonic and paracrine proarrhythmic mechanisms in myocardial cell cultures. Circ Arrhythm Electrophysiol. 2013; 6: 380-91.

Assiri, A. et al., Epidemiological, demographic, and clinical characteristics of 47 cases of Middle East respiratory syndrome coronavirus disease from Saudi Arabia: a descriptive study, Lancet Inf. Dis. (2013) 13: 752-61.

Augello, A. et al., Mesenchymal stem cells: a perspective from in vitro cultures to in vivo migration and niches. Eur. Cells and Materials (2010) (20): 121-33.

Baarsma, HA and Konigshoff M., 'WNT-er is coming': WNT signalling in chronic lung diseases. Thorax 2017; 72: 746-759.

Baban, B. et al., Indoleamine 2,3-dioxygenase expression is restricted to fetal trophoblast giant cells during murine gestation and is maternal genome specific. J Reprod Immunol, 2004, 61: 67-77.

Bai ZM, et al., Arterially transplanted mesenchymal stem cells in a mouse reversible unilateral ureteral obstruction model: in vivo bioluminescence imaging and effects on renal fibrosis. Chin Med J (Engl) 126: 1890-1894, 2013.

Balaji, S. et al. The Role of Mesenchymal Stem Cells in the Regenerative Wound Healing Phenotype. Adv. Wound Care (2012) 1(40): 159-65.

Balana, B, et al., 5-Azacytidine induces changes in electrophysiological properties of human mesenchymal stem cells. Cell Res. 16: 949-960; 2006.

Balasubramian et al., Bone marro-derived angiogenic cells restore lung alveolar and vascular structure after neonatal hyperoxia in infant mice. Am J Physiol Lung Cell Mol Physiol. 2010; 298: L315-23.

Balke B., A Simple Field Test for the Assessment of Physical Fitness REP 63-6, Rep Civ Aeromed Res Inst US. 1963 (53): 1-8.

Balkom B.W., et al., Endothelial cells require miR-214 to secrete exosomes that suppress senescence and induce angiogenesis in human and mouse endothelial cells, Blood. 2013;121:S1-S15.

Barkhem, T., Nilsson, S., and Gustafsson, J. A., Molecular mechanisms, physiological consequences and pharmacological implications of estrogen receptor action. (2004) Am. J. Pharmacogenomics 4, 19-28.

Baron F, et al., Cotransplantation of mesenchymal stem cells might prevent death from graft-versus-host disease (GVHD) without abrogating giall-versus-tumor effects after HLA-mismatched allogeneic transplantation following nonmyeloablative conditioning, Biol Blood Marrow Transplant 2010; 16: 838-847.

Barreiro TJ, Perillo I., An approach to interpreting spirometry, Am Fam Physician. Mar. 1, 2004; 69(5): 1107-14.

Bartel, DP., MicroRNAs: genomics, biogenesis, mechanism, and function, Cell (2004) 116: 281-97.

Bauer Y, et al. A novel genomic signature with translational significance for human idiopathic pulmonary fibrosis. Am J Respir Cell Mol Biol 2015; 52: 217-231.

Bauer Y, et al. MMP-7 is a predictive biomarker of disease progression in patients with idiopathic pulmonary fibrosis. ERJ Open Res 2017; 3.

Beach A, et al. Exosomes: an overview of biogenesis, composition and role in ovarian cancer. Journal of ovarian research. 2014;7(1):14.

Beers, MF and Morrisey, EE, The 3 R's of lung health and disease—repair, remodeling and regeneration. J. Clin. Invest. (2011) 121: 2065-73.

Bellon, M. et al. Deregulation of microRNA involved in hematopoiesis and the immune response in HTLV-I adult T-cell leukemia. Blood (2009) 113:4914-4917.

Bellusci et al., Fibroblast Growth Factor 10 (FGF10) and branchburg morphongenesis in the embryonic mouse lung, Development. Dec. 1997; 124(23): 4867-78.

Benaroch, P. et al., HIV-1 assembly in macrophages, retroviral. (2010) 7: 29.

Benirschke, K. et al., Early Development of the Human Plecenta, P. Pathology of the human placenta. New York, Springer-Verlag, 2000, 42-46, 116, 281-297.

Schlndorff D., The glomerular mesangial cell: an expanding role for a specialized pericyte. FASEB J. (1987) 1(4): 272-81.

Schmittgen TD, Livak KJ. Analyzing real-time PCR data by the comparative C(T) method. Nat Protoc 2008; 3: 1101-1108.

Schniedermann et al., Mouse lung contains endothelial progenitors with high capacity to form blood and lymphatic vessesls. BMC Cell Biol. 2010; 11: 50.

Schouten, LR et al., Age-dependent differences in pulmonary host responses in ARDS: a prospective observational cohort study, Ann. Intensive Care (2019) 9: 55.

Schrier D. et al., The role of strain variation in murine bleomycin-induced pulmonary fibrosis, Am Rev Respir Dis., 127 (1): 63-6, 1983.

Schriner SE, et al. Extension of murine life span by overexpression of catalase targeted to mitochondria. Science. 2005;308(5730):1909-1911.

Schumacker PT, et al. Mitochondria in lung biology and pathology: more than just a powerhouse. Am J Physiology Lung Cell Mol Physiol. 2014;306(11):L962-L974.

Sedgwick JB, et al., Effects of inflammatory cytokines on the permeability of human lung microvascular endothelial cell monolayers and differential eosinophil transmigration. J Allergy Clin Immunol. 2002; 110: 752-756.

(56) References Cited

OTHER PUBLICATIONS

Seki E, et al., TLR4 enhances TGF-β signaling and hepatic fibrosis. Nat Med 2007; 13: 1324-32.

Selman M, et al. Idiopathic Pulmonary Fibrosis: Aberrant Recapitulation of Developmental Programs?. PLoS medicine 2008; 5: e62.

Selman M, et al., Idiopathic pulmonary fibrosis: prevailing and evolving hypotheses about its pathogenesis and implications for therapy. Ann Intern Med, 134(2): 136-151, 2001.

Selman M, Pardo A. Revealing the pathogenic and aging-related mechanisms of the enigmatic idiopathic pulmonary fibrosis. an integral model. Am J Respir Crit Care Med 2014;189(10):1161-1172.

Semedo P, et al. Mesenchymal Stem Cells Attenuate Renal Fibrosis Through Immune Modulation and Remodeling Properties in a Rat Remnant Kidney Model. Stem Cells 27: 3063-3073, 2009.

Senoo H., Structure and function of hepatic stellate cells. Med Electron Microsc. Mar. 2004; 37(1): 3-15.

Seo, H. S., et al. Estrogenic and anti-estrogenic regulation of estrogen receptor in MCF-7 breast-cancer cells : Comparison of immunocytochemical data with biochemical measurements. (1998) Int. J. Cancer 78, 760-765.

Serrano AL, et al., Chapter seven—Cellular and Molecular Mechanisms Regulating Fibrosis in Skeletal Muscle Repair and Disease. Curr Top Dev Biol: 167-201, 2011.

Shake JG, et al. Mesenchymal stem cell implantation in a swine myocardial infarct model: engraftment and functional affects. Ann Thoracic Surg: 73:1919-1926, 2002.

Shan et al., Centrifugal Migration of Mesenchymal Cells in Embryonic Lung. Dev Dyn. 2008; 237: 750-757.

Shannon & Deterding. Epithelial-mesenchymal interactions in lung development. In: McDonald JA, ed. Lung Biology in Health and Disease. vol. 100. New York: Marcel Dekker Inc., 1997, pp. 81-118.

Shapira SD, et al., A physical and regulatory map of host-influenza interactions reveals pathways in H1N1 infection, (2009) Cell 139: 1255-1267.

Sharplin J, Franko AJ., A quantitative histological study of strain-dependent differences in the effects of irradiation on mouse lung during the early phase. Radiat Res. 1989; 119: 1-14.

Shen, Q. et al., Paracrine factors from mesenchymal stem cells attenuate epithelial injury and lung fibrosis.Mol. Med. Re. (2015) 11: 2831-37.

Shilo, S., et al. MicroRNA in Cutaneous Wound Healing: A New Paradigm. DNA Cell Biol. (2007) 26: 227-37.

Shim, WS, et al., Ex vivo differentiation of human adult bone marrow stem cells into cardiomyocyte-like cells. Biochem. Biophys. Res. Commun. 324: 481-488; 2004.

Shu T, et al., HO-1 modified mesenchymal stem cells modulate MMPs/TIMPs system and adverse remodeling in infarcted myocardium. Tissue Cell: 217-222, 2010.

Sica A, Mantovani A., Macrophage plasticity and polarization: in vivo veritas. J Clin Investig. 2012; 122: 787-795.

Siegfried JM, Stabile LP. Estrogenic steroid hormones in lung cancer. Seminars in oncology 2014; 41: 5-16.

Silva J., et al., Vesicle-related microRNAs in plasma of nonsmall cell lung cancer patients and correlation with survival, Eur Respir J. 2011;37:617-623.

Silva, F., Nardi, N., From leading role to the backstage: mesenchymal stem cells as packaging cell lines for in situ production of viral vectors, Med. Hypoth. (2006) 67:922-925.

Simons M., et al., Exosomes-vesicular carriers for intercellular communication, Curr Opin Cell Biol. 2009;21:575-581.

Simpson, RJ, et al., Proteomic profiling of exosomes: current perspectives, Proteomics (2008) 8: 4083-99.

Singh A, et al., Mesenchymal stem cells in cardiac regeneration: a detailed progress report of the last 6 years (2010-2015). Stem Cell Res Ther. 2016; 7: 82.

Sinnott, J. T., et al. Respiratory syncytial virus pneumonia in a cardiac transplant recipient. J. Infect. Dis. (1988) 158:650-651, Wendt, C. H. Community respiratory viruses: organ transplant recipients. Am. J. Med. (1997) 102:31-36, 42-43.

Skog J., et al., Glioblastoma microvesicles transport RNA and proteins that promote tumour growth and provide diagnostic biomarkers, Nat Cell Biol. 2008;10:1470-1476.

Skurikhin, E.G. et al., Differentiation of Mesenchymal Multipotent Stromal Cells of the Lungs in Pneumofibrosis. Bull Exp. Biol. Med. (2013) 154: 537-43.

Smith W, Hood M. Arrhythmias, in Cardiothoracic Critical Care, 2007.

Snider et al., Chronic interstitial pulmonary fibrosis produced in hamsters by endotracheal bleomycin. Lung volumes, volume-pressure relations, carbon monoxide uptake, and arterial blood gas studied. Am Rev Respir Dis. Feb. 1978;117(2):289-97.

Sobo-Vujanovic, A. et al., Dendritic-cell exosomes cross-present Toll-like receptor-ligands and activate bystander dendritic cells, Cell Immunol. (2014) 289: 119-127.

Soncini, M. et al.,Isolation and characterization of mesenchymal cells from human fetal membranes, J Tissue Eng Regen Med, 2007, 1:296-305.

Song JW, et al. Blood biomarkers MMP-7 and SP-A: predictors of outcome in idiopathic pulmonary fibrosis. Chest 2013; 143: 1422-1429.

Song L, , et al. Silencing suppressors: viral weapons for countering host cell defenses. Protein Cell. (2011) 2: 273-81.

Spach MS, Boineau JP., Microfibrosis produces electrical load variations due to loss of side-to-side cell connections: a major mechanism of structural heart disease arrhythmias. Pacing Clin Electrophysiol 1997; 20: 397-413.

Spees JL, et al. Bone marrow progenitor cells contribute to repair and remodeling of the lung and heart in a rat model of progressive pulmonary hypertension. FASEB J. 2008; 22(4):1226-1236.

Spees JL, et al. Engraftment of bone marrow progenitor cells in a rat model of asbestos-induced pulmonary ?brosis. Am J Resp Crit Care Med. 2007;176(4):385-394.

Spinale FG., Myocardial Matrix Remodeling and the Matrix Metalloproteinases: Influence on Cardiac Form and Function. Physiol Rev 2007; 87: 1285-342.

Squillaro T, Peluso G, Galderisi U. Clinical Trials With Mesenchymal Stem Cells: An Update. Cell Transplant 2016; 25: 829-848.

Srour, N. and Thebaud, B., Mesenchymal Stromal Cells in Animal Bleomycin Pulmonary Fibrosis Models: A Systematic Review., Stem Cells Trans. Med. (2015) 4:1500-1510.

Stambolic, V et al., "Negative regulation of PKB/Akt-dependent cell survival by the tumor suppressor PTEN," Cell (1998) 95: 29-39.

Starcher B. et al., Increased elastin and collagen content in the lungs of hamsters receiving an intratracheal injection of bleomycin, Am Rev Respir Dis., 117(2): 299-305, 1978.

Starkel P, Leclercq IA. Animal models for the study of hepatic fibrosis. Best Pract Res Clin Gastroenterol. 2011; 25: 319-333.

Ogata-Kawata H., et al., Circulating exosomal microRNAs as biomarkers of colon cancer, PLoS One. 2014;9:e92921.

Oh DY, et al., Potently immunosuppressive 5-fluorouracil-resistant mesenchymal stromal cells completely remit an experimental autoimmune disease, J Immunol 2012; 188: 2207-2217.

Ohshima K., et al., Let-7 microRNA family is selectively secreted into the extracellular environment via exosomes in a metastatic gastric cancer cell line, PLoS One. 2010;5:e13247.

Oikonomidi et al. Matrix Metalloproteinases in Respiratory Diseases: From Pathogenesis to Potential Clinical Implications. Curr Med Chem. 2009; 16(10): 1214-1228.

Olivera S., Tomic-Canic M. (2013) Human Ex Vivo Wound Healing Model. In: Gourdie R., Myers T. (eds) Wound Regeneration and Repair. Methods in Molecular Biology (Methods and Protocols), vol. 1037. Humana Press, Totowa pp. 255-264.

Olman MA, et al., Microarray analysis indicates that pulmonary edema fluid from patients with acute lung injury mediates inflammation, mitogen gene expression, and fibroblast proliferation through bioactive interleukin-1. Chest. 2002; 121: 69S-70S.

Omrani, AS et al., Ribavirin and interferon alfa-2a for severe Middle East respiratory syndrome coronavirus infection: a retrospective cohort study, Lancet Infect. Dis. (2014) 14: 1090-5.

(56) References Cited

OTHER PUBLICATIONS

Ono M, et al. Exosomes from bone marrow mesenchymal stem cells contain a microRNA that promotes dormancy in metastatic breast cancer cells. Sci Signal 2014; 7:332, pp. ra63.
Orom, UA et al. MicroRNA-10a Binds the 5'UTR of Ribosomal Protein mRNAs and Enhances Their Translation. (2008) Mol. Cell 30: 460-71.
Ortiz LA, et al. Mesenchymal stem cell engraftment in lung is enhanced in response to bleomycin exposure and ameliorates its fibrotic effects. Proc Natl Acad Sci U S A 2003; 100: 8407-8411.
Oshida K, Waxman DJ, Corton JC. Chemical and Hormonal Effects on STAT5b-Dependent Sexual Dimorphism of the Liver Transcriptome. PLoS One 2016; 11: e0150284.
Osong Public Health Res. Perspect., Middle East Respiratory Sndrome Coronavirus Outbreak in the Republic of Korea, (2015) 6: 269-78.
Paley, MA et al., Progenitor and terminal subsets of CD8+ T cells cooperate to contain chronic viral infection, Science (2012) 338: 1220-125.
Pandit KV, Milosevic J, Kaminski N. MicroRNAs in idiopathic pulmonary fibrosis. Transl Res 2011; 157: 191-199.
Pandit KV, Milosevic J. MicroRNA regulatory networks in idiopathic pulmonary fibrosis. Biochem Cell Biol 2015; 93: 129-137.
Pardo A, Selman M., Matrix metalloproteases in aberrant fibrotic tissue remodeling. Proc Am Thorac Soc. Jun. 2006; 3(4): 383-8.
Pastar I, et al. Skin Metabolite, Farnesyl Pyrophosphate, Regulates Epidermal Response to Inflammation, Oxidative Stress, and Migration. J Cell Physiol. 2016;231(11):2452-63.
Patel AS, et al. Epithelial cell mitochondrial dysfunction and PINK1 are induced by transforming growth factor-beta1 in pulmonary fibrosis. PLoS One. 2015;10(3):e0121246.
Patel, PH, et al. GW-Bodies and P-Bodies Constitute Two Separate Pools of Sequestered Non-Translating RNAs. PLos One (2016) 11(3): e0150291.
Paul, W. E., "Chapter 1: The immune system: an introduction," Fundamental Immunology, 4th Edition, Ed. Paul, W. E., Lippicott-Raven Publishers, Philadelphia, (1999), at p. 102.
Pavenstadt, H, Roles of the podocyte in glomerular function. Am. J. Physiol. Renal Physiol. (2000) 278 (2): F173-F179.
Pedersen, IM, et al, Interferon modulation of cellular microRNAs as an antiviral mechanism. Nature (2007) 449:919-922.
Pegtel, DM et al., Functional delivery of viral miRNAs via exosomes, Proc. Nat. Acad. Sci. USA (2010) 107: 6328-33.
Peigue-Lafeuille, HN, et al., Severe respiratory syncytial virus pneumonia in an adult renal transplant recipient: successful treatment with ribavirin. Scand. J. Infect. Dis. (1990) 22:87-89.
Peiris, JS, et al., Clinical progression and viral load in a community outbreak of coronavirus-associated SARS pneumonia: a prospective study, Lancet (2003) 361: 1767-72.
Pelchen Matthews, A., et al., Endosomes, exosomes and Trojan viruses Trends Microbiol. (2004) 12: 310-316.
Peng et al., Comparative Analysis of Mesenchymal Stem Cells from Bone Marrow, Cartilage, and Adipose Tissue, Stems Cells and Development, 17: 761-774, 2008.
Peng L, et al. Autologous Bone Marrow Mesenchymal Stem Cell Transplantation in Liver Failure Patients Caused by Hepatitis B: Short-Term and Long-Term Outcomes. Hepatology. 2011; 54: 820-828.
Peng R, et al. Bleomycin induces molecular changes directly relevant to idiopathic pulmonary fibrosis: a model for "active" disease. PLoS One 2013; 8: e59348.
Perez-Simon JA, et al. , Mesenchymal stem cells expanded in vitro with human serum for the treatment of acute and chronic graft-versus-host disease: results of a phase I/II clinical trial, Haematologica 2011; 96: 1072-1076.
Phan, S. et al., A comparative study of pulmonary fibrosis induced by bleomycin and an O2 metabolite producing enzyme system, Chest., 83(5 Suppl): 44S-45S, 1983.
Phan, S. et al., Bleomycin-induced pulmonary fibrosis in rats: biochemical demonstration of increased rate of collagen synthesis, Am Rev Respir Dis 121: 501-506, 1980.
Phillips RJ, Burdick MD, Hong K, et al. Circulating ?brocytes traf?c to the lungs in response to CXCL12 and mediate ? brosis. J Clin Invest. 2004;114(3): 438-446.
Phinney DG, et al. Biological Activities Encoded by the Murine Mesenchymal Stem Cell Transcriptome Provide a Basis tor Their Developmental Potential and Broad Therapeutic Efficacy. Stem Cells 2006; 24: 186-198.
Phinney, DG and Pittenger, MF., Concise Review: MSC-Derived Exosomes for Cell-Free Therapy. Stem Cells (2017) 35: 851-58.
Pittenger et al., Multilineage potential of adult human mesenchymal stem cells, Science 284: 143-47 (1999).
Poisson J, et al., Liver sinusoidal endothelial cells: Physiology and role in liver diseases. J Hepatol. Jan. 2017; 66(1): 212-227.
Porter DW, et al., Time course of pulmonary response of rats to inhalation of crystalline silica: NF-kappa B activation, inflammation, cytokine production, and damage. Inhalation Toxicol. 2002; 14: 349-367.
Portmann-Lanz, C. et al., Placental mesenchymal stem cells as potential autologous graft for pre- and perinatal neuroregeneration, Am J Obstet Gynecol, 2006, 194: 664-673.
Prasse A, et al. A Vicious Circle of Alveolar Macrophages and Fibroblasts Perpetuates Pulmonary Fibrosis via CCL18. Am J Respir Crit Care Med. 2006; 173(7): 781-92.
Prasse A, et al. CCL18 as an Indicator of Pulmonary Fibrotic Activity in Idiopathic Interstitial Pneumonias and Systemic Sclerosis. Arthritis Rheum. 2007; 56(5): 1685-93.
Prasse A, et al. Serum CC-Chemokine Ligand 18 Concentration Predicts Outcome in Idiopathic Pulmonary Fibrosis. Am J Respir Crit Care Med. 2009; 179(8): 717-23.
Preisler-Mashek, M. T., et al. Ligand-specific regulation of proteasome-mediated proteolysis of estrogen receptor-alpha. (2002) Am. J. Physiol. Endocrinol. Metab. 282, 891-898.
Prusa AR, et al., Amniotic fluid cells and human stem cell research: a new connection, Med Sci Monit. Nov. 2002; 8(11): RA253-7.
Qazi, KR, et al., Proinflammatory exosomes in bronchoalveolar lavage fluid of patients with sarcoidosis, Thorax, (2010) 65 (11): 1016-1024.
Qin, X et al., 4E-BP1, a multifactor regulated multifunctional protein, Cell Cycle (2016) 15(6): 781-86.
Qu J.L., et al., Gastric cancer exosomes promote tumour cell proliferation through PI3K/Akt and MAPK/ERK activation, Dig Liver Dis. 2009;41:875-8.
Quarmby S, et al., Irradiation Induces Upregulation of CD31 in Human Endothelial Cells. Arterioscler Thromb Vasc Biol. 1999; 19: 588-597.
Rabani V, et al. Mesenchymal stem cell infusion therapy in a carbon tetrachloride-induced liver fibrosis model affects matrix metalloproteinase expression. Cell Biol Int. 2010; 34: 601-605.
Rabinowits G., et al., Exosomal microRNA: a diagnostic marker for lung cancer, Clin Lung Cancer. 2009;10:42-46.
Liang J, et al. Allogenic mesenchymal stem cells transplantation in refractory systemic lupus erythematosus: a pilot clinical study. Ann Rheum Dis. 2010; 69(8):1423-1429.
Liang X, Ding Y, Zhang Y, Tse HF, and Lian Q. Paracrine mechanisms of Mesenchymal Stem cell-based therapy: Current status and perspectives. Cell transplantation. 2013.
Liang X, et al. Exosomes secreted by mesenchymal stem cells promote endothelial cell angiogenesis by transferring miR-125a. J Cell Sci 2016; 129: 2182-2189.
Liao J., et al., Expression profiling of exosomal miRNAs derived from human esophageal cancer cells by Solexa high-throughput sequencing, Int J Mol Sci. 2014;15:15530-15551.
Ling, L. et al., Wnt signaling controls the fate of mesenchymal stem cells. Gene (2009) 433: 1-7.
Lino Cardenas CL, et al. miR-199a-5p Is upregulated during fibrogenic response to tissue injury and mediates TGFbeta-induced lung fibroblast activation by targeting caveolin-1. PLoS Genet 2013; 9: e1003291.
Lino Cardenas CL, Kaminski N, Kass DJ. Micromanaging microRNAs: using murine models to study microRNAs in lung fibrosis. Drug Discov Today Dis Models 2013; 10: e145-e151.
Lion, T., et al. Intestinal adenovirus infection with increasing viral load in stool is an early indicator of impending disseminated disease

(56) References Cited

OTHER PUBLICATIONS in children undergoing T-cell depleted allogeneic stem cell transplantation. Blood (2003) 102:196a.

Liu H, et al. The Role of SDF-1-CXCR4/CXCR7 Axis in the Therapeutic Effects of Hypoxia-Preconditioned Mesenchymal Stem Cells for Renal Ischemia/Reperfusion Injury. PLoS One. 2012; 7: e34608.

Liu XJ, et al., Reciprocal effect of mesenchymal stem cell on experimental autoimmune encephalomyelitis is mediated by transforming growth factor-beta and interleukin-6, Clin Exp Immunol 2009; 158: 37-44.

Liu Y, et al., Therapeutic potential of human umbilical cord mesenchymal stem cells in the treatment of rheumatoid arthritis, Arthritis Res Ther 2010; 12: R210.

Liu Y., Cellular and molecular mechanisms of renal fibrosis. Nat Rev Nephrol 2011; 7: 684-96.

Liu, A. et al., Wnt5a through noncanonical Wnt/JNK or Wnt/PKC signaling contributes to the differentiation of mesenchymal stem cells into type II alveolar. PLoS One (2014) 9: e90229.

Liu, AR. J., Activation of canonical wnt pathway promotes differentiation of mouse bone marrow-derived MSCs into type II alveolar epithelial cells, confers resistance to oxidative stress, and promotes their migration to injured lung tissue in vitro. Cell Physiol. (2013) 228: 1270-83.

Lonard, D. M., et al. The 26S proteasome is required for estrogen receptor-alpha and coactivator turnover and for efficient estrogen receptor-a transactivation. (2000) Mol. Cell 5, 939-948.

Long, X and Nephew, KP, Fulvestrant (ICI 182,780)-dependent interacting proteins mediate immobilization and degradation of estrogen receptor-alpha. J. Biological Chem. (2006) 281: 9607-15.

Lopez-Verrilli et al. Mesenchymal stem cell-derived exosomes from different sources selectively promote neuritic butgrowth. Neuroscience 2016; 320: 129-139.

Lotvall, J., Valadi, H. Cell to Cell Signalling via Exosomes Through esRNA. Cell Adhesion & Migration (2007) 1:3, 156-58.

Loutfy, MR et al., Interferon alfacon-1 plus corticosteroids in severe acute respiratory syndrome: a preliminary study, JAMA (2003) 290: 3222-28.

Luzina IG, et al. CCL18-stimulated upregulation of collagen production in lung fibroblasts requires Sp1 signaling and basal Smad3 activity. J Cell Physiol. 2006; 206(1): 221-8.

Mack, M. et al., Transfer of the chemokine receptor CCR5 between cells by membrane-derived microparticles: a mechanism for cellular human immunodeficiency virus 1 infection, Nat. Med. (2000) 6: 769-75.

MacIntyre N., Current issues in mechanical ventilation for respiratory failure, Chest, 128:561 S-567, 2005.

Madhi, S. A., B. et al. Increased burden of respiratory viral associated severe lower respiratory tract infections in children infected with human immunodeficiency virus type-1. J. Pediatr. (2000) 137:78-84.

Madhi, S. A., L. et al. Five-year cohort study of hospitalization for respiratory syncytial virus associated lower respiratory tract infection in African children. J Clin. Virol. (2006) 36:215-221.

Madhi, S. A., N. Lower respiratory tract infections associated with influenza A and B viruses in an area with a high prevalence of pediatric human immunodeficiency type 1 infection. Pediatr. Infect. Dis. J. (2002) 21:291-297133.

Madrid, R. et al., Nef-induced alteration of the early/recycling endosomal compartment correlates with enhancement of HIV-1 infectivity, J. Biol. Chem. (2005) 280: 5032-44.

Mailleuix et al., Fgf10 expression indentifies parabronchial smooth muscle cell pregenitors and is required for entry into the smooth muscle cell lineage, Development. May 2005; 132(9): 2157-66.

Mair-Jenkins, J. et al., The effectiveness of convalescent plasma and hyperimmune immunoglobulin for the treatment of severe acute respiratory infections of viral etiology: a systematic review and exploratory meta-analysis, J. Infect. Dis. (2015) 211: 80-90.

Majumdar, et al., Phenotypic and functional comparison of cultures of marrow-derived mesenchymal stem cells (MSCs) and stromal cells, J. Cell Physiol. 176: 57-66 (1998).

Makkar RR, et al., Intramyocardial injection of allogenic bone marrow-derived mesenchymal stem cells without immunosuppression preserves cardiac function in a porcine model of myocardial infarction. J Cardiovasc Pharmacol Ther: 225-233, 2005.

Manachery, VD, et al. , Pathogenic influenza viruses and coronaviruses utilize similar and contrasting approaches to control interferon-stimulated gene responses, Mol. Bio. (2014) 5: e01174-14.

Marenzana M, Vande Velde G. Refine, reduce, replace: Imaging of fibrosis and arthritis in animal models. Best Pract Res Clin Rheumatol 2015; 29: 715-740.

Margadant, C, Sonnenberg A., Integrin-TGF-b crosstalk in fibrosis, cancer and wound healing. EMBO Rep 2010; 11: 97-105.

Markova MS, et al., A role for the androgen receptor in collagen content of the skin. A role for the androgen receptor in collagen content of the skin. J Invest Dermatol 2004; 123: 1052-1056.

Marquez-Curtis, LA and Janowska-Wieczork, A., Enhancing the Migration Ability of Mesenchymal Stromal Cells by Targeting the SDF-1/CXCR4 Axis. BioMed. Res. Int. (2013): 2013; 561098.

Martin M, et al. TGF-beta1 and radiation fibrosis: a master switch and a specific therapeutic target? Int J Radiat Oncol Biol Phys. 2000; 47: 277-290.

Martin ML, Blaxall BC., Cardiac Intercellular Communication: Are myocytes and fibroblasts fair-weather friends? J Cardiovasc Transl Res 2012; 5: 768-82.

Martin-Medina A, et al. Increased Extracellular Vesicles Mediate WNT5A Signaling in Idiopathic Pulmonary Fibrosis. Am J Respir Grit Care Med. vol. 198, Iss 12, pp. 1527-1538, Dec. 15, 2018. [Originally Published in Press as DOI: 10.1164/rccm.201708-1580OC on Jul. 25, 2018].

Masyuk, Al, et al., Exosomes in the pathogenesis, diagnostics and therapeutics of liver diseases, Journal of Hepatology (2013) 59 (3): 621-625.

Mathew M, Thomas SM. In: Li X, editor. The Cellular Microenvironment of Head and Neck Squamous Cell Carcinoma, InTech; 2012. pp. 163-174.

Matsui F, et al. Mesenchymal stem cells protect against obstruction-induced renal fibrosis by decreasing STAT3 activation and STAT3-dependent MMP-9 production. Am J Physiol Renal Physiol. Jan. 1, 2017; 312(1): F25-F32.

Matsuura et al. Transplantation of cardiac progenitor cells ameliorates cardiac dysfunction after myocardial infarction in mice. J. Clin. Invest., 119 (2009): 2204-2217.

McBride JD, et al. Bone marrow mesenchymal stem cell-derived cd63+ exosomes transport wnt3a exteriorly and enhance dermal fibroblast proliferation, migration, and angiogenesis in vitro. Stem Cells Dev. Oct. 1, 2017;26(19) :1384-1398.

McDonald JA, ed. Lung Biology in Health and Disease. vol. 100. New York: Marcel Dekker Inc., 1997, pp. 81-118.

McGee SP, Zhang H, Karmaus W, Sabo-Attwood T. Influence of sex and disease severity on gene expression profiles in individuals with idiopathic pulmonary fibrosis. Int J Mol Epidemiol Genet 2014; 5: 71-86.

McNamara, PS, Van Doorn, HR, Respiratory viruses and atypical bacteria. In Manson's Tropical Infectious Diseases (23rd Ed.) (2014), 215-224.

McQualter & Bertoncello., Concise Review: Deconstructing the Lung to Reveal Its Regenerative Potential. Stem Cells. May 2012; 30(5); 811-16.

McQualter et al. Evidence of an epithelial stem/progenitor cell hierarchy in the adult mouse lung. Proc Natl Acad Sci USA 2010; 107: 1414-19.

McQualter et al., Endogenous Fibroblastic Progenitor Cells in the Adult Mouse Lung Are Highly Enriched in the Sca-1 Positive Cell Fraction. Stem Cells. (2009); 27: 623-633.

Meckes D.G., Jr., et al., Human tumor virus utilizes exosomes for intercellular communication, Proc Natl Acad Sci U S A. 2010;107:20370-20375.

Chimenti et al., Relative roles of direct regeneration versus paracrine effects of human cardiosphere-derived cells transplanted into infarcted mice. Circ. Res., 106 (2010): 971-980.

(56) References Cited

OTHER PUBLICATIONS

Chithra P, et al., Influence of Aloe vera on the glycosaminoglycans in the matrix of healing dermal wounds in rats. J Ethnopharmacol. 1998; 59: 179-186.

Cho J.A., et al., Exosomes from breast cancer cells can convert adipose tissue-derived mesenchymal stem cells into myofibroblast-like cells, Int J Oncol. 2012;40:130-138.

Choi, M. et al., Therapeutic Use of Stem Cell Transplantation for Cell Replacement or Cytoprotective Effect of Microvesicle Released from Mesenchymal Stem Cell. Mol. Cells (2014) 37: 133-139.

Choi, WS, et al., Clinical Presentation and Outcomes of Middle East Respiratory Syndrome in the Republic of Korea, Infect. Chemother. (2016) 48: 118-26.

Chou SH, et al., Mesenchymal stem cell insights: prospects in cardiovascular therapy. Cell Transplant. 2014; 23(4-5): 513-29.

Chu, CM et al., Role of lopinaviriritonavir in the treatment of SARS: initial virological and clinical findings, Thorax (2004) 59: 252-56.

Chu, KH et al., Acute renal impairment in coronavirus-associated severe acute respiratory syndrome, Kidney Int. (2005) 67: 98-705.

Chung, YS, et al., Cardiac injury protection from mouse bone marrow stromal cells with in utero transplantation followed by secondary postnatal boost. Chin. J. Physiol. 54: 205-218; 2011.

Cikaluk, D.E. et al., GERp95, a membrane-associated protein that belongs to a family of proteins involved in stem cell differentiation. Mol. Biol. Cell (1999) 10: 3357-72.

Coker and Laurent, Pulmonary fibrosis: cytokines in the balance. Eur Respir J, 1998, 11: 1218-1221.

Collard HR, et al. A new era in idiopathic pulmonary fibrosis: considerations for future clinical trials. Eur Respir J 2015.

Collino, F. et al., Microvesicles derived from adult human bone marrow and tissue specific mesenchymal stem cells shuttle selected pattern of miRNAs. PLoS One (2010) 5: e11803.

Colter DC, et al., Identification of a subpopulation of rapidly self-renewing and multipotential adult step cells in colonies of human marrow stromal cells, Proc Natl Acad Sci USA 98, 78415.

Connick P, et al., Autologous mesenchymal stem cells for the treatment of secondary progressive multiple sclerosis: an open-label phase 2a proof-of-concept study, Lancet Neurol 2012; 11: 150-156.

Connick P, et al., The mesenchymal stem cells in multiple sclerosis (MSCIMS) trial protocol and baseline cohort characteristics: an open-label pre-test: post-test study with blinded outcome assessments, Trials 2011; 12: 62.

Conroy KP, et al. alphav integrins: key regulators of tissue fibrosis. Cell Tissue Res 2016.

Crivellato, The role of angiogenic growth factors in organogenesis, Int J Dev Biol. 2011; 55(4-5): 365-75.

Cruz FF, et al., Systemic Administration of Human Bone Marrow-Derived Mesenchymal Stromal Cell Extracellular Vesicles Ameliorates Aspergillus Hyphal Extract-Induced Allergic Airway Inflammation in Immunocompetent Mice. Stem Cells Transl Med. Nov. 2015; 4(11): 1302-16.

Cui R, et al., Human mesenchymal stromal/stem cells acquire immunostimulatory capacity upon cross-talk with natural killer cells and might improve the NK cell function of immunocompromised patients, Stem Cell Res Ther. 2016; 7: 88.

Cunningham, F. et al., The placenta and fetal membranes, Williams Obstetrics, 20th ed. Appleton and Lange, 1997, 95-125.

Cushing L, et al. miR-29 is a major regulator of genes associated with pulmonary fibrosis. Am J Respir Cell Mol Biol 2011; 45: 287-294.

Da Silva AF, et al., Bone Marrow-Derived Mesenchymal Stem Cells and Their Conditioned Medium Attenuate Fibrosis in an Irreversible Model of Unilateral Ureteral Obstruction. Cell Transplant 24: 2657-2666, 2015.

Damarla, M. et al., Mitogen activated protein kinase activated protein kinase 2 regulates actin polymerization andvascular leak in ventilator associated lung injury, PLoS One, 4(2): E4600, 2009.

Dancer RCA, et al. Metalloproteinases in idiopathic pulmonary fibrosis. Eur Respir J. 2011; 38(6): 1461-67.

Darby IA, et al., Fibroblasts and myofibroblasts in wound healing. Clin Cosmet Investig Dermatol. 2014; 7: 301-311.

Darby IA, Hewitson TD., Fibroblast differentiation in wound healing and fibrosis. Int Rev Cytol. 2007; 257: 143-179.

Darley-Usmar V, Halliwell B., Blood radicals: reactive nitrogen species, reactive oxygen species, transition metal ions, and the vascular system. Pharm Res. 1996; 13: 649-662.

Das, KM, et al., Acute Middle East Respiratory Syndrome Coronavirus: Temporal Lung Changes Observed on the Chest Radiographs of 55 Patients, Am. J. Roentgenol. (2015) 205: W267-74.

Das, KM, et al., CT correlation with outcomes in 15 patients with acute Middle East respiratory syndrome coronavirus, Am. J. Roentgenol. (2015) 204: 736-42.

DaSilva, LL. et al., Human immunodeficiency virus type 1 Nef protein targets CD4 to the multivesicular body pathway, J. Virol. (2009) 83: 6578-90.

Database NCBI—Access No. NP_187864 heat shock protein 70-4 [*Arabidopsis thaliana*] (Jan. 22, 2014) 3 pages.

De Coppi P, et al., Isolation of amniotic stem cell lines with potential for therapy, Nature Biotechnol. Jan. 2007; 25(1): 100-6.

De Langhe E, et al. Quantification of lung fibrosis and emphysema in mice using automated micro-computed tomography. PLoS One 2012; 7: e43123.

De Langhe et al., Levels of mesenchymal FGFR2 signaling modulate smooth muscle progenitor cell commitment in the lung, Biol. Nov. 1, 2006; 299(1): 52-62.

De Lisio M, et al., Substrate and strain alter the muscle-derived mesenchymal stem cell secretome to promote myogenesis. Stem Cell Res Ther: 74, 2014.

De Vleeschauwer SI, Rinaldi M, De Vooght V, Vanoirbeek JA, Vanaudenaerde BM, Verbeken EK, Decramer M, Sayan-Ramirez GN, Verleden GM, Janssens W. Repeated invasive lung function measurements in intubated mice: an approach for longitudinal lung research. Lab Anim 2011; 45: 81-89.

Del Fattore, A. et al. Differential effects of extracellular vesicles secreted by mesenchymal stem cells from different sources on glioblastoma cells. Expert Opin. Biol. Ther. (2015) 15: 495-504.

Delanian S, et al., Abnormal phenotype of cultured fibroblasts in human skin with chronic radiotherapy damage. Radiotherapy and Oncology 1997; 47: 255-261.

Delanian S, et al., Cu/Zn superoxide dismutase modulates phenotypic changes in cultured fibroblasts from human skin with chronic radiotherapy damage. Radiotherapy and Oncology, 2001; 58: 325-331.

Denham JW, Hauer-Jensen M., The radiotherapeutic injury—a complex 'wound'. Radiother Oncol J Eur Soc Ther Radiol Oncol. 2002; 63: 129-145.

Deuse et al. Hepatocyte Growth Factor or Vascular Endothelial Growth Factor Gene Transfer Maximizes Mesenchymal Stem Cell-Based Myocardial Salvage After Acute Myocardial Infarction. Circulation, 120 (2009): S247-S254.

Devine SM, et al. Mesenchymal stem cells distribute to a wide range of tissues following systemic infusion into nonhuman primates. Blood. 2003; 101: 2999-3001.

Dignan, F., C. et al. Parainfluenza type 3 infection post stem cell transplant: high prevalence but low mortality. J. Hosp. Infect. (2006) 63:452-458.

Ding et al., Endothelial-derived angiocrine signals induce and sustain regenerative lung alveolarization. Cell. Oct. 28, 2011;147(3):539-53.

Doeppner TR, et al., Extracellular Vesicles Improve Post-Stroke Neuroregeneration and Prevent Postischemic Immunosuppression, Stem Cells Transl Med 2015; 4: 1131-1143.

Doppler SA, et al., Cardiac regeneration: current therapies—future concepts. J Thorac Dis. 2013; 5: 683-97.

Dorr W, Hendry JH., Consequential late effects in normal tissues. Radiotherapy and Oncology. 2001; 61: 223-231.

Doublier S, et al., Testosterone and 17beta-estradiol have opposite effects on podocyte apoptosis that precedes glomerulosclerosis in female estrogen receptor knockout mice. Kidney Int 2011; 79: 404-413.

Doublier S, Lupia E, Catanuto P, Elliot SJ. Estrogens and progression of diabetic kidney damage. Curr Diabetes Rev 2011; 7: 28-34.

(56) References Cited

OTHER PUBLICATIONS

Steiner, DF, et al., MicroRNA-29 regulates T-box transcription factors and interferon-? production in helper T cells, Immunity (2011) 35: 169-81.
Stenmark, H., Rab GTPases as coordinators of vesicle traffic, Nat. Rev. Mol. Cell Biol. (2009) 10: 513-25.
Stojadinovic O, Tomic-Canic M. Human ex vivo wound healing model. Methods Mol Biol 2013; 1037: 255-264.
Stoorvogel, W. et al., The biogenesis and functions of exosomes, Traffic (2002) 3: 321-330.
Straub JM, et al., Rediation-induced fibrosis: mechanisms and implications for therapy. J Cancer Res Clin Oncol. Nov. 2015; 141(11): 1985-1994.
Strickland, LT et al. Axotomy-lnduced miR-21 Promotes Axon Growth in Adult Dorsal Root Ganglion Neurons. PLoS One (2011) 6(8): e23423.
Strieter, R., Chest, Pathogenesis and natural history of usual interstitial pneumonia: the whole story or the last chapter of a long novel. 128 (5 Suppl 1): 526S-532S, 2005.
Sueblinvong V, et al. Predisposition for disrepair in the aged lung. Am J Med Sci 2012; 344: 41-51.
Summer et al., Isolation of an Adult Mouse Lung Mesenchymal Progenitor Cell Population, Am J Respir Cell Mol Biol. 2007; 37: 152-9.
Sun D, et al. Therapeutic Effects of Human Amniotic Fluid-Derived Stem Cells on Renal Interstitial Fibrosis in a Murine Model of Unilateral Ureteral Obstruction. PLoS One 8: e65042, 2013.
Sun JC, et al., Dendritic cells-mediated CTLs targeting hepatocellular carcinoma stem cells, Cancer Biol Ther 2010; 10: 368-375.
Sun L, et al., Mesenchymal stem cell transplantation reverses multiorgan dysfunction in systemic lupus erythematosus mice and humans, Stem Cells 2009; 27: 1421-1432.
Sun, Z. et al., Inhibition of Wnt/β-catenin signaling promotes engraftment of mesenchymal stem cells to repair lung injury. J. Cell Physiol (2014) 229: 213-24.
Sung, T. L., and A. P. Rice. 2009. miR-198 inhibits HIV-1 gene expression and replication in monocytes and its mechanism of action appears to involve repression of cyclin T1. PLoS Pathog. 5:e1000263.
Swaminathan S, et al., Nephrogenic systemic fibrosis, gadolinium, and iron mobilization. N Engl J Med 2007; 357: 720-2.
Swigris JJ, et al. The SF-36 and SGRQ: validity and first look at minimum important differences in IPF. Respir Med 2010; 104: 296-304.
Tager et al., The lysophosphatidic acid receptor LPA1 links pulmonary fibrosis to lung injury by mediating fibroblast recruitment and vascular leak, Nat. Med. 14:45-54, 2008.
Tak JK, Park JW., The use of ebselen for radioprotection in cultured cells and mice. Free Radic Biol Med. 2009; 46: 1177-1185.
Takahashi H, et al. Serum surfactant proteins A and D as prognostic factors in idiopathic pulmonary fibrosis and their relationship to disease extent. Am J Respir Crit Care Med 2000; 162: 1109-1114.
Tam, S. et al. MicroRNA-143 expression in dorsal root ganglion neurons. Cell Tissue Res. (2011) 346: 163-73.
Tan CY, et al. Mesenchymal stem cell-derived exosomes promote hepatic regeneration in drug-induced liver injury models. Stem Cell Res Ther. 2014; 5(3): 76.
Tan J, et al., Induction therapy with autologous mesenchymal stem cells in living-related kidney transplants: a randomized controlled trial. JAMA 307: 1169-1177, 2012.
Tan JL, et al. Amnion Epithelial Cell-Derived Exosomes Restrict Lung Injury and Enhance Endogenous Lung Repair. Stem Cells Transl Med. 2018;7(2):180-96.
Tan-P-H et al. MicroRNA-based therapy in pain medicine: Current progress andfuture prospects. Acta AnaesthesiologicaTaiwanica 51 (2013) 171-76.
Tanaka K, et al., Spatial Distribution of Fibrosis Governs Fibrillation Wave Dynamics in the Posterior Left Atrium During Heart Failure. Circ Res 2007; 101: 839-47.
Tang GN, et al. MicroRNAs Involved in Asthma After Mesenchymal Stem Cells Treatment. Stem Cells Dev 2016; 25: 883-896.
Tang J, et al., Mesenchymal stem cells modified with stromal cell-derived factor 1 alpha improve cardiac remodeling via paracrine activation of hepatocyte growth factor in a rat model of myocardial infarction. Molecules Cells: 9-19, 2010.
Tang, N. et al., Lysophosphatidic acid accelerates lung fibrosis by inducing differentiation of mesenchymal stem cells into myofibroblasts. J. Cell Mol. Med. (2014) 18: 156-69.
Tanimoto H, et al. Improvement of liver fibrosis by infusion of cultured cells derived from human bone marrow. Cell Tissue Res. 2013; 354: 717-728.
Tao B, et al. Percutaneous Intramyocardial Delivery of Mesenchymal Stem Cells Induces Superior Improvement in Regional Left Ventricular Function Compared with Bone Marrow Mononuclear Cells in Porcine Myocardial Infarcted Heart. Theranostics, 5(2): 196-205, 2015.
Tashiro J, et al. Therapeutic benefits of young, but not old, adipose-derived mesenchymal stem cells in a chronic mouse model of bleomycin-induced pulmonary fibrosis. Transl Res 2015; 166: 554-567.
Tavares-Ferreira, D. et al. Correlation of miRNA expression with intensity of neuropathic pain in man. Molecular Pain (2019) 15: 1-16.
Taylor AH, Al-Azzawi F. Immunolocalisation of oestrogen receptor beta in human tissues. J Mol Endocrinol 2000; 24: 145-155.
Taylor D.D., et al., MicroRNA signatures of tumor-derived exosomes as diagnostic biomarkers of ovarian cancer, Gynecol Oncol 2008;110:13-21.
Terasaki Y, et al., Hydrogen therapy attenuates irradiation-induced lung damage by reducing oxidative strss. Am J Physiol Lung Cell Mol Physiol. 2011; 301: L415-L426.
Tesselaar, MET et al., Microparticle-associated tissue factor activity: a link between cancer and thrombosis?, Journal of Thrombosis and Haemostasis (2007) 5 (3): 520-527.
Thannickal VJ, et al. Blue journal conference. Aging and susceptibility to lung disease. Am J Respir Crit Care Med. 2015;191(3):261-269.
Thannickal, V. et al., Evolving Concepts of Apoptosis in Idiopathic Pulmonary Fibrosis. Proc Am Thorac Soc., 3(4): 350-356, 2006.
Thebaud & Yoder. Pulmonary endothelial progenitor cells. In: Voelkel NF, Rounds S, eds. The Pulmonary Endothelium: Function in Health and Disease. Chichester, West Sussex: Wiley, 2009: 203-16.
Theofilopoulos AN, et al., The multiple pathways to autoimmunity, Nat Immunol. Jun. 20, 2017; 18(7): 716-724.
Thery C, Zitvogel L, and Amigorena S. Exosomes: composition, biogenesis and function. Nat Rev Immunol. 2002;2(8):569-79.
Thery, C. , et al., Membrane vesicles as conveyors of immune responses, Nat. Rev. Immunol. (2009) 9: 581-93.
Thomas, T. et al., MAPKAP kinase 2-deficiency prevents neurons from cell death by reducing neuroinflammation—relevance in a mouse model of Parkinson's disease. J Neurochem., 105(5): 2039-52, 2008.
Thompson WW, et al. (2003) Mortality associated with influenza and respiratory syncytial virus in the United States. JAMA 289: 179-186.
Thompson WW, et al. (2004) Influenza-associated hospitalizations in the United States. JAMA 292: 1333-1340.
Thompson, Clustal W: improving the sensitivity of progressive multiple sequence alignment through sequence weighting, position-specific gap penalties and weight matrix choice, Nucl Acids Res. 2 (1994), 4673-4680.
Thrall R. et al., Bleomycin-induced pulmonary fibrosis in the rat: inhibition by indomethacin, Am J Pathol., 95(1): 117-30, 1979.
Tian T., et al., Dynamics of exosome internalization and trafficking, J Cell Physiol. 2013;228:1487-1495.
Timmermans et al., Endothelial progenitor cells: identity defined? J Cell Mol Med. 2009; 13: 87-102.
Timmers et al. Reduction of myocardial infarct size by human mesenchymal stem cell conditioned medium. Stem Cell Res., 1 (2008): 129-137.

(56) References Cited

OTHER PUBLICATIONS

Berardis S, et al., Use of mesenchymal stem cells to treat liver fibrosis: current situation and future prospects. World J Gastroenterol. Jan. 21, 2015; 21(3): 742-758.
Bernardo ME, Fibbe WE., Mesenchymal stromal cells: sensors and switchers of inflammation, Cell Stem Cell. Oct. 3, 2013; 13(4): 392-402.
Bessout R, et al., Mesenchymal stem cell therapy induces glucocorticoid synthesis in colonic mucosa and suppresses radiation-activated T cells: new insights into MSC immunomodulation, Mucosal Immunol 2014; 7: 656-669.
Bian S, et al., Extracellular vesicles derived from human bone marrow mesenchymal stem cells promote angiogenesis in a rat myocardial infarction model. J Mol Med (Berlin) 2014; 92: 387-397.
Boerma M, Hauer-Jensen M., Potential Targets for Intervention-Induced Heart Disease. Curr Drug Targets. 2010; 11: 1405-1412.
Bonfeld TL, et al. Human mesenchymal stem cells suppress chronic airway inflammation in the murine ovalbumin asthma model. Am J Physiol. 2010;299(6):L760-L770.
Boonacker, E., Van Noorden, CJ., The multifunctional or moon-lighting protein CD26/DPPIV, Eur. J. Cell Biol. (2003) 82: 53-73.
Booth, CM, et al., Clinical features and short-term outcomes of 144 patients with SARS in the greater Toronto area, JAMA (2003) 289: 2801-9.
Borzone G, et al., Bleomycin-induced chronic lung damage does not resemble human idiopathic pulmonary fibrosis. Am J Respir Crit Care Med. Jun. 2001; 163(7):1648-53.
Boscher, C, Nabi, IR, Caveolin-1: role in cell signaling, Adv. Exp. Med. Biol. (2012) 729: 29-50.
Bourne, GL, The microscopic anatomy of the human amnion and chorion. Am. J. Obstet. & Gynec. (1960) 79 (6): 1070-1073.
Bowie et al., A method to identify protein sequences that fold into a known three-dimensional structure, Science 253:164 (1991).
Brack AS, et al., Increased Wnt signaling during aging alters muscle stem cell fate and increases fibrosis. Science: 807-810, 2007.
Brennecke, J. et al., Principles of microRNA-target recognition, PLoS Biol. (2005) 3: e85.
Brogaard, L. et al., Late regulation of immune genes and microRNAs in circulating leukocytes in a pig model of influenza A (H1N2) infection, Sci. Reports (2016) 6:21812.
Brognard, J et al., "PHLPP and a second isoform, PHLPP2, differentially attenuate the amplitude of Akt signaling by regulating distinct Akt isoforms," Mol Cell (2007) 25: 917-931.
Brouillette J, Rivard K, Lizotte E, Fiset C. Sex and strain differences in adult mouse cardiac repolarization: importance of androgens. Cardiovasc Res 2005; 65: 148-157.
Brownell et al., Precision Medicine: The New Frontier in Idiopathic Pulmonary Fibrosis, American Journal of Respiratory and Critical Care Medicine, Jun. 1, 2016, vol. 193, No. 11, pp. 1213-1218.
Bruno S, et al. Mesenchymal stem cell-derived microvesicles protect against acute tubular injury. J of the Am Society of Nephrology : JASN. 2009;20(5):1053-67.
Brutlag, Improved sensitivity of biological sequence database searches, Comp. App. Biosci. 6 (1990), 237-245.
Bueno M, et al., PINK1 deficiency impairs mitochondrial homeostasis and promotes lung fibrosis. J Clin Investig. 2015;125(2):521-538.
Burchfield JS, et al., Pathological Ventricular Remodeling, Mechanisms: Part 1 of 2. Circulation 2013; 128: 388-400.
Burger A, et al., Molecular and cellular basis of radiation fibrosis. Int J Radiat Biol. 1998; 73: 401-408.
Buyanovskaya OA, et al. Spontaneous aneuploidy and clone formation in adipose tissue stem cells during different periods of culturing. Bull Exp Biol Med 148, 109 (2009).
Cai, SX et al., Activation of Wnt/β-catenin signalling promotes mesenchymal stem cells to repair injured alveolar epithelium induced by lipopolysaccharide in mice. Stem Cell Res Ther. (2015) 6: 65.

Calveley VL, et al., Partial volume rat lung irradiation: temporal fluctuations of in-field and out-of-field DNA damage and inflammatory cytokines following irradiation. Int J Radiat Biol. 2005; 81: 887-899.
Campana F, et al., Topical superoxide dismutase reduces post-irradiation breast cancer fibrosis. J Cell Mol Med. 2004; 8: 109-116.
Campbell, TD et al., HIV-1 Nef protein is secreted into vesicles that can fuse with target cells and virions, ethn. Dis. (2008) 18: S2-S9.
Caplan, A. and Correa, D., The MSC: an injury drugstore. Cell Stem Cell (2011) 9: 11-15.
Carey MA, Card JW, Voltz JW, Germolec DR, Korach KS, Zeldin DC. The impact of sex and sex hormones on lung physiology and disease: lessons from animal studies. American journal of physiology Lung cellular and molecular physiology 2007; 293: L272-278.
Carmussi, et al., Exosomes/microvesicles as a mechanism of cell-to-cell communication. Kidney Int. (2010) 78: 838-848.
Carthew, RW and Sontheimer, EJ., Origins and Mechanisms of miRNAs and siRNAs. Cell (2009) 136: 642-55.
Carvalho PP, et al., Xenofree enzymatic products for the isolation of human adipose-derived stromal/stem cells. Tissue Eng Part C Meth. 2013; 19(6): 473-8.
Casey, M. and MacDonald P., Interstitial collagen synthesis and processing in human amnion: a property of the mesenchymal cells, Biol Reprod, 1996, 55: 1253-1260.
Cavanaugh D, et al. Quantification of bleomycin-induced murine lung damage in vivo with micro-computed tomography. Acad Radiol 2006; 13: 1505-1512.
Chambers DC, et al. A phase 1b study of placenta-derived mesenchymal stromal cells in patients with idiopathic pulmonary ?brosis. Respirology. 2014;19(7):1013-1018.
Chamoto et al. CD34+ Progenitor to Endothelial Cell Transition in Post-Pneumonectomy Angiogenesis. Am J Respir Cell Mol Biol. Mar. 2012; 46(3): 283-9.
Chan, JF, et al., Broad-spectrum antivirals for the emerging Middle East respiratory syndrome coronavirus, J. Infect. (2013) 67: 606-16.
Chan, JF, et al., Treatment With Lopinavir/Ritonavir or Interferon-β1b Improves Outcome of MERS-CoV Infection in a Nonhuman Primate Model of Common Marmoset, J. Infect. Dis. (2015) 212: 1904-13.
Chan, KS, et al., SARS: prognosis, outcome and sequelae, Respirology (2003) 8-Suppl.: S36-40.
Chang JW, et al., Therapeutic effects of umbilical cord blood-derived mesenchymal stem cell transplantation in experimental lupus nephritis, Cell Transplant 2011; 20: 245-257.
Chang YJ, et al., Mesenchymal stem cells facilitate recovery from chemically induced liver damage and decrease liver fibrosis. Life Sci. 2009; 85: 517-525.
Chattopadhyay, S. et al., Cytokine regulation of MMP-9 in peripheral glia: implications for pathological processes and pain in injured nerve. Brain Behav. Immun. (20007) 21: 561-8.
Chaudiere J, Ferrari-Iliou R., Intracellular antioxidants: from chemical to biochemical mechanisms. Food Chem Toxicol. 1999; 37: 949-962.
Chen J, et al., EGFR Signaling Promotes TGFb-Dependent Renal Fibrosis. J Am Soc Nephrol 2012; 23: 215-24.
Chen X, et al., Role of matrix metalloproteinases in skeletal muscle: migration, differentiation, regeneration and fibrosis. Cell Adhesion Migration: 337-341, 2009.
Chen, TS et al., Mesenchymal stem cell secretes microparticles enriched in pre-microRNAs. Nucleic Acids Res. (2010) 38: 215-224.
Cheresh P, Kim SJ, Tulasiram S, Kamp DW. Oxidative stress and pulmonary fibrosis. Biochim Biophys Acta. 2013;1832(7):1028-104.
Chiba H, Otsuka M, Takahashi H. Significance of molecular biomarkers in idiopathic pulmonary fibrosis: A mini review. Respir Investig 2018; 56: 384-391.
Chilosi M, et al., Aberrant Wnt/beta-catenin pathway activation in idiopathic pulmonary fibrosis. Am J Pathol 2003; 162: 1495-1502.
Zaki, AM et al., Isolation of a Novel Coronavirus from a Man with Pneumonia in Saudi Arabia, N. Engl. J. Med. (2012) 367: 1814-20.

(56) References Cited

OTHER PUBLICATIONS

Zappia E, et al., Mesenchymal stem cells ameliorate experimental autoimmune encephalomyelitis inducing T-cell anergy, Blood 2005; 106: 1755-1761.

Zeisberg EM, et al., Endothelial-to-mesenchymal transition contributes to cardiac fibrosis. Nat Med 2007; 13: 952-61.

Zhang et al. Human Umbilical Cord Mesenchymal Stem Cell Exosomes Enhance Angiogenesis Through the Wnt4/ b-Catenin Pathway. Stem Cells Transl Med. May 2015; 4(5): 513-22.

Zhang et al., Successful immortalization of mesenchymal progenitor cells derived from human placenta and the differentiation abilities of immortalized cells, Biochem Biophys Res Commun, 2006, 351: 853-859.

Zhang H, et al., The Development of Classically and Alternatively Activated Macrophages Has Different Effects on the Varied Stages of Radiation-induced Pulmonary Injury in Mice. J Radiat Res. 2011; 52: 717-726.

Zhang Q, et al., Mesenchymal stem cells derived from human gingiva are capable of immunomodulatory functions and ameliorate inflammation-related tissue destruction in experimental colitis, J Immunol 2009; 183: 7787-7798.

Zhang Y et al., Regulation of Matrix Metalloproteines-2 Secretion from Scleral Fibroblasts and Retinal Pigment Epithelial Cells by miR-2 BioMed Research International, 2017.

Zhang Y, et al. Exosomes derived from mesenchymal stromal cells promote axonal growth of cortical neurons. Mol Neurobiol (2017) 54(4): 2659-73.

Zhang Y, et al. Histopathologic and Molecular Analysis of Idiopathic Pulmonary Fibrosis Lungs from Patients Treated with Pirfenidone or Nintedanib. Histopathology 2018.

Zhang, et al. Regulation of Matrix Metalloproteinase-2 Secretion from Scleral Fibroblasts and Retinal Pigment Epithelial Cells by miR-29a. Biomed Research International, May 29, 2017, vol. 2017, Art. 2647879, pp. 1-8.

Zhang, J. et al., Exosome and exosomal microRNA: trafficking, sorting, and function, Genomics Proteomics Bioinformatics (2015) 13: 17-24.

Zhang, X., et al., Mesenchymal progenitor cells derived from chorionic villi of human placenta for cartilage tissue engineering, Biochem Biophys Res Commun, 2006, 340: 944-952.

Zhang, Y, et al., Enhanced IL-1 beta and tumor necrosis factor-alpha release and messenger RNA expression in macrophages from idiopathic pulmonary fibrosis or after asbestos exposure. J. Immunol. 150(9): 4188-4196, 1993.

Zhao DC, et al. Bone marrow-derived mesenchymal stem cells protect against experimental liver fibrosis in rats. World J Gastroenterol. 2005; 11: 3431-3440.

Zhao W, Robbins ME., Inflammation and chronic oxidative stress in radiation-induced late normal tissue injury: therapeutic implications. Curr Med Chem. 2009; 16: 130-143.

Zhao, BQ, et al. Role of matrix metalloproteinases in delayed cortical responses after stroke. Nat. Med. (2006) 12: 441-45.

Zhao, F. et al., Therapeutic effects of bone marrow-derived mesenchymal stem cells engraftment on bleomycin-induced lung injury in rats. Transplant Proc (2008) 40: 1700-1705.

Zhao, P. et al., Human amniotic mesenchymal cells have some characteristics of cardiomyocytes, Transplantation, 2005, 79: 528-535.

Zheng P, et al. Diagnostic value of KL-6 in idiopathic interstitial pneumonia. J Thorac Dis 2018; 10: 4724-4732.

Zheng SQ, et al., MiR-101 regulates HSV-1 replication by targeting ATP5B, Antiviral Res (2011) 89: 219-226.

Zhou B, et al., Administering human adipose-derived mesenchymal stem cells to prevent and treat experimental arthritis, Clin Immunol 2011; 141: 328-337.

Zhou H, Collection, storage, preservation, and normalization of human urinary exosomes for biomarker discovery, Kidney International (2006) 69, 1471-1476.

Zhou H, et al., Efficacy of bone marrow-derived mesenchymal stem cells in the treatment of sclerodermatous chronic graft-versus-host disease: clinical report, Biol Blood Marrow Transplant 2010; 16: 403-412.

Zhou W., et al., Cancer-secreted miR-105 destroys vascular endothelial barriers to promote metastasis, Cancer Cell. 2014;25:501-515.

Zhou Y, et al., Mesenchymal stromal cells augment CD4+ and CD8+ T-cell proliferation through a CCL2 pathway, Cytotherapy. Oct. 2013; 15(10): 1195-207.

Zhou, Q. et al. MicroRNA-29a Regulates Intestinal Membrane Permeability in Patients with Irritable Bowel Syndrome. Gut (2010) 59: 775-84.

Zhu XY, et al. Mesenchymal Stem Cells and Endothelial Progenitor Cells Decrease Renal Injury in Experimental Swine Renal Artery Stenosis Through Different Mechanisms. Stem Cells. 2013; 31: 117-125.

Zhu XY, et al., Concise Review: Mesenchymal Stem Cell Treatment for Ischemic Kidney Disease. Stem Cells. Sep. 2013; 31(9): 1731-1736.

Zhu, H. et al., The Role of the Hyaluronan Receptor CD44 in Mesenchymal Stem Cell Migration in the Extracellular Matrix Stem Cells (2006) 24: 928-35.

Zhu, L. et al., Artificial Cells, nanomedicine and biotechnology, Novel alternatives to extracellular vesicle-based immunotherapy—exosome mimetics derived from natural killer cells, (2018) 46 (53): S166-S179.

Zhuo W, et al. Efficiency of endovenous versus arterial administration of mesenchymal stem cells for ischemia-reperfusion-induced renal dysfunction in rats. Transplant Proc. 2013; 45: 503-510.

Zomer, A. et al., Exosomes: Fit to deliver small RNA, Commun. Integr. Biol. (2010) 3: 447-50.

Zonta S, et al. Experimental transplantation: Which Is the Most Suitable and Effective Route of Administration for Mesenchymal Stem Cell-Based Immunomodulation Therapy in Experimental Kidney Transplantation: Endovenous or Arterial? Transplant Proc. 2010;42:1336-1340.

Zonta S, et al., Which is the most suitable and effective route of administration for mesenchymal stem cell-based immunomodulation therapy in experimental kidney transplantation: endovenous or arterial?, Transplant Proc. 2010;42:1336-1340.

Zou, Z. et al. More insight into mesenchymal stem cells and their effects inside the body. Expert Opin. Biol. Thera. (2010) 10: 215-30.

Zu, J. et al., Cyclophosphamide Combined with Bone Marrow Mesenchymal Stromal Cells Protects against Bleomycin-induced Lung Fibrosis in Mice. Ann. Clin. Lab. Sci. (2015) 45: 292-300.

Zuk PA., et al. Human Adipose Tissue Is a Source of Multipotent Stem Cells. Mol Biol Cell. 2002, 13(12): 4279-95.

Raghu G, Chen SY, Hou Q, Yeh WS, Collard HR. Incidence and prevalence of idiopathic pulmonary fibrosis in US adults 18-64 years old. Eur Respir J 2016; 48: 179-18.

Raghu G, et al., American Thoracic Society ERSJRS, Latin American Thoracic S. Diagnosis of Idiopathic Pulmonary Fibrosis. An Official ATS/ERS/JRS/ALAT Clinical Practice Guideline. Am J Respir Crit Care Med 2018; 198: e44-e68.

Raghu G, et al. An official ATS/ERS/JRS/ALAT statement: idiopathic pulmonary Fibrosis: evidence-based guidelines for diagnosis and management. Am J Resp Crit Care Med. 183(6):788-824 (2011).

Raghu G, et al. Idiopathic pulmonary fibrosis in US Medicare beneficiaries aged 65 years and older: incidence, prevalence, and survival, Nov. 2001. Lancet Respir Med 2014; 2: 566-572.

Raghu G, et al. Idiopathic pulmonary Fibrosis: clinically meaningful primary endpoints in phase 3 clinical trials. Am J Resp Crit Care Med. 2012;185(10):1044-1048.

Raghu G. et al., An Official ATS/ERS/JRS/ALAT Statement: Idiopathic Pulmonary Fibrosis: Evidenced-based Guidlines for Diagnosis and Management. Am J Resp Crit Care Med., 183(6): 788-824, 2011.

Raiden, S., et al. Nonpeptide antagonists of AT1 receptor for angiotensin II delay the onset of acute respiratory distress syndrome, Pharmacol. Exp. Ther. (2002) 303: 45-51.

(56) References Cited

OTHER PUBLICATIONS

Ramachandran P, Iredale JP., Macrophages: Central regulators of hepatic fibrogenesis and fibrosis resolution. J Hepatol 2012; 56: 1417-9.
Ramasamy et al. Fgf10 dosage is critical for the amplification of epithelial cell progenitors andfor the formation of multiple mesenchymal lineages during lung development. Dev Biol. Jul. 15, 2007; 307(2): 237-47.
Ranganath SH, et al. Harnessing the Mesenchymal Stem Cell Secretome for the Treatment of Cardiovascular Disease. Cell Stem Cell. 2012;10(3):244-58.
Rangappa, S, et al., Transformation of adult mesenchymal stem cells isolated from the fatty tissue into cardiomyocytes. Ann. Thorac. Surg. 75: 775-779; 2003.
Record M, et al. Exosomes as intercellular signalosomes and pharmacological effectors,.(2010), doi:10.1016/j.ocp.2011.02.011 published in Biochem. Pharmacol. 2011; 81: 1171-82.
Redente EF, et al. Age and sex dimorphisms contribute to the severity of bleomycin-induced lung injury and fibrosis. Am J Physiol Lung Cell Mol Physiol 2011; 301: L510-518.
Redente EF, et al. Tumor necrosis factor-alpha accelerates the resolution of established pulmonary fibrosis in mice by targeting profibrotic lung macrophages. Am J Respir Cell Mol Biol 2014; 50: 825-837.
Reid, G., et al. Cyclic, proteasome-mediated turnover of unliganded and liganded ERalpha on responsive promoters is an integral feature of estrogen signaling. (2003) Mol. Cell 11, 695-707.
Reid, G., et al. Human estrogen receptor-alpha : Regulation by synthesis, modification and degradation. (2002) Cell. Mol. Life Sci. 59, 821-831.
Reis LA, et al., Bone marrow-derived mesenchymal stem cells repaired but did not prevent gentamicin-induced acute kidney injury through paracrine effects in rats, PLoS One 2012; 7: e44092.
Ren J, et al. Global transcriptome analysis of Human Bone Marrow Stromal Cells (BMSCs) reveals proliferative, mobile, and Interactive cells that produce abundant extracellular matrix proteins, some of which may affect BMSC Potency. Cytotherapy 2011; 13: 661-674.
Ren, et al., Therapeutic potential of mesenchymal stem cells producing IFN-a in a mouse melanoma lung metastasis model, Stem Cells (2008) 26: 2332-38.
Ricciardi M. et al., Comparison Between Bone Marrow Mesenchymal Stromal Cells (BM-MSC) and Lung Mesenchyma Stromal Cells (Lung-MSC) For Epithelial Regeneration, Blood (2013) 122: 5414.
Richards et al, Peripheral Blood Proteins Predict Mortality in Idiopathic Pulmonary Fibrosis. Am J Respir Crit Care Med, 2012, 185: 67-76.
Richards TJ et al., Peripheral Blood Proteins Predict Mortslity in Idiopathic Pulmonary Fibrosis, Am. J. of Respir. and Crit. Care Medicine, 2012, vol. 185 : 67-76.
Richeldi L, et al. Efficacy and safety of nintedanib in idiopathic pulmonary fibrosis. N Engl J Med 2014; 370: 2071-2082.
Richeldi L, et al. Nintedanib in patients with idiopathic pulmonary ?brosis: Combined evidence from the TOMORROW and INPULSIS((R)) trials. Res Med. 2016;113:74-79.
Ringden O, et al., Mesenchymal stem cells for treatment of therapy-resistant graft-versus-host disease, Transplantation 2006; 81: 1390-1397.
Ringe, J. et al., Towards in situ tissue repair: human mesenchymal stem cells express chemokine receptors CXCR1, CXCR2 and CCR2, and migrate upon stimulation with CXCL8 but not CCL2. et al. J. Cell Biochem. (2007) 101: 135-46.
Rockey DC et al., Fibrosis—A Common Pathway to Organ Injury and Failure. N Engl J Med. Mar. 19, 2015; 372(12): 1138-49.
Rockey DC, et al., Activation-dependent contractility of rat hepatic lipocytes in culture and in vivo. J Clin Invest 1993; 92: 1795-804.
Rockey DC., Advances In Translational Science, Translating an Understanding of the Pathogenesis of Hepatic Fibrosis to Novel Therapies. Clin Gastroenterol Hepatol 2013; 11(3): 224-31.
Rodemann HP, Bamberg M., Cellular basis of radiation-induced fibrosis. Radiotherpy and Oncology 1995; 35: 83-90.
Rojas M, Xu J, Woods CR, et al. Bone marrow-derived mesenchymal stem cells in repair of the injured lung. Am J Resp Cell Mol Bio. 2005;33(2):145-152.
Rong, Q. et al., Bone marrow-derived mesenchymal stem cells are capable of mediating hepatitis B virus infection in injured tissues, J. Viral Hepatitis (2008) 15:607-614.
Rosas IO, et al. MMP1 and MMP7 as Potential Peripheral Blood Biomarkers in Idiopathic Pulmonary Fibrosis. PLoS Med. 2008; 5(4): e93.
Rosenberg, GA. Matrix Metalloproteinases in Neuroinflammation. GLIA (2002) 39: 279-91.
Roush S, Slack FJ., The let-7 family of microRNAs. Trends Cell Biol. 2008; 18: 505-516.
Rubenfeld GD, et al. Incidence and Outcomes of Acute Lung Injury. N Engl J Med. Oct. 20, 2005; 353(16): 1685-93.
Rubia GA et al., Mesenchymal stromal cells prevent bleomycin-induced lung and skin fibrosis in aged mice and restore wound healing, J Cell Physiol. Aug. 2018; 233(8): 5503-5512.
Rubio GA, Elliot SJ, Glassberg MK. What Should Be Chronic: The Animal, the Model, or Both? Stem Cells Transl Med 2016; 5: 703.
Rubio, et al. Mesenchymal stromal cells prevent bleomycin-induced lung and skin fibrosis in aged mice and restore wound healing. Journal of Cellular Physiology. Aug. 2018;233(8):5503-5512.
Rudolph R, et al., Slowed growth of cultured fibroblasts from human radiation wounds. Plast Reconstr Surg. 1988; 82: 669-677.
Russo RC, et al. Phosphoinositide 3-kinase gamma plays a critical role in bleomycin-induced pulmonary inflammation and fibrosis in mice. J Leukoc Biol 2011; 89: 269-282.
Saad, M. et al., Clinical aspects and outcomes of 70 patients with Middle East respiratory syndrome coronavirus infection: a single-center experience in Saudi Arabia, Int. J. Infect. Dis. (2014) 29: 301-6.
Saito Y, et al. Pirfenidone exerts a suppressive effect on CCL18 expression in U937-derived macrophages partly by inhibiting STAT6 phosphorylation. Immunopharmacol Immunotoxicol. 2016; 38(6): 46471.
Salazar KD, et al. Mesenchymal stem cells produce Wnt isoforms and TGF-beta1 that mediate proliferation and procollagen expression by lung ?broblasts. Am J Physiol. 2009;297(5):L1002-L1011.
Sanchez Freire, et al. MicroRNAs May Mediate the Down-Regulation ofNeurokinin-1 Receptor in Chronic Bladder Pain Syndrome. (2010) Am. J.Pathol. 176: 288-303.
Sandow SL, et al., Expression of homocellular and heterocellular gap junctions in hamster arterioles and feed arteries. Cardiovasc. Res. (2003); 60(3): 643-653.
Sanyal AJ, et al., Portal hypertension and its complications. Gastroenterology 2008; 134: 1715-28.
Sarbassov, DD et al., "Phosphorylation and regulation of Akt/PKB by the rictor-mTOR complex," (2005) Science 307: 1098-1101.
Sathish V, Martin YN, Prakash YS. Sex steroid signaling: implications for lung diseases. Pharmacol Ther 2015; 150: 94-108.
Sathish V; Prakash Y. Sex differences in pulmonary anatomy and physiology: Implications for health and disease. Sex differences in physiology; 2016. p. 89-106.
Drosten, C. et al., Identification of a Novel Coronavirus in Patients with Severe Acute Respiratory Syndrome, N.Engl. J. Med. (2003) 348: 1967-76.
Du Bois RM, et al. Forced vital capacity in patients with idiopathic pulmonary fibrosis: test properties and minimal clinically important difference. Am J Respir Crit Care Med 2011; 184: 1382-1389.
Duijvestein M, et al., Autologous bone marrow-derived mesenchymal stromal cell treatment for refractory luminal Crohn's disease: results of a phase I study, Gut 2010; 59: 1662-1669.
Duong et al., Pro-angiogenic Hematopoietic Progenitor Cells and Endothelial Colony Forming Cells in Pathological Angiogenesis of Bronchial and Pulmonary Circulation. Angiogenesis. 2011: 411-22.
Eakin EG, et al. Validation of a new dyspnea measure: the UCSD Shortness of Breath Questionnaire. University of California, San Diego. Chest 1998; 113: 619-624.

(56) References Cited

OTHER PUBLICATIONS

Eckert, R. L., et al. Estrogen Receptor Synthesis and Turnover in MCF-7 Breast Cancer Cells Measured by a Density Shift Technique. (1984) Endocrinology 114, 629-637.

Eggenhofer e, et al., The life and fate of mesenchymal stem cells, Front Immunol. 2014; 5: 148.

Eirin A, et al. Adipose Tissue-Derived Mesenchymal Stem Cells Improve Revascularization Outcomes to Restore Renal Function in Swine Atherosclerotic Renal Artery Stenosis. Stem Cells. 2012; 30: 1030-1041.

El Khissiin, A., and Leclercq, G. Implication of proteasome in estrogen receptor degradation. (1999) FEBS Lett. 448, 160-166.

Elliot SJ, Karl M, Berho M, Potier M, Zheng F, Leclercq B, Striker GE, Striker LJ. Estrogen deficiency accelerates progression of glomerulosclerosis in susceptible mice. The American journal of pathology 2003; 162: 1441-1448.

Elliot SJ, Karl M, Berho M, Xia X, Pereria-Simon S, Espinosa-Heidmann D, Striker GE. Smoking induces glomerulosclerosis in aging estrogen-deficient mice through cross-talk between TGF-beta1 and IGF-I signaling pathways. J Am Soc Nephrol 2006; 17: 3315-3324.

Escola, JM., Selective enrichment of tetraspan proteins on the internal vesicles of multivesicular endosomes and on exosomes secreted by human B-lymphocytes, J. Biol. Chem. (1998) 273: 20121-27.

Escrevente C., et al., Interaction and uptake of exosomes by ovarian cancer cells, BMC Cancer. 2011;11:108.

Evans P. and Halliwell B. Free Radicals and Hearing: Cause, Consequence, and Criteria. Ann N Y Acad Sci. 2006; 884: 19-40.

Fabbri M., et al., MicroRNAs bind to Toll-like receptors to induce prometastatic inflammatory response, Proc Natl Acad Sci U S A. 2012;109:E2110-E2116.

Fan, E. et al., Ventilatory management of acute lung injury and acute respiratory distress syndrome, JAMA, 294:2889-2896, 2005.

Fan, M., Bigsby, R. M., and Nephew, K. P. The NEDD8 pathway is required for proteasome-mediated degradation of human estrogen receptor (ER)-alpha and essential for the antiproliferative activity of ICI 182 780 in ERalpha-positive breast cancer cells. (2003) Mol. Endocrinol. 17, 356-365.

Fan, M., Nakshatri, H., and Nephew, K. P. Inhibiting proteasomal proteolysis sustains estrogen receptor-alpha activation. (2004) Mol Endocrinol. 18, 2603-2615.

Fan, M., Park, A., and Nephew, K. P. Chip (Carboxyl Terminus of Hsc70-lnteracting Protein) Promotes Basal and Geldanamycin-Induced Degradation of Estrogen Receptor-alpha. (2005) Mol Endocrinol. 19, 2901-2914.

Fang S, et al. Umbilical Cord-Derived Mesenchymal Stem Cell-Derived Exosomal MicroRNAs Suppress Myofibroblast Differentiation by Inhibiting the Transforming Growth Factor-b/SMAD2 Pathway During Wound Healing. Stem Cells Transl Med. Oct. 2016; 5(10): 1425-1439.

Farsad K. Exosomes: novel organelles implicated in immunomodulation and apoptosis. The Yale journal of biology and medicine. 2002;75(2):95-101.

Favereaux, A. et al. Bidirectional integrative regulation of Cav1.2 calcium channel by microRNA miR-103: role in pain. EMBO J. (2011) 30: 3830-41.

Feng, J et al., "Identification of a PKB/Akt hydrophobic motif Ser-473 kinase as DNA-dependent protein kinase," J Biol Chem (2004) 279: 41189-41196.

Feng, Y. et al. Ischemic Preconditioning Potentiates the Protective Effect of Stem Cells through Secretion of Exosomes by Targeting Mecp2 via miR-22. PLoS One (2014) 9: e88685.

Finkelstein JN, et al., Particulate-Cell Interactions and Pulmonary Cytokine Expression. Environ Health Perspect. 1997; 105(Suppl 5): 1179-1182.

Finlay GA, et al., Transforming Growth Factor-b1-Induced Activation of the EFK Patway/AP-1 in Human Lung Fibroblasts Requires the Autocrine Induction of Basic Fibroblast Growth Factor. J Biol Chem. 2000; 275: 27650-27656.

Fischer UM, et al. Pulmonary Passage is a Major Obstacle for Intravenous Stem Cell Delivery: The Pulmonary First-Pass Effect. Stem Cells Dev. 2009; 18: 683-692.

Flomenberg, P., J., et al. Increasing incidence of adenovirus disease in bone marrow transplant recipients. J. Infect. Dis. (1994) 169:775-781.

Ford AQ, et al., Adoptive transfer of iL-4Ra+macrophages is sufficient to enhance eosinophilic inflammation in a mouse model of allergic lung inflammation. BMC Immunol. 2012; 13: 6.

Fouts DE, et al., Bacterial translocation and changes in the intestinal microbiome in mouse models of liver disease. J Hepatol 2012; 56: 1283-92.

Frank F., et al., Structural basis for 5'-nucleotide base-specific recognition of guide RNA by human AGO2, Nature. 2010;465:818-822.

Franzdottir et al. Airway branching morphogenesis in three dimensional culture. Respir Res. 2010; 11: 162.

Friedman SL, Sheppard D, Duffield JS, Violette S. Therapy for fibrotic diseases: nearing the starting line. Sci Transl Med 2013; 5: 167sr161.

Fujishima S, et al. Production and Activation of Matrix Metalloproteinase 7 (Matrilysin 1) in the Lungs of Patients With Idiopathic Pulmonary Fibrosis. Arch Pathol Lab Med. 2010; 134(8): 1136-42.

Gallagher, TM, Coronavirus spike proteins in viral entry and pathogenesis, Buchmeier, MJ. Virology (2001) 279: 371-74.

Garcia O, et al. Amniotic fluid stem cells inhibit the progression of bleomycin-induced pulmonary fibrosis via CCL2 modulation in bronchoalveolar lavage. PLoS One 2013; 8: e71679.

Giangreco et al., Molecular phenotype of airway side population cells. Am J Physiol Lung Cell Mol Physiol. Apr. 2004;286(4):L624-30.

Gibbings, D, Voinnet, O., Control of RNA silencing and localization by endolysosomes, Trends Cell Biol. (2010) 20: 491-501.

Gimble J, Guilak F., Adipose-derived adult stem cells: isolation, characterization, and differentiation potential. Cytotherapy. 2003; 5(5): 362-9.

Gimble JM, Bunnell BA, and Guilak F. Human adipose-derived cells: an update on the transition to clinical translation. RegenMed. 2012;7(2):225-35.

Glassberg MK, Choi R, Manzoli V, Shahzeidi S, Rauschkolb P, Voswinckel R, Aliniazee M, Xia X, Elliot SJ. 17beta-estradiol replacement reverses age-related lung disease in estrogen-deficient C57BL/6J mice. Endocrinology 2014; 155: 441-448.

Glassberg MK, et al. Estrogen deficiency promotes cigarette smoke-induced changes in the extracellular matrix in the lungs of aging female mice. Transl Res 2016; 178: 107-117.

Glassberg MK, et al. 17beta-estradiol replacement reverses age-related lung disease in estrogen-deficient C57BL/6J mice. Endocrinology 2014; 155: 441-448.

Glassberg MK, et al. Activation of the estrogen receptor contributes to the progression of pulmonary lymphangioleiomyomatosis via matrix metalloproteinase-induced cell invasiveness. J Clin Endocrinol Metab 2008; 93: 1625-1633.

Glassberg MK, et al. Allogeneic Human Mesenchymal Stem Cells in Patients With Idiopathic Pulmonary Fibrosis via Intravenous Delivery (AETHER): A Phase I Safety Clinical Trial. Chest 2017; 151: 971-981.

Gnecchi et al., Paracrine mechanisms in adult stem cell signaling and therapy, Circ. Res., 103 (2008): 1204-1219.

Goldstein et al., Failure of mechanical properties to parallel changes in lung connective tissue composition in bleomycin-induced pulmonary fibrosis in hamsters. Am Rev Respir Dis. Jul. 1979;120(1):67-73.

Golpanian S, et al. Rationale and design of the allogeneic human mesenchymal stem cells (hMSC) in patients with aging frailty via intravenous delivery (CRATUS) study: a phase I/II, randomized, blinded and placebo controlled trial to evaluate the safety and potential ef?cacy of allogeneic human mesenchymal stem cell infusion in patients with aging frailty. Oncotarget. 2016;7(11):11899-11912.

(56) References Cited

OTHER PUBLICATIONS

Golpanian S, et al., Rebuilding the Damaged Heart: Mesenchymal Stem Cells, Cell-Based Therapy, and Engineered Heart Tissue. Physiol Rev. Jul. 2016; 96(3): 1127-1168.

Gonzalez MA, et al., Treatment of experimental arthritis by inducing immune tolerance with human adipose-derived mesenchymal stem cells, Arthritis Rheum 2009; 60: 1006-1019.

Gordon S, Martinez FO., Alternative activation of macrophages: mechanism and functions. Immunity. 2010; 32: 593-604.

Gould, SJ et al., The Trojan exosome hypothesis, Proc. Nat. Acad. Sci. USA (2003) 100: 10592-97.

Greenberger JS, Epperly MW., Antioxidant Gene Therapeutic Approaches to Normal Tissue Radioprotection and Tumor Radiosensitization. In vivo. 2007; 21: 141-146.

Greene KE, et al. Serum surfactant proteins-A and -D as biomarkers in idiopathic pulmonary fibrosis. Eur Respir J 2002; 19: 439-446.

Gregory, PA, et al. 2008. The miR-200 family and miR-205 regulate epithelial to mesenchymal transition by targeting ZEB1 and SIP1. Nat. Cell Biol. 2008) 10:593-6011.

Grinnell & Harrington. Pulmonary endothelial cell interactions with the extracellular matrix. In: Voelkel NF, Rounds S, eds. The Pulmonary Endothelium: Function in Health and Disease. Chichester, West Sussex: Wiley-Blackwell, 2009: 51-72.

Gross JC, et al. Active Wnt proteins are secreted on exosomes. Nat Cell Biol 2012; 14: 1036-1045.

Gu Z, et al., Transplantation of umbilical cord mesenchymal stem cells alleviates lupus nephritis in MRL/Ipr mice, Lupus 2010; 19: 1502-1514), GvHD.

Guduric-Fuchs J., et al., Selective extracellular vesicle-mediated export of an overlapping set of microRNAs from multiple cell types, BMC Genomics. 2012;13:357.

Guertin DA et al., "Ablation in mice of the mTORC components raptor, rictor, or mLST8 reveals that mTORC2 is Yequired for signaling to Akt-FOXO and PKC?, but not S6K1," Dev Cell (2006) 11: 859-871.

Guiot J, Moermans C, et al. Blood Biomarkers in Idiopathic Pulmonary Fibrosis. Lung 2017; 195: 273-280.

Guiot, J. et al. Blood Biomarkers in Idiopathic Pulmonary Fibrosis. Lung (2017) 195(3): 273-280.

Gujral TS, et al. A Noncanonical Frizzled2 PathwayRegulates Epithelial-MesenchymalTransition and Metastasis. Cell. Nov. 6, 2014; 159(4): 844-56.

Guo J, et al., Xenogeneic immunosuppression of human umbilical cord mesenchymal stem cells in a major histocompatibility complex-mismatched allogeneic acute graft-versus-host disease murine model, Eur J Haematol 2011;87: 235-243.

Guo, L. et al. The role of microRNAs in self-renewal and differentiation of mesenchymal stem cells. Exptl Hematol. (2011) 39: 608-616.

György B, et al. Therapeutic Applications of Extracellular Vesicles: Clinical Promise and Open Questions. Annu Rev Pharmacol Toxicol. 2015; 55: 439-464.

Hakkarainen, T. et al., Human mesenchymal stem cells lack tumor tropism but enhance the antitumor activity of oncolytic adenoviruses in orthotopic lung and breast tumors, Human Gene Therapy (2007) 18:627-641.

Hallahan DE, et al., Effects of Intercellular Adhesion Molecule 1 (ICAM-1) Null Mutation on Radiation-Induced Pulmonary Fibrosis and Respiratory Insufficiency in Mice. J Natl Cancer Inst. 2002; 94: 733-741.

Hamai K, et al. Comparative Study of Circulating MMP-7, CCL18, KL-6, SP-A, and SP-D as Disease Markers of Idiopathic Pulmonary Fibrosis. Dis Markers 2016: 4759040.

Hara, Y, et al. In vivo effect of bone marrow-derived mesenchymal stem cells in a rat kidney transplantation model with prolonged cold ischemia. Transpl Int 24: 1112-1123, 2011.

Hare JM, et al. Comparison of allogeneic vs autologous bone marrow-derived mesenchymal stem cells delivered by transendocardial injection in patients with ischemic cardiomyopathy: the POSEIDON randomized trial. JAMA. 2012;308(22):2369-2379.

Hare JM, Traverse JH, Henry TD, et al. A randomized, double-blind, placebo-controlled, dose-escalation study of intravenous adult human mesenchymal stem cells (prochymal) after acute myocardial infarction. J Am Coll Cardiol. 2009;54(24):2277-2286.

Harrison JD, Stather JW., The assessment of doses and effects from intakes of radioactive particles. J Anat. 1996; 189 (Pt 3): 521-530.

Hart, BJ, et al., Interferon-β and mycophenolic acid are potent inhibitors of Middle East respiratory syndrome coronavirus in cell-based assays, J. Gen. Virol. (2014) 95: 571-77.

Hartvigsen et al., Postprandial effects of test meals including concentrated arabinoxylan and whole grain rye in subjects with the metabolic syndrome: a randomised study. Eur J Clin Nutr. May 2014;68(5):567-74.

Hashimoto N, Jin H, Liu T, Chensue SW, Phan SH. Bone marrow-derived progenitor cells in pulmonary fibrosis. J Clin Invest. 2004; 113(2): 243-252.

Haston CK, Travis EL., Murine Susceptibility to Radiation-induced Pulmonary Fibrosis Is Influenced by a Genetic Factor Implicated in Susceptability to Bleomycin-induced Pulmonary Fibrosis. Cancer Res 1997; 57: 5286-5291.

Hecker L, et al. Reversal of persistent fibrosis in aging by targeting Nox4-Nrf2 redox imbalance. Sci Transl Med 2014; 6: 231ra247.

Hecker L. et al., NADPH oxidase-4 mediates myofibroblast activation and fibrogenic responses to lung injury, Nat. Med., 15(9): 1077-81, 2009.

Hegab et al,. Isolation and Characterization of Murine Multipotent Lung Stem Cells. Stem Cells Dev. 2010; 19: 523-36.

Hegyi L, et al., Primary cardiac sarcomas may develop from resident or bone marrow-derived mesenchymal stem cells: use of immunohistochemistry including CD44 and octamer binding protein 3/4. Histopathology 2012; 61: 966-73.

Heldman AW, et al. Transendocardial mesenchymal stem cells and mononuclear bone marrow cells for ischemic cardiomyopathy: the TAC-HFT randomized trial. JAMA. 2014;311(1):62-73.

Henderson NC, et al., Selective av integrin depletion identifies a core, targetable molecular pathway that regulates fibrosis across solid organs. Nat Med 2013; 19: 1617-24.

Henikoff, Amino acid substitution matrices from protein blocks, Proc. Natl. Acad. Sci., USA, 89, (1989), 10915.

Herberts CA, et al., Risk factors in the development of stem cell therapy. J Transl Med. 2011; 9: 29.

Herrera MB, et al. Exogenous mesenchymal stem cells localize to thekidney by means of CD44 following acute tubularinjury. Kidney Int 72: 430-441, 2007.

Herrera MB, et al. Mesenchymal stem cells contribute to the renal repair of acute tubular epithelial injury. Int J Mol Med 14: 1035-1041, 2004.

Hieshima K, et al. A novel human CC chemokine PARC that is most homologous to macrophage-inflammatory protein-1 alpha/LD78 alpha and chemotactic for T lymphocytes, but not for monocytes.. J Immunol. 1997; 159(3): 1140-49.

Hill JA, Olson EN., Cardiac plasticity. N Engl J Med 2008; 358: 1370-80.

Hinz B, et al., Biological Perspectives, The Myofibrobladt, One Function, Multiple Origins. Am J Pathol 2007; 170: 1807-16.

Hinz B., The role of myofibroblasts in wound healing. Curr Res Transl Med. Oct.-Dec. 2016; 64(4): 171-177.

Hoffman et al., Lung-Derived Mesenchymal Stromal Cell Post-Transplantation Survival, Persistence, Paracrine Expression, and Repair of Elastase-Injured Lung, Stem Cells Dev. (2011); 20: 1779-92.

Hofmann, H. et al., Human coronavirus NL63 employs the severe acute respiratory syndrome coronavirus receptor for cellular entry, Proc. Natl Acad. Sci. USA (2005) 102: 7988-93.

Hoogduijn MJ, et al., Donor-derived mesenchymal stem cells remain present and functional in the transplanted human heart. Am J Transplant. Jan. 2009; 9(1): 222-30.

Huang X., et al., Characterization of human plasma-derived exosomal RNAs by deep sequencing, BMC Genomics. 2013;14:319.

Huang XP, et al., Differentiation of allogeneic mesenchymal stem cells induces immunogenicity and limits their long-term benefits for myocardial repair. Circulation. 2010; 122: 2419-29.

(56) References Cited

OTHER PUBLICATIONS

Huang, J, et al.,. Cellular microRNAs contribute to HIV-1 latency in resting primary CD4+ T lymphocytes. Nat. Med. (2007) 13:1241-1247.

Hughes G, et al. Real World Experiences: Pirfenidone and Nintedanib are Effective and Well Tolerated Treatments for Idiopathic Pulmonary Fibrosis. J Clin Med 2016; 5.

Huleihel L, et al. Modified mesenchymal stem cells using miRNA transduction alter lung injury in a bleomycin model. Am J Physiol Lung Cell Mol Physiol 2017: ajplung 00323 02016.

Hunninghake GM. A new hope for idiopathic pulmonary fibrosis. N Engl J Med 2014; 370: 2142-2143.

Tkach M, Thery C. Communication by Extracellular Vesicles: Where We Are and Where We Need to Go. Cell 2016; 164: 1226-1232.

Tolar J, Le Blanc K, Keating A, and Blazar BR. Concise Review: Hitting the Right Spot with Mesenchymal Stromal Cells. Stem Cells. 2010;28(8):1446-55.

Toma C, et al., Human Mesenchymal Stem Cells Differentiate to a Cardiomyocyte Phenotype in the Adult Murine Heart. Circulation: 93-98, 2002.

Tomasek JJ, et al., Myofibroblasts and mechano-regulation of connective tissue remodelling. Nat Rev Mol Cell Biol. 2002; 3: 349-363.

Tomasoni S, et al. Transfer of Growth Factor Receptor mRNA Via Exosomes Unravels the Regenerative Effect of Mesenchymal Stem Cells. Stem Cells Dev 2013; 22: 772-780.

Tomé M, et al. miR-335 orchestrates cell proliferation, migration and differentiation in human mesenchymal stem cells. Cell Death and Differentiation. 2011;18(6):985-95.

Toonkel RL, et al. Mesenchymal stem cells and idiopathic pulmonary fibrosis. Potential for clinical testing. Am J Respir Crit Care Med 2013; 188: 133-140.

Torrisani, J., et al. Enjoy the Silence: The Story of let-7 MicroRNA and Cancer. Curr. Genomics. 2007; 8: 229-233.

Toussaint O, et al., Approach of evolutionary theories of ageing, stress, senescence-like phenotypes, calorie restriction and hormesis from the view point of far-from-equilibrium thermodynamics. Mech Ageing Dev. 2002; 123: 937-946.

Trachtenberg B., et al. Rationale and design of the Transendocardial Injection of Autologous Human Cells (bone marrow or mesenchymal) in Chronic Ischemic Left Ventricular Dysfunction and Heart Failure Secondary to Myocardial Infarction (TAC-HFT) trial: a randomized, double-blind, placebo-controlled study of safety and efficacy. Am Heart J. 2011; 161(3):487-493.

Travis EL, Organizational response of normal tissues to irradiation. Semin Radiat Oncol. Jul. 2001; 11(3): 184-96.

Travis WD, et al. Idiopathic nonspecific interstitial pneumonia: report of an American Thoracic Society project. Am J Resp Crit Care Med. 2008;177(12):1338-1347.

Tremain N, et al. MicroSAGE Analysis of 2,353 Expressed Genes in a Single Cell-Derived Colony of Undifferentiated Human Mesenchymal Stem Cells Reveals mRNAs of Multiple Cell Lineages. Stem Cells 2001; 19: 408-418.

Triboulet R, et al., Suppression of microRNA-silencing pathway by HIV-1 during virus replication, Science (2007)315: 1579-1582.

Triebner K, et al. Menopause Is Associated with Accelerated Lung Function Decline. Am J Respir Crit Care Med 2017; 195: 1058-1065.

Tsai Al, et al., Tsai Al, et al., Biomed Res Int. 2017: 2851906, Biomed Res Int. 2017: 2851906.

Tsai MS, et al., Isolation of human multipotent mesenchymal stem cells from second-trimester amniotic fluid using a novel two-stage culture protocol, Hum Reprod. Jun. 2004; 19(6): 1450-6.

Tzouvelekis A, et al. A prospective, non-randomized, no placebo-controlled, phase lb clinical trial to study the safety of the adipose derived stromal cells—stromal vascular fraction in idiopathic pulmonary Fibrosis. J Transl Med. 2013;11:171.

Tzouvelekis, A. et al., Stem cell therapy in pulmonary fibrosis, Curr. Opinion. Pulm. Med. (2011) 17: 368-73.

Tögel F, et al. Administered mesenchymal stem cells protect against ischemic acute renal failure through differentiation-independent mechanisms. Am J Physiol Renal Physiol 289: F31-F42, 2005.

Tögel F, et al. Renal SDF-1 signals mobilization and homing of CXCR4-positive cells to the kidney after ischemic injury. Kidney Int 67: 1772-1784, 2005.

Tögel FE, Westenfelder C. Kidney Protection and Regeneration Following Acute Injury: Progress Through Stem Cell Therapy. Am J Kidney Dis 60: 1012-1022, 2012.

Umehara H, et al., A novel clinical entity, IgG4-related disease (IgG4RD): general concept and details. Mod Rheumatol 2012; 22: 1-14.

Umezawa, H. et al., Studies on bleomycin, Cancer 20: 891-895, 1967.

Umezawa, H., Chemistry and mechanism of action of bleomycin, Fed Proc, 33: 2296-2302, 1974.

Umezu T., et al., Leukemia cell to endothelial cell communication via exosomal miRNAs, Oncogene. 2013;32:2747-2755.

Valadi, H. et al., Exosome-mediated transfer of mRNAs and microRNAs is a novel mechanism of genetic exchange between cells, Nat. Cell Biol. (2007) 9: 654-59.

Van Dommelen, SM et al., Microvesicles and exosomes: opportunities for cell-derived membrane vesicles in drug delivery, J. Control. Release (2011) 161: 635-44.

Van Koppen A, et al. Human Embryonic Mesenchymal Stem Cell-Derived Conditioned Medium Rescues Kidney Function in Rats with Established Chronic Kidney Disease. PLoS One 7: e38746, 2012.

Van Rooij, E. et al., Dysregulation of microRNAs after myocardial infarction reveals a role of miR-29 in cardiac fibrosis, Proc. Natl. Acad. Sci. USA (2008) 105: 13027-32.

Vande Velde G, et al. Longitudinal micro-CT provides biomarkers of lung disease that can be used to assess the effect of therapy in preclinical mouse models, and reveal compensatory changes in lung volume. Dis Model Mech 2016; 9: 91-98.

Vander Haar, E et al., "Insulin signalling to mTOR mediated by the Akt/PKB substrate PRAS40," Nat Cell Biol (2007) 9: 316-323.

Varin A, Gordon S., Alternative activation of macrophages: immune function and cellular biology. Immunobiology. 2009; 214: 630-641.

Vasudevan, S.et al. Switching from Repression to Activation: MicroRNAs Can Up-Regulate Translation. Science (2007) 318: 1931-34.

Venkataraman et al., Overactive epidermal growth factor receptor signaling leads to increased fibrosis after severe acute respiratory syndrome coronavirus infection, J. Virol. (2017) 91 (12): e00182-17.

Vermeulen A, Kaufman JM, Goemaere S, van Pottelberg I. Estradiol in elderly men. Aging Male 2002; 5: 98-102.

Vespasiani-Gentilucci U, et al., Hepatic toll-like receptor 4 expression is associated with portal inflammation and fibrosis in patients with NAFLD. Liver Int 2015; 35: 569-81.

Vij R, Noth I. Peripheral Blood Biomarkers in Idiopathic Pulmonary Fibrosis. Transl Res. 2012; 159(4): 218-27.

Villarroya-Beltri C., et al., Sumoylated hnRNPA2B1 controls the sorting of miRNAs into exosomes through binding to specific motifs, Nat Commun. 2013;4:2980.

Vittal, R. et al., Effects of the protein kinase inhibitor, imatinib mesylate, on epithelial/mesenchymal phenotypes: implications for treatment of fibrotic diseases, J Pharmacol Exp Ther., 321(1): 35-44, 2007.

Vittal, R. et al., Modulation of prosurvival signaling in fibroblasts by a protein kinase inhibitor protects against fibrotic tissue injury, Am J Pathol., 166(2): 367-75, 2005.

Volckaert et al., Parabronchial smooth muscle constitutes an airway epithelial stem cell niche in the mouse lung after injury, J Clin Invest. 2011; 121: 4409-19.

Voltz JW, Card JW, Carey MA, Degraff LM, Ferguson CD, Flake GP, Bonner JC, Korach KS, Zeldin DC. Male sex hormones exacerbate lung function impairment after bleomycin-induced pulmonary fibrosis. Am J Respir Cell Mol Biol 2008; 39: 45-52.

Von Grotthuss, M. et al., mRNA cap-1 methyltransferase in the SARS genome, Cell (2003) 113: 701-2.

(56) References Cited

OTHER PUBLICATIONS

Vuga LJ, et al. WNT5A Is a Regulator of Fibroblast Proliferation and Resistance to Apoptosis. Am J Respir Cell Mol Biol. Nov. 2009; 41(5): 583-9.
Wakitani, S, et al., Myogenic cells derived from rat bone marrow mesenchymal stem cells exposed to 5-azacytidine. Muscle Nerve 18: 1417-1426; 1995.
Wang B, et al. Mesenchymal Stem Cells Deliver Exogenous MicroRNA-let7c via Exosomes to Attenuate Renal Fibrosis. Mol Ther 2016.
Wang D, et al., Umbilical cord mesenchymal stem cell transplantation in active and refractory systemic lupus erythematosus: a multicenter clinical study, Arthritis Res Ther 2014; 16: R79.
Wang K, et al., Impact of serum SP-A and SP-D levels on comparison and prognosis of idiopathic pulmonary fibrosis: A systematic review and meta-analysis, Medicine (2017) 96 (23): e7083.
Wang X, et al. Cellular microRNA expression correlates with susceptibility of monocytes/macrophages to HIV-1 Infection. Blood. (2009) 113:671-4.
Wang X, et al. Exosomal miR-223 Contributes to Mesenchymal Stem Cell-Elicited Cardioprotection in Polymicrobial Sepsis. Sci Rep 2015; 5: 13721.
Wang Y, et al. Adipose derived mesenchymal stem cells transplantation via portal vein improves microcirculation and ameliorates liver fibrosis induced by CCl4 in rats. J Transl Med. 2012; 10: 133.
Wang, FZ et al, 2008. Human cytomegalovirus infection alters the expression of cellular microRNA species that affect its replication. J. Virol. (2008) 82:9065-9074.
Wang, J-F et al., Crocin Alleviates Pain Hyperalgesia in AIA Rats by Inhibiting the Spinal Wnt5a/ β-Catenin Signaling Pathway and Glial Activation, Neural Plasticity (2020) 4297483.
Wang, JS, et al., Marrow stromal cells for cellular cardiomyoplasty: feasibility and potential clinical advantages. J. Thorac. Cardiovasc. Surg. 120: 999-1005; 2000.
Wansleeben, C. et al, Stem cells of the adult lung: their development and role in homeostasis, regeneration and disease. Wiley Interdiscip. Rev. Dev. Biol. (2013) 2: 131-148.
Ware, L. and Matthay, The Acute Respiratory Distress Syndrome, M., N Engl J Med, 342:1334-1349, 2000.
Waterman RS, et al., A new mesenchymal stem cell (MSC) paradigm: polarization into a pro-inflammatory MSC1 or an Immunosuppressive MSC2 phenotype, PLoS One. Apr. 26, 2010; 5(4): e10088.
Webb P, Lopez GN, Greene GL, Baxter JD, Kushner PJ. The limits of the cellular capacity to mediate an estrogen response. Mol Endocrinol 1992; 6: 157-167.
Webber J., et al., Cancer exosomes trigger fibroblast to myofibroblast differentiation, Cancer Res. 2010;70:9621-9630.
Wei J. et al., Human amnion-isolated cells normalize blood glucose in streptozotocin-induced diabetic mice, Cell Transplant, 2003, 12: 545-552.
Weiss DJ, et al. A placebo-controlled, randomized trial of mesenchymal stem cells in COPD. Chest. 2013;143(6):1590-1598.
Weiss, SR, Leibowitz, IL, Coronavirus Pathogenesis, Coronavirus pathogenesis. Adv. Virus Res. (2011) 81: 85-164.
Wernig G, et al. Unifying mechanism for different fibrotic diseases. Proc Natl Acad Sci U S A 2017; 114: 4757-4762.
Westenfelder C, Togel FE. Protective actions of administered mesenchymalstem cells in acute kidney injury: relevance toclinical trials. Kidney Int Suppl (2011) 1: 103-106, 2011.
Whimbey, E., R. B., et al. Respiratory syncytial virus pneumonia in hospitalized adult patients with leukemia. (1995) Clin. Infect. Dis. 21:376-379.
Widagdo, W. et al., Differential Expression of the Middle East Respiratory Syndrome Coronavirus Receptor in the Upper Respiratory Tracts of Humans and Dromedary Camels, J. Vir. (2016) 90: 4838-42.
Wijayaratne, A. L., and McDonnell, D. P. The human estrogen receptor-alpha is a ubiquitinated protein whose stability is affected differentially by agonists, antagonists, and selective estrogen receptor modulators. (2001) J. Biol. Chem. 276, 35684-35692.
Wijayaratne, A. L., et al. Comparative Analyses of Mechanistic Differences Among Antiestrogens. (1999) Endocrinology 140, 5828-5840.
Williams AE. Functional aspects of animal microRNAs. Cellular and molecular life sciences : CMLS. 2007;65(4):545-62.
Williams JP, et al., Treatment for Radiation-Induced Pulmonary Late Effects: Spoiled for Choice or Looking in the Wrong Direction? Curr Drug Targets. 2010; 11: 1386-1394.
Wilson and Wynn, Pulmonary fibrosis: pathogenesis, etiology and regulation. Mucosal Immunol., 2009, 3(2): 103-121.
Wilson JG, Liu KD, Zhuo H, et al. Mesenchymal stem (stromal) cells for treatment of ARDS: a phase 1 clinical trial. Lancet. 2015;3(1):24-32.
Wolbank, S. et al., Dose-dependent immunomodulatory effect of human stem cells from amniotic membrane: a comparison with human mesenchymal stem cells from adipose tissue, Tissue Eng, 2007, 13: 1173-1183.
Wong TC, et al., Association Between Extracellular Matrix Expansion Quantified by Cardiovascular Magnetic Resonance and Short Term Mortality. Circulation 2012; 126: 1206-16.
Woo, PC et al., Clinical features and molecular epidemiology of coronavirus-HKU1-associated community-aquired pneumonia, Hong Kong Med. J. (2008) 15 (Suppl. 9): 46-47.
Wu et al., MicroRNA machinery responds to peripheral nerve lesion in an injury-regulated pattern. Neuroscience (2011) 190: 386-97.
Wu KC, et al., Late gadolinium enhancement by cardiovascular magnetic resonance heralds an adverse prognosis in nonischemic cardiomyopathy. J Am Coll Cardiol 2008; 51: 2414-21.
Wynn TA., Common and unique mechanisms regulate fibrosis in various fibroproliferative diseases. J Clin Invest 2007; 117: 524-9.
Wynn TA., Fibrotic disease and the TH1/TH2 paradigm. Rev Immunol 2004; 4: 583-94.
Wäster P, et al. IUltraviolet exposure of melanoma cells induces fibroblast activation protein-a in fibroblasts: Implications for melanoma invasion. Int J Oncol. Jul. 2011; 39(1): 193-202.
Xiao J, et al., Transplantation of adipose-derived mesenchymal stem cells into a murine model of passive chronic immune thrombocytopenia, Transfusion 2012; 52: 2551-2558.
Xin H, et al. MiR-133b Promotes Neural Plasticity and Functional Recovery After Treatment of Stroke with Multipotent Mesenchymal Stromal Cells in Rats Via Transfer of Exosome-Enriched Extracellular Particles. Stem Cells. Dec. 2013; 31(12): 2737-46.
Xu, J. et al., Role of the SDF-1/CXCR4 axis in the pathogenesis of lung injury and fibrosis. Am. J. Respir. Cell Mol. Biol. (2007) 37: 291-99.
Xu, W, et al., Mesenchymal stem cells from adult human bone marrow differentiate into a cardiomyocyte phenotype in vitro. Exp. Biol. Med. 229: 623-631; 2004.
Yamamoto et al., Epithelial-vascular cross talk mediated by VEGF-A and HGF signaling directs primary septae formation during distal lung morphogenesis. Dev Biol. Aug. 1, 2007;308(1):44-53.
Yamout B, et al., Bone marrow mesenchymal stem cell transplantation in patients with multiple sclerosis: a pilot study, J Neuroimmunol 2010; 227: 185-189.
Yang G, et al. Discovery and validation of extracellular/circulating microRNAs during idiopathic pulmonary fibrosis disease progression. Gene 2015; 562: 138-144.
Yang T, et al. miR-29 mediates TGFbeta1-induced extracellular matrix synthesis through activation of PI3K-AKT pathway in human lung fibroblasts. J Cell Biochem 2013; 114: 1336-1342.
Yang, IV et al., Gene expression profiling of familial and sporadic interstitial pneumonia. Am. J. Respir. Crit. Care Med. (2007) 175: 45-54.
Yamold J, Brotons MC., Pathogenetic mechanisms in radiation fibrosis. Radiother Oncol J Eur Soc Ther Radiol Oncol. 2010; 97: 149-161.
Yeager, CL et al., Human aminopeptidase N is a receptor for hman coronavirus 229E, Nature (1992) 357: 420-22.
Yeung ML, et al., Changes in microRNA expression profiles in HIV-1-transfected human cells, Retrovirology (2005) 2: 81.
Yin, Y., Wunderink, RG, MERS, SARS and other coronaviruses as causes of pneumonia, Respirology (2018) 23 (2): 130-37.

(56) References Cited

OTHER PUBLICATIONS

Yoder, MC, Progenitor cells in the pulmonary circulation, Proc Am Thorac Soc. 2011; 8: 466-70.
Yoshioka, T, et al., Repair of Infarcted Myocardium Mediated by Transplanted Bone Marrow-Derived CD34+ Stem Cells in a Non-human Primate Model. Stem Cells 23: 355-364; 2005.
Young HY, et al., Human reserve pluripotent mesenchymal stem cells are present in the connective tissues of skeletal muscle and dermis derived from fetal, adult, and geriatric donors, Anat Rec 264, 51-62.
Yu S, et al. Tumor Exosomes Inhibit Differentiation of Bone Marrow Dendritic Cells. J. Immunol. 2007; 178: 6867-75.
Yusuf, U. et al. Cidofovir for the treatment of adenoviral infection in pediatric hematopoietic stem cell transplant patients. Transplantation (2006) 81:1398-1404.
Hunter, IC et al. Transmission of Middle East respiratory syndrome coronavirus infections in healthcare settings, Abu Dhabi. Emerg. Infect. Dis. (2016) 22: 647-56.
Idell, S. et al., Angiotensin converting enzyme in bronchoalveolar lavage in ARDS, Chest (1987) 91: 52-56.
Iglesias, DM et al. Stem Cell Microvesicles Transfer Cystinosin to Human Cystinotic Cells and Reduce Cystine Accumulation In Vitro. PLoS One (2012) 7(8): e42840.
Imai, Y., et al., Angiotensin-Converting Enzyme 2 (ACE2) in Disease Pathogenesis, Cir. J. (2010) 74: 405-10.
Ingerslev et al., Resistant starch and arabinoxylan augment SCFA absorption, but affect postprandial glucose and insulin responses differently. Br J Nutr. May 2014;111(9):1564-76.
Ishikawa N, Hattori N, Yokoyama A, Kohno N. Utility of KL-6/MUC1 in the clinical management of interstitial lung diseases. Respir Investig 2012; 50: 3-13.
Ishizawa K, et al. Bone marrow-derived cells contribute to lung regeneration after elastase-induced pulmonary emphysema. FEBS Lett. 2004; 556(1-3):249-252.
Ital J, Identification of hematopoietic progenitor cells in human amniotic fluid before the 12th week of gestation, Anat Embryol. Apr.-Jun. 1993; 98(2): 119-26.
Izbicki G, et al. Time course of bleomycin-induced lung fibrosis. Int J Exp Pathol 2002; 83: 111-119.
Izbicki G. et al., Time course of bleomycin-induced lung fibrosis, Int J Exp Pathol., 83(3): 111-9, 2002.
Jameel MN, et al. Long-term functional improvement and gene expression changes after bone marrow-derived multipotent progenitor cell transplantation in myocardial infarction. Am J Physiol Heart Circ Physiol: 298: H1348-H1356, 2010.
Jang YO, et al. Histological improvement following administration of autologous bone marrow-derived mesenchymal stem cells for alcoholic cirrhosis: a pilot study. Liver Int. 2014; 34: 33-41.
Janick-Buckner, D. et al., Alteration of bronchoalveolar lavage cell populations following bleomycin treatment in mice, Toxicol Appl Pharmacol., 100(3): 465-73, 1989.
Janowska-Wieczorek A., et al., Microvesicles derived from activated platelets induce metastasis and angiogenesis in lung cancer, Int J Cancer. 2005;113:752-760.
Jeong JO, et al. Malignant tumor formation after transplantation of short-term cultured bone marrow mesenchymal stem cells in experimental myocardial infarction and diabetic neuropathy. Circ Res. 2011; 108: 1340-7.
Ji, R-R et al, Matrix metalloprotease regulation of neuropathic pain, Trends Pharmacol. Sci. (2009) 30 (7): 336-40.
Jinnin M. J, Mechanisms of skin fibrosis in systemic sclerosis. Dermatol 2010; 37: 11-25.
Johkoh T, Muller NL, Cartier Y, et al. Idiopathic interstitial pneumonias: diagnostic accuracy of thin-section CT in 129 patients. Radiology. 1999;211(2):555-560.
Johnson A, DiPietro LA., Apoptosis and angiogenesis: an evoling mechanism for fibrosis. FASEB J 2013; 27: 3893-901.
Jones, et al., Isolation and Characterization of Bone Marrow Multipotential Mesenchymal Progenitor Cells. 2002 Arthritis Rheum. 46: 3349-60.
Jong, AY et al., Large-scale isolation and cytotoxicity of extracellular vesicles derived from activated human natural killer cells, J. Extracell. Vesicles (2017) 6: 1294368.
Jopling, CL, et al., Modulation of hepatitis C virus RNA abundance by a liver-specific microRNA. Science (2005) 309:1577-1581.
Jung KH, et al. Effect of human umbilical cord blood-derived mesenchymal stem cells in a cirrhotic rat model. Liver Int. 2009; 29: 898-909.
Kadivar, M, et al. In vitro cardiomyogenic potential of human umbilical vein-derived mesenchymal stem cells. Biochem. Biophys. Res. Commun. 340: 639-647; 2006.
Kaissling B, et al., Renal epithelial injury and fibrosis. Biochim Biophys Acta 2013; 1832: 931-9.
Kamath PS, Kim WR. The Model for End-Stage Liver Disease (MELD). Hepatology. 2007; 45: 797-805.
Kang, CK, et al., Clinical and Epidemiologic Characteristics of Spreaders of Middle East Respiratory Syndrome Coronavirus during the 2015 Outbreak in Korea, J. Korean Med. Sci. (2017) 32: 744-49.
Kang, et al., A paradoxical role for IFN-gamma in the immune properties of mesenchymal stem cells during viral challenge, Exp. Hematol. (2005) 33: 796-803.
Kapetanaki MG, Mora AL, Rojas M. Influence of age on wound healing and fibrosis. J Pathol 2013; 229: 310-322.
Karl M, et al. Differential effects of continuous and intermittent 17beta-estradiol replacement and tamoxifen therapy on the prevention of glomerulosclerosis: modulation of the mesangial cell phenotype in vivo. The American journal of pathology 2006; 169: 351-361.
Karlas, A. et al., Genome-wide RNAi screen identifies human host factors crucial for influenza virus replication, Nature (2010) 463 (7282): 818-22.
Karlson, et al., Mesenchymal stem cells exert differential effects on alloantigen and virus-specific T-cell responses, Blood (2008) 112:532-541.
Karussis D, et al., Safety and Immunological Effects of Mesenchymal Stem Cell Transplantation in Patients With Multiple Sclerosis and Amyotrophic Lateral Sclerosis, Arch Neurol 2010; 67: 1187-1194.
Katakowski M, et al. Exosomes from marrow stromal cells expressing miR-146b inhibit glioma growth. Cancer Lett 2013; 335: 201-204.
Katsuda T, et al. Human adipose tissue-derived mesenchymal stem cells secrete functional neprilysin-bound exosomes. Sci Rep (2013); 3: 1197.
Kawasaki A, et al. Wnt5a promotes adhesion of human dermal fibroblasts by triggering a phosphatidylinositol-3 kinase/Akt signal. Cell Signal. Dec. 2007; 19(12): 2498-506.
Kebriaei P, et al., Adult human mesenchymal stem cells added to corticosteroid therapy for the treatment of acute graft versus-host disease, Biol Blood Marrow Transplant 2009; 15: 804-811.
Keller, S. et al., Exosomes: from biogenesis and secretion to biological function, Immunol. Lett (2006) 107: 102-108.
Kennedy B, et al. Biomarkers to identify ILD and predict lung function decline in scleroderma lung disease or idiopathic pulmonary fibrosis. Sarcoidosis Vase Diffuse Lung Dis 2015; 32: 228-236.
Khan MA, et al., Partial volume rat lung irradiation; assessment of early DNA damage in different lung regions and effect of radical scavengers. Radiother Oncol J Eur Soc Ther Radiol Oncol. 2003; 66: 95-102.
Khimji AK, Rockey DC., Endothelin—biology and disease. Cell Signal 2010; 22: 1615-25.
Kim EY, et al., The potential of mesenchymal stem cells derived from amniotic membrane and amniotic fluid for neuronal regenerative therapy, BMB Rep. Mar. 2014; 47(3): 135-140.
Kim PJ, et al., Direct Evaluation of Myocardial Viability and Stem Cell Engraftment Demonstrates Salvage of the Injured Myocardium. Circ Res: e40-e50, 2015.
Kim SJ, et al. The role of mitochondrial DNA in mediating alveolar epithelial cell apoptosis and pulmonary fibrosis. Int J Mol Sci. 2015;16(9):21486-21519.
Kim, OY, et al., Extracellular vesicle mimetics: Novel alternatives to extracellular vesicle-based theranostics, drug delivery, and vaccines, Semin. Cell Dev. Biol. (2017) 67: 74-82.

(56) References Cited

OTHER PUBLICATIONS

Kim, S-J et al., "Mitochondrial catalase overexpressed transgenic mice are protected against lung fibrosis in part via preventing alveolar epithelial cell mitochondrial DNA damage," (2016) Free Radic. Biol. Med. 101: 482-90).

Kinder BW, et al. Serum surfactant protein-A is a strong predictor of early mortality in idiopathic pulmonary fibrosis. Chest 2009; 135: 1557-1563.

King et al., Structural and functional characteristics of lung macro- and microvascular endothelial cell phenotypes, Microvasc Res. 2004; 67: 139-51.

King TE Jr., Bradford WZ, Castro-Bernardini S, et al. A phase 3 trial of pirfenidone in patients with idiopathic pulmonary ?brosis. N Engl J Med. 2014;370(22):2083-2092.

King TE, Jr., et al. A phase 3 trial of pirfenidone in patients with idiopathic pulmonary fibrosis. N Engl J Med 2014; 370: 2083-2092.

Meckes, DG et al., Microvesicles and viral infection, J. virol. (2011) 85: 12844-54.

Meng XM, et al., Inflammatory processes in renal fibrosis. Nat Rev Nephrol 2014; 10: 493-503.

Mercer PF, et al. Exploration of a potent PI3 kinase/mTOR inhibitor as a novel anti-fibrotic agent in IPF. Thorax 2016.

Meyerholz, DK et al., Dipeptidyl Peptidase 4 Distribution in the Human Respiratory Tract: Implications for the Middle East Respiratory Syndrome, Am. J. Pathol. (2016) 186: 78-86.

Meyers and Miller, Optimal alignments in linear space, puter Applic. Biol. Sci., 4:11-17 (1988).

Mezzano SA, et al., Angiotensin II and Renal Fibrosis. Hypertension 2001; 38: 635-8.

Mias C, et al., Mesenchymal Stem Cells Promote Matrix Metalloproteinase Secretion by Cardiac Fibroblasts and Reduce Cardiac Ventricular Fibrosis After Myocardial Infarction. Stem Cells: 2734-2743, 2009.

Millimaggi D., et al., Tumor vesicle-associated CD147 modulates the angiogenic capability of endothelial cells, Neoplasia. 2007;9:349-357.

Miragoli M, et al., Electrotonic Modulation of Cardiac Impulse Conduction by Myofibroblasts. Circ Res 2006; 98: 801-10.

Miragoli M, Myofibroblasts induce ectopic activity in cardiac tissue, et al. Circ Res 2007; 101: 755-8.

MMWR (2010) Estimates of Deaths Associated with Seasonal Influenza—United States, 1976-2007. Atlanta, GA: Centers for Disease Control and Prevention. pp. 1057-1062.

Moertel CA, et al., Pseudomosaicism, true mosaicism, and maternal cell contamination in amniotic fluid processed with in situ culture and robotic harvesting, 1992; Prenat Diagn 12, 671-683.

Molina EJ, et al., Reverse remodeling is associated with changes in extracellular matrix proteases and tissue inhibitors after mesenchymal stem cell (MSC) treatment of pressure overload hypertrophy. J Tissue Engineering Regenerative Med: 85-91, 2009.

Monastyrskaya, K. et al. miR-199a-5p Regulates Urothelial Permeability and May Play a Role in Bladder Pain Syndrome. Am. J. Pathol. (2013) 182: 431-48.

Monsel A, et al. Therapeutic Effects of Human Mesenchymal Stem Cell-derived Microvesicles in Severe Pneumonia in Mice. Am J Respir Crit Care Med. Aug. 1, 2015; 192(3): 324-36.

Monsel, A. et al., Mesenchymal stem cell derived secretome and extracellular vesicles for acute lung injury and other inflammatory lung diseases. Expert Opin. Biol. Ther. (2016) 16: 859-71.

Montgomery RL, et al. MicroRNA mimicry blocks pulmonary fibrosis. EMBO Mol Med 2014; 6: 1347-1356.

Moodley Y, et al. Anti-inflammatory effects of adult stem cells in sustained lung injury: a comparative study. PLoS One 2013; 8: e69299.

Moodley Y, et al. Human umbilical cord mesenchymal stem cells reduce fibrosis of bleomycin-induced lung injury. Am J Pathol 2009; 175: 303-313.

Moon, SY, Son, JS., Infectivity of an Asymptomatic Patient with Middle East Respiratory Syndrome Coronavirus Infection, CM. Infect. Dis. (2017) 64: 1457-58.

Moore-Morris T, et al., Resident fibroblast lineages mediate pressure overload-induced cardiac fibrosis. J Clin Invest 2014; 124: 2921-34.

Mora, AL, Rojas, M., Aging and lung injury repair: a role for bone marrow derived mesenchymal stem cells. J. Cell Biochem. (2008) 105: 641-47.

Morando S, et al., The therapeutic effect of mesenchymal stem cell transplantation in experimental autoimmune encephalomyelitis is mediated by peripheral and central mechanisms, Stem Cell Res Ther 2012; 3: 3.

Morgenstem, B. et al., Ribavirin and interferon-beta synergistically inhibit SARS-associated coronavirus replication in animal and human cell lines, Biochem. Biophys. Res. Commun. (2005) 326: 905-8.

Morigi M, et al. Mesenchymal Stem Cells Are Renotropic, Helping to Repair the Kidney and Improve Function in Acute Renal Failure. J Am Soc Nephrol 15: 1794-1804, 2004.

Morrisey & Hogan, Preparing for the first breath: genetic and cellular mechanisms in lung development, Dev Cell. Jan. 19, 2010; 18(1): 8-23.

Moscoso, I, et al., Differentiation "In vitro" of primary and immortalized porcine mesenchymal stem cells into cardiomyocytes for cell transplantation. Transplant. Proc. 37: 481-482; 2005.

Mossman BT, et al. Pulmonary endpoints (lung carcinomas and asbestosis) following inhalation exposure to asbestos. J Toxicol Environ Health Part B, 2011;14:76-121.

Muggia, F. et al., Pulmonary toxicity of antitumor agents, Cancer Treat Rev, 10: 221-243, 1983.

Mulcahy L.A., et al., Routes and mechanisms of extracellular vesicle uptake, J Extracell Vesicles. (2014) 3: 103402/iev/v3/24641.

Muller I, et al., Application of multipotent mesenchymal stromal cells in pediatric patients following allogeneic stem cell transplantation, Blood Cells Mol Dis 2008; 40: 25-32.

Munich S., Sobo-Vujanovic A., Buchser W.J., Beer-Stolz D., Vujanovic N.L. Dendritic cell exosomes directly kill tumor mils and activate natural killer cells via TNF superfamily ligands. Oncoimmunology. 2012;1:1074-1083.

Naik, et al., Viral Infection and aging as cofators for the development of pulmonary fibrosis, Expert Review of Respiratory Medicine, Dec. 31, 2010, Vo. 4, No. 6, pp. 759-771.

Nardulli, A. M., and Katzenellenbogen, B. S. Dynamics of Estrogen Receptor Turnover in Uterine Cells in Vitro and in Uteri in Vivo. (1986) Endocrinology 119, 2038-2046.

Nawaz, Z., et al. Proteasome-dependent degradation of the human estrogen receptor. (1999) Proc. Natl. Acad. Sci. U. S. A. 96, 1858-1862.

Neininger A. et al., MK2 Targets Au-rich Elements and Regulates Biosynthesis of Tumor Necrosis Factor and Interleukin-6 Independently at Different Post-transcriptional Levels. J Biol. Chem., 277(5): 3065-8, 2002.

Nelson AW, Tilley WD, Neal DE, Carroll JS. Estrogen receptor beta in prostate cancer: friend or foe? Endocrine-related cancer 2014; 21: T219-234.

Nelson JF, Felicia LS, Osterburg HH, Finch CE. Altered profiles of estradiol and progesterone associated with prolonged estrous cycles and persistent vaginal comification in aging C57BL/6J mice. Biol Reprod 1981; 24: 784-794.

Neven KY, et al. Extracellular Vesicles: How the External and Internal Environment Can Shape Cell-To-Cell Communication. Curr Environ Health Rep. 2017.

Nicholls, J., Peiris, M., Good Ace, bad ACE do bathe in lung injury, SARS, Nature Medicine (2005) 11 (8): 821-22.

Nichols, W.G. et al., Respiratory Viruses other than influenza virus: impact and therapeutic advances. Clin. Microbiol. Rev. (2008) 21(2): 274-90.

Nielsen et al., Diets high in resistant starch and arabinoxylan modulate digestion processes and SCFA pool size in the large intestine and faecal microbial composition in pigs. Br J Nutr. Dec. 14, 2014;112(11):1837-49.

Niknejad, H. et al, Properties of the amniotic membrane for potential use in tissue engineering, Eur. Cells and Materials (2008) 15: 88-99.

(56) References Cited

OTHER PUBLICATIONS

Ning H, et al., The correlation between cotransplantation of mesenchymal stem cells and higher recurrence rate in hematologic malignancy patients: outcome of a pilot clinical study, Leukemia 2008; 22: 593-599.

Ninichuk V, et al. Multipotent mesenchymal stem cells reduceinterstitial fibrosis but do not delay progression of chronic cidney disease in collagen4A3-deficient mice. Kidney Int 70: 121-129, 2006.

Nishimura K, et al. Usual interstitial pneumonia: histologic correlation with high-resolution CT. Radiology. 1992;182(2):337-342.

Noble, P. and Homer R., Idiopathic pulmonary fibrosis: new insights into pathogenesis. Clin Chest Med, 25(4): 749-58, 2004.

Nolte-'t Hoen, EN et al., Activated T cells recruit exosomes secreted by dendritic cells via LFA-1, Blood. 2009;113:1977-1981.

Nuckton T. et al., Pulmonary dead-space fraction as a risk factor for death in the acute respiratory distress syndrome, N Engl J Med, 346:1281-1286, 2002.

Oberbauer E, et al., Enzymatic and non-enzymatic isolation systems for adipose tissue-derived cells: current state of the art. Cell Regen 2015; 4: 7.

Kinnaird et al, Local Delivery of Marrow-Derived Stromal Cells Augments Collateral Perfusion Through Paracrine Mechanisms., Circulation 109: 1543-49 (2004).

Kliment CR, et al. A novel method for accurate collagen and biochemical assessment of pulmonary tissue utilizing one animal. Int J Clin Exp Pathol 2011; 4: 349-355.

Ko IK, Kim BS., Mesenchymal stem cells for treatment of myocardial infarction. Int J Stem Cells. 2008; 1: 49-54.

Kolb, M., et al., Transient expression of IL-1b induces acute lung injury and chronic repair leading to pulmonary fibrosis. J. Clin. Invest, 107(12): 1529-1536, 2001.

Konigshoff M, et al. Functional Wnt Signaling Is Increased in Idiopathic Pulmonary Fibrosis. PLoS One 2008; 3: e2142.

Kono M, et al. Androgen Receptor Function and Androgen Receptor-Targeted Therapies in Breast Cancer: A Review. JAMA Oncol 2017; 3: 1266-1273.

Kopers-Lalic, D. et al., Virus-modified exosomes for targeted RNA delivery; a new approach in nanomedicine, Adv. Drug delivery rev. (2012) doi: 10.1016/j.addr.2012.07.006.

Koppers-Lalic D., et al., Nontemplated nucleotide additions distinguish the small RNA composition in cells from exosomes. Cell Rep. 2014;8:1649-1658.

Kosaka N., et al., Neutral sphingomyelinase 2 (nSMase2)-dependent exosomal transfer of angiogenic microRNAs regulate cancer cell metastasis, J Biol Chem. 2013;288:10849-10859.

Kosuma, GD, et al. Stem Cells Dev. (2017) 26: 617-31.

Koften, D.N. and Morrisey, E.E., Lung regeneration: mechanisms, applications and emerging stem cell populations. Nat. Med.(2014) 20(8): 822-32.

Koumangoye R.B., et al., Detachment of breast tumor cells induces rapid secretion of exosomes which subsequently mediate cellular adhesion and spreading, PLoS One. 2011;6:e24234.

Kuba, K. et al., A crucial role of angiotensin converting enzyme 2 (ACE2) in SARS coronavirus-induced lung injury, Nat. Med. (2005) 11: 875-79.

Kupferberg DH, et al. Minimal clinically important difference for the UCSD Shortness of Breath Questionnaire. J Cardiopulm Rehabil 2005; 25: 370-377.

Kusuma, et al. To Protect and to Preserve: Novel Preservation Strategies for Extracellular Vesicles. Front Pharmacol. 2018; 9: 1199.

Kusuma, GD, et al. Effect of the Microenvironment on Mesenchymal Stem Cell Paracrine Signaling: Opportunities to Engineer the Therapeutic Effect. Stem Cells Dev. (2017) 26: 617-31.

Kynast, KL, et al. Modulation of central nervous system-specific microRNA-124a alters the inflammatory response in the formalin test in mice. Pain (2013) 154: 368-76.

Lagos D, et al., miR-132 regulates antiviral innate immunity through suppression of the p300 transcriptional co-activator, Nature Cell Biology (2010) 12: 513-519.

Lai C-C, et al., Asymptomatic carrier state, acute respiratory disease, and pneumonia due to severe acute respiratory syndrome coronavirus 2 (SARS-CoV-2): Facts and myths. J. Microbiol. Immunol. Infect. (2020) doi.org/10.1016/j.imii.2020.02.012.

Lai et al. Derivation and characterization of human fetal MSCs: An alternative cell source for large-scale production of cardioprotective microparticles. J. Mol. Cell. Cardiol. (2010) 48: 1215-1224.

Lai et al. Exosome secreted by MSC reduces myocardialischemia/reperfusion injury. Stem Cell Res., 4 (2010): 214-222.

Lakhal, S. et al. Exosome nanotechnology: an emerging paradigm shift in drug delivery: exploitation of exosome nanovesicles for systemic in vivo delivery of RNAi heralds new horizons for drug delivery across biological barriers, Bioessays (2011) 33: 737-41.

Lama VN, et al., Evidence for tissue-resident mesenchymal stem cells in human adult lung from studies of transplanted allografts, J Clin Invest. Apr. 2007; 117(4): 989-96).

Lama VN, Phan SH. The extrapulmonary origin of ?broblasts: stem/progenitor cells and beyond. Proc Am Thorac Soc. 2006; 3(4):373-376.

Lamparski, J Immunol, Production and characterization of clinical grade exosomes derived from dendritic cells, Methods. 2002; 270: 211-226.

Lau, SK et al., Delayed induction of proinflammatory cytokines and suppression of innate antiviral response by the novel Middle East respiratory syndrome coronavirus: implications for pathogenesis and treatment, J. Gen. Virol. (2013) 94: 2679-90.

Lawson W. et al., Increased and prolonged pulmonary fibrosis in surfactant protein C-deficient mice following intratracheal bleomycin, Am J Pathol. 2005; 167(5): 1267-1277.

Le Blanc K, et al. Mesenchymal stem cells for treatment of steroid-resistant, severe, acute graft-versus-host disease: a phase II study Lancet. 2008;371(9624):1579-1586.

Lee HY, et al. Targeted expression of catalase to mitochondria prevents age-associated reductions in mitochondrial function and insulin resistance. Cell Metab. 2010;12(6):668-674.

Lee JW, et al. Allogeneic human mesenchymal stem cells for treatment of E. coli endotoxin-induced acute lung injury in the ex vivo perfused human lung. Proc Natl Acad Sci U S A. 2009;106(38): 16357-16362.

Lee SH, et al. The effect of adipose stem cell therapy on pulmonary fibrosis induced by repetitive intratracheal bleomycin in mice. Exp Lung Res 2014; 40: 117-125.

Lee SR, et al. Repeated administration of bone marrow-derived mesenchymal stem cells improved the protective effects on a remnant kidney model. Ren Fail. 2010; 32: 840-848.

Lee Y, et al. Exosomes and microvesicles: extracellular vesicles for genetic information transfer and gene therapy. Hum Mol Genet 2012; 21: R15-134.

Lee, N. et al. A major outbreak of severe acute respiratory syndrome in Hong Kong. N. Engl. J. Med. (2003) 348: 1986-94.

Lee, N. et al., Effects of early corticosteroid treatment on plasma SARS-associated Coronavirus RNA concentrations in adult patients, J. Clin. Virol. (2004) 31: 304-9.

Lee, SH et al., Modulation of cytokine and nitric oxide by mesenchymal stem cell transfer in lung injury/fibrosis. Respir. Res. (2010) 11: 16.

Lefaix JL, Daburon F., Diagnosis of acute localized irradiation lesions: review of the French experimental experience. Health Phys. 1998; 75: 375-384.

Leri A, et al., Cardiac stem cell niches. Stem Cell Res: 631-646, 2014.

Levine D, et al., Expression of the Integrin a8b1 during Pulonary and Hepatic Fibrosis. Am J Pathol 2000; 156: 1927-35.

Ley B, et al. Unified baseline and longitudinal mortality prediction in idiopathic pulmonary Fibrosis. Eur Resp J. 2015;45(5): 1374-1381.

Ley, K. and Zarbock, A., From lung injury to fibrosis, Nat. Med. 14: 20-21; 2008.

Li et al., Paracrine factors released by GATA-4 overexpressed mesenchymal stem cells increase angiogenesis and cell survival. Am. J. Physiol. Heart Circ. Physiol., 299 (2010): H1772-H1781.

Li M, Jendrossek V, Belka C., The role of PDGF in radiation oncology. Radiat Oncol. 2007; 2: 5.

(56) References Cited

OTHER PUBLICATIONS

Li MO, et al., Transforming growth factor-beta regulation of immune responses. Annu Rev Immunol. 2006; 24: 99-146.

Li Q, et al. In Vivo Tracking and Comparison of the Therapeutic Effects of MSCs and HSCs for Liver Injury. PLoS One. 2013; 8: e62363.

Li Y, et al., Androgen contributes to gender-related cardiac hypertrophy and fibrosis in mice lacking the gene encoding guanylyl cyclase-A. Endocrinology 2004; 145: 951-958.

Li, W. et al. Angiotensin-converting enzyme 2 is a functional receptor for the SARS coronavirus. Nature (2003) 426: 450-54.

Li, Xiaohong, et al., Mesenchymal stem cells in idiopathic pulmonary fibrosis. (2017) Oncotarget 8(60): 102600-102616.

Li, Y, et al., Insulin-like growth factor 1 enhances the migratory capacity of mesenchymal stem cells, 2007 Biochem. Biophys. Res. Communic. 356(3): 780-784.

Li, Y., et al., MicroRNA expression and virulence in pandemic influenza virus-infected mice, J. Virol. (2010) 84(6): 3023-32.

Ji, R-R, et al. MMP-2 and MMP-9-Investigations in Neuropathic Pain Phases. US Neurology, 2008;4(2):71-74.

\* cited by examiner

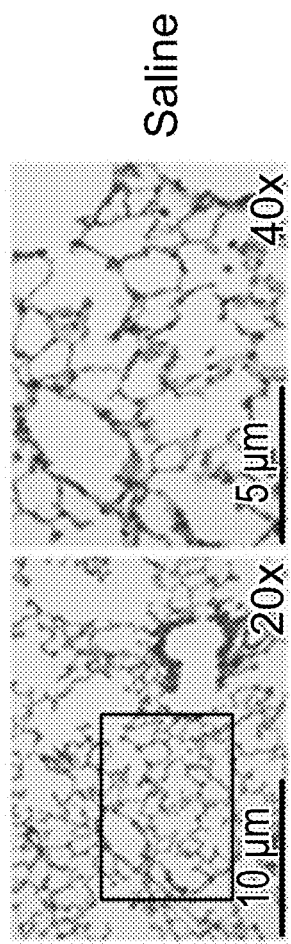
FIG. 4A Saline
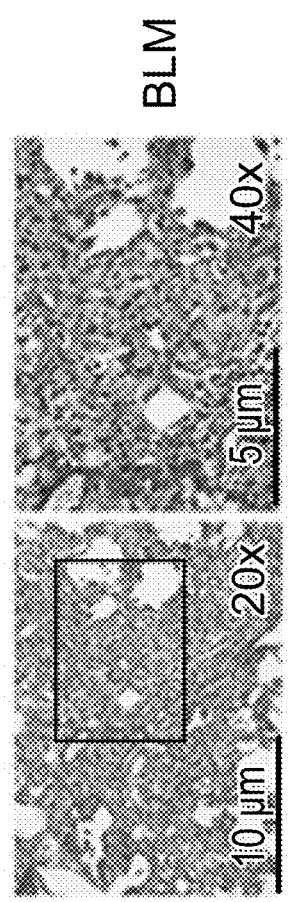
FIG. 4B BLM
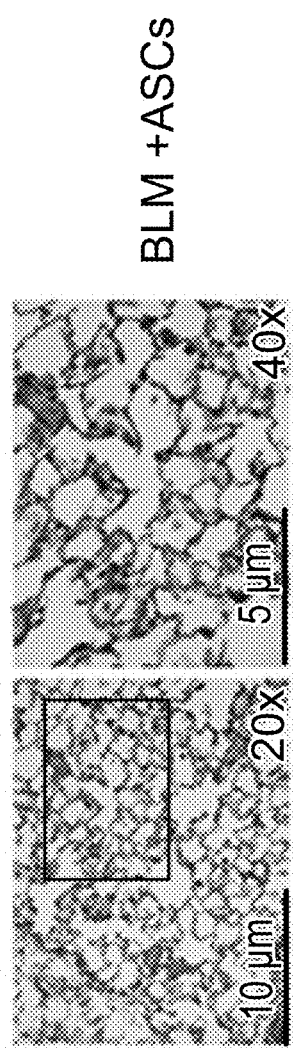
FIG. 4C BLM +ASCs 20x
40x

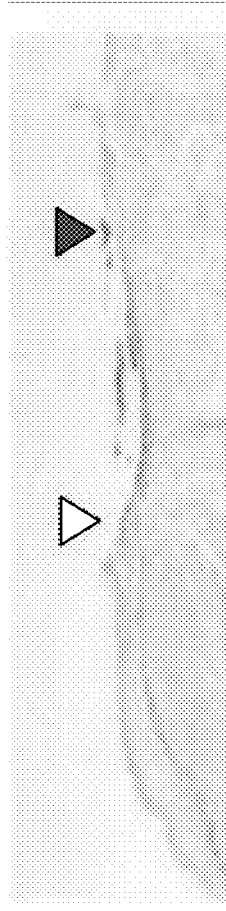
FIG. 18A Whole cell MSC
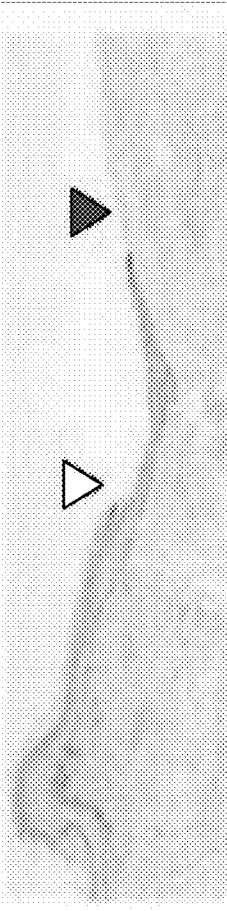
FIG. 18B Exosomes
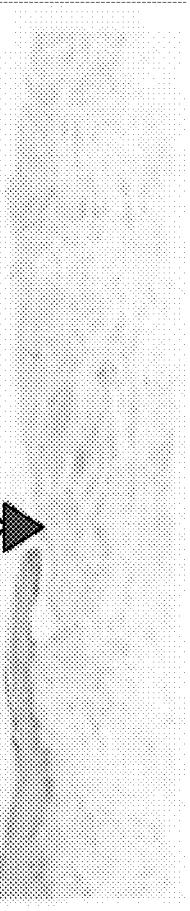
FIG. 18C Control

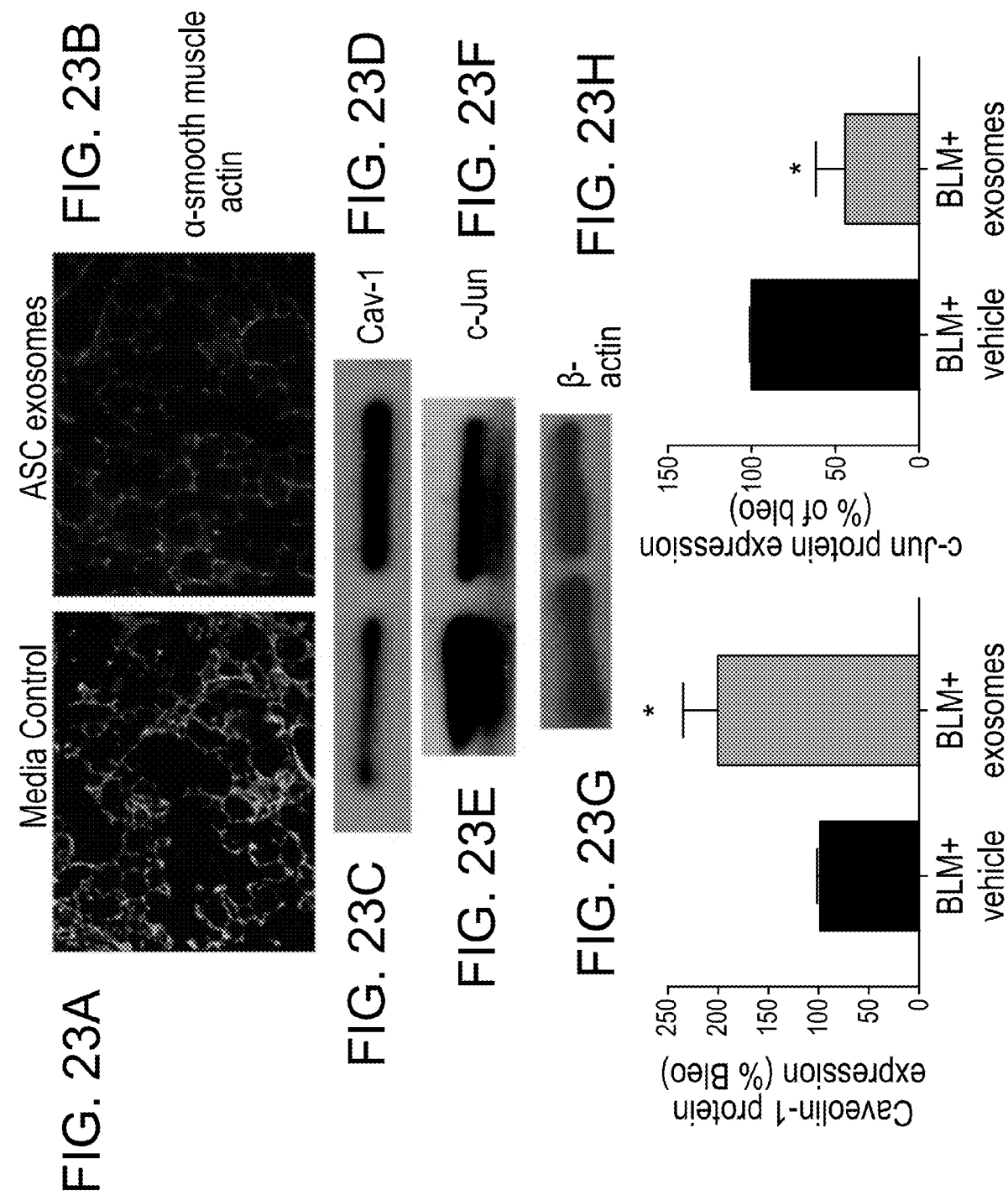

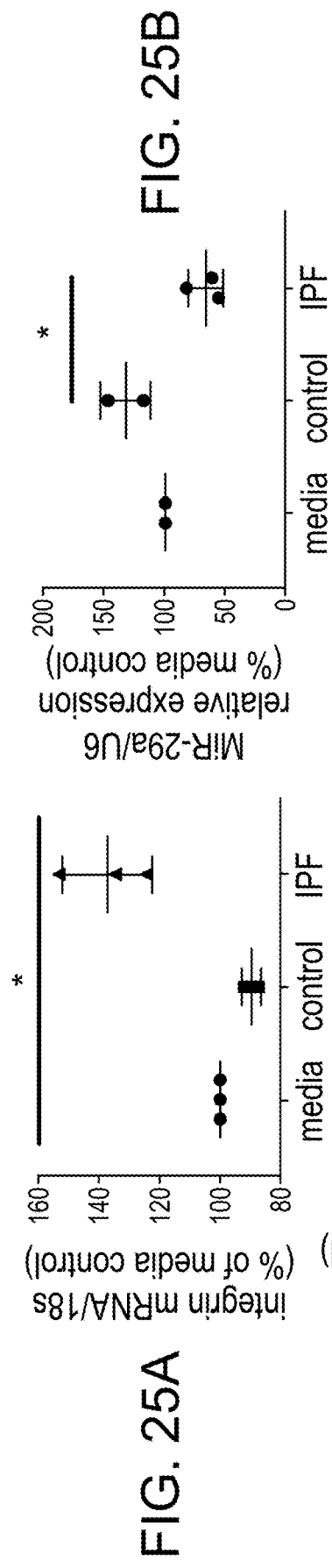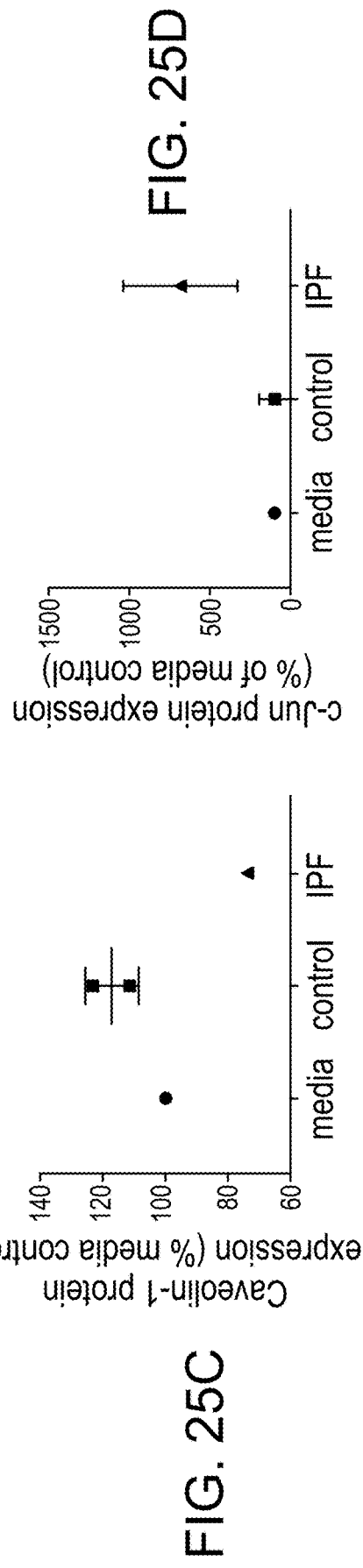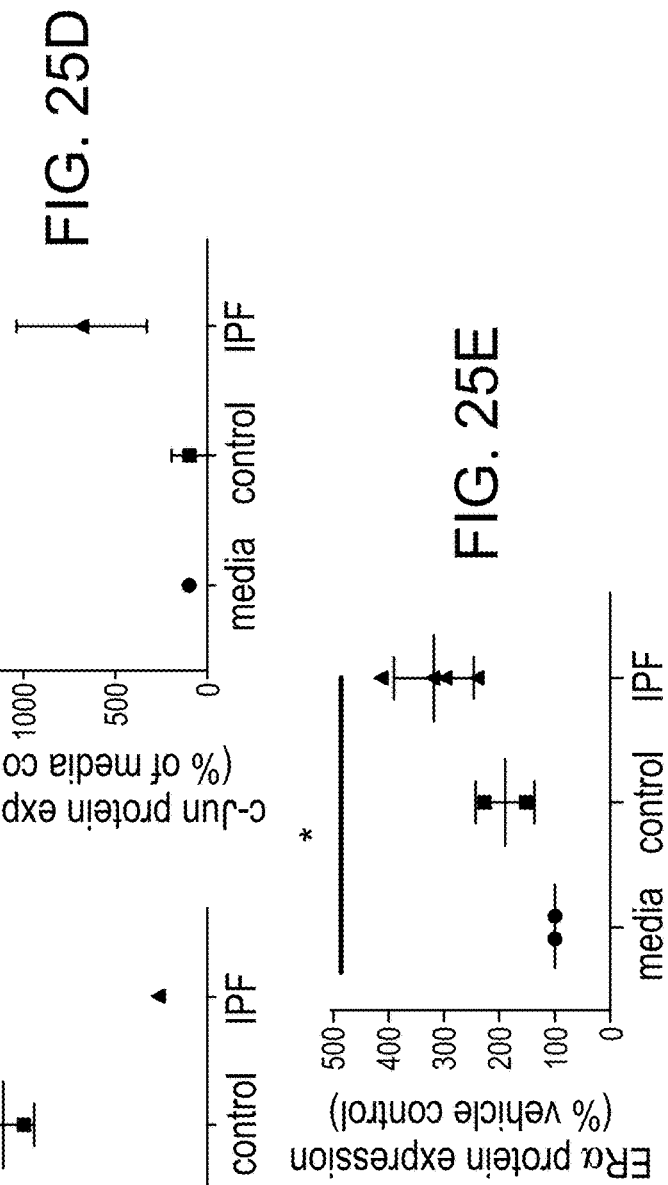

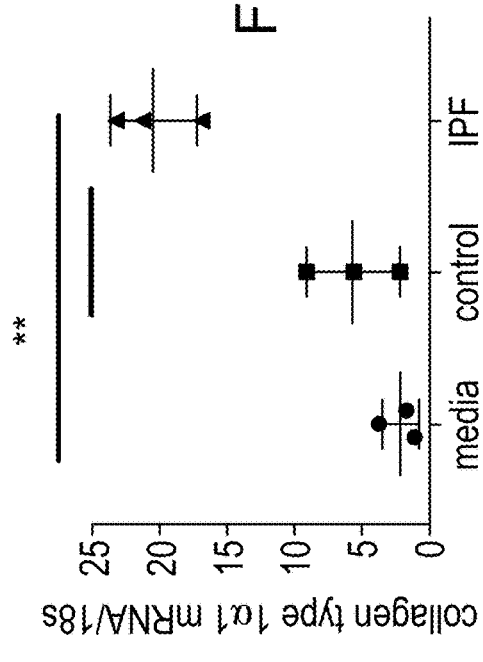
FIG. 26B
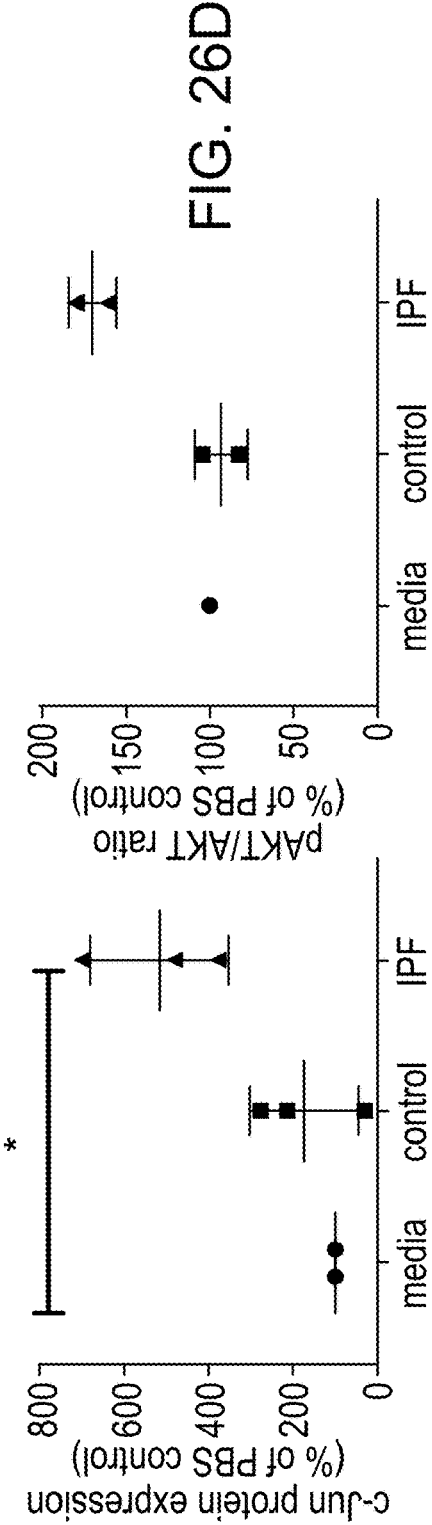
FIG. 26D
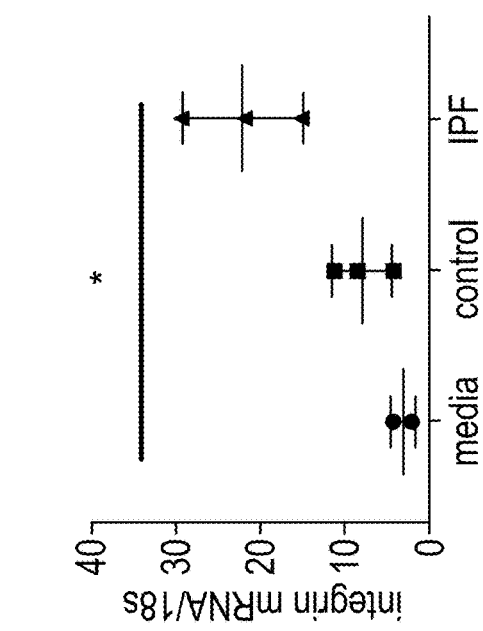
FIG. 26A
FIG. 26C

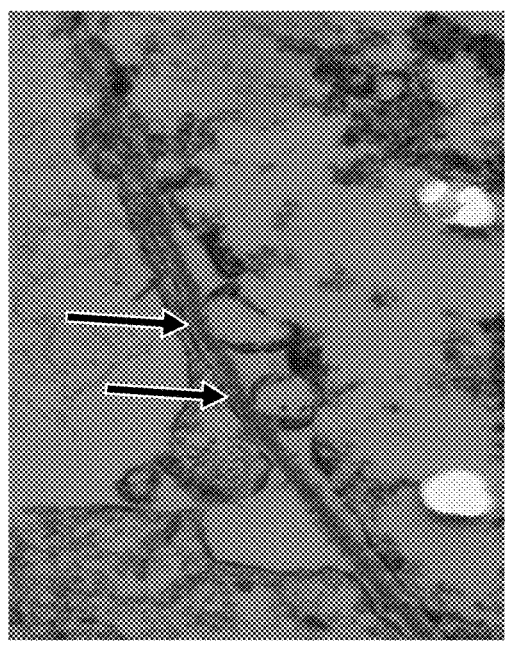
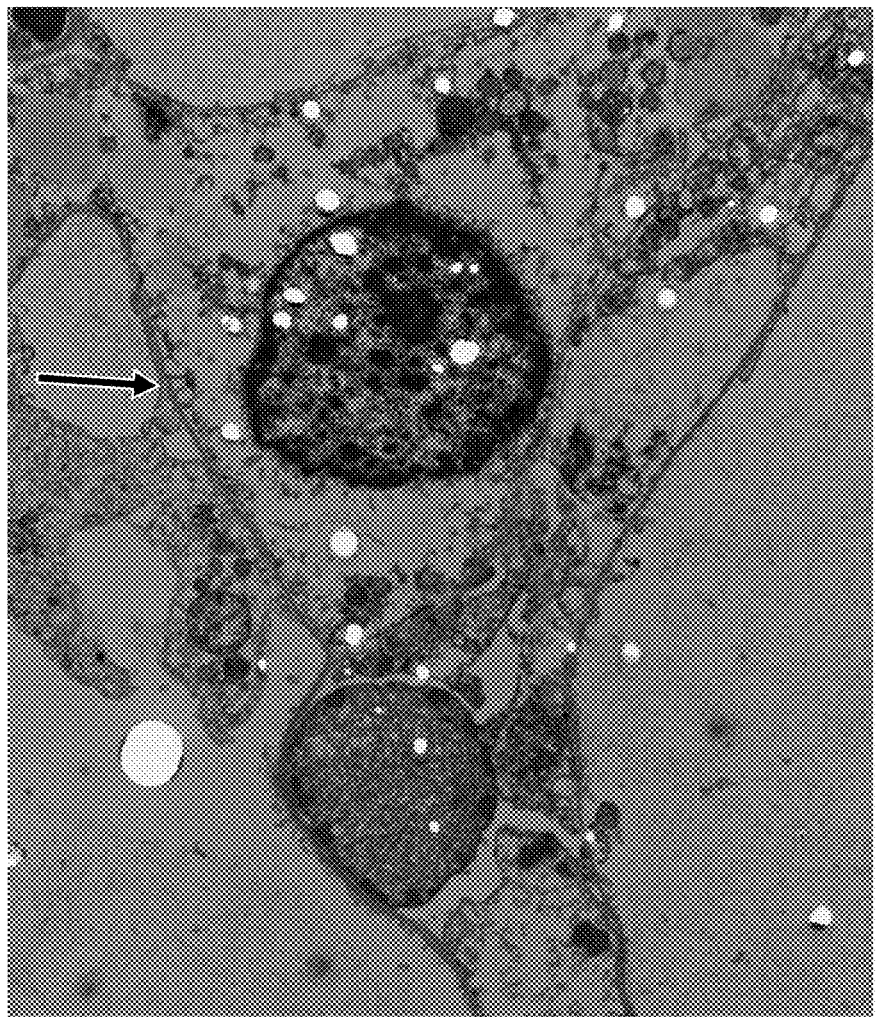

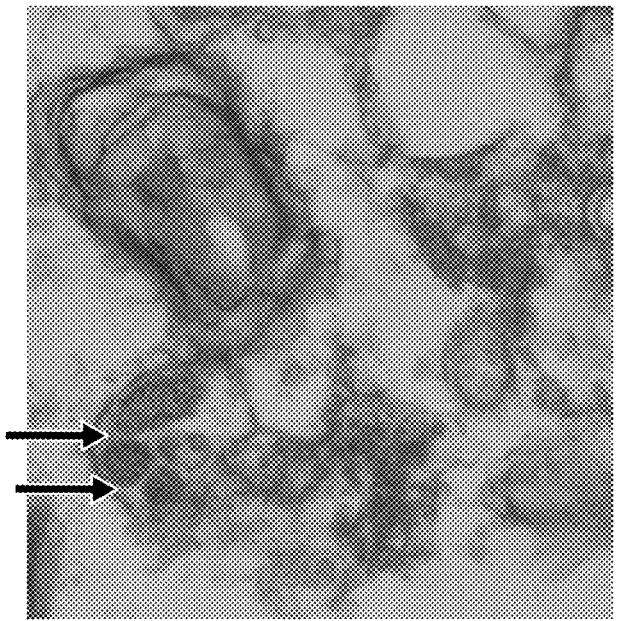
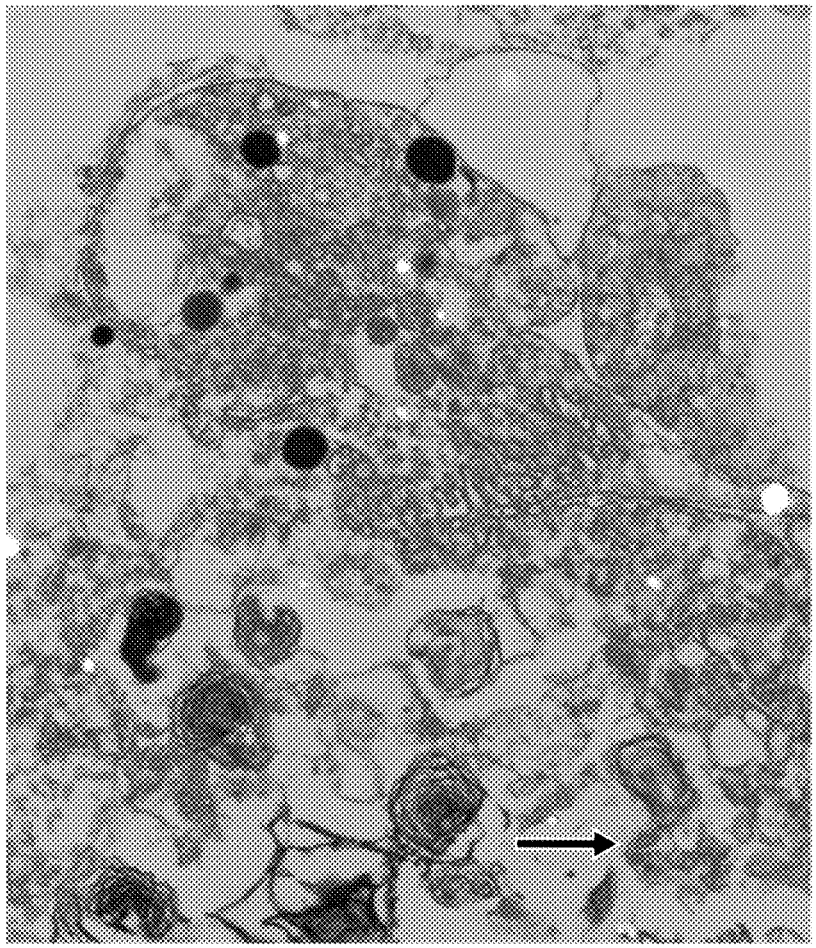

MESENCHYMAL STEM CELL-DERIVED EXTRACELLULAR VESICLES AND USES THEREOF FOR TREATING AND DIAGNOSING FIBROTIC DISEASES

CROSS-REFERENCE TO RELATED APPLICATIONS

This application claims the benefit of priority to U.S. provisional applications 63/023,365 (filed May 12, 2020), 62/945,917 (filed Dec. 10, 2019) and 62/858,154 (filed Jun. 6, 2019). Each of these applications is incorporated herein by reference in its entirety.

FIELD OF INVENTION

The described invention generally relates to mesenchymal stem cell-derived extracellular vesicles, compositions thereof, and uses thereof.

SEQUENCE LISTING

The instant application contains a Sequence Listing which has been submitted electronically in ASCII format and is hereby incorporated by reference in its entirety. Said ASCII copy, created on Jun. 4, 2020, is named 130309-00104_SL.txt and is 9015 bytes in size.

BACKGROUND

Fibrosis as a Pathology

Fibrosis represents the formation or development of excess fibrous connective tissue in an organ or tissue, which is formed as a consequence of the normal or abnormal/reactive wound healing response leading to a scar. Although the fibrogenic response may have adaptive features in the short term, when it progresses over a prolonged period of time, parenchymal scarring and ultimately cellular dysfunction and organ failure ensue (Rockey D C et al., N Engl J Med. 2015 Mar. 19; 372(12): 1138-49). Fibrosis is characterized by, for example, without limitation, an aberrant deposition of an extracellular matrix protein, an aberrant promotion of fibroblast proliferation, an aberrant induction of differentiation of a population of fibroblasts into a population of myofibroblasts, an aberrant promotion of attachment of myofibroblasts to an extracellular matrix, or a combination thereof.

There are four major phases of the fibrinogenic response. First is initiation of the response, driven by primary injury to the organ. The second phase is the activation of effector cells, and the third phase is the elaboration of extracellular matrix, both of which overlap with the fourth phase, during which the dynamic deposition (and insufficient resorption) of extracellular matrix promotes progression to fibrosis and ultimately to end-organ failure (Id.).

The fact that diverse diseases in different organ systems are associated with fibrotic changes suggests common pathogenic pathways (Id.). This "wounding response" is orchestrated by complex activities within different cells in which specific molecular pathways have emerged. Cellular constituents include inflammatory cells (e.g., macrophages and T cells), epithelial cells, fibrogenic effector cells, endothelial cells, and others. Many different effector cells, including fibroblasts, myofibroblasts, cells derived from bone marrow, fibrocytes, and possibly cells derived from epithelial tissues (epithelial-to-mesenchymal transition) have been identified; there is some controversy regarding the identity of specific effectors in different organs. Beyond the multiple cells essential in the wounding response, core molecular pathways are critical; for example, the transforming growth factor beta (TGF-β) pathway is important in virtually all types of fibrosis (Id.).

As fibrosis progresses, myofibroblasts proliferate and sense physical and biochemical stimuli in the local environment by means of integrins and cell-surface molecules; contractile mediators trigger pathological tissue contraction. This chain of events, in turn, causes physical organ deformation, which impairs organ function. Thus, the biology of fibrogenesis is dynamic, although the degree of plasticity appears to vary from organ to organ (Id.).

Acute and chronic inflammation often trigger fibrosis (Id.). Inflammation leads to injury of resident epithelial cells and often endothelial cells, resulting in enhanced release of inflammatory mediators, including cytokines, chemokines, and others. This process leads to the recruitment of a wide range of inflammatory cells, including lymphocytes, polymorphonuclear leukocytes, eosinophils, basophils, mast cells, and macrophages. These inflammatory cells elicit the activation of effector cells, 1 which drive the fibrogenic process (Id., citing Wynn T A. Nat Rev Immunol 2004; 4: 583-94). In addition, macrophages can play a prominent role in interstitial fibrosis, often driven by the TGF-β pathway (Id., citing Meng X M, et al. Nat Rev Nephrol 2014; 10: 493-503). However, some inflammatory cells may be protective. For example, certain populations of macrophages phagocytose apoptotic cells that promote the fibrogenic process and activate matrix-degrading metalloproteases (Id., citing Ramachandran P, Iredale J P. J Hepatol 2012; 56: 1417-9). Fibroblasts and myofibroblasts have been identified as key fibrosis effectors in many organs, and as such are responsible for the synthesis of extracellular matrix proteins (Id., citing Hinz B, et al. Am J Pathol 2007; 170: 1807-16).

The matrix proteins that compose the fibrotic scar, which are highly conserved across tissues, consist predominantly of interstitial collagens (types I and III), cellular fibronectin, basement-membrane proteins such as laminin, and other, less abundant elements. In addition, myofibroblasts, which by definition are cells that express smooth-muscle proteins, including actin (ACTA2), are contractile (Id., citing Rockey D C, et al. J Clin Invest 1993; 92: 1795-804). The contraction of these cells contributes to the distortion of parenchymal architecture, which can promote disease pathogenesis and tissue failure. However, myofibroblasts also contribute to the normal wound healing process by contracting the edges of the wound and synthesizing and depositing extracellular matrix components (Hinz B. Curr Res Transl Med. 2016 October-December; 64(4): 171-177; Darby I A, et al. Clin Cosmet Investig Dermatol. 2014; 7: 301-311).

The molecular processes driving fibrosis are wide-ranging and complex. The TGF-β cascade, which plays a major role in fibrosis, involves the binding of a ligand to a serine-threonine kinase type II receptor that recruits and phosphorylates a type I receptor. This type I receptor subsequently phosphorylates SMADs, which function as downstream effectors, typically by modulating target gene expression. TGF-β, which is a potent stimulator of the synthesis of extracellular matrix proteins in most fibrogenic cells, and is synthesized and secreted by inflammatory cells and by effector cells, thereby functioning in both an autocrine and paracrine fashion (Id.).

Platelet-derived growth factor (PDGF), connective-tissue growth factor (CTGF), and vasoactive peptide systems (especially angiotensin II and endothelin-1) play important roles (Id., citing Wynn T A. J Clin Invest 2007; 117: 524-9).

Among vasoactive systems, endothelin plays a role in fibrosis in virtually all organ systems, acting through G-protein-coupled endothelin-A or endothelin-B cell-surface receptors or both (Id., citing Khimji A K, Rockey D C. Cell Signal 2010; 22: 1615-25). Furthermore, angiogenic pathways may be important in fibrosis (Id., citing Johnson A, DiPietro L A. FASEB J 2013; 27: 3893-901). Integrins, which link extracellular matrix to cells, are considered critical in the pathogenesis of fibrosis (Id., citing Levine D, et al. Am J Pathol 2000; 156: 1927-35; Henderson N C, et al. Nat Med 2013; 19: 1617-24).

Pulmonary Fibrosis

Pulmonary fibrosis (PF) occurs in association with a wide range of diseases, including scleroderma (systemic sclerosis), sarcoidosis, and infection, and as a result of environmental exposures (e.g., silica dust or asbestos), but in most patients it is idiopathic and progressive. Pulmonary fibrosis is characterized by parenchymal honeycombing (meaning the characteristic appearance of variably sized cysts in a background of densely scarred lung tissue. Microscopically, enlarged airspaces surrounded by fibrosis with hyperplastic or bronchiolar type epithelium are present. From https://emedicine.medscape.com/article/2078590-overview), reduced lung compliance, and restrictive lung function (meaning a decreased lung capacity or volume, so a person's breathing rate often increases to meet the oxygen needs on inhalation). Fibrosis of the interstitial spaces (meaning the walls of the air sacs of the lungs (alveoli) and the spaces around blood vessels and small airways) hinders gas exchange, culminating in abnormal oxygenation and clinical dyspnea (meaning shortness of breath, inability to take a deep breath, or chest tightness). Progressive pulmonary fibrosis also leads to pulmonary hypertension, right-sided heart failure, and ultimately respiratory failure (Id.).

Idiopathic Pulmonary Fibrosis (IPF)

Idiopathic Pulmonary fibrosis (IPF, also known as cryptogenic fibrosing alveolitis, CFA, or Idiopathic Fibrosing Interstitial Pneumonia) is defined as a specific form of chronic, progressive fibrosing interstitial pneumonia of uncertain etiology that occurs primarily in older adults, is limited to the lungs, and is associated with the radiologic and histological pattern of usual interstitial pneumonia (UIP) (Raghu G. et al., Am J Respir Crit Care Med., 183(6): 788-824, 2011; Thannickal, V. et al., Proc Am Thorac Soc., 3(4): 350-356, 2006). It may be characterized by abnormal and excessive deposition of fibrotic tissue in the pulmonary interstitium. On high-resolution computed tomography (HRCT) images, UIP is characterized by the presence of reticular opacities often associated with traction bronchiectasis. As IPF progresses, honeycombing becomes more prominent (Neininger A. et al., J Biol. Chem., 277(5): 3065-8, 2002). Pulmonary function tests often reveal restrictive impairment and reduced diffusing capacity for carbon monoxide (Thomas, T. et al., J Neurochem., 105(5): 2039-52, 2008). Studies have reported significant increases in TNF-α and IL-6 release in patients with idiopathic pulmonary fibrosis (IPF) (Zhang, Y, et al. J. Immunol. 150(9): 4188-4196, 1993), which has been attributed to the level of expression of IL-1β (Kolb, M., et al. J. Clin. Invest, 107(12): 1529-1536, 2001). The onset of IPF symptoms, shortness of breath and cough, are usually insidious but gradually progress, with death occurring in 70% of patients within five years after diagnosis. This grim prognosis is similar to numbers of annual deaths attributable to breast cancer (Raghu G. et al., Am J Respir Crit Care Med., 183(6): 788-824, 2011).

IPF afflicts nearly 130,000 patients in the United States, with approximately 50,000 new patients annually and nearly 40,000 deaths each year worldwide (Raghu G. et al., Am J Respir Crit Care Med., 183(6): 788-824, 2011). While these data are notable, a recent study reported that IPF may be 5-10 times more prevalent than previously thought, perhaps due to increasing prevalence or enhanced diagnostic capabilities (Thannickal, V. et al., Proc Am Thorac Soc., 3(4): 350-356, 2006). Lung transplantation is considered a definitive therapy for IPF, but the five year survival post lung transplantation is less than 50%. Accordingly, even lung transplantation cannot be considered a "cure" for IPF. In addition to the physical and emotional toll on the patient, IPF is extremely expensive to treat and care for, with national healthcare costs in the range of $2.8 billion dollars for every 100,000 patients annually.

Previous studies have suggested that superimposed environmental insults may be important in the pathogenesis of IPF. In most reported case series, up to 75 percent of index patients with IPF are current or former smokers. In large epidemiologic studies, cigarette smoking has been strongly associated with IPF. In addition, many of the inflammatory features of IPF are more strongly linked to smoking status than to the underlying lung disease. Thus, cigarette smoking may be an independent risk factor for IPF. Latent viral infections, especially those of the herpes virus family, have also been reported to be associated with IPF.

Histopathologically, IPF can be described as accumulation of activated myofibroblasts (or mesenchymal cells) in fibroblastic foci (Thannickal, V. et al., Proc Am Thorac Soc., 3(4): 350-356, 2006). Impaired apoptosis of myofibroblasts may result in a persistent and dysregulated repair process that culminates in tissue fibrosis. Arguably, inflammation also plays a critical role in IPF, perhaps through cyclic acute stimulation of fibroblasts. These findings point to potential targets for therapeutic intervention.

Pathogenesis of Idiopathic Pulmonary Fibrosis (IPF)

While pathogenic mechanisms are incompletely understood, the currently accepted paradigm proposes that injury to the alveolar epithelium is followed by a burst of pro-inflammatory and fibroproliferative mediators that invoke responses associated with normal tissue repair. For unclear reasons, these repair processes never resolve and progressive fibrosis ensues (Selman M, et al., Ann Intern Med, 134(2): 136-151, 2001; Noble, P. and Homer R., Clin Chest Med, 25(4): 749-58, 2004; Strieter, R., Chest, 128 (5 Suppl 1): 526S-532S, 2005).

Cardiac Fibrosis

The heart undergoes extensive structural and functional remodeling (meaning a group of molecular, cellular and interstitial changes that manifest clinically as changes in size, mass, geometry and function of the heart) in response to injury, central to which is the hypertrophy (meaning an increase in size of the individual muscle cells without changing their total number) of cardiac myocytes, with excessive deposition of extracellular matrix (Rockey D C et al., N Engl J Med. 2015 Mar. 19; 372(12): 1138-49, citing Hill J A, Olson E N. N Engl J Med 2008; 358: 1370-80). Myocardial fibrosis is commonly categorized as one of two types: reactive fibrosis or replacement fibrosis. Reactive fibrosis occurs in perivascular spaces (meaning the fluid-filled space that surrounds a blood vessel or organ) and corresponds to similar fibrogenic responses in other tissues; replacement fibrosis occurs at the site of myocyte loss.

In the heart, fibrosis is attributed to cardiac fibroblasts, the most abundant cell type in the myocardium, the middle muscular layer of the heart wall. These cells are derived from fibroblasts that are native to the myocardium, from circulating fibroblasts, and from fibroblasts that emerge from epithelial-to-mesenchymal transition (Id., citing Zeisberg E M, et al. Nat Med 2007; 13: 952-61; Moore-Morris T, et al. J Clin Invest 2014; 124: 2921-34). All these cell types proliferate and differentiate into myofibroblasts in response to injury, a process that is driven by classic factors such as TGF-β1, endothelin-1, and angiotensin II (Id., citing Burchfield J S, et al. Circulation 2013; 128: 388-400). Cross-talk and feedback also occurs between cells in this case, between activated fibroblasts and cardiomyocytes—which further fuels fibrogenesis (Id., citing Martin M L, Blaxall B C. J Cardiovasc Transl Res 2012; 5: 768-82).

Cardiac fibrosis contributes to both systolic and diastolic dysfunction and to perturbations of electrical excitation; it also disrupts repolarization (Id., citing Spinale F G. Physiol Rev 2007; 87: 1285-342). Proarrhythmic effects (meaning worsening of existing arrhythmias) are the most prominent. Collagenous septa in the failing heart contribute to arrhythmogenesis by inducing a discontinuous slowing of conduction (Id., citing Spach M S, Boineau J P. Pacing Clin Electrophysiol 1997; 20: 397-413). Areas of arrhythmogenic fibrosis slow conduction through junctions in the heterocellular gap (meaning intercellular channels that allow direct diffusion of ions and small molecules between adjacent cells) that couple fibroblasts and cardiomyocytes (Id., citing Miragoli M, et al. Circ Res 2006; 98: 801-10). Conduction of vasoconstrictor and vasodilator responses in the microcirculation involves electrical coupling through gap junction channels among cells of the vascular wall (Sandow S L, et al. Cardiovasc. Res. (2003); 60(3): 643-653). Endocardial breakthrough of microreentrant circuits (meaning small areas of continuous circulating electricity in which an impulse reenters and repetitively excites a region of the heart; reentrant circuits are the basis of most clinical arrhythmias. Smith W, Hood M. Arrhythmias, in Cardiothoracic Critical Care, 2007) occurs as a result of the heterogeneous spatial distribution of fibrosis and the triggering of activity caused by the depolarization of myocytes by electrically coupled myofibroblasts (Rockey D C et al., N Engl J Med. 2015 Mar. 19; 372(12): 1138-49, citing Tanaka K, et al. Circ Res 2007; 101: 839-47; Miragoli M, et al. Circ Res 2007; 101: 755-8).

Fibrotic scarring in the heart correlates strongly with an increased incidence of arrhythmias and sudden cardiac death (Id., citing Wu K C, et al. J Am Coll Cardiol 2008; 51: 2414-21). For example, a 3% increase in the extracellular volume fraction of fibrous tissue (measured by means of magnetic resonance imaging after the administration of gadolinium) is associated with a 50% increase in the risk of adverse cardiac events (Id., citing Wong T C, et al. Circulation 2012; 126: 1206-16).

Hepatic Fibrosis

The liver is made up of two lobes, each of which is made up of thousands of hexagonally-shaped lobules. Each lobule is made up of numerous liver cells, called hepatocytes, that are cuboidal epithelial cells that line up in radiating rows and make up the majority of cells in the liver. Hepatocytes perform most of the liver's functions—metabolism, storage, digestion, and bile production. Between each row are sinusoids, which are small blood vessels lined by hepatocytes that diffuse oxygen and nutrients through their capillary walls into the liver cells. The lobules are connected to small bile ducts that connect with larger ducts to ultimately form the hepatic duct. Hepatic biliary cells, which line the bile ducts, are targets of liver injury, but also orchestrate liver repair. They undergo extensive morphogenesis to form a complex network of intrahepatic biliary ducts. This network functions to drain the bile produced by hepatocytes to the intestine. Hepatic stellate cells exist in the space between parenchymal cells and sinusoidal endothelial cells of the hepatic lobule and store 80% of retinoids in the whole body as retinyl palmitate in lipid droplets in the cytoplasm. In physiological conditions, these cells play pivotal roles in the regulation of retinoid homeostasis, which contributes to many diverse functions including vision, inflammatory/immune response, adipogenesis, cell differentiation, and insulin sensitivity. In pathological conditions such as liver fibrosis, hepatic stellate cells lose retinoids and synthesize a large amount of extracellular matrix (ECM) components including collagen, proteoglycan, and adhesive glycoproteins (Senoo H. Med Electron Microsc. 2004 March; 37(1): 3-15). Healthy sinusoidal endothelial cells maintain hepatic stellate cell quiescence, thus inhibiting their vasoconstrictive effect (Poisson J, et al. J Hepatol. 2017 January; 66(1): 212-227).

Hepatic fibrosis typically results from an inflammatory process that affects hepatocytes or biliary cells. Inflammation leads to the activation of effector cells, which results in the deposition of extracellular matrix. Although a variety of effectors synthesize extracellular matrix in the liver, hepatic stellate cells appear to be the primary source of extracellular matrix. Abundant evidence suggests that the stellate cell is pericyte-like (pericytes are spatially isolated contractile cells on capillaries which control blood flow), undergoing a transformation into a myofibroblast in response to injury (Rockey D C et al., N Engl J Med. 2015 Mar. 19; 372(12): 1138-49, citing Rockey D C, et al. J Clin Invest 1993; 92: 1795-804).

In the liver, multiple cell types, including stellate cells, endothelial cells, Kupffer cells (the resident macrophages of the liver), bile-duct cells, and immune cells, orchestrate the cellular and molecular response to injury (Id., citing Rockey D C. Clin Gastroenterol Hepatol 2013; 11(3): 224-31). Numerous molecular pathways, similar to those found in other organs, are involved. A pathway that appears to be unique to the liver involves toll-like receptor 4 (TLR4); TLR4 is activated on the surface of stellate cells by intestinal bacterial lipopolysaccharides derived from the gut (i.e., translocated bacteria), triggering cell activation and fibrogenesis and thereby linking fibrosis to the microbiome (Id., citing Seki E, et al. Nat Med 2007; 13: 1324-32; Fouts D E, et al. J Hepatol 2012; 56: 1283-92). TLR4 expression is associated with portal inflammation and fibrosis in patients with fatty liver disease (Id., citing Vespasiani-Gentilucci U, et al. Liver Int 2015; 35: 569-81).

The end result of hepatic fibrogenesis is cirrhosis, an ominous parenchymal lesion that underlies a wide range of devastating complications that have adverse effects on survival. Portal hypertension (meaning an increase in the pressure within the portal vein, which carries blood from the digestive organs to the liver), a devastating result of injury, develops during the fibrogenic response after disruption of the normal interaction between sinusoidal endothelial cells and hepatic stellate cells; the resulting activation and contraction of pericyte-like stellate cells leads to sinusoidal constriction (sinusoidal capillaries are a special type of capillary that have a wide diameter) and increased intrahepatic resistance (meaning the resistance in the liver vascular bed to the flow that reaches the liver via the portal vein, which can be assessed experimentally, based on Ohm's law, by measuring portal pressure changes when an increasing portal venous flow is applied). This increase in resistance in turn activates abnormal signaling by smooth-muscle cells in mesenteric vessels. An increase in angiogenesis and collateral blood flow follows, resulting in an increase in mesenteric blood flow (meaning blood flow to the intestines) and a worsening of portal hypertension (Id., citing Sanyal A J, et al. Gastroenterology 2008; 134: 1715-28). The major clinical sequelae of portal hypertension, variceal hemorrhage (varices are dilated blood vessels caused by portal hypertension; they cause no symptoms unless they rupture and bleed, which can be life threatening) and ascites (meaning an abnormal accumulation of protein-containing fluid within the abdomen), emerge relatively late, after the portal pressure rises to a hepatic venous pressure gradient of more than 12 mm Hg (Id.).

Renal Fibrosis

Events that initiate renal fibrosis are diverse, ranging from primary renal injury to systemic diseases (Id., citing Liu Y. Nat Rev Nephrol 2011; 7: 684-96; Kaissling B, et al. Biochim Biophys Acta 2013; 1832: 931-9). The kidneys are susceptible to hypertension and diabetes, the two leading causes of renal fibrosis. As is true in other organs, fibrosis of the kidney is mediated by cellular elements (e.g., inflammatory cells) and molecular elements (e.g., cytokines, TGF-β1, CTGF, PDGF, and endothelin-1) (Id., citing Liu Y. Nat Rev Nephrol 2011; 7: 684-96; Kaissling B, et al. Biochim Biophys Acta 2013; 1832: 931-9; Chen J, et al. J Am Soc Nephrol 2012; 23: 215-24; Mezzano S A, et al. Hypertension 2001; 38: 635-8). The intrarenal renin-angiotensin-aldosterone axis (a signaling pathway that regulates the body's blood pressure by homeostatic control of arterial pressure, tissue perfusion, and extracellular volume) is particularly important in hypertension-induced fibrosis (Id., citing Mezzano S A, et al. Hypertension 2001; 38: 635-8).

The kidney's unique cellular architecture consists of the glomeruli (meaning a tuft formed of capillary loops at the beginning of each nephiric tubule in the kidney; this tuft with its capsule (Bowman's capsule) constitutes the Malpighian body), tubules (meaning the portion that extends from the Bowman capsule in the kidney cortex (meaning the outer part of the kidney between the renal capsule and the renal medulla) into the kidney medulla (meaning the innermost part of the kidney), interstitium (meaning the intertubular, extraglomerular, extravascular space of the kidney), and capillaries. Injury at any of these sites triggers the deposition of extracellular matrix (Id., citing Burchfield J S, et al. Circulation 2013; 128: 388-400). The location of the initial injury is an important determinant of the clinical consequences. Injuries that initially target glomeruli elicit patterns of disease that are different from those that are elicited by injuries to the tubular-interstitial environment. For example, NSAIDs, urinary obstruction, polycystic kidney disease, and infections can provoke tubulointerstitial fibrosis (a progressive detrimental connective tissue deposition on the kidney parenchyma), whereas glomerular immune deposition (e.g., the deposition of IgA in the glomeruli) leads to glomerulonephritis (meaning acute inflammation of the kidney, typically caused by an immune response) (Id., citing Miragoli M, et al. Circ Res 2007; 101: 755-8; Wu K C, et al. J Am Coll Cardiol 2008; 51: 2414-21). Glomeruli and podocytes (highly specialized cells of the kidney glomerulus that wrap around capillaries and that neighbor cells of the Bowman's capsule, see Reiser J and Altintas M M. Podocytes. *F1000Research* 2016, 5(F1000 Faculty Rev): 114) are sensitive to systemic and local immunologic insults; high glomerular capillary pressure, exacerbated by systemic hypertension and diabetes, leads to proteinuria (meaning the presence of abnormal quantities of protein in the urine), the activation of cytokines and complement, and the infiltration of immune cells, resulting in epithelial cell and interstitial fibrosis (Id., citing Wong T C, et al. Circulation 2012; 126: 1206-16; Rockey D C. Clin Gastroenterol Hepatol 2013; 11(3): 224-31). Podocytes cooperate with mesangial cells (contractile cells that constitute the central stalk of the glomerulus) to support the structure and function of the glomerulus (see, e.g., Pavenstadt, H, Am. J. Physiol. Renal Physiol. (2000) 278 (2): F173-F179). Mesangial cells have characteristics of a modified smooth muscle cell, but also are capable of generation of prostaglandins and mediators of inflammation; production and breakdown of basement membrane and other biomatrix material; synthesis of cytokines, and uptake of macromolecules, including immune complexes (see Schlndorff D., FASEB J. (1987) 1(4): 272-81).

Glomerular fibrosis, regardless of the cause, diminishes renal blood flow, which leads to hypoxia and the activation of hypoxia-inducible factor 1, a dimeric protein complex that plays an integral role in the body's response to low oxygen concentrations, or hypoxia, which in turn triggers nephron collapse and fibrotic replacement by means of rarefaction (meaning a decrease in the capillary density) (Id., citing Seki E, et al. Nat Med 2007; 13: 1324-32). The renal interstitium and capillaries contribute substantially to tubulointerstitial disease, as peritubular pericytes migrate into the interstitium, where they are transformed into myofibroblasts (Id., citing Fouts D E, et al. J Hepatol 2012; 56: 1283-92).

Regardless of the initiating insult, renal fibrosis leads to loss of function and organ failure. Homeostasis can be maintained with a glomerular filtration rate as low as approximately 10% of the normal rate. As the mechanisms maintaining homeostasis are progressively disrupted, anemia develops and the regulation of electrolyte balance and pH is disrupted (Id.).

Radiation Fibrosis

Patients with cancer often receive external beam ionizing radiation therapy either alone or in combination with surgery and/or chemotherapy. Ionizing radiation induces damage not only in rapidly proliferating tumor cells but also in normal tissue in the radiation field. A significant contributor to patient morbidity is radiation-induced fibrosis (RIF), which may occur in the skin and subcutaneous tissue, lungs, gastrointestinal and genitourinary tracts, as well as any other organs in the treatment field. Radiation injury triggers inflammation and ultimately stimulates transdifferentiation of fibroblasts into myofibroblasts. In addition to their excessive proliferation, these myofibroblasts produce excess collagen and other extracellular matrix (ECM) components, which is compounded by a reduction in remodeling enzymes. Subsequent fibrosis reduces tissue compliance and—in a majority of cancer patients and particularly those with head and neck cancer—causes cosmetic and functional impairment that significantly impacts quality of life (Straub J M, et al. J Cancer Res Clin Oncol. 2015 November; 141(11): 1985-1994).

RIF usually occurs 4-12 months after radiation therapy and progresses over several years. It affects almost every part of the body that is exposed to radiation. The clinical presentation depends on the type of tissue exposed to irradiation. In general, RIF may manifest as skin induration and thickening, muscle shortening and atrophy, limited joint mobility, lymphedema, mucosal fibrosis, ulceration, fistula, hollow organ stenosis, and pain (Id., citing Don W, Hendry J H. Radiother Oncol J Eur Soc Ther Radiol Oncol. 2001; 61: 223-231).

The mechanism of RIF is similar to that of any chronic wound healing process. An initial injury incites an acute response that leads to inflammation, followed by fibroblast recruitment and activation with extracellular matrix deposition. Radiation is energy in the form of waves or high-speed particles. The term "ionizing" indicates that said energy is strong enough to displace bound electrons. Ionizing radiation refers to three types of emissions—alpha, beta, and gamma—with therapeutic radiation being predominantly gamma (Id., citing Harrison J D, Stather J W. J Anat. 1996; 189(Pt 3): 521-530). Radiation injury results from two primary mechanisms: direct DNA damage and the generation of reactive oxygen species (ROS) (Id., citing Travis E L. Semin Radiat Oncol. 2001 July; 11(3): 184-96). The latter is more prominent in RIF and involves the interaction of ionizing radiation with water molecules to form free radicals, including superoxide, hydrogen peroxide, and hydroxyl radical (Id., citing Tak J K, Park J W. Free Radic Biol Med. 2009; 46: 1177-1185), the last of which accounts for 60-70% of the total damage (Id., citing Terasaki Y, et al. Am J Physiol Lung Cell Mol Physiol. 2011; 301: L415-L426; Zhao W, Robbins M E. Curr Med Chem. 2009; 16: 130-143). Reactive nitrogen species (RNS) also likely play a role in radiation injury, as treatment with the inducible nitric oxide synthase (iNOS) inhibitor, L-nitroarginine methyl ester (L-NAME), prevented acute lung injury in rats (Id., citing Khan M A, et al. Radiother Oncol J Eur Soc Ther Radiol Oncol. 2003; 66: 95-102). Free radicals damage all components of cells, including proteins, nucleic acids, and lipids (Id., citing Terasaki Y, et al. Am J Physiol Lung Cell Mol Physiol. 2011; 301: L415-L426; Zhao W, Robbins M E. Curr Med Chem. 2009; 16: 130-143). Superoxide dismutase, catalase, and glutathione peroxidase are responsible for controlling free radical damage (Id., citing Greenberger J S, Epperly M W. In vivo. 2007; 21: 141-146). A deficiency in these enzymes or excess ROS/RNS leads to oxidative stress in tissues (Id., citing Chaudiere J, Ferrari-Iliou R. Food Chem Toxicol. 1999; 37: 949-962; Darley-Usmar V, Halliwell B. Pharm Res. 1996; 13: 649-662; Evans P, Halliwell B. Ann N Y Acad Sci. 1999; 884: 19-40). Injured cells release chemoattractant molecules that trigger nonspecific inflammation (Id., citing Denham J W, Hauer-Jensen M. Radiother Oncol J Eur Soc Ther Radiol Oncol. 2002; 63: 129-145; Travis E L. Semin Radiat Oncol. 2001 July; 11(3): 184-96; Williams J P, et al. Curr Drug Targets. 2010; 11: 1386-1394). Furthermore, thrombosis and ischemia exacerbate local injury leading to further release of inflammatory chemokines and cytokines (Id., citing Boerma M, Hauer-Jensen M. Curr Drug Targets. 2010; 11: 1405-1412; Lefaix J L, Daburon F. Health Phys. 1998; 75: 375-384).

Neutrophils are the first inflammatory cells to arrive at the site of injury (Id., citing Abreu M T, et al. J Immunol. 2005; 174: 4453-4460). Increased expression of intercellular adhesion molecule 1 (ICAM-1) (Id., citing Hallahan D E, et al. J Natl Cancer Inst. 2002; 94: 733-741) and platelet endothelial cell adhesion molecule 1 (PECAM-1) (Id., citing Quarmby S, et al. Arterioscler Thromb Vasc Biol. 1999; 19: 588-597) on disrupted endothelial surfaces contributes to neutrophil extravasation and transmigration into tissues (Id., citing Lefaix J L, Daburon F. Health Phys. 1998; 75: 375-384). When these cells come into contact with collagen fragments and fibronectin, they release proinflammatory cytokines like tumor necrosis factor alpha (TNF-α), IL-1, and IL-6 that perpetuate the development of ROS and lead to even greater local inflammation (Id., citing Calveley V L, et al. Int J Radiat Biol. 2005; 81: 887-899; Finkelstein J N, et al. Environ Health Perspect. 1997; 105(Suppl 5): 1179-1182; Olman M A, et al. Chest. 2002; 121: 69S-70S; Porter D W, et al. Inhalation Toxicol. 2002; 14: 349-367; Sedgwick J B, et al. J Allergy Clin Immunol. 2002; 110: 752-756). The next cells to arrive are the monocytes and lymphocytes (Id., citing Haston C K, Travis E L. Cancer Res. 1997; 57: 5286-5291; Sharplin J, Franko A J. Radiat Res. 1989; 119: 1-14), which interact with each other to lead to the differentiation of monocytes into two subsets of macrophages (Id., citing Gordon S, Martinez F O. Immunity. 2010; 32: 593-604; Sica A, Mantovani A. J Clin Investig. 2012; 122: 787-795; Varin A, Gordon S. Immunobiology. 2009; 214: 630-641): classically activated pro-inflammatory M1 or alternatively activated anti-inflammatory M2 (Id., citing Ford A Q, et al. BMC Immunol. 2012; 13: 6; Zhang H, et al. J Radiat Res. 2011; 52: 717-726). Platelet-derived growth factor (PDGF) secreted from the M2 subset promotes neoangiogenesis and stimulates the migration of fibroblasts into the injured tissue from either the surrounding stroma or from circulating mesenchymal stem cells (Id., citing Li M, JendrossekV, Belka C. Radiat Oncol. 2007; 2: 5; Mathew M, Thomas S M. In: Li X, editor. Squamous cell carcinoma. InTech; 2012. pp. 163-174). They also secrete TGF-β, which is heavily implicated in RIF (Id., citing Li M O, et al. Annu Rev Immunol. 2006; 24: 99-146). Indeed, TGF-β is responsible for a number of functions that contribute to the pathogenesis of this condition, including the production of fibroblasts from bone marrow progenitors (Id., citing Campana F, et al. J Cell Mol Med. 2004; 8: 109-116; Rodemann H P, Bamberg M. Radiother Oncol J Eur Soc Ther Radiol Oncol. 1995; 35: 83-90) and the differentiation of fibroblasts into myofibroblasts (Id., citing Yarnold J, Brotons M C. Radiother Oncol J Eur Soc Ther Radiol Oncol. 2010; 97: 149-161), whereby a phenotypic change in the fibroblasts results in increased expression of alpha-smooth muscle actin (α-SMA), followed by subsequent transformation into protomyofibroblasts and eventual maturation into myofibroblasts (Id., citing Tomasek J J, et al. Nat Rev Mol Cell Biol. 2002; 3: 349-363). These myofibroblasts may also derive from circulating bone marrow-derived progenitor cells known as fibrocytes or from epithelial cells undergoing epithelial-mesenchymal transition (EMT) (Id., citing Darby I A, Hewitson T D. Int Rev Cytol. 2007; 257: 143-179). In response to TGF-β, myofibroblasts secrete excess collagen, fibronectin, and proteoglycans (Id., citing Chithra P, et al. J Ethnopharmacol. 1998; 59: 179-186), and in doing so they are responsible for the increased stiffness and thickening of the tissue (Id., citing Lefaix J L, Daburon F. Health Phys. 1998; 75: 375-384; Martin M, et al. Int J Radiat Oncol Biol Phys. 2000; 47: 277-290). Furthermore, TGF-β promotes decreased matrix metalloproteinase (MMP) activity (especially MMP-2 and MMP-9) and increased activity of tissue inhibitors of metalloproteinases (TIMPs), compounding the already excessive ECM deposition (Id., citing Pardo A, Selman M. Proc Am Thorac Soc. 2006 June; 3(4): 383-8). Lastly, although myofibroblasts promote endothelial cell proliferation and angiogenesis through the secretion of basic fibroblast growth factor (bFGF) (Id., citing Finlay G A, et al. J Biol Chem. 2000; 275: 27650-27656), excess collagen reduces vascularity over time (Id., citing Lefaix J L, Daburon F. Health Phys. 1998; 75: 375-384). This makes fibrotic areas susceptible to physical trauma and gradual ischemia, which may lead to loss of function, tissue atrophy, reduction in the number fibroblasts, or necrosis (Id., citing Burger A, et al. Int J Radiat Biol. 1998; 73: 401-408; Delanian S, et al. Radiother Oncol J Eur Soc Ther Radiol Oncol. 1998; 47: 255-261; Delanian S, et al. Radiother Oncol J Eur Soc Ther Radiol Oncol. 2001; 58: 325-331; Denham J W, Hauer- Jensen M. Radiother Oncol J Eur Soc Ther Radiol Oncol. 2002; 63: 129-145; Rudolph R, et al. Plast Reconstr Surg. 1988; 82: 669-677; Toussaint O, et al. Mech Ageing Dev. 2002; 123: 937-946).

Other Forms of Fibrosis

Fibrosis also occurs in the joints, bone marrow, brain, eyes, intestines, peritoneum and retroperitoneum, pancreas, and skin. Retroperitoneal fibrosis is a rare condition characterized by inflammation and fibrosis in the retroperitoneal space; most cases are idiopathic, but secondary causes include drugs, infections, autoimmune and inflammatory stimuli, and radiation. Patients may present with pain, and the major clinical sequelae of this condition are related to its involvement with structures in the retroperitoneum, including arteries (leading to acute and chronic renal failure) and ureters (leading to hydronephrosis, the swelling of a kidney due to a build-up of urine). Currently, there is no treatment available for this primary fibrosing disorder. In certain cancers, fibrosis is linked to TGF-β-integrin signaling (Rockey D C et al., N Engl J Med. 2015 Mar. 19; 372(12): 1138-49, citing Margadant C, Sonnenberg A. EMBO Rep 2010; 11: 97-105). TGF-β affects integrin-mediated cell adhesion and migration by regulating the expression of integrins, their ligands and integrin-associated proteins. Conversely, several integrins directly control TGF-β activation. In addition, a number of integrins can interfere with both Smad-dependent and Smad-independent TGF-β signaling in different ways, including the regulation of the expression of TGF-β signalling pathway components, the physical association of integrins with TGF-β receptors and the modulation of downstream effectors. Reciprocal TGF-β integrin signalling is implicated in normal physiology, as well as in a variety of pathological processes including systemic sclerosis, idiopathic pulmonary fibrosis, chronic obstructive pulmonary disease and cancer (Margadant C, Sonnenberg A. EMBO Rep. 2010 February; 11(2): 97-105). In scleroderma, the prototypical fibrosing skin disease, skin fibroblasts and myofibroblasts are activated through the TGF-β-SMAD signaling pathway (Rockey D C et al., N Engl J Med. 2015 Mar. 19; 372(12): 1138-49, citing Jinnin M. J Dermatol 2010; 37: 11-25). Nephrogenic systemic fibrosis, a debilitating condition that is marked by widespread organ fibrosis, occurs in patients with renal insufficiency who have been exposed to gadolinium-based contrast material. Initial systemic inflammatory-response reactions and the reaction of gadolinium (Gd3+) ions with circulating proteins and heavy metals lead to the deposition of insoluble elements in tissue (Id., citing Swaminathan S, et al. N Engl J Med 2007; 357: 720-2). Since no effective therapies have been identified, prevention is key (Id.). A recently recognized IgG4-related disease appears to involve autoimmune-driven inflammation that provokes fibrosis in multiple organs, including the pancreas, retroperitoneum, lung, kidney, liver, and aorta (Id., citing Umehara H, et al. Mod Rheumatol 2012; 22: 1-14).

Wound Healing

The term "wound healing" refers to the process by which the body repairs trauma to any of its tissues, especially those caused by physical means and with interruption of continuity.

A wound-healing response often is described as having three distinct phases-injury, inflammation and repair. Generally speaking, the body responds to injury with an inflammatory response, which is crucial to maintaining the health and integrity of an organism. If, however, it goes awry, it can result in tissue destruction.

Although these three phases are often presented sequentially, during chronic or repeated injury, these processes function in parallel, placing significant demands on regulatory mechanisms. (Wilson and Wynn, Mucosal Immunol., 2009, 3(2): 103-121).

Phase I: Injury

Injury caused by factors including, but not limited to, autoimmune or allergic reactions, environmental particulates, or infection or mechanical damage, often results in the disruption of normal tissue architecture, initiating a healing response. Damaged epithelial and endothelial cells must be replaced to maintain barrier function and integrity and prevent blood loss, respectively. Acute damage to endothelial cells leads to the release of inflammatory mediators and initiation of an anti-fibrinolytic coagulation cascade, temporarily plugging the damaged vessel with a platelet and fibrin-rich clot. For example, lung homogenates, epithelial cells or bronchoalveolar lavage fluid from idiopathic pulmonary fibrosis (IPF) patients contain greater levels of the platelet-differentiating factor, X-box-binding protein-1, compared with chronic obstructive pulmonary disease (COPD) and control patients, suggesting that clot-forming responses are continuously activated. In addition, thrombin (a serine protease required to convert fibrinogen into fibrin) is also readily detected within the lung and intra-alveolar spaces of several pulmonary fibrotic conditions, further confirming the activation of the clotting pathway. Thrombin also can directly activate fibroblasts, increasing proliferation and promoting fibroblast differentiation into collagen-producing myofibroblasts. Damage to the airway epithelium, specifically alveolar pneumocytes, can evoke a similar anti-fibrinolytic cascade and lead to interstitial edema, areas of acute inflammation, and separation of the epithelium from the basement membrane.

Platelet recruitment, degranulation and clot formation rapidly progress into a phase of vasoconstriction with increased permeability, allowing the extravasation (movement of white blood cells from the capillaries to the tissues surrounding them) and direct recruitment of leukocytes to the injured site. The basement membrane, which forms the extracellular matrix underlying the epithelium and endothelium of parenchymal tissue, precludes direct access to the damaged tissue. To disrupt this physical barrier, zinc-dependent endopeptidases, also called matrix metalloproteinases (MMPs), cleave one or more extracellular matrix constituents allowing extravasation of cells into, and out of, damaged sites.

Phase II: Inflammation

Once access to the site of tissue damage has been achieved, chemokine gradients recruit inflammatory cells. Neutrophils, eosinophils, lymphocytes, and macrophages are observed at sites of acute injury with cell debris and areas of necrosis cleared by phagocytes.

The early recruitment of eosinophils, neutrophils, lymphocytes, and macrophages providing inflammatory cytokines and chemokines can contribute to local TGF-β and IL-13 accumulation. Following the initial insult and wave of inflammatory cells, a late-stage recruitment of inflammatory cells may assist in phagocytosis, in clearing cell debris, and in controlling excessive cellular proliferation, which together may contribute to normal healing. Late-stage inflammation may serve an anti-fibrotic role and may be required for successful resolution of wound-healing responses. For example, a late-phase inflammatory profile rich in phagocytic macrophages, assisting in fibroblast clearance, in addition to IL-10-secreting regulatory T cells, suppressing local chemokine production and TGF-β, may prevent excessive fibroblast activation.

The nature of the insult or causative agent often dictates the character of the ensuing inflammatory response. For example, exogenous stimuli like pathogen-associated molecular patterns (PAMPs) are recognized by pathogen recognition receptors, such as toll-like receptors and NOD-like receptors (cytoplasmic proteins that have a variety of functions in regulation of inflammatory and apoptotic responses), and influence the response of innate cells to invading pathogens. Endogenous danger signals also can influence local innate cells and orchestrate the inflammatory cascade.

The nature of the inflammatory response dramatically influences resident tissue cells and the ensuing inflammatory cells. Inflammatory cells themselves also propagate further inflammation through the secretion of chemokines, cytokines, and growth factors. Many cytokines are involved throughout a wound-healing and fibrotic response, with specific groups of genes activated in various conditions. Fibrotic lung disease (such as idiopathic pulmonary fibrosis) patients more frequently present pro-inflammatory cytokine profiles (including, but not limited to, interleukin-1 alpha (IL-1α), interleukin-1 beta (IL-1β), interleukin-6 (IL-6), tumor necrosis factor alpha (TNF-α), transforming growth factor beta (TGF-β), and platelet-derived growth factors (PDGFs)). Each of these cytokines has been shown to exhibit significant pro-fibrotic activity, acting through the recruitment, activation and proliferation of fibroblasts, macrophages, and myofibroblasts.

Phase III: Tissue Repair and Contraction

The closing phase of wound healing consists of an orchestrated cellular reorganization guided by a fibrin (a fibrous protein that is polymerized to form a "mesh" that forms a clot over a wound site)-rich scaffold formation, wound contraction, closure and re-epithelialization. The vast majority of studies elucidating the processes involved in this phase of wound repair have come from dermal wound studies and in vitro systems.

Myofibroblast-derived collagens and smooth muscle actin (α-SMA) form the provisional extracellular matrix, with macrophage, platelet, and fibroblast-derived fibronectin forming a fibrin scaffold. Collectively, these structures are commonly referred to as granulation tissues. Primary fibroblasts or alveolar macrophages isolated from IPF patients produce significantly more fibronectin and α-SMA than control fibroblasts, indicative of a state of heightened fibroblast activation. It has been reported that IPF patients undergoing steroid treatment had similar elevated levels of macrophage-derived fibronectin as IPF patients without treatment. Thus, similar to steroid resistant IL-13-mediated myofibroblast differentiation, macrophage-derived fibronectin release also appears to be resistant to steroid treatment, providing another reason why steroid treatment may be ineffective. From animal models, fibronectin appears to be required for the development of pulmonary fibrosis, as mice with a specific deletion of an extra type III domain of fibronectin (EDA) developed significantly less fibrosis following bleomycin administration compared with their wild-type counterparts.

In addition to fibronectin, the provisional extracellular matrix consists of glycoproteins (such as PDGF), glycosaminoglycans (such as hyaluronic acid), proteoglycans and elastin. Growth factor and TGF-β-activated fibroblasts migrate along the extracellular matrix network and repair the wound. Within skin wounds, TGF-β also induces a contractile response, regulating the orientation of collagen fibers. Fibroblast to myofibroblast differentiation, as discussed above, also creates stress fibers and the neo-expression of α-SMA, both of which confer the high contractile activity within myofibroblasts. The attachment of myofibroblasts to the extracellular matrix at specialized sites called the "fibronexus" or "super mature focal adhesions" pull the wound together, reducing the size of the lesion during the contraction phase. The extent of extracellular matrix laid down and the quantity of activated myofibroblasts determines the amount of collagen deposition. To this end, the balance of matrix metalloproteinases (MMPs) to tissue inhibitor of metalloproteinases (TIMPs) and collagens to collagenases vary throughout the response, shifting from pro-synthesis and increased collagen deposition towards a controlled balance, with no net increase in collagen. For successful wound healing, this balance often occurs when fibroblasts undergo apoptosis, inflammation begins to subside, and granulation tissue recedes, leaving a collagen-rich lesion. The removal of inflammatory cells, and especially α-SMA-positive myofibroblasts, is essential to terminate collagen deposition. Interestingly, in IPF patients, the removal of fibroblasts can be delayed, with cells resistant to apoptotic signals, despite the observation of elevated levels of pro-apoptotic and FAS-signaling molecules.

Several studies also have observed increased rates of collagen-secreting fibroblast and epithelial cell apoptosis in IPF, suggesting that yet another balance requires monitoring of fibroblast apoptosis and fibroblast proliferation. From skin studies, re-epithelialization of the wound site re-establishes the barrier function and allows encapsulated cellular re-organization. Several in vitro and in vivo models, using human or rat epithelial cells grown over a collagen matrix, or tracheal wounds in vivo, have been used to identify significant stages of cell migration, proliferation, and cell spreading. Rapid and dynamic motility and proliferation, with epithelial restitution from the edges of the denuded area, occur within hours of the initial wound. In addition, sliding sheets of epithelial cells can migrate over the injured area assisting wound coverage. Several factors have been shown to regulate re-epithelialization, including serum-derived transforming growth factor alpha (TGF-α), and matrix metalloproteinase-7 (MMP-7) (which itself is regulated by TIMP-1).

Collectively, the degree of inflammation, angiogenesis, and amount of extracellular matrix deposition all contribute to ultimate development of a fibrotic lesion.

Pro-Inflammatory Mediators

Accumulating evidence has suggested that polypeptide mediators known as cytokines, including various lymphokines, interleukins, and chemokines, are important stimuli to collagen deposition in fibrosis. Released by resident tissue cells and recruited inflammatory cells, cytokines are thought to stimulate fibroblast proliferation and increased synthesis of extracellular matrix proteins, including collagen. For example, an early feature in the pathogenesis of idiopathic pulmonary fibrosis is alveolar epithelial and/or capillary cell injury. This promotes recruitment into the lung of circulating immune cells, such as monocytes, neutrophils, lymphocytes and eosinophils. These effector cells, together with resident lung cells, such as macrophages, alveolar epithelial and endothelial cells, then release cytokines, which stimulate target cells, typically fibroblasts, to replicate and synthesize increased amounts of collagen. Breakdown of extracellular matrix protein also may be inhibited, thereby contributing to the fibrotic process. (Coker and Laurent, Eur Respir J, 1998, 11: 1218-1221)

Numerous cytokines have been implicated in the pathogenesis of fibrosis, including, without limitation, transforming growth factor-β (TGF-β), tumor necrosis factor-α (TNF- α), platelet-derived growth factor (PDGF), insulin-like growth factor-1 (IGF-1), endothelin-1 (ET-1) and the interleukins, interleukin-1 (IL-1), interleukin-6 (IL-6), interleukin-8 (IL-8), and interleukin-17 (IL-17). Chemokine leukocyte chemoattractants, including the factor Regulated upon Activation in Normal T-cells, Expressed and Secreted (RANTES), are also thought to play an important role. Elevated levels of pro-inflammatory cytokines, such as Interleukin 8 (IL-8), as well as related downstream cell adhesion molecules (CAMs) such as intercellular adhesion molecule-1 (ICAM-1) and vascular cell adhesion molecule-1 (VCAM-1), matrix metalloproteinases such as matrix metalloproteinase-7 (MMP-7), and signaling molecules such as S100 calcium-binding protein A12 (S100A12, also known as calgranulin C), in the peripheral blood have been found to be associated with mortality, lung transplant-free survival, and disease progression in patients with IPF (Richards et al, Am J Respir Crit Care Med, 2012, 185: 67-76).

The TGF-β family of proteins has a potent stimulatory effect on extracellular matrix deposition, and in fact has been used in constructing induced animal models of fibrosis through gene transfer. In vitro studies show that TGF-β1, secreted as a latent precursor, promotes fibroblast procollagen gene expression and protein synthesis. The data suggest that the other mammalian isoforms, TGF-β2 and TGF-β3, also stimulate human lung fibroblast collagen synthesis and reduce breakdown in vitro. In animal models of pulmonary fibrosis, enhanced TGF-β1 gene expression is temporally and spatially related to increased collagen gene expression and protein deposition. TGF-β1 antibodies reduce collagen deposition in murine bleomycin-induced lung fibrosis, and human fibrotic lung tissue shows enhanced TGF-β1 gene and protein expression.

TNF-α can stimulate fibroblast replication and collagen synthesis in vitro, and pulmonary TNF-α gene expression rises after administration of bleomycin in mice. Soluble TNF-α receptors reduce lung fibrosis in murine models, and pulmonary overexpression of TNF-α in transgenic mice is characterized by lung fibrosis. In patients with IPF or asbestosis (a chronic inflammatory and fibrotic medical condition affecting the parenchymal tissue of the lungs caused by the inhalation and retention of asbestos fibers), bronchoalveolar lavage fluid-derived macrophages release increased amounts of TNF-α compared with controls.

Endothelin (ET-1) also fulfills the criteria for a profibrotic cytokine. This molecule promotes fibroblast proliferation and chemotaxis and stimulates procollagen production. It is present in the lungs of patients with pulmonary fibrosis, and a recent report suggests that bosentan, an ET-1 receptor antagonist, ameliorates lung fibrosis when administered to experimental animals.

Regenerative Cells of the Lungs

The lung is a highly quiescent tissue, previously thought to have limited reparative capacity and a susceptibility to scarring. It is now known that the lung has a remarkable reparative capacity, when needed, and scarring or fibrosis after lung injury may occur infrequently in scenarios where this regenerative potential is disrupted or limited (Kotten, D. N. and Morrisey, E. E., "Lung regeneration: mechanisms, applications and emerging stem cell populations," Nat. Med. (2014) 20(8): 822-32, citing Beers, M F and Morrisey, E E, "The 3 R's of lung health and disease—repair, remodeling and regeneration," J. Clin. Invest. (2011) 121: 2065-73; and Wansleeben, C. et al, "Stem cells of the adult lung: their development and role in homeostasis, regeneration and disease," Wiley Interdiscip. Rev. Dev. Biol. (2013) 2: 131-148). Thus, the tissues of the lung may be categorized as having facultative progenitor cell populations that can be induced to proliferate in response to injury as well as to differentiate into one or more cell types.

The adult lung comprises at least 40-60 different cell types of endodermal, mesodermal, and ectodermal origin, which are precisely organized in an elaborate 3D structure with regional diversity along the proximal-distal axis. In addition to the variety of epithelial cells, these include cartilaginous cells of the upper airways, airway smooth muscle cells, interstitial fibroblasts, myofibroblasts, lipofibroblasts, and pericytes as well as vascular, microvascular, and lymphatic endothelial cells, and innervating neural cells. The regenerative ability of lung epithelial stem/progenitor cells in the different regions of the lung are thought to be determined not only by their intrinsic developmental potential but also by the complex interplay of permissive or restrictive cues provided by these intimately associated cell lineages as well as the circulating cells, soluble and insoluble factors and cytokines within their niche microenvironment (McQualter & Bertoncello., Stem Cells. 2012 May; 30(5); 811-16).

The crosstalk between the different cell lineages is reciprocal, multidirectional, and interdependent. Autocrine and paracrine factors elaborated by mesenchymal and endothelial cells are required for lung epithelial cell proliferation and differentiation (Yamamoto et al., Dev Biol. 2007 Aug. 1; 308(1): 44-53; Ding et al., Cell. 2011 Oct. 28; 147(3): 539-53), while endothelial and epithelial cell-derived factors also regulate mesenchymal cell proliferation and differentiation, extracellular matrix deposition and remodeling, and adhesion-mediated signaling (Crivellato. Int J Dev Biol. 2011; 55(4-5): 365-75; Grinnell & Harrington. Pulmonary endothelial cell interactions with the extracellular matrix. In: Voelkel N F, Rounds S, eds. The Pulmonary Endothelium: Function in Health and Disease. Chichester, West Sussex: Wiley-Blackwell, 2009: 51-72). Chemotactic factors elaborated by these cell lineages also orchestrate the recruitment of inflammatory cells, which participate in the remodeling of the niche and the regulation of the proliferation and differentiation of its cellular constituents (McQualter & Bertoncello. Stem Cells. 2012 May; 30(5); 811-16).

Stem Cell Niches

Adult tissue compartments contain endogenous niches of adult stem cells that are capable of differentiating into diverse cell lineages of determined endodermal, mesodermal or ectodermal fate depending on their location in the body. For example, in the presence of an appropriate set of internal and external signals, bone marrow-derived adult hematopoietic stem cells (HSCs) have the potential to differentiate into blood, endothelial, hepatic and muscle cells; brain-derived neural stem cells (NSCs) have the potential to differentiate into neurons, astrocytes, oligodendrocytes and blood cells; gut- and epidermis-derived adult epithelial stem cells (EpSCs) have the potential to give rise to cells of the epithelial crypts and epidermal layers; adipose-derived stem cells (ASCs) have the potential to give rise to fat, muscle, cartilage, endothelial cells, neuron-like cells and osteoblasts; and bone-marrow-derived adult mesenchymal stem cells (MSCs) have the potential to give rise to bone, cartilage, tendon, adipose, muscle, marrow stroma and neural cells.

Endogenous adult stem cells are embedded within the ECM component of a given tissue compartment, which, along with support cells, form the cellular niche. Such cellular niches within the ECM scaffold together with the surrounding microenvironment contribute important biochemical and physical signals, including growth factors and transcription factors required to initiate stem cell differentiation into committed precursors cells and subsequent precursor cell maturation to form adult tissue cells with specialized phenotypic and functional characteristics.

Lung Mesenchymal Stem/Progenitor Cells

Tracheal and distal embryonic lung mesenchyme have been demonstrated to have inductive properties for the regional specification of the embryonic epithelium (Shannon & Deterding. Epithelial-mesenchymal interactions in lung development. In: McDonald J A, ed. Lung Biology in Health and Disease. Vol. 100. New York: Marcel Dekker Inc., 1997, pp. 81-118). During lung development, mesenchymal stromal cells at the distal tip of the branching epithelium are known to secrete fibroblast growth factor (FGF)-10, which influences the fate and specificity of early lung epithelial progenitor cells (Bellusci et al. Development. 1997 December; 124(23): 4867-78; Ramasamy et al. Dev Biol. 2007 Jul. 15; 307(2): 237-47). FGF-10 is a component of a multifaceted epithelial-mesenchymal cell signaling network involving BMP, Wnt, and Shh pathways which coordinate the proliferation and differentiation of progenitor cells in the developing lung (reviewed in Morrisey & Hogan. Dev Cell. 2010 Jan. 19; 18(1): 8-23). Lineage tracing studies have also revealed that FGF-10+ mesenchymal cells residing at the branching tip of the epithelium function as stem/progenitor cells for smooth muscle cells, which become distributed along the elongating airways (De Langhe et al., Dev Biol. 2006 Nov. 1; 299(1): 52-62; Mailleuix et al., Development. 2005 May; 132(9): 2157-66). In other studies, mesenchymal stromal cells adjacent to the trachea and extrapulmonary bronchi have also been shown to give rise to bronchiolar smooth muscle cells (Shan et al., Dev Dyn. 2008; 237: 750-5). Collectively, these studies suggest that at least two distinct populations of mesenchymal stromal cells endowed with epithelial modulating properties emerge during development.

Several studies have identified resident mesenchymal stromal cells in adult lungs with the capacity for adipogenic, chondrogenic, osteogenic, and myogenic differentiation. These cells have been clonally expanded from heterogeneous populations of mixed lineage cells defined by their ability to efflux Hoechst 33342 (Giangreco et al., Am J Physiol Lung Cell Mol Physiol. 2004; 286: L624-30; Summer et al., Am J Respir Cell Mol Biol. 2007; 37: 152-9), by their capacity for outgrowth from lung explant cultures (Hoffman et al., Stem Cells Dev. (2011); 20: 1779-92), or by their characteristic expression of Sca-1 (McQualter et al., Stem Cells. (2009); 27: 612-22; Hegab et al., Stem Cells Dev. 2010; 19: 523-36). In addition, further enrichment of CD45− CD31− Sca-1+ mesenchymal stromal cells has been achieved based on their lack of EpCAM expression, which selectively labels epithelial lineage cells (McQualter et al. Proc Natl Acad Sci USA 2010; 107: 1414-19). Resolution of the mesenchymal and epithelial lineages has revealed that the endogenous lung mesenchymal stromal cell population is necessary and sufficient to support the proliferation and differentiation of bronchiolar epithelial stem/progenitor cells in coculture (Id.). This suggests that adult mesenchymal stromal cells share similar epithelial inductive properties to their embryonic counterparts and are an important element of the epithelial stem/progenitor cell niche in the adult lung. This concept is also supported by in vivo studies showing that following naphthalene injury of club cells, parabronchial mesenchymal cells secrete FGF-10 to support epithelial regeneration from surviving epithelial stem/progenitor cells (Volckaert et al., J Clin Invest. 2011; 121: 4409-19).

Lung Endothelial Progenitor Cells

Endothelial-epithelial cell interactions and angiogenic and angiocrine factors elaborated in the lung epithelial stem/progenitor cell microenvironment also play a role in the regulation of endogenous lung epithelial stem/progenitor cell regeneration and repair (Yamamoto et al., Dev Biol. 2007 Aug. 1; 308(1): 44-53; Ding et al., Cell. 2011 Oct. 28; 147(3): 539-53; Crivellato. Int J Dev Biol. 2011; 55(4-5): 365-75; Grinnell & Harrington. Pulmonary endothelial cell interactions with the extracellular matrix. In: Voelkel N F, Rounds S, eds. The Pulmonary Endothelium: Function in Health and Disease. Chichester, West Sussex: Wiley-Blackwell, 2009: 51-72). For example, it has been reported that the coculture of human vascular endothelial cells with a human bronchial epithelial cell line promotes the generation of branching bronchoalveolar epithelial structures in a 3D culture system (Frazdottir et al. Respir Res. 2010; 11: 162). While considerable progress has been made in understanding the heterogeneity, functional diversity, and pathophysiological behavior of lung vascular and microvascular endothelial cells, the immunophenotypic profiling, quantitation, and functional analysis of lung endothelial progenitor cells (EPC) lags far behind. As for EPC derived from human umbilical cord blood, bone marrow, and mobilized peripheral blood (Timmermans et al., J Cell Mol Med. 2009; 13: 87-102), the rarity of EPC in the lung, their lack of distinguishing markers, and the inability to discriminate circulating EPC and tissue resident EPC have been major impediments in assessing the contribution of endogenous lung EPC in lung vascular repair, and lung regeneration and remodeling (Thebaud & Yoder. Pulmonary endothelial progenitor cells. In: Voelkel N F, Rounds S, eds. The Pulmonary Endothelium: Function in Health and Disease. Chichester, West Sussex: Wiley, 2009: 203-16; Yoder. Proc Am Thorac Soc. 2011; 8: 466-70).

Lung macrovascular and microvascular endothelial cells can be resolved on the basis of their preferential binding to the lectins *Helix pomatia* and *Griffonia simplicifolica*, respectively (King et al., Microvasc Res. 2004; 67: 139-51), but there are no other cell surface markers that can discriminate mature lung endothelial cells and EPC (Yoder. Proc Am Thorac Soc. 2011; 8: 466-70). In addition, the rarity of EPC has necessitated the ex vivo expansion and passaging of adherent heterogeneous rat (Alvarez et al., Am J Physiol Lung Cell Mol Physiol. 2008; 294: L419-30) or mouse (Schniedermann et al., BMC Cell Biol. 2010; 11: 50) lung endothelial cells in liquid culture prior to quantitation and flow cytometric and functional analysis of lung-derived EPC in in vitro assays. These assays suggest that the lung microvasculature is a rich source of EPC. However, the incidence, immunophenotypic and functional properties of EPC in the primary explanted endothelial cells compared with their ex vivo manipulated, selected, and expanded counterparts remains indeterminate. The ability of these endogenous lung EPCs to contribute to vascular repair and remodeling in vivo is also unproven (Yoder. Proc Am Thorac Soc. 2011; 8: 466-70). Studies suggest it likely that both circulating EPC and resident lung EPC contribute to endothelial cell regeneration and repair (Balasubramian et al., Am J Physiol Lung Cell Mol Physiol. 2010; 298: L315-23; Duong et al., Angiogenesis. 2011: 411-22; Chamoto et al. Am J Respir Cell Mol Biol. 2012 March; 46(3): 283-9).

Mesenchymal Stem Cells (MSCs)

Mesenchymal stem cells (MSCs) (also known as stromal stem cells) are non-blood adult stem cells found in a variety of tissues. They are characterized by their spindle-shape morphologically, by the expression of specific markers on their cell surface, and by their ability, under appropriate conditions, to differentiate along a minimum of three lineages (osteogenic, chondrogenic, and adipogenic).

No single marker that definitely delineates MSCs in vivo has been identified due to a lack of consensus regarding the MSC phenotype, but it generally is considered that MSCs are positive for cell surface markers CD105, CD166, CD90, and CD44, and that MSCs are negative for typical hematopoietic antigens, such as CD45, CD34, and CD14. As for the differentiation potential of MSCs, studies have reported that populations of bone marrow-derived MSCs have the capacity to develop into terminally differentiated mesenchymal phenotypes both in vitro and in vivo, including bone, cartilage, tendon, muscle, adipose tissue, and hematopoietic-supporting stroma. Studies using transgenic and knockout mice and human musculoskeletal disorders have reported that MSC differentiate into multiple lineages during embryonic development and adult homeostasis.

Analyses of the in vitro differentiation of MSCs under appropriate conditions that recapitulate the in vivo process have led to the identification of various factors essential for stem cell commitment. Among them, secreted molecules and their receptors (e.g., transforming growth factor-(3), extracellular matrix molecules (e.g., collagens and proteoglycans), the actin cytoskeleton, and intracellular transcription factors (e.g., Cbfa1/Runx2, PPARγ, Sox9, and MEF2) have been shown to play important roles in driving the commitment of multipotent MSCs into specific lineages, and maintaining their differentiated phenotypes.

MSCs are known to undergo phenotypic rearrangements during ex vivo manipulations, losing expression of some markers while also acquiring new ones. (Augello, A. et al. Eur. Cells and Materials (2010) (20): 121-33, citing Jones, et al. 2002 Arthritis Rheum. 46: 3349-60).

Role of MSCs in Wound Healing

MSCs are thought to orchestrate wound repair by: (1) structural repair via cellular differentiation; (2) immune-modulation; (3) secretion of growth factors that drive neovascularization and re-epithelialization; and (4) mobilization of resident stem cells. (Balaji, S. et al. Adv. Wound Care (2012) 1(40): 159-65).

MSC Migration In Vivo

Results indicate that MSCs play several simultaneous roles: limiting inflammation through releasing cytokines; aiding healing by expressing growth factors; altering host immune responses by secreting immuno-modulatory proteins; enhancing responses from endogenous repair cells; and serving as mature functional cells in some tissues such as bone (Phinney, D G and Pittenger, M F. Stem Cells (2017) 35: 851-58). When labeled and delivered in vivo, MSCs will migrate to sites of tissue injury (Id.). CD44-HA interaction is involved in MSC migratory activities (Zhu, H. et al. Stem Cells (2006) 24: 928-35).

Several reports indicate that the SDF-1/CXCR4 axis is present and functional in MSC populations (Augello, A. et al. Eur. Cells and Materials (2010) (20): 121-33, citing Wynn et al. 2004 Blood 104: 2643-45; Dar et al. 2005 Nat. Immunol. 6: 1038-46). MSCs also can respond to chemotactic signaling molecules acting on pathways other than the SDF-1/CXCR-4 axis, including monocyte chemotactic protein-3 (MCP-3) (Id.).

MSCs for Cell-Based Therapy

While pre-clinical studies in experimental animal models of immune and inflammatory disorders have shown great promise using autologous, allogeneic and even xenogeneic MSCs, clinical studies in human subjects have yielded mixed results (Theofilopoulos A N, et al. Nat Immunol. 2017 Jun. 20; 18(7): 716-724).

In experimental disease models including colitis (Id., citing Zhang Q, et al. J Immunol 2009; 183: 7787-7798), radiation proctitis (Id., citing Bessout R, et al. Mucosal Immunol 2014; 7: 656-669), immune thrombocytopenia (Id., citing Xiao J, et al. Transfusion 2012; 52: 2551-2558) and autoimmune encephalomyelitis (Id., citing Zappia E, et al. Blood 2005; 106: 1755-1761), MSCs reduce T-cell proliferation, suppress the inflammatory infiltrates and cytokines and express anti-inflammatory cytokines (Id.). Similarly, prominent immunosuppressive effects of MSCs for animal immune disorder models of arthritis (Id., citing Zhou B, et al. Clin Immunol 2011; 141: 328-337; Gonzalez M A, et al. Arthritis Rheum 2009; 60: 1006-1019; Liu Y, et al. Arthritis Res Ther 2010; 12: R210), SLE (Id., citing Sun L, et al. Stem Cells 2009; 27: 1421-1432; Chang J W, et al. Cell Transplant 2011; 20: 245-257; Sun J C, et al. Cancer Biol Ther 2010; 10: 368-375; Gu Z, et al. Lupus 2010; 19: 1502-1514), GvHD (Id., citing Guo J, et al. Eur J Haematol 2011; 87: 235-243), and multiple sclerosis (Id., citing Oh D Y, et al. J Immunol 2012; 188: 2207-2217; Morando S, et al. Stem Cell Res Ther 2012; 3: 3; Liu X J, et al. Clin Exp Immunol 2009; 158: 37-44) have been well documented.

MSCs have been used in clinical trials as an immunomodulator in the treatment of diseases such as GvHD, organ transplantation, diabetes, multiple sclerosis and Crohn's disease. Several clinical trials on GvHD and multiple sclerosis have shown complete or partial responses in some patients, with no serious adverse effects (Id., citing Le Blanc K, et al. Lancet 2008; 371: 1579-1586; Perez-Simon J A, et al. Haematologica 2011; 96: 1072-1076; Muller I, et al. Blood Cells Mol Dis 2008; 40: 25-32; Baron F, et al. Biol Blood Marrow Transplant 2010; 16: 838-847; Arima N, et al. Cytotherapy 2010; 12: 265-268; Zhou H, et al. Biol Blood Marrow Transplant 2010; 16: 403-412; Kebriaei P, et al. Biol Blood Marrow Transplant 2009; 15: 804-811; Ringden O, et al. Transplantation 2006; 81: 1390-1397; Connick P, et al. Trials 2011; 12: 62; Connick P, et al. Lancet Neurol 2012; 11: 150-156; Karussis D, et al. Arch Neurol 2010; 67: 1187-1194; Yamout B, et al. J Neuroimmunol 2010; 227: 185-189).

Other trials have shown no difference between placebo control and treatment groups, or even a worsening of the condition (Id., citing Osiris therapeutics, Inc., 2009 (http://clinicaltrials.gov/show/NCT00366145; http://investor.osiris.com/releasedetail.cfm? Release ID=407404); Duijvestein M, et al. Gut 2010; 59: 1662-1669; Ning H, et al. Leukemia 2008; 22: 593-599; Wang D, et al. Arthritis Res Ther 2014; 16: R79).

Recent evidence has shown that, in certain settings, MSCs can even be immunostimulatory. The mechanisms involved in this process are largely unknown. Zhou et al. (2013) showed that when mouse spleen T cells were stimulated with allogeneic mixed lymphocyte reaction (MLR) or anti-CD3/CD28 beads and treated with autologous bone marrow MSC or MSC-conditioned medium, MSCs had both suppressive and stimulatory functions toward T cells (Zhou Y, et al. Cytotherapy. 2013 October; 15(10): 1195-207). This depended on the ratio of MSC to responder T cells, with low numbers of MSC increasing and higher numbers inhibiting T-cell proliferation. Immunostimulatory function was mediated, in part, by soluble factors. MSC immunosuppression of the MLR was indirect and related to inhibition of antigen-presenting cell maturation. Direct effects of MSC-conditioned medium during anti-CD3/CD28 stimulated proliferation were entirely stimulatory and required the presence of the T-cell receptor. MSC supernatant contained both CCL2 and CCL5 at high levels, but only CCL2 level correlated with the ability to augment proliferation. An anti-CCL2 antibody blocked this proliferative activity. It was therefore determined that CCL2 plays an important role in the immunostimulatory function of MSC, and that the immunomodulatory role of MSC is determined by a balance between inhibitory and stimulatory factors, suggesting the need for caution when these cells are investigated in clinical protocols.

Additionally, Cui et al. (2016) found that MSCs can acquire immunostimulatory properties in certain contexts. MSCs cultured with natural killer (NK) cells primed the NK cells for increased release of IFN-γ (a cytokine critical for innate and adaptive immunity) in response to IL-12 and IL-18 (interleukins produced by activated antigen-presenting cells). Priming of NK cells by MSCs occurred in a cell-cell contact-independent manner and was impaired by inhibition of the CCR2, the receptor of CCL2, on NK cells (Cui R, et al. Stem Cell Res Ther. 2016; 7: 88). Waterman et al. (2010) have suggested that MSCs may polarize into two distinctly acting phenotypes following specific TLR stimulation, resulting in different immune modulatory effects and distinct secretomes (Bernardo M E, Fibbe W E. Cell Stem Cell. 2013 Oct. 3; 13(4): 392-402, citing Waterman R S, et al. PLoS One. 2010 Apr. 26; 5(4): e10088).

This ability of MSCs to adopt a different phenotype in response to sensing an inflammatory environment is not captured in assays that are commonly used to characterize these cells, but it is crucial for understanding their therapeutic potential in immune-mediated disorders. Much of the characterization of these properties has been conducted in vitro, and there are outstanding questions about the degree to which they represent activities that are functionally relevant for endogenous and/or transplanted cells in vivo (Id.).

Mesenchymal Stem Cells in IPF

MSC administration has been proposed as an effective therapy to alleviate bleomycin-induced lung injury and fibrosis. The mechanisms involve multiple biological effects of MSCs, including homing, differentiation, secretome, and promotion of lung endogenous antidamage ability. However, a large proportion of these studies have explored the early inflammatory stage rather than the late fibrotic stage (Li, Xiaohong, et al. (2017) Oncotarget 8(60): 102600-102616).

For example, MSCs have been used as a cell therapy to treat pulmonary fibrosis (Id., citing Tzouvelekis, A. et al., Curr. Opinion. Pulm. Med. (2011) 17: 368-73). Bone marrow-MSC (BM-MSC) transplants significantly reduced lung injury and fibrosis in animal bleomycin-induced PF models (Id., citing Srour, N. and Thebaud, B. Stem Cells Trans. Med. (2015) 4: 1500-1510). In 2003, Ortiz reported that BM-MSC injection ($5\times10^5$/mouse in 200 µl of PBS) through the jugular vein immediately after challenge with BLM can significantly reduce pulmonary fibrosis (Id., citing Ortiz, L A, et al. Proc. Natl Acad. Sci. USA (2003) 100: 8407-8411). In a $SiO_2$-induced IPF mice model, human mesenchymal stem cell (hMSC) transplantation directly replaced fibrosis with normal lung cells and reduced IPF symptoms, such as collagen deposition and inflammation (Id., citing Choi, M. et al. Mol. Cells (2014) 37: 133-39). Bleomycin-induced lung injury and fibrosis were significantly reduced by injection of BM-MSCs by downregulating proinflammatory and angiogenic cytokines and nitric oxide metabolites after 4 days of BLM inhalation (Id., citing Lee, S H et al. Respir. Res. (2010) 11: 16). Zhao et al. also showed the therapeutic effects of BM-MSC engraftment in bleomycin-induced lung damage in rats (Id., citing Zhao, F. et al. Transplant Proc (2008) 40: 1700-1705). Cyclophosphamide alone did not improve PF and may even aggravate PF, but the combination with BM-MSCs can protect against bleomycin-induced lung fibrosis in mice (Id., citing Zu, J. et al. Ann. Clin. Lab. Sci. (2015) 45: 292-300). Moreover, data from MSC-based clinical trials support the safety of a single infusion of hMSC in patients with IPF (Id., citing Glassberg, M K, et al. Chest (2017) 151: 971-81).

Some results have suggested that BM-MSCs home to the lungs after damage, exhibiting epithelioid phenotypes and reducing inflammation and collagen deposition in BLM-induced animal models (Id., citing Ortiz L A, et al. Proc. Natl Acad. Sci. USA (2003) 100: 8407-8411; Ricciardi M. et al. Blood (2013) 122: 5414). Akram et al. found that hMSCs showed a strong migratory response to alveolar epithelial cell injury in a 3D direct-contact wound repair model (Id., citing Akram K M, et al. Respir. Res. (2013) 14: 9).

The migration of BM-MSCs is mediated by some chemotactic factors and their receptors. The chemokine SDF-1 is crucial for migration to injured tissues via interacting with its cognate receptor CXCR4 on the cellular surface (Id., citing Marquez-Curtis, L A and Janowska-Wieczork, A. BioMed. Res. Int. (2013): 2013; 561098). Xu et al. found that SDF-1 significantly promoted the chemotactic migration of BM-MSCs, but this effect was mimicked by lung extracts from mice after bleomycin treatment and was completely inhibited by TN14003, a synthetic specific CXCR4 antagonist (Id., citing Xu, J. et al. Am. J. Respir. Cell Mol. Biol. (2007) 37: 291-99). SDF-1 and CXCR4 were increased in lungs of IPF patients compared to normal human lungs, and the concentration of SDF-1 in serum and bronchoalveolar lavage fluid (BALF) and the expression level of CXCR4 in lungs were elevated in BLM-induced animal models (Id.). On day 7 after bleomycin challenge, SDF-1a mRNA levels in the lungs increased significantly compared with saline groups and remained on day 14 (Id., citing Hashimoto, N. et al. J. Clin. Invest. (2004) 113: 243-52). SDF-1 expression was also increased in the lungs of patients with idiopathic interstitial pneumonia (Id., citing Yang, I V et al. Am. J. Respir. Crit. Care Med. (2007) 175: 45-54). Another study showed chemokine CXCL8 (interleukin-8) also promoted the migration of hMSCs (Id., citing Ringe, J. et al. J. Cell Biochem. (2007) 101: 135-46).

After homing to injured lungs, MSCs can differentiate into type II alveolar epithelial cells (AECs) and be involved in the renewal of the alveolar epithelium in vitro and in vivo (Id., citing Liu, A R. J. Cell Physiol. (2013) 228: 1270-83; Cai, S X et al. Stem Cell Res. Ther. (2015) 6: 65; Liu, A. et al. PLoS One (2014) 9: e90229). MSC differentiation into type II AECs is mainly mediated by the Wnt pathway (Id., citing Ling, L. et al. Gene (2009) 433: 1-7). Liu et al. found that β-catenin and glycogen synthase kinase-3β (GSK-3β) in the canonical Wnt pathway were activated during the differentiation of mouse MSCs into type II AECs (Id., citing Liu, A R. J. Cell Physiol. (2013) 228: 1270-83). Overexpression of β-catenin in mouse MSCs to activate the canonical Wnt/β-catenin pathway further improved their protective effect against epithelial impairment and therapeutic effects for ARDS in mice (Id., citing Cai, S X et al. Stem Cell Res. Ther. (2015) 6: 65). Further studies indicated that Wnt5a contributes to MSC differentiation into type II AECs through noncanonical c-Jun N-terminal kinase (JNK) or protein kinase C (PKC) signaling in vitro (Id., citing Liu, A. et al. PLoS One (2014) 9: e90229).

However, the role of MSCs in resistance to PF through differentiation into epithelial cells remains controversial. In HCl-induced models of acute lung injury (ALI), MSCs did not improve the pathologic changes of ALI and PF (Id., citing Sun, Z. et al. J. Cell Physiol. (2014) 229: 213-24). It was found that the activation of canonical Wnt/β-catenin signaling induced most MSCs to differentiate into fibroblasts or myofibroblasts, and that blocking this signal after MSC transplantation ameliorated PF and improved pulmonary function in vivo. Tang et al. also showed that BM-MSCs induce α-SMA-positive myofibroblasts in a transplanted BM model (Id., citing Tang, N. et al. J. Cell Mol. Med. (2014) 18: 156-69). MSCs administered to mice during the fibrotic stage of a radiation-induced PF model likewise differentiated into fibroblast-like phenotype and aggravated the fibrotic lesion (Id., citing Mora, A L, Rojas, M. J. Cell Biochem. (2008) 105: 641-47). MSCs isolated from bleomycin-injured mice lungs also were more likely to differentiate into fibroblasts in vitro (Id., citing Skurikhin, E. G. et al. Bull Exp. Biol. Med. (2013) 154: 537-43).

MSC-derived conditioned medium (MSC-CM) can also exert a protective effect against BLM-induced lung injury and fibrosis (Id., citing Shen, Q. et al. Mol. Med. Re. (2015) 11: 2831-37). In the bleomycin-induced rat model, MSC-CM prevented PF by reducing pulmonary inflammation, fibrosis score, collagen deposition, and cell apoptosis. MSC-CM also protected human non-small-cell lung cancer epithelial cells (A549) from bleomycin-induced apoptosis. However, unlike fibrosis, bleomycin injury does resolve in some cases, and also responds to use of anti-inflammatory and antifibrotic agents (Borzone G, et al. Am J Respir Crit Care Med. 2001 June; 163(7):1648-53).

MSCs have been proposed to possess the capacity to secrete a broad range of bioactive molecules, such as growth factors, cytokines, and chemokines (Li, Xiaohong, et al. (2017) Oncotarget 8(60): 102600-102616, citing Monsel, A. et al. Expert Opin. Biol. Ther. (2016) 16: 859-71; Caplan, A. and Correa, D. Cell Stem Cell (2011) 9: 11-15; Kosuma, G D, et al. Stem Cells Dev. (2017) 26: 617-31). These bioactive molecules regulate local immune response to establish a regenerative microenvironment and subsequently inhibit inflammation and repair the injured tissues (Id.).

MSCs in Cardiac Fibrosis

MSCs have been intensively studied in basic cardiovascular research (Chou S H, et al. Cell Transplant. 2014; 23(4-5): 513-29). Since Wakitani et al. reported that MSCs can differentiate in vitro into a myogenic phenotype, there has been a growing body of evidence that MSCs are effective in improving the cardiac performance of the ischemia/reperfusion (IR) heart (Id., citing Wakitani, S, et al. Muscle Nerve 18: 1417-1426; 1995). In vitro differentiation of MSCs into cells resembling cardiomyocytes prompted early expectation of their capacity to regenerate these cells in vivo. Exposure of the cells to a chemical 5-azacytidine (5-Aza), a DNA-methylating agent, has been the most common strategy for inducing their cardiac differentiation in vitro (Id., citing Balana, B, et al. Cell Res. 16: 949-960; 2006; Wakitani, S, et al. Muscle Nerve 18: 1417-1426; 1995). Under this condition, stromal cell lines, primary stromal cells and MSCs, from different species and different tissue sources exhibited a modified phenotype with the adoption of myotube morphology, expression of immature action potentials, and a variety of cardiac-specific genes (e.g., MEF-2A/MEF-2D) and peptides (e.g., myosin, desmin, actinin, atrial natriuretic peptides) (Id., citing Chung, Y S, et al. Chin. J. Physiol. 54: 205-218; 2011; Moscoso, I, et al. Transplant. Proc. 37: 481-482; 2005; Rangappa, S, et al. Ann. Thorac. Surg. 75: 775-779; 2003; Wang, J S, et al. J. Thorac. Cardiovasc. Surg. 120: 999-1005; 2000; Xu, W, et al. Exp. Biol. Med. 229: 623-631; 2004). Further, functional differentiation has been indicated by the formation of gap junctions and spontaneous cell contractibility (Id., citing Kadivar, M, et al. Biochem. Biophys. Res. Commun. 340: 639-647; 2006). Recently, in vitro alternative methods to cardiomyocyte transdifferentiation included culturing in medium enriched with dexamethasone and ascorbic acid, bone morphogenetic protein-2, and fibroblast growth factor-4, and coculture with cardiomyocytes have also been tried (Id., citing Rangappa, S, et al. Ann. Thorac. Surg. 75: 775-779; 2003; Shim, W S, et al. Biochem. Biophys. Res. Commun. 324: 481-488; 2004; Yoshioka, T, et al. Stem Cells 23: 355-364; 2005). However, it is currently unknown whether in vitro differentiation of MSCs into cardiomyocytes will enhance the reparative effects of these cells once they are transplanted in vivo.

Engraftment and differentiation rates of MSCs are relatively low compared with other cellular effects they render, including their paracrine actions (Golpanian S, et al. Physiol Rev. 2016 July; 96(3): 1127-1168, citing Leri A, et al. Stem Cell Res: 631-646, 2014). Still, numerous reports regarding these mechanisms of action for both autologous and allogeneic MSCs exist in the literature, albeit conflicting evidence (Id., citing Kim P J, et al. Circ Res: e40-e50, 2015; Makkar R R, et al. J Cardiovasc Pharmacol Ther: 225-233, 2005; Price M J, et al. Int J Cardiol: 231-239, 2006; Shake J G, et al. Ann Thoracic Surg: 1919-1926, 2002; Silva G V, et al. Circulation: 150-156, 2005; Toma C, et al. Circulation: 93-98, 2002). For example, porcine hearts directly injected with autologous, Di-I-labeled MSCs into the infarct zone, 2 wk following left anterior descending (LAD) artery occlusion, were found to have marked engraftment in the host myocardium as well as markers for myocardial-specific proteins troponin T, tropomyosin, myosin heavy chain, and α-actinin (Id., citing Shake J G, et al. Ann Thoracic Surg: 1919-1926, 2002). Similarly, allogeneic bromodeoxyuridine-labeled MSCs, delivered via direct intramyocardial injections 1 mo after M I induction, engrafted in the peri-infarct zone and differentiated into cardiomyocytes (Id., citing Makkar R R, et al. J Cardiovasc Pharmacol Ther: 225-233, 2005).

Others have found little to no engraftment or differentiation in myocardial injury models (Id., citing Kim P J, et al. Circ Res: e40-e50, 2015; Toma C, et al. Circulation: 93-98, 2002). Human β-galactosidase$^+$ MSCs transdiaphragmatically delivered to rat left ventricles engrafted in host myocardium at a rate of only 0.44% 4 days following injection (Id., citing Toma C, et al. Circulation: 93-98, 2002). Significantly, most cells were found in the lungs, spleen, and liver. The engrafted cells however began to appear morphologically indistinguishable from the host cardiac myocytes and, starting as early as 2 wk post-injection, revealed de novo expression of desmin, β-myosin heavy chain, α-actinin, cardiac troponin T, and phospholamban with sarcomeric organization of contractile proteins (Id., citing Toma C, et al. Circulation: 93-98, 2002). In another study, mouse hearts that were administered human placenta-derived amniotic MSCs (AMCs) following left anterior descending (LAD) artery ligation did not demonstrate any immunohistological evidence of engraftment, while those that were treated with c-kit$^+$ AMCs showed engraftment yet no cardiac differentiation of cells (Id., citing Kim P J, et al. Circ Res: e40-e50, 2015). These inconsistent findings on MSC survival have led to the concept of cell transiency, suggesting that MSCs' engraftment persists only for a limited time (Id., citing Jameel M N, et al. Am J Physiol Heart Circ Physiol: H1348-H1356, 2010). Although the reasons behind this phenomenon are not exactly clear, they may possibly be related to the MSC source, mode of delivery (Id., citing Tao B, et al. Theranostics: 196-205, 2015), and/or disease model employed (i.e., acute vs. chronic).

Formation of scar not only initiates cardiac remodeling to a spherical shape but is also closely interrelated with endogenous myogenesis. Type I collagen is the most frequently found collagen in fibrotic tissues, and the presence of tissue fibrosis has been associated with dysregulation of myocyte regeneration and repair (Id., citing Alexakis C, et al. Am J Physiol Cell Physiol: C661-C669, 2007; Brack A S, et al. Science: 807-810, 2007). Indeed, exposure of MSCs to type I collagen leads to a downregulation of growth and inflammatory gene factors with a resultant decrease in MSC-induced myoblast proliferation potential (Id., citing De Lisio M, et al. Stem Cell Res Ther: 74, 2014). Matrix metalloproteinases (MMPs) are a group of essential molecules that maintain extracellular matrix (ECM) homeostasis and ECM remodeling plays a large role in regulating myocyte migration, differentiation, and regeneration (Id., citing Chen X, et al. Cell Adhesion Migration: 337-341, 2009). MSCs release a combination of various MMPs and tissue inhibitors that are involved in extracellular remodeling (Id., citing Molina E J, et al. J Tissue Engineering Regenerative Med: 85-91, 2009). Notably, the ratio of MMPs to tissue inhibitors can be modulated by overexpression of certain factors, which can reverse the process of cardiac remodeling (Id., citing Shu T, et al. Tissue Cell: 217-222, 2010; Tang J, et al. Molecules Cells: 9-19, 2010). Moreover, MSCs are capable of regulating the ECM degradative potential of cardiac fibroblasts, thereby supporting an indirect antifibrotic mechanism (Id., citing Mias C, et al. Stem Cells: 2734-2743, 2009). Indeed, the reduction of fibrosis in scarred tissues, which involves ECM degradation, aids in improving the renegerative capacity of endogenous myocytes (Id., citing Serrano A L, et al. Curr Top Dev Biol: 167-201, 2011). Regardless of the method of cardiac neomyogenesis, the process seems to occur under significant manipulation in vitro while biological in vivo influences may not be adequate for driving cardiac regeneration (Id., citing Toma C, et al. Circulation: 93-98, 2002).

Although many studies involving multipotent MSCs have not reported any major health concerns, implying the safety of MSC therapy, some trials have recounted serious adverse events (Singh A, et al. Stem Cell Res Ther. 2016; 7: 82, citing Herberts C A, et al. J Transl Med. 2011; 9: 29), such as malignant tumour formation on transplantation of unmodified BM-MSCs in the peri-infarct area of a mouse model (Id., citing Jeong J O, et al. Circ Res. 2011; 108: 1340-7). In a study conducted to observe an infarcted heart region, several calcified or ossified encapsulated structures were identified after the injection of MSCs (Id., citing Ko I K, Kim B S. Int J Stem Cells. 2008; 1: 49-54). A study on arrhythmic mechanisms established the proarrhythmic effects of hMSCs in neonatal rat cardiomyocytes and the pattern of the MSCs was said to be determinant of the arrhythmic severity of the myocardial tissue (Id., citing Askar S F, et al. Circ Arrhythm Electrophysiol. 2013; 6: 380-91). Another study concluded the possibility of primary cardiac sarcoma formation from MSCs, which can further develop into tumours with multi-lineage differentiation (Id., citing Hegyi L, et al. Histopathology. 2012; 61: 966-73). According to a study conducted by Huang et al., allogeneic MSC transplantation in the myocardium exhibited a biphasic immune response of these cells, resulting in a shift from an immune-privileged state to an immunogenic phenotype after differentiation leading to characteristics such as fractional shortening and progressive ventricular dysfunction (Id., citing Huang X P, et al. Circulation. 2010; 122: 2419-29). Many pathways and underlying processes concerning MSCs still exist that remain unexplored in the field of reparative medicine. Cell therapy has been adopted as a novel therapeutic strategy for treatment of cardiac disorders such as severe heart failure and CAD. Unfortunately, although these approaches have led to advancements in the field of safety and efficacy of these cell therapies, the mediocre success rates in terms of functional improvement serve as a disappointment in the field (Id., citing Doppler S A, et al. J Thorac Dis. 2013; 5: 683-97).

MSCs in Renal Fibrosis

Mesenchymal stem cell-based therapies have been shown to confer renal protection in several models of acute kidney injury (AKI) (Matsui F, et al. Am J Physiol Renal Physiol. 2017 Jan. 1; 312(1): F25-F32, citing Hara, Y, et al. Transpl Int 24: 1112-1123, 2011; Herrera M B, et al. Int J Mol Med 14: 1035-1041, 2004; Herrera M B, et al. Kidney Int 72: 430-441, 2007; Kim J H, et al. Am J Physiol Renal Physiol 302: F1141-F1150, 2012; Morigi M, et al. J Am Soc Nephrol 15: 1794-1804, 2004; Rigel F, et al. Am J Physiol Renal Physiol 289: F31-F42, 2005; Tögel F, et al. Kidney Int 67: 1772-1784, 2005; Zhu X Y, et al. Stem Cells 31: 117-125, 2013), and early clinical trials have demonstrated the safety and efficacy of MSCs in protecting against renal dysfunction and reducing both the length of stay and need for hospital readmission in cardiac surgery patients at high risk for postoperative AKI (Id., citing Tögel F E, Westenfelder C. Am J Kidney Dis 60: 1012-1022, 2012; Westenfelder C, Togel F E. Kidney Int Suppl (2011) 1: 103-106, 2011). A decreased incidence of acute rejection has also been demonstrated in patients receiving MSCs at the time of kidney transplantation (Id., citing Tan J, et al. JAMA 307: 1169-1177, 2012).

Although MSC therapy may be an attractive strategy for renal repair, most clinical trials involve only early phases of kidney disease (Id., citing Squillaro T, et al. Cell Transplant 25: 829-848, 2016), and the potential of MSC-based therapy to prevent or ameliorate chronic kidney disease (CKD) is only beginning to be elucidated. Unlike acute alterations elicited in AKI, regression of longstanding structural remodeling like fibrosis is difficult to attain with any therapeutic intervention (Zhu X Y, et al. Stem Cells. 2013 September; 31(9): 1731-1736). Several recent animal studies show the capacity of exogenously administered MSCs to reduce tubulointerstitial fibrosis, preserve peritubular capillary density, and prevent epithelial mesenchymal transition in multiple different models of chronic renal injury (Matsui F, et al. Am J Physiol Renal Physiol. 2017 Jan. 1; 312(1): F25-F32, citing Asanuma H, et al. J Surg Res 168: e51-e59, 2011; Bai Z M, et al. Chin Med J (Engl) 126: 1890-1894, 2013; da Silva A F, et al. Cell Transplant 24: 2657-2666, 2015; Ninichuk V, et al. Kidney Int 70: 121-129, 2006; Semedo P, et al. Stem Cells 27: 3063-3073, 2009; Sun D, et al. PLoS One 8: e65042, 2013; van Koppen A, et al. PLoS One 7: e38746, 2012). Results have also demonstrated a significant reduction in obstruction-induced collagen I and III mRNA expression, collagen deposition, fibronectin and α-SMA expression, and fibronectin and α-SMA deposition in the kidney in the presence of MSCs (Id.).

The route of MSC delivery, intravenous, intra-arterial, or intra-parenchymal, may affect their efficiency for kidney repair. When labeled MSC intravenously infused into baboons were observed for 9-21 months, estimated levels of engraftment in the kidney, lung, liver, thymus, and skin ranged from 0.1-2.7% (Zhu X Y, et al. Stem Cells. 2013

September; 31(9): 1731-1736, citing Devine S M, et al. Blood. 2003; 101: 2999-3001). Indeed, the intravenous route lags in delivery efficiency, because MSC may initially be trapped in the lungs (Id., citing Fischer U M, et al. Stem Cells Dev. 2009; 18: 683-692). Intra-arterial infusion of MSC was the most effective route to achieve immunomodulation in rat kidney transplantation, possibly by avoiding lodging in the pulmonary circulation, allowing MSC to home to the injured kidney (Id., citing Zonta S, et al. Transplant Proc. 2010; 42:1336-1340). Indeed, a retention of 12-14% of intra-arterially injected MSC was observed in one study of experimental ischemic CKD (Id., citing Eirin A, et al. Stem Cells. 2012; 30: 1030-1041). Contrarily, a recent study found similar functional efficacy, with most MSC label diminished within 7 days after either intravenous or intra-arterial infusion in rat ischemia-reperfusion injury (IRI) (Id., citing Zhuo W, et al. Transplant Proc. 2013; 45: 503-510). Intra-parenchymal administration of MSC also reduces renal fibrosis and promoted functional recovery, but is impractical for clinical applications, especially when kidney pathology is diffuse (Id., citing Alfarano C, et al. Cell Transplant. 2012; 21: 2009-2019).

How long the effects of MSC on kidney protection can last also remains unclear. In a pilot study, ARAS (atherosclerotic renal artery stenosis, the major cause of ischemic CKD) pigs were studied 4 or 12 weeks after injection of MSC (Id., citing Zhu X Y, et al. Stem Cells. 2013; 31: 117-125). Very few pre-labeled MSC were detectable in the kidney by 12 weeks, possibly because of dilution and decay of the label. Nevertheless, comparable improvements in RBF were observed at both time-points, suggesting that their beneficial effects are sustained for at least 3 months. The decrease over time in the paracrine/endocrine effects of MSC may be more important for CKD than AKI, in which the injurious trigger might have been removed. Repeated weekly administration of MSC improves their protective effects in the rat remnant kidney, primarily via paracrine effects (Id., citing Lee S R, et al. Ren Fail. 2010; 32: 840-848). Whether CKD would benefit from multiple MSC administration awaits further testing in CKD models. Furthermore, hypoxic preconditioning enhances MSC recruitment and functional recovery from IRI (Id., citing Liu H, et al. PLoS One. 2012; 7: e34608), but remains to be tested in CKD.

MSCs in Hepatic Fibrosis

Several pre-clinical in vivo studies have been performed over the past several years to evaluate the therapeutic potential of MSCs in the context of liver fibrosis (Berardis S, et al. World J Gastroenterol. 2015 Jan. 21; 21(3): 742-758). In most of the studies, liver fibrosis was induced by intraperitoneal or subcutaneous injection of $CCl_4$ (carbon tetrachloride, a potent hepatotoxin). This model has the advantage of being the best characterized model with respect to histological, biochemical, cellular and molecular changes associated with the development of liver fibrosis. Moreover, it can reproduce the pattern of most of the diseases observed in human fibrosis. However, this model has some limitations. First, it is not a suitable model to study all types of liver fibrosis, such as biliary fibrosis. Second, it cannot provide a perfect simulation of a human disease because there are large species differences in immune reactions, gene expression/regulation, and metabolic, pharmacological and tissue responses (Id., citing Starkel P, Leclercq I A. Best Pract Res Clin Gastroenterol. 2011; 25: 319-333).

The results of the in vivo studies are promising because they report a decrease in the liver fibrosis with frequent improvement of hepatic functions. In addition to an improvement in liver fibrosis and liver function, one study reported an improvement in liver microcirculation after MSC injection (Id., citing Wang Y, et al. J Transl Med. 2012; 10: 133). In two other studies, the decrease in the collagen deposition was correlated to a decrease in α-SMA expression, a classical marker of activated stellate cells (Id., citing Zhao D C, et al. World J Gastroenterol. 2005; 11: 3431-3440; Tanimoto H, et al. Cell Tissue Res. 2013; 354: 717-728). Most of the time, these results are observed 4 weeks after cell infusion. It is unknown whether the observed anti-fibrotic effect persists over time, because the $CCl_4$ injections need to be continued after MSC injection to avoid a regression of liver fibrosis. This represents an obstacle to long-term studies, because animals can hardly support $CCl_4$ injections over a long period of time (Id.).

In vivo studies highlight the controversy that remains concerning the exact mechanisms by which MSCs may exert a beneficial effect. Indeed, some studies have mentioned the differentiation of MSCs into hepatocyte-like cells (Id., citing Jung K H, et al. Liver Int. 2009; 29: 898-909; Li Q, et al. PLoS One. 2013; 8: e62363) and/or the expression of metalloproteinases by MSCs (Id., citing Chang Y J, et al. Life Sci. 2009; 85: 517-525; Rabani V, et al. Cell Biol Int. 2010; 34: 601-605; Tanimoto H, et al. Cell Tissue Res. 2013; 354: 717-728). The promotion of hepatocyte proliferation and modulation of inflammation have also been proposed (Id., citing Li Q, et al. PLoS One. 2013; 8: e62363).

Over the past few years, several clinical trials using human MSCs to treat patients presenting liver fibrosis have been published. The endpoints of the studies were to evaluate the safety and efficacy of bone marrow and umbilical cord MSCs transplantation. The cells were mostly infused intravenously, although two studies reported infusions via the hepatic artery (Id., citing Peng L, et al. Hepatology. 2011; 54: 820-828; Jang Y O, et al. Liver Int. 2014; 34: 33-41), and in one study, the cells were injected into the spleen (Id., citing Amin M A, et al. Clin Transplant. 2013; 27: 607-612). There was also great variation in the number of cells infused per patient and in the frequency of injection in the different trials. The results of the studies seemed promising in terms of improvement of liver function and model for end-stage liver disease score, which is based on objective variables (INR, serum albumin and serum bilirubin) and has been validated as a predictor of survival among patients with advanced liver disease (Id., citing Kamath P S, Kim W R. Hepatology. 2007; 45: 797-805).

However, there is a lack of data regarding the evaluation of liver histology after cell transplantation, and globally, the size of the samples is small in most studies and there is a lack of controls in five of the studies. The follow up period is quite short, except in one study with a 192-wk follow up. Thus it is crucial to evaluate the long term efficacy, prognosis and safety before proposing this therapy routinely in the clinical practice. The use of MSCs in clinical practice is currently hindered by the incapacity to monitor the transplanted cells in the patients and by the lack of standardized transplantation protocols (Id.).

Therapeutic Effects of MSCs Mediated by Stem Cell Secretion

A 'paracrine hypothesis' that the observed therapeutic effects of MSCs are partly mediated by stem cell secretion has gained much attention and is supported by experimental data (Arlan, F. et al. Stem Cell Res. (2013) 10: 301-12, citing Gnecchi et al. Circ. Res., 103 (2008): 1204-1219). It has been shown that MSC-CM enhanced cardiomyocyte and/or progenitor survival after hypoxia-induced injury (Id., citing Chimenti et al. Circ. Res., 106 (2010): 971-980; Deuse et al.

Circulation, 120 (2009): S247-S254; Gnecchi et al. Circ. Res., 103 (2008): 1204-1219; Matsuura et al. J. Clin. Invest., 119 (2009): 2204-2217; Rogers et al., 2011). Furthermore, MSC-CM induces angiogenesis in infarcted myocardium (Id., citing Chimenti et al. Circ. Res., 106 (2010): 971-980; Deuse et al. Circulation, 120 (2009): S247-S254; Li et al. Am. J. Physiol. Heart Circ. Physiol., 299 (2010): H1772-H1781). In both murine and porcine models of myocardial ischemia/reperfusion (FR) injury it has been shown that MSC-CM reduces infarct size (Id., citing Timmers et al. Stem Cell Res., 1 (2007): 129-137).

High performance liquid chromatography (HPLC) and dynamic light scatter (DLS) analyses revealed that MSCs secrete cardioprotective microparticles with a hydrodynamic radius ranging from 50 to 65 nm (Id., citing Chen et al., 2011; Lai et al. J. Mol. Cell. Cardiol. (2010) 48: 1215-1224). The therapeutic efficacy of MSC-derived extracellular vesicles (EVs) was independent of the tissue source of the MSCs. For example, exosomes from human embryonic stem cell-derived MSCs were similar to those derived from other fetal tissue sources (e.g. limb, kidney). This suggested that secretion of therapeutic EVs may be a general property of all MSCs (Id., citing Lai et al. Stem Cell Res., 4 (2010): 214-222).

MSC-Derived EVs Comprising Exosomes and Microvesicles

MSC-derived EVs, which include exosomes and microvesicles (MV), are involved in cell-to-cell communication, cell signaling, and altering cell or tissue metabolism at short or long distances in the body, and can influence tissue responses to injury, infection, and disease (Phinney, D G and Pittenger, M F. Stem Cells (2017) 35: 851-58). Their content includes cytokines and growth factors, signaling lipids, mRNAs, and regulatory miRNAs (Id.). The content of MSC EVs is not static; they are a product of the MSC tissue origin, its activities, and the immediate intercellular neighbors of the MSCs (Id.).

MSCs secrete a plethora of biologically active proteins (Id., citing Tremain N, et al. Stem Cells 2001; 19: 408-418; Phinney D G, et al. Stem Cells 2006; 24: 186-198; Ren J, et al. Cytotherapy 2011; 13: 661-674).

Most cells produce EVs as a consequence of intracellular vesicle sorting, including both microvesicles of >200 nm, and exosomes of 50-200 nm diameter. The microvesicles are shed from the plasma membrane, whereas exosomes originate from early endosomes and, as they mature into late endosomes/multivesicular bodies, acquire increasing numbers of intraluminal vesicles, which are released as exosomes upon fusion of the endosome with the cell surface (Id., citing Lee Y, et al. Hum Mol Genet 2012; 21: R15-134; Tkach M, Thery C. Cell 2016; 164: 1226-1232).

Although MSC-derived EVs recapitulate to a large extent the immensely broad therapeutic effects previously attributed to MSCs, most studies fall short of rigorously validating this hypothesis (Id.) For example, various groups have compared the potency of MSCs versus MSC-derived EVs, and in some cases MSC-conditioned media, in animal models of myocardial infarction (Id., citing Bian S, et al. J Mol Med (Berlin) 2014; 92: 387-397), focal cerebral ischemia (Doeppner T R, et al. Stem Cells Transl Med 2015; 4: 1131-1143), gentamicin-induced kidney injury (Reis L A, et al. PLoS One 2012; 7: e44092), and silicosis (Choi M, et al. Mol Cells 2014; 37: 133-1394). While most studies report that MSC-derived EVs are equally effective as MSCs in sparing tissue and/or promoting functional recovery from injury, this desired outcome is compromised by lack of appropriate controls, comparable dosing, evaluation of the different disease endpoints, variations in frequency and timing of dosage, and absence of dose-dependent effects, thereby making it difficult to draw reliable conclusions about comparable efficacy and potency (Id.)

MSC-derived EVs may function largely via horizontal transfer of mRNAs, miRNAs, and proteins, which then function by a variety of mechanisms to alter the activity of target cells. For example, it has been reported that transfer of IGF-1R mRNA from MSC-derived exosomes to cisplatin-damaged proximal tubular epithelial cells sensitized the epithelial cells to the renal-protective effects of locally produced IGF-1 (Id., citing Tomasoni S, et al. Stem Cells Dev 2013; 22: 772-780). With respect to miRNAs, those contained within MSC-derived EVs have been shown to inhibit tumor growth (Id., citing Katakowski M, et al. Cancer Lett 2013; 335: 201-204; Ono M, et al. Sci Signal 2014; 7: ra63), reduce cardiac fibrosis following myocardial infarction (Feng, Y. et al. PLoS One (2014) 9: e88685), stimulate axonal growth from cortical neurons (Id., citing Zhang Y, et al. Mol Neurobiol (2017) 54(4): 2659-73), promote neurite remodeling and functional recovery after stroke (Id., citing Xin H, et al. Stem Cells 2013; 31: 2737-2746), and stimulate endothelial cell angiogenesis (Id., citing Liang X, et al. J Cell Sci 2016; 129: 2182-2189).

Several studies have validated a direct role for exosome-derived miRNAs in modulating target cell function via use of loss-of-function approaches (Id., citing Wang X, et al. Sci Rep 2015; 5: 13721; Xin H, et al. Stem Cells 2013; 31: 2737-2746). Other studies have shown that EVs secreted by bone marrow-derived MSCs contain cystinosin (CTNS), a cystine efflux channel in the lysosomal membrane, and that coculture of fibroblasts and proximal tubular cells from cystinosis patients with MSC-derived EVs resulted in a dose-dependent decrease in cellular cystine levels (Id., citing Iglessias, D M et al. PLoS One (2012) 7: e42840).

It has been demonstrated that exosomes produced from adipose-derived MSCs (ASCs) contain neprilysin, an enzyme that degrades the amyloid beta (Aβ) peptide, and that coculture of N2a cells engineered to overexpress human Aβ with ASCs significantly reduced the levels of secreted Aβ40 and Aβ342 by exosome-mediated transfer of neprilysin (Id., citing Katsuda T, et al. Sci Rep (2013); 3: 1197). A separate study reported that MSC-derived exosomes suppress human-into-mouse graft-versus-host disease (GvHD) by inhibiting Th1 cell effector function via the release of CD73 containing exosomes, which, when taken up by CD39-expressing CD4+Th1 cells, resulted in enhanced adenosine production and increased Th1 cell apoptosis (Id., citing Amarnath A, et al. Stem Cells (2015) 33: 1200-1212). Together, these studies indicate that dissecting the therapeutic effects of MSC-derived EVs and their mechanism of action in vivo may be equally as challenging as determining that for the parent MSCs (Id.).

Not all MSC-derived EVs are equivalent. For example, it has been reported that exosomes isolated from adipose-derived MSCs contain up to fourfold higher levels of enzymatically active neprilysin, as compared to bone marrow-derived MSCs (Id., citing Katsuda T, et al. Sci Rep (2013) 3: 1197). EVs from marrow and umbilical cord-derived MSCs were shown to inhibit the growth and to induce apoptosis of U87MG glioblastoma cells in vitro whereas those from adipose-derived MSCs promoted cell growth but had no effect on U87MG survival (Id., citing Del Fattore, A. et al. Expert Opin. Biol. Ther. (2015) 15: 495-504). Moreover, it has been shown that exosomes prepared from different tissue-specific MSCs have measurably different effects on neurite outgrowth in primary cortical neurons and dorsal root ganglia explant cultures (Id., citing Lopez-Verrilli et al. Neuroscience 2016; 320: 129-139).

Small RNAs as Critical Regulators in the Expression and Function of Eukaryotic Genes and Genomes Small (about 20-30 nucleotide (nt)) noncoding RNAs regulate eukaryotic genes and genomes (Carthew, R W and Sontheimer, E J. Cell (2009) 136: 642-55). This regulation can occur at multiple levels of genome function, including chromatin structure, chromosome segregation, transcription, RNA processing, RNA stability, and translation (Id.). The effects of small RNAs on gene expression and control are generally inhibitory, and the corresponding regulatory mechanisms are therefore collectively subsumed under the heading of RNA silencing (Id.). The central theme that runs throughout is that the small RNAs serve as specificity factors that direct bound effector proteins to target nucleic acid molecules via base-pairing interactions (Id.). Invariably, the core component of the effector machinery is a member of the Argonaute protein superfamily (Id.).

There are three main categories of small RNAs: short interfering RNAs (siRNAs), microRNAs (miRNAs), and piwi-interacting RNAs (piRNAs) (Id.). siRNAs and miRNAs are the most broadly distributed in both phylogenetic and physiological terms and are characterized by the double-stranded nature of their precursors (Id.). In contrast, piRNAs are primarily found in animals, exert their functions most clearly in the germline, and derive from precursors that are poorly understood, but appear to be single stranded (Id.). Where siRNAs and miRNAs bind to members of the Ago clade of Argonaute proteins, piRNAs bind to members of the Piwi clade (Id.).

The signature components of RNA silencing are Dicers, Agos, and 21-23 nt duplex-derived RNAs (Id.). Both siRNA and miRNA small RNAs depend on Dicer enzymes to excise them from their precursors, and Ago proteins to support their silencing effector functions (Id.).

RNase III enzymes, which are dsRNA-specific nucleases, are the source of miRNA/siRNA biogenesis (Id.). One class of large RNase III enzymes has several domains in a specific order from the amino to carboxy terminus: a DEXD/H ATPase domain, a DUF283 domain, a PAZ domain, two tandem RNase III domains, and a dsRNA-binding domain (Id.). Some members of this family differ slightly from this arrangement (Id.).

The PAZ and RNase III domains play central roles in excising siRNAs preferentially from ends of dsRNA molecules. PAZ domains are shared with Argonaute proteins and are specialized to bind RNA ends, especially duplex ends with short (2 nt) 3' overhangs. An end engages the Dicer PAZ domain, and the substrate dsRNA then extends approximately two helical turns along the surface of the protein before it reaches a single processing center that resides in a cleft of an intramolecular dimer involving the RNase III domains. Each of the two RNase IIII active sites cleaves one of the two strands, leading to staggered duplex scission to generate new ends with 2-3' nt overhangs. The reaction leaves a 5' monophosphate on the product ends, consistent with a requirement for this group during later stages of silencing. This general model pertains equally to pre-miRNA stem-loop substrates and to long, perfectly base-paired dsRNAs. In some species, different functional categories of small RNAs exhibit slightly different lengths; this appears to be dictated by the distance between the PAZ domain and the processing center in the relevant Dicer enzyme (Id.).

The roles of the ATPase domain probably vary among different forms of Dicer (Id.). ATP promotes dsRNA processing by *Drosophila* Dicer 2 and *C. elegans* Dcr-1, and mutations predicted to cripple ATPase activity in *Drosophila* Dicer-2 specifically abolish dsRNA processing. In contrast, ATP is dispensable for dsRNA processing by human Dcr (hDcr), and an ATPase defective mutant exhibits no processing defect (Id.).

Dicers isolated from their natural sources generally are found in a heterodimeric complex with a protein that contains two or three double stranded Ras binding domains (dsRBDs); the Ras-binding domain (RBD) is an independent domain of about 75 residues, which is sufficient for GTP-dependent binding of Ras and other G alpha GTPases. Both hDcr and *Drosophila* Dcr-2 process dsRNAs effectively in the absence of the heterodimeric partner (TRBP and R2D2, respectively). In at least some cases, the role of Dicer in silencing extends beyond dsRNA processing and into the pathway of RISC assembly; this activity is much more dependent on the dsRBD partner protein (Id.).

Argonautes

The Argonaute superfamily can be divided into three separate subgroups: the Piwi clade that binds piRNAs, the Ago clade that associates with miRNAs and siRNAs, and a third clade described in nematodes. All gene regulatory phenomena involving 20-30 nt RNAs are thought to require one or more Argonaute proteins, which are the central, defining components of an RNA-induced silencing complex (RISC). The double-stranded products of Dicer enter into a RISC assembly pathway that involves duplex unwinding, culminating in the stable association of only one of the two strands with the Ago effector protein. This guide strand directs target recognition by Watson-Crick base pairing; the other strand of the original small RNA duplex (the passenger strand) is discarded (Id.).

Argonaute proteins are defined by the presence of four domains: the PAZ domain (shared with Dicer enzymes), the PIWI domain that is unique to the Argonaute superfamily, and the N and Mid domains. The overall protein structure is bi-lobed, with one lobe consisting of the PAZ domain and the other lobe consisting of the PIWI domain flanked by N-terminal (N) and middle (Mid) domains. The Argonaute PAZ domain has RNA 3' terminus binding activity, and the co-crystal structures reveal that this function is used in guide strand binding. The other end of the guide strand engages a 5' phosphate binding pocket in the Mid domain, and the remainder of the guide tracks along a positively charged surface to which each of the domains contributes. The protein-DNA contacts are dominated by sugar-phosphate backbone interactions. Guide strand nucleotides 2-6, which are especially important for target recognition, are stacked with their Watson-Crick faces exposed and available for base pairing (Id.).

The PIWI domain adopts an RNase H-like fold that in some cases can catalyze guide strand-dependent endonucleolytic cleavage of a base pair target. This initial cut represents the critical first step in a subset of small RNA silencing events that proceed through RNA destabilization. Not all Argonaute proteins have endonucleolytic activity, and those that lack it usually also lack critical active-site residues that coordinate a presumptive catalytic metal ion (Id.).

In humans, four of the eight Argonaute proteins are from the Ago clade and associate with both siRNAs and miRNAs (Id.).

MicroRNAs

MicroRNAs are found in plant and animal branches of Eukaryotes and are encoded by a bewildering array of genes. Transcription of miRNAs is typically performed by RNA polymerase II, and transcripts are capped and polyadenylated. Although some animal miRNAs are individually produced from separate transcription units, many more are produced from transcription units that make more than one product. A transcript may encode clusters of distinct miRNAs, or it may encode an miRNA and protein. The latter type of transcript is organized such that the miRNA sequence is located within an intron. Many new animal miRNAs are thought to arise from accumulation of nucleotide sequence changes and not from gene duplication (Id.).

The resulting primary or pri-miRNA transcript extends both 5' and 3' from the miRNA sequence, and two sequential processing reactions trim the transcript into the mature miRNA. Processing depends on the miRNA sequence folding into a step-loop structure. A typical animal pri-miRNA consists of an imperfectly paired stem of ~33 bp, with a terminal loop and flanking segments. The first processing step, which occurs in the nucleus, excises the stem-loop from the remainder of the transcript to create a pre-miRNA product. For most pri-miRNAs, a nuclear member of the RNase III family (Drosha in animals) carries out this cleavage reaction. Although Drosha catalyzes pri-miRNA processing, it depends on a protein cofactor, which contains two dsRBD domains and stably associates with the ribonuclease to form the microprocessor complex (Id.).

An alternative pathway uses splicing of pri-miRNA transcripts to liberate introns that precisely mimic the structural features of pre-miRNAs. These introns then enter the miRNA processing pathway without the aid of the Microprocessor (Id.).

The second processing step excises the terminal loop from the pre-miRNA stem to create a mature miRNA duplex of approximately 22 bp length. In animals, the pre-miRNA is exported from the nucleus, and the canonical Dicer enzyme carries out the cleavage reaction in the cytoplasm (Id.).

MicroRNAs behave like traditional polymeric products of gene activity, such that most species of a miRNA have highly exact ends, although there is a little variation. This feature of miRNAs has probably allowed them to interact with greater specificity on substrate mRNAs without a need for stringent complementarity or large overlap (Id.).

Consequently, the processing machinery is constructed to produce miRNA duplexes with highly exact ends. The first cut, carried out by Drosha with the aid of its dsRBD domain binding partner protein (called DGCR8), is most critical. DGCR8 directly interacts with the pri-miRNA stem and flanking single-stranded segments. The cleavage site is determined by the distance from the stem-flank junction, which is precisely one turn of a dsRNA helix (11 bp) and is the minimal processing length for an RNase III enzyme. Although Drosha carries out the cleavage reaction, it relies upon DGCR8 to serve as a molecular anchor that properly positions Drosha's catalytic site the correct distance from the stem-flank junction. Thus, the endpoint of the stem is a critical determinant for one end of the mature miRNA (Id.).

The second cut performed by Dicer defines the other end of the mature miRNA. Dicer will cleave anywhere along a dsRNA molecule but has a strong preference for the terminus. The PAZ domain of Dicer interacts with the 3' overhang at the terminus and determines the cleavage site in a ruler-like fashion. The RNase III catalytic sites are positioned two helical turns or 22 bp away from the terminus/PAZ portion of the Dicer-RNA complex (Id.).

While regulation of miRNA biogenesis has not been extensively studied, a surprising number of miRNA genes are formed under the control of the very targets that they regulate. A rationale behind these double-negative regulatory relationships is that tight regulation of miRNA biogenesis is crucial. Misexpression of miRNAs frequently mimics loss of function phenotypes for their targets. This would be prevented if biogenesis of a miRNA is strictly controlled by its targets. The restriction would also explain how off-targeting effects by wayward miRNAs are carefully limited (Id.).

MicroRNA Associations

The mature miRNA duplex is a short-lived entity; it is rapidly unwound when it associates with an Ago protein. Unwinding occurs so rapidly after duplex formation, because the two processes are physically coupled due to Ago2's presence in a complex with Dicer and TRBP, the double-stranded RNA binding protein that loads siRNA into the RISC (Id.).

miRNA unwinding is accompanied by differential strand retention, i.e., one strand is retained while the other strand is lost. Strand retention is based on the relative thermodynamic stability of the duplex's ends. Although the rule is that the 5' terminus of the retained strand is at the less stably base-paired end of the duplex, this rule is not absolute. The other strand is appreciably detected in Ago complexes, lending ambiguity to the notion of strand asymmetry. Although either strand can become stably associated with Ago proteins, the more commonly associate strand is termed the miRNA strand; the other strand is called the miRNA* strand. miRNA unwinding is not accompanied by cleavage of the ejected strand by the associated Ago (Id.).

The mammalian Dicer/Ag/miRNA complex is associated with other proteins, e.g., Gemin3, Gemin4, Mov10, and Imp8, as well as the mammalian protein GW182, associate with Ago2. GW182 is both necessary and sufficient for miRNA-bound Ago to silence gene expression. Thus miRNA-bound Ago in association with GW182 can be thought of as the miRISC complex (Id.).

Post-Transcriptional Repression by miRNAs

An miRNA acts as an adaptor for miRISC to specifically recognize and regulate particular mRNAs. If miRISC is tethered to a heterologous RNA recognition factor, the factor enables miRISC to recognize and repress mRNAs that lack miRNA-binding sites. With few exceptions, miRNA-binding sites in animal mRNAs lie in the 3' untranslated region (UTR) and are usually present in multiple copies. Most animal miRNAs bind with mismatches and bulges, although a key feature of recognition involves Watson-Crick base pairing of miRNA nucleotides 2-8, representing the seed region (Id.).

While it was thought that perfect complementarity allows Ago-catalyzed cleavage of the mRNA strand, whereas central mismatches exclude cleavage and promote repression of mRNA translation, it appears that translational repression is the default mechanism by which miRNAs repress gene expression, both in animals and plants. Perfectly complementary miRNAs may additionally engage in mRNA cleavage such that their effects are the result of both mechanisms (Id.).

The mechanisms by which miRISC regulates translation have been subject to ongoing debate. The fundamental issue of whether repression occurs at translation initiation or post-initiation has not yet been resolved. There are three competing models for how miRISC represses initiation. One proposes that there is competition between miRISC and eIF4E for binding to the mRNA 5' cap structure. A second model has proposed that miRISC stimulates de-adenylation of the mRNA tail; translation is repressed because the cap and PABP1-free tail of the deadenylated mRNA are unable to circularize. A third model has proposed that miRISC blocks association of the 60S ribosomal subunit with the 40S preinitiation complex, i.e., the recruitment of eIF6 by miRISC may repress translation by preventing the assembly of translationally competent ribosomes at the start codon (Id.).

It is unclear why some targets are degraded and others are not (Id.).

Without being limited by any particular theory, it appears that the mode of regulation of any miRNA (repression vs. activation) in the context of the whole cell and the myriad activities that affect posttranscriptional gene regulation may be context dependent (Id.).

The cell's position in the cell cycle is one such context. For example, miRNA let-7 and an artificial miRNA (CXCR-4) repress translation in proliferating human cells, but change into translational activators when the cell cycle is arrested at the G1 checkpoint by serum starvation. Aphidicollin-induced arrest at G1 also generates translational activation, whereas nocodazole-induced arrest at G2/M generates translational repression. Lymphocyte growth arrest induces TNFα expression that is required for macrophage maturation; miR-369-3p switches from a repressor to an activator of TNFα translation when cells in culture are growth arrested (Id., citing Vasudevan, S. et al. Science (2007) 318: 1931-34).

Binding site position is another context. Interaction of miR-10a with the 5'UTR of certain ribosomal subunit mRNAs leads to their activated translation, whereas interaction with the 3'UTR leads to repression (Id., citing Orom, U A et al. (2008) Mol. Cell 30: 460-71).

Another context is how small RNA regulation is organized and modulated within the cell. Ago proteins are frequently associated with membrane trafficking compartments, such as the Golgi and ER (Id., citing Cikaluk, D. E. et al. Mol. Biol. Cell (1999) 10: 3357-72). It has been hypothesized that miRISC factors might become anchored in certain subcellular compartments, e.g., P bodies or GW bodies, two separate pools of sequestered non-translating RNAs (Patel, P H, et al. PLos One (2016) 11(3): e015029). Subunits of miRISC (miRNAs, Ago and GW1821) and their repressed targets also are enriched in GW bodies. While GW bodies are not essential for miRNA repression, GW body formation requires an intact miRNA pathway (Carthew, R W and Sontheimer, E J. Cell (2009) 136: 642-55).

Role of miRNAs in the Proliferation and Differentiation of MSCs in Wound Healing Little attention has been paid to the role of miRNAs in the proliferation and differentiation of MSCs in the setting of wound healing (Guo, L. et al. Exptl Hematol. (2011) 39: 608-616, citing Silo, S., et al. DNA Cell Biol. (2007) 26: 227-37). Using a skin excision model, altered expression in a panel of miRNAs, including upregulated expression of miR-31, -21, -223, -142, -205, -203, -18b, -19a, -130b, -16, -26b, -125b, and let-7f, and down regulated expression of miR-133a, -181, -30a-3p, -193b, -30a-5p, -204, -200b, -96, -127, -181c, -182 and -130a was demonstrated in wounded tissue in the stage of active granulation formation (Id., citing Zou, Z. et al. Expert Opin. Biol. Thera. (2010) 10: 215-30). Further, Zou et al. found that TGFβ, a key growth factor elevated in the wound site, stimulated upregulation of miR-21 in MSCs as well as in multipotential C3H10T1/2 cells, and promoted proliferation and differentiation of these cells in vitro. Consistently, knockdown of miR-21 in the wound bed delayed the healing process. These results suggest that miR-21 regulates gene expression and, subsequently, the behavior of MSCs in wound healing.

miRNA Expression in MSCs and Microvesicles

Recent studies have shown that MSCs secrete microvesicles (MVs) (Id., citing Bruno S, et al. J. Am. Soc. Neprhol. (2009) 20: 1053-67; Collino, F. et al. PLoS One (2010) 5: e11803). An miRNA profile on MVs from MSCs and HLSCs showed that MVs contained a pattern of miRNAs shared with their cells of origin (Collino F, et al. PLoS One (2010) 5: e11803).

MVs are circular fragments of membrane released from the endosomal compartment as exosomes or shed from the surface membranes of most cell types (Guo, L. et al. Exptl Hematol. (2011) 39: 608-616, citing Lotvall, J., Valadi, H. Cell Adh. Mgr. (2007) 1: 156-58). Accumulating data suggest that MVs may serve as a means of cell-to-cell communication through which genetic information or gene products are transferred and cell activities are regulated (Id., citing Carmussi, et al. Kidney Int. (2010) 78: 838-848; Lotvall, J., Valadi, H. Cell Adh. Mgr. (2007) 1: 156-58). MSC EVs have been shown to harbor a variety of mRNAs and miRNAs (Carmussi, et al. Kidney Int. (2010) 78: 838-848; Lotvall, J., Valadi, H. Cell Adh. Mgr. (2007) 1: 156-58; Chen, T S et al. Nucleic Acids Res. (2010) 38: 215-224). Differential miRNA expression profiles in MSCs and MVs derived from MSCs have been observed (Carmussi, et al. Kidney Int. (2010) 78: 838-848; Chen, T S et al. Nucleic Acids Res. (2010) 38: 215-224). Microarray analysis for the presence of miRNAs revealed that the secreted RNA contained many miRNAs that were essentially a subset of those in MSCs. 9 of the 13 members in one of the most highly conserved and developmentally important human let-7 family were expressed in MSCs (citing Jerome T, et al. Curr. Genomics. 2007; 8: 229-233; Roush S, Slack F J. Trends Cell Biol. 2008; 18: 505-516). They were: hsa-let-7a, hsa-let-7b, hsa-let-7c, hsa-let-7d, hsa-let-7e, hsa-let-7f, hsa-let-7g, hsa-let-7i, and hsa-miR-98. Of these, only hsa-let-7a, -7b, -7c, and -7d were detected in the conditioned medium (CM) (Chen, T S et al. Nucleic Acids Res. (2010) 38: 215-224). The passenger miRNA sequences of -7b and -7d also were detected in the CM and not detectable in MSCs (Id.). These differences suggested that secretion of miRNAs including passenger miRNA sequences is a selective, and not a random process, by MSCs (Id.). Microarray analysis also revealed the presence of miRNA-923, a degradative product of ribosomal RNA (Id.). Therefore, while the secretion did not contain intact rRNA, it contained degraded ribosomal RNA and possibly degraded mRNA (Id.). MSCs were found to preferentially secrete miRNA in the precursor instead of the mature form; these pre-miRNAs were enriched in MVs, which were readily taken up by neighbor cells, suggesting a potential mechanism in regulation of activities of other cells (Id.).

Role of miRNAs in Pain Conditions

The analysis and validation of miRNAs in different tissue and pain conditions have been extensively reported. (Tan-P-H et al. Acta Anaesthesiologica Taiwanica 51 (2013) 171-76). Among the miRNAs dysregulated in the dorsal root gangion (DRG), miR-21 expression is consistently shown to increase after multiple types of peripheral nerve injury. (Id., citing Strickland, L T et al. PLoS One (2011) 6: e23423; Wu et al., Neuroscience (2011) 190: 386-97). miR-124a has been shown to be involved in inflammatory nociception by regulation of relevant target proteins. (Id., citing Kynast, K L, et aql. Pain (2013) 154: 368-76). miR-143 was shown to be expressed in nociceptive neurons; it has been suggested that miR-143 could selectively contribute to mRNA regulation in specific populations of nociceptors. (Id., citing Tam, S. et al. Ell Tissue Res. (2011) 346: 163-73). A functional study showed that miR-103 is downregulated in neuropathic animals and that intrathecal applications of miR-103 successfully relieve pain. (Id., citing Favereaux, A. et al. EMBO J. (2011) 30: 3830-41). miRNA functions have also been investigated in animal models of chronic pelvic pain including of bladder pain syndrome (BPS) and irritable bowel syndrome (IBS). these studies indicate that miRNAs are involved in the onset and progression of neural sensitization and play an important role in inflammatory, neuropathic and visceral nociception. Therefore, these studies provided targets miRNAs for treatment of inflammatory, neuropathic, and visceral pain. Using cell-based models, 31 differentially expressed miRNAs were identified in bladder pain syndrome (BPS) patients and a direct correlation demonstrated between miR-449b, miR-500, miR-328, and miR-320 and a downregulation of NK1 receptor mRNA and/or protein levels. (Id., citing Sanchez Freire, et al. (2010) Am. J. Pathol. 176: 288-303). Defects in urothelial integrity resulting in leakage and activation of underlying sensory nerves are possible causative factors of bladder pain syndrome. [Id.] A possible link between miR-199a-5p expression and the control of urothelial permeability in bladder pain syndrome has been suggested. (Id., citing Monastyrskaya, K. et al. Am. J. Pathol. (2013) 182: 431-48). It has also been suggested that upregulation of miR-199a-5p and concomitant downregulation of its multiple targets might determine the impact of a tight urothelial barrier, leading to chronic bladder pain syndrome. (Id., citing Monastyrskaya, K. et al. Am. J. Pathol. (2013) 182: 431-48). In IBS patients with increased intestinal membrane permeability, increased expression of miR-29a was found in blood microvesicles, small bowel, and colon tissues. miR-29a has a complementary site in the 3'-UTRs of the glutamate-ammonia ligase gene that leads to decreased glutamine synthetase levels, increased intestinal permeability and chronic visceral pain in IBS patients. Suppressing the expression of miR-29a in vitro restored intestinal permeability. (Id., citing Zhou, Q. et al. Gut (2010) 59: 775-84).

Has-miR-29a expression was reduced in lingual nerve neuromas pf patients with higher pain visual analogue scare (VAS) scores (painful group), compared with patients with lower pain VAS scores (non-painful group. A statistically significant negative correlation was observed between the expression of both hs-miR-29a and hs-miR-500a, and the pain VAS score, indicating that reduced levels of both of these miRNAs are associated with the presence of pain. Tavares-Ferreira, D. et al. Molecular Pain (2019) 15: 1-16.

MSC EVs in Treatment of Organ Fibrosis

MSC-derived EVs have shown protective effects in several models of organ injury and fibrosis. In murine models of kidney injury, MSC-derived EVs protected against renal injury by reducing levels of creatinine, uric acid, lymphocyte response and fibrosis through shuttling miR-let7c to induce renal tubular cell proliferation (Kusuma G D, et al. Front Pharmacol. 2018; 9: 1199, citing Wang B, et al. Mol Ther. 2016 August; 24(7): 1290-301). In a murine model of carbon tetrachloride-induced hepatic injury, concurrent treatments of MSC-EVs attenuated the injury by increasing the proliferation, survival and prevented the apoptosis of hepatocytes (Id., citing Tan C Y, et al. Stem Cell Res Ther. 2014; 5(3): 76). In animal models of lung injury, MSC and hAEC-EVs have been shown to reduce pulmonary inflammation, improved lung tissue recovery and supported the proliferation of alveolar type II and bronchoalveolar stem cells (Id., citing Rubenfeld G D, et al. N Engl J Med. 2005 Oct. 20; 353(16): 1685-93; Cruz F F, et al. Stem Cells Transl Med. 2015 November; 4(11): 1302-16; Monsel A, et al. Am J Respir Crit Care Med. 2015 Aug. 1; 192(3): 324-36; Tan J L, et al. Stem Cells Transl Med. 2018 February; 7(2): 180-196). In models of stroke, MSC-EVs delivery of miR-133b directly to neurite cells reportedly enhanced the outgrowth of neurites resulting in increased proliferation of neuroblasts and endothelial cells (Id., citing Xin H, et al. Stem Cells. 2013 December; 31(12): 2737-46). Additionally, Anderson et al. showed through a comprehensive proteomic analysis that MSC-derived EVs mediated angiogenesis via NF-κB signaling (Anderson J D, et al. Stem Cells. 2016 March; 34(3): 601-13), while Zhang et al. (Stem Cells Transl Med. 2015 May; 4(5): 513-22) showed that UC MSC-EVs mediated angiogenesis via the Wnt4/β-catenin pathway. However, EV composition is determined not only by the cell type but also by the physiological state of the producer cells. This diversity of mechanisms by which EVs are generated and confer effects provides both opportunities and challenges for developing EV-based therapeutics (György B, et al. Annu Rev Pharmacol Toxicol. 2015; 55: 439-464). As described above, MSCs have been shown to be both immunosuppressive and immunostimulatory, depending on the context, and many questions about EVs remain. For example, many methods are used to isolate EVs, and EV contents and properties overlap with those of the cells of origin and other EV types. Formalizing EV nomenclature and defining attributes is a work in progress. There is a pressing need for useful standards to enable cross-lab comparisons and reproduction of results. The mechanisms of EV uptake and content delivery (or degradation) vary among EV types and recipient cell types. Elucidating and understanding these processes is critical for harnessing EVs as therapeutic delivery vehicles. Multiple lines of evidence indicate that EVs can transfer biomolecules to modulate recipient cell state in vivo, for example, following bolus injection of purified or concentrated EVs. However, the extent to which such processes naturally shape cellular function and intercellular communication, particularly under homeostatic conditions, remains poorly understood. Moreover, we do not understand the relative importance of EV-mediated transfer between proximal cells, for example, when diffusional barriers lead to local accumulation of secreted EVs rather than transfer of EVs via the circulation, where EV concentrations may be lower. EV-mediated signaling is dose-dependent (Id., citing Yu S, et al. J. Immunol. 2007; 178: 6867-75), so the tuning of EV dose may enable the balancing of potential deleterious and therapeutic effects of EV administration. Understanding the role of EV dose is also important for achieving therapeutic efficacy.

EV binding is mediated by receptors that interact with either universal EV molecules, such as lipids and carbohydrates, or specific peptides present on subsets of EVs. Following initial binding, cells internalize EVs by processes that include receptor-mediated phagocytosis or endocytosis via receptors that include T cell immunoglobulin- and mucin-domain-containing molecule-4 (TIM4), which binds to phosphatidylserine (PS) on EVs; scavenger receptors; integrins; and complement receptors (Id., citing Record M, et al. Biochem. Pharmacol. 2011; 81: 1171-82). How EV cargo is released into the cytoplasm after entry into recipient cells is unclear. Furthermore, uptake of cargo into a cell is not equivalent to cargo functionality. For instance, EVs may potentially pass through cells within the multivesicular body compartment, which could explain how EVs cross the blood-brain barrier (BBB) (i.e., via a transendothelial route). Endocytotic mechanisms must circumvent the lysosomal degradative pathway, and direct fusion between the EV and target cell plasma membrane or endocytotic membrane does not always ensure functionality of the contents. In many cases, EV cargo can be degraded by recipient cells, thereby inhibiting therapeutic delivery but limiting the impact of off-target delivery. In general, the fate of EVs within the body and cells remains poorly understood and requires additional investigation to elucidate how these processes impact functional EV-mediated delivery (Id.).

Alterations in the WNT signaling pathways are known to contribute to cellular (dys)functions in pulmonary fibrosis (Martin-Medina A, et al. Am J Respir Crit Care Med. 2018 Jul. 25, citing Konigshoff M, et al. PLoS One 2008; 3: e2142; Chilosi M, et al. Am J Pathol 2003; 162: 1495-1502; Selman M, et al. PLoS medicine 2008; 5: e62) and more recently, it has been demonstrated that secreted WNT proteins can be transported by EVs to exert their intercellular communication (Id., citing Gross J C, et al. Nat Cell Biol 2012; 14: 1036-1045). The vast majority of research has focused on the role of the WNT/β-catenin pathway in pulmonary fibrosis, which has been linked to disturbed lung epithelial cell function and impaired repair (Id., citing Konigshoff M, et al. PLoS One 2008; 3: e2142; Chilosi M, et al. Am J Pathol 2003; 162: 1495-1502; Selman M, et al. PLoS medicine 2008; 5: e62; Baarsma H A, Konigshoff M. Thorax 2017; 72: 746-759). β-catenin independent WNT signaling in lung fibrosis is much less studied. The WNT protein WNT-5A is largely known to exert its effects β-catenin independent and has been found upregulated in IPF fibroblasts (Id., citing Vuga L J, et al. Am J Respir Cell Mol Biol. 2009 November; 41(5): 583-9).

A recent study showed that lung fibroblasts are a source of EVs and demonstrate autocrine effects of EVs on fibroblast proliferation, which was enhanced by TGF-β (Id.). Similarly, MSC-derived exosomes were found to induce dermal fibroblast proliferation (Id., citing McBride J D, et al. Stem Cells Dev. 2017 Oct. 1; 26(19):1384-1398). Fibroblast-derived EVs did not promote myofibroblast differentiation, but rather decreased mRNA levels of myofibroblast markers. MSC-EVs have also been reported to suppress myofibroblast differentiation (Id., citing Fang S, et al. Stem Cells Transl Med. 2016 October; 5(10): 1425-1439). The proliferative effect of EVs on fibroblasts was to a large extent mediated by WNT-5A, as it was demonstrated that this effect could not only be attenuated by siRNA-mediated WNT-5A knockdown, but also by antibody-mediated neutralization of WNT-5A on EVs or upon destruction of EV structure (Id.). WNT transport on EVs has important implications with respect to the signaling range of WNT proteins, which is generally thought to be rather short and limited to close neighboring cells. EV-mediated transport can contribute to a larger signaling range of WNT proteins and thus determine the signaling outcome on other cells. WNT-5A has also been reported to promote processes as fibroblast adhesion (Id., citing Kawasaki A, et al. Cell Signal. 2007 December; 19(12): 2498-506) or invasion (Id., citing Waster P, et al. Int J Oncol. 2011 July; 39(1): 193-202), as well as epithelial-mesenchymal transition (Id., citing Gujral T S, et al. Cell. 2014 Nov. 6; 159(4): 844-56). WNT-5A bound EVs in IPF bronchoalveolar lavage fluid (BALF) were shown to contribute to the functional effects, thus suggesting that fibroblast derived EVs can be found in IPF BALF. This work further raises the more general question whether EVs promote lung fibrosis development or might have a protective role in vivo (Id.).

Although many of the cellular and molecular processes underlying fibrosis are understood, there are few effective therapies and fewer that target fibrogenesis specifically (Rockey D C., N Engl J Med. 2015 Mar. 19; 372(12):1138-49). Since there is no known effective treatment for fibrosis, in particular for IPF, including lung transplantation, there remains a critical need for the development of novel therapeutics. There are a variety of therapeutic approaches currently being investigated, including anti-fibrotic therapies that may slow or inhibit the body's ability to produce scar or fibrotic tissue and pulmonary vasodilators to increase the tissue area for gas exchange in the lung. Aside from lung transplantation, potential IPF treatments have included corticosteroids, azathioprine, cyclophosphamide, anticoagulants, and N-acetylcysteine (Raghu G. et al., Am J Respir Crit Care Med., 183(6): 788-824, 2011). In addition, supportive therapies such as oxygen therapy and pulmonary rehabilitation are employed routinely. However, none of these have definitely impacted the long term survival of IPF patients, which further highlights the unmet medical need for treatment options in IPF. As an example, despite mixed clinical program results, InterMune's oral small-molecule Esbriet® (pirfenidone) received European and Japanese approvals for patients with IPF. Esbriet® thus became the first medication specifically indicated for the treatment of IPF; due to equivocal trial outcomes and drug side effects, the drug's utility is viewed with skepticism in the United States, and did not receive an FDA approval based on the data submitted at that time. A large, double-blind, placebo-controlled phase 3 clinical trial to assess the safety and efficacy of pirfenidone in patients with IPF was completed in 2017.

The described invention provides another therapeutic approach.

SUMMARY OF THE INVENTION

According to one aspect, the described invention provides a composition comprising a population of isolated EVs transfected with an miR-29a mimic, an miR-199-3p inhibitor, or both, wherein the EVs are derived from mesenchymal stem cells (MSCs). According to some embodiments, the miR-29a mimic has at least about 70% sequence homology with SEQ ID NO: 1. According to some embodiments, the miR-199-3p inhibitor has at least about 70% sequence homology with SEQ ID NO: 2. According to some embodiments, the MSCs are obtained from a human subject. According to some embodiments, the MSCs are derived from a tissue selected from the group consisting of amniotic membrane, chorionic membrane, umbilical cord tissue, bone marrow, and adipose tissue. According to some embodiments, the EVs are characterized by: sedimentation at about 100,000×g, a buoyant density in sucrose of about 1.10-1.21 g/ml, and an average diameter of from about 30 nm to about 200 nm. According to some embodiments, the average diameter of the EVs ranges from about 140 nm to about 150 nm.

According to some embodiments, the composition is a pharmaceutical composition comprising: (i) a therapeutic amount of the composition according to claim 1; and (ii) a pharmaceutically acceptable carrier. According to some embodiments, the pharmaceutical composition is formulated for administration by inhalation. According to some embodiments, the pharmaceutically acceptable carrier comprises a pulmonary surfactant. According to some embodiments, the pharmaceutical composition is formulated for intravenous administration. According to some embodiments, the pharmaceutical composition further comprises one or a combination of an immunomodulator, an analgesic, an anti-inflammatory agent, an anti-fibrotic agent, or a proton pump inhibitor. According to some embodiments, the immunomodulator is a corticosteroid. According to some embodiments, the corticosteroid is selected from prednisone, azathioprine, mycophenolate, mycophenolate mofetil, colchicine, interferon-gamma 1b, and combinations thereof. According to some embodiments, the analgesic is selected from codeine, hydrocodone, oxycodone, methadone, hydromorphone, morphine, fentanyl, and combinations thereof. According to some embodiments, the anti-inflammatory agent is selected from aspirin, celecoxib, diclofenac, diflunisal, etodolac, ibuprofen, indomethacin, ketoprofen, ketorolac nabumetone, naproxen, nintedanib, oxaprozin, pirfenidone, piroxicam, salsalate, sulindac, tolmetin, and combinations thereof. According to some embodiments, the anti-fibrotic agent is selected from nintedanib, pirfenidone, and combinations thereof. According to some embodiments, the proton pump inhibitor is selected from omeprazole, lansoprazole, dexlansoprazole, esomeprazole, pantoprazole, rabeprazole, ilaprazole, and combinations thereof.

According to another aspect, the described invention provides a method of treating a fibrotic condition of an organ in a subject in need thereof comprising administering to the subject a therapeutic amount of a pharmaceutical composition comprising a population of synthetic EVs comprising an miR-29a mimic, an miR-199-3p inhibitor, or both, and a pharmaceutically acceptable carrier, wherein the EVs are derived from mesenchymal stem cells (MSCs), and wherein the pharmaceutical composition is effective to upregulate expression of miR-29a, downregulate miR-199-3p, or both. According to some embodiments, the upregulated expression of miR-29a is effective to decrease expression of MMP-2. According to some embodiments, the downregulated expression of miR-199-3p is effective to upregulate CAV-1 expression. According to some embodiments, the miR-29a mimic has at least about 70% sequence homology with SEQ ID NO: 1. According to some embodiments, the miR-199-3p inhibitor has at least about 70% sequence homology with SEQ ID NO: 2.

According to some embodiments, the MSCs are obtained from a human subject. According to some embodiments, the MSCs are derived from a tissue selected from the group consisting of amniotic membrane, chorionic membrane, umbilical cord tissue, bone marrow, and adipose tissue. According to some embodiments, the EVs are characterized by: sedimentation at about 100,000×g, a buoyant density in sucrose of about 1.10-1.21 g/ml, and an average diameter of from about 30 nm to about 200 nm. According to some embodiments, the average diameter of the EVs ranges from about 140 nm to about 150 nm.

According to some embodiments, the fibrotic condition of an organ is a fibrotic condition of lung, heart, kidney, nerves, the central nervous system, or liver. According to some embodiments, the fibrotic condition of lung is interstitial lung disease. According to some embodiments, the fibrotic condition of lung is pulmonary fibrosis. According to some embodiments, the pulmonary fibrosis is idiopathic pulmonary fibrosis (IPF). According to some embodiments, the step of administering occurs nasally, intratracheally, orally, parenterally, or by inhalation.

According to some embodiments, the pharmaceutical composition further comprises at least one additional therapeutic agent. According to some embodiments, the additional therapeutic agent is selected from one or a combination of an immunomodulator, an analgesic, an anti-inflammatory compound, an anti-fibrotic compound, or a proton pump inhibitor. According to some embodiments, the immunomodulator is a corticosteroid. According to some embodiments, the corticosteroid is selected from prednisone, azathioprine, mycophenolate, mycophenolate mofetil, colchicine, interferon-gamma 1b, and combinations thereof. According to some embodiments, the analgesic is selected from capsaicin; codeine, hydrocodone, lidocaine, oxycodone, methadone, hydromorphone, morphine, fentanyl, and combinations thereof. According to some embodiments, the anti-inflammatory agent is selected from aspirin, celecoxib, diclofenac, diflunisal, etodolac, ibuprofen, indomethacin, ketoprofen, ketorolac nabumetone, naproxen, nintedanib, oxaprozin, pirfenidone, piroxicam, salsalate, sulindac, tolmetin, and combinations thereof. According to some embodiments, the anti-fibrotic agent is selected from nintedanib, pirfenidone, and combinations thereof. According to some embodiments, the proton pump inhibitor is selected from omeprazole, lansoprazole, dexlansoprazole, esomeprazole, pantoprazole, rabeprazole, ilaprazole, and combinations thereof. According to some embodiments, the subject also receives oxygen therapy.

According to some embodiments, a method of preparing the pharmaceutical composition comprises: isolating a population of mesenchymal stem cells (MSCs) from a tissue sample; transfecting the isolated population of MSCs in (a) with one or more plasmids comprising an miR-29a mimic, an miR-199-3p inhibitor, or both; preparing a purified population of EVs comprising the miR-29a mimic, miR-199-3p inhibitor, or both from the isolated population of MSCs in (b); and adding a pharmaceutically acceptable carrier to form the pharmaceutical composition. According to some embodiments, the MSCs are obtained from a human subject. According to some embodiments, the MSCs are derived from a tissue selected from the group consisting of amniotic membrane, chorionic membrane, umbilical cord tissue, bone marrow, and adipose tissue. According to some embodiments, the EVs are purified by one or more of: a) ultracentrifugation; b) sucrose density gradient centrifugation; c) column chromatography; d) size exclusion; or e) filtration through a device containing an affinity matrix selective towards the EVs. According to some embodiments, the EVs are characterized by: sedimentation at about 100,000×g, a buoyant density in sucrose of about 1.10-1.21 g/ml, and an average diameter of from about 30 nm to about 200 nm. According to some embodiments, the average diameter of the EVs ranges from about 140 nm to about 150 nm. According to some embodiments, the EVs comprise microvesicles whose diameter is >200 nm.

According to another aspect, the described invention provides a precision medicine method for optimizing therapeutic benefit for a subject, comprising: obtaining a urine sample from the subject and from a healthy control; isolating EVs from the urine sample obtained from the subject and healthy control; measuring a level of expression of each of a plurality of miRNAs in the EVs from the urine sample from the subject and in the EVs from the urine sample from the healthy control; determining that expression of the one or more of the miRNAs in the EVs from the subject is dysregulated compared to the healthy control; identifying the patient as one that can benefit therapeutically from being treated for a fibrotic disease: (1) when the presence of one or more dysregulated miRNAs in the EVs from the urine sample obtained from the subject is detected; (2) when an increase in levels of one or more WNT proteins in the EVs from the urine sample from the subject compared to the control is detected; or (3) when the presence of one or more dysregulated miRNAs and an increase in levels of one or more WNT proteins in the EVs from the urine sample from the subject compared to the control is detected; and tailoring an effective medical treatment for the fibrotic disease based on genetic, environmental and lifestyle factors.

According to some embodiments, the dysregulated miRNAs comprise one or more of miR-134-5p, miR-196b-5p, miR-629-5p, miR-206, miR-192-5p, miR-320c, miR-125a-3p, miR-215-5p, miR-642a-3p, miR-576-3p, miR-3679-5p, miR-134-5p, miR-196b-5p, miR-629-5p, or miR-206. According to some embodiments, the one or more miRNAs is downregulated compared to the healthy control. According to some embodiments, the one or more miRNAs is upregulated compared to the healthy control. According to some embodiments, the EVs are characterized by: sedimentation at about 100,000×g, a buoyant density in sucrose of 1.10-1.21 g/ml, and an average diameter of from 30 nm to about 200 nm. According to some embodiments, the average diameter of the EVs ranges from about 140 nm to about 150 nm.

According to some embodiments, the method further comprises the step of detecting a level of expression of one or more WNT proteins in the EVs from the urine samples and determining that expression of one or more of the WNT proteins in the urine sample from the subject is dysregulated compared to the healthy control. According to some embodiments, the one or more WNT proteins comprise WNT-5A.

According to some embodiments, the method further comprises obtaining a blood or serum sample from the subject and from the healthy control; detecting a level of expression of one or more biomarkers selected from KL-6/MUC1, SP-A, SP-D, CCL18, MMP-1, and MMP-7 in the samples; and comparing the levels of expression of the one or more biomarkers in the samples from the subject and from the healthy control; wherein an increase in the levels of the one or more biomarkers in the sample from the subject compared to the healthy control indicates a poor prognosis in the subject.

According to some embodiments, the method further comprises the steps of obtaining a bronchoalveolar lavage fluid (BALF) sample from the subject and from the healthy control; isolating EVs from the BALF samples; detecting a level of expression of one or more WNT proteins in the EVs; and comparing the level of expression of the one or more WNT proteins in the EVs from the subject and from the healthy control; wherein an increase in the levels of the one or more WNT proteins in the EVs from the subject indicates the subject has a fibrotic disease. According to some embodiments, the one or more WNT proteins comprise WNT-5A.

According to some embodiments, the fibrotic disease is selected from one or more of a fibrotic lung disease, a fibrotic cardiac disease, a fibrotic renal disease, a fibrotic hepatic disease, a fibrotic skin disease, a fibrotic pancreatic disease, a fibrotic eye disease, a fibrotic joint disease, a fibrotic bone marrow disease, a fibrotic brain disease, a fibrotic intestinal disease, a fibrotic peritoneum disease, a fibrotic retroperitoneum disease, a fibrotic condition of the nerves or nervous system (e.g, CNS, PNS, ANS), a nerve compression, or an injury due to fibrosis. According to some embodiments, the fibrotic disease is a fibrotic lung disease.

According to another aspect, the described invention provides a method of diagnosing and treating a fibrotic disease in a subject in need thereof comprising (a) obtaining a urine sample from the subject and from a healthy control; (b) isolating EVs from the urine sample obtained from the subject and healthy control; (c) detecting a level of expression of miRNAs in the EVs from the urine sample from the subject and in the EVs from the urine sample from the healthy control; (d) determining that expression of one or more of the miRNAs in the EVs from the subject is dysregulated compared to the healthy control; and (e) identifying the subject as one that can benefit therapeutically from being treated for a fibrotic disease: (i) when the presence of one or more dysregulated miRNAs in the EVs from the urine sample obtained from the subject is detected; (ii) when an increase in levels of one or more WNT proteins in the EVs from the urine sample from the subject compared to the healthy control is detected; or (iii) when the presence of one or more dysregulated miRNAs and an increase in levels of one or more WNT proteins in the EVs from the urine sample from the subject compared to the healthy control is detected; and (f) administering a therapeutic amount of a pharmaceutical composition comprising either: (i') at least about 1×108 whole MSCs comprising synthetic exosomes comprising a therapeutic amount of an miR-29a mimic, an miR-199-3p inhibitor, or both to the diagnosed subject; or (ii') a therapeutic amount of a purified and enriched population of synthetic exosomes comprising an miR-29a mimic, an miR-199-3p inhibitor, or both to the diagnosed subject; wherein the therapeutic amount is effective to upregulate expression of miR-29a, to downregulate expression of miR-199-3p, or both, and to effectively treat the fibrotic disease.

According to some embodiments, the sequence of the miR-29a mimic is at least about 70% homologous with SEQ ID NO: 1. According to some embodiments, the sequence of the miR-199-3p inhibitor is at least about 70% homologous with SEQ ID NO: 2. According to some embodiments, the upregulated expression of miR-29a is effective to decrease expression of MMP-2. According to some embodiments, the downregulated expression of miR-199-3p is effective to upregulate CAV-1 expression. According to some embodiments, the fibrotic disease is selected from one or more of a fibrotic lung disease, a fibrotic cardiac disease, a fibrotic renal disease, a fibrotic hepatic disease, a fibrotic skin disease, a fibrotic pancreatic disease, a fibrotic eye disease, a fibrotic joint disease, a fibrotic bone marrow disease, a fibrotic brain disease, a fibrotic intestinal disease, a fibrotic peritoneum disease, a fibrotic retroperitoneum disease, a fibrotic condition of the nerves or nervous system (e.g, CNS, PNS, ANS), a nerve compression, or an injury due to fibrosis. According to some embodiments, the fibrotic disease is fibrotic lung disease.

According to another aspect, the described invention provides a method of treating a fibrotic disease in a subject in need thereof comprising administering to the subject a therapeutic amount of a pharmaceutical composition comprising a population of synthetic EVs comprising an miR-29a mimic, an miR-199-3p inhibitor, or both, and a pharmaceutically acceptable carrier, wherein the EVs are derived from mesenchymal stem cells (MSCs), and wherein the pharmaceutical composition is effective to upregulate expression of miR-29a, downregulate miR-199-3p, or both. According to some embodiments, the upregulated expression of miR-29a is effective to decrease expression of MMP-2. According to some embodiments, the downregulated expression of miR-199-3p is effective to upregulate CAV-1 expression. According to some embodiments, the miR-29a mimic has at least about 70% sequence homology with SEQ ID NO: 1. According to some embodiments, the miR-199-3p inhibitor has at least about 70% sequence homology with SEQ ID NO: 2.

According to some embodiments, the MSCs are obtained from a human subject. According to some embodiments, the MSCs are derived from a tissue selected from the group consisting of amniotic membrane, chorionic membrane, umbilical cord tissue, bone marrow, and adipose tissue. According to some embodiments, the EVs are characterized by: sedimentation at about 100,000×g, a buoyant density in sucrose of about 1.10-1.21 g/ml, and an average diameter of from about 30 nm to about 200 nm. According to some embodiments, the average diameter of the EVs ranges from about 140 nm to about 150 nm. According to some embodiments, the fibrotic disease is selected from one or more of a fibrotic lung disease, a fibrotic cardiac disease, a fibrotic renal disease, a fibrotic hepatic disease, a fibrotic skin disease, a fibrotic pancreatic disease, a fibrotic eye disease, a fibrotic joint disease, a fibrotic bone marrow disease, a fibrotic brain disease, a fibrotic intestinal disease, a fibrotic peritoneum disease, a fibrotic retroperitoneum disease, a fibrotic condition of the nerves or or nervous system (e.g, CNS, PNS, ANS), a nerve compression, or an injury due to fibrosis. According to some embodiments, the fibrotic disease is fibrotic lung disease.

According to some embodiments, the step of administering occurs nasally, intratracheally, orally, parenterally, topically, or by inhalation. According to some embodiments, the pharmaceutical composition further comprises at least one additional therapeutic agent. According to some embodiments, the additional therapeutic agent is selected from one or a combination of an immunomodulator, an analgesic, an anti-inflammatory compound, an anti-fibrotic compound, or a proton pump inhibitor. According to some embodiments, the immunomodulator is a corticosteroid. According to some embodiments, the corticosteroid is selected from prednisone, azathioprine, mycophenolate, mycophenolate mofetil, colchicine, interferon-gamma 1b, and combinations thereof. According to some embodiments, the analgesic is selected from capsaisin, codeine, hydrocodone, oxycodone, methadone, hydromorphone, lidocaine, morphine, fentanyl, resiniferatoxin, and combinations thereof. According to some embodiments, the anti-inflammatory agent is selected from aspirin, celecoxib, diclofenac, diflunisal, etodolac, ibuprofen, indomethacin, ketoprofen, ketorolac nabumetone, naproxen, nintedanib, oxaprozin, pirfenidone, piroxicam, salsalate, sulindac, tolmetin, and combinations thereof. According to some embodiments, the anti-fibrotic agent is selected from nintedanib, pirfenidone, and combinations thereof. According to some embodiments, the proton pump inhibitor is selected from omeprazole, lansoprazole, dexlansoprazole, esomeprazole, pantoprazole, rabeprazole, ilaprazole, and combinations thereof.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2A: Changes in mean % predicted FVC for overall study period. FIG. 2B: Changes in % predicted diffusing capacity of the lungs for carbon monoxide (Dlco). FIG. 2C: Changes in 6-min walk test (6-MWT) distance. N=7 for all data. FIG. 2D: A representative HRCT scan at baseline, week 24, and week 48, showing decreasing fibrotic reticulation in all lobes at $100 \times 10^6$ dose.

FIG. 3A: Representative μCT transverse and coronal lung sections acquired from aged (22 month-old) male C57BL/6 mice at baseline (left) and 7 days following intratracheal bleomycin (BLM, 2.0 units/kg) administration (right) demonstrating increased lung density and loss of airspaces. FIG. 3B: Saline treatment did not result in evidence of lung injury on μCT scan at baseline (left) or 7 days post-instillation (right).

FIG. 4A-FIG. 4E show that allogeneic adipose-derived mesenchymal stem cells (ASCs) administered 12 days after bleomycin (BLM)-instillation reduce severity of pulmonary fibrosis and collagen content in aged mice. Histological sections of lung tissue were stained with Masson's-Trichrome. FIGS. 4A and 4B show representative photomicrographs (20× and 40× magnification) of lung sections from saline-treated control mice (FIG. 4A) and BLM-treated mice (FIG. 4B). FIG. 4C: Administration of ASCs 12 days after BLM-instillation resulted in reduced severity of pulmonary fibrosis. FIG. 4D: Degree of pulmonary fibrosis on histological sections was measured by semi-quantitative Ashcroft score. BLM instillation resulted in increased Ashcroft score compared to saline controls. Treatment with ASCs 12 days following BLM administration resulted in decreased Ashcroft score. FIG. 4E: Intratracheal BLM instillation increased lung collagen content as measured by hydroxyproline assays. Mice treated with ASCs on day 12 post-BLM had decreased lung collagen content compared to BLM only controls. Data are graphed as mean±standard error of the mean (n=6-8/group). *$P<0.05$; $P<0.01$; *$P<0.001$; ****$P<0.0001$.

FIG. 6C: BLM lung injury resulted in increased MMP-2 activity in lungs of aged C56Bl/6 mice measured at 21-day sacrifice. Intravenous infusion of ASCs on day 12 post-BLM resulted in decreased MMP-2 activity compared to BLM-only control mice. Zymography was performed on protein extracts from lung tissue from saline, BLM or BLM+ASC treated mice exposure to measure MMP-2 activity. Insert (top) is a representative zymogram of 2 mice per group. Data are graphed as the mean±standard error of the mean of n=3/group. *P<0.05. FIG. 6D: Cav-1 protein expression was determined by western analysis. Inset (top) is a representative western blot of two mice per group and β-actin loading control. Data are graphed as mean±standard error of the mean (n=3/group).

FIG. 9A compares ERα protein expression for pre-menopausal and post-menopausal tissue. FIG. 9B compares ERβ protein expression for pre-menopausal and post-menopausal tissue. FIG. 9C (premenopausal) and FIG. 9D (post-menopausal) show the ratio of luciferase/B-gal for samples V, 0.1, 1, 1, 10, ICI (ICI 182,780 stands for filvestrant, an estrogen receptor antagonist), E2 is estradiol; 1ICI/E2(1) and ICI/E2 (10) in nM concentration.

FIG. 11 panels 1, 5, 9: control-preASCs; FIG. 11 panels 2, 6, 8: pre-ASCs transfected with catalase inhibitor ("inh."); FIG. 11 panels 3, 7, 10: post-ASC control; FIG. 11 panels 4, 8, 12: post-hASCs transfected with catalase activator. Infusion of pre-hASC transfected with inhibitor (hASCs+inh, FIG. 11 panels 6 and 8) did not reduce severity of fibrosis in the lung compared to post-hASCs transfected with catalase activator (hASCs+activator, FIG. 11, panels 10 and 12).

FIG. 13A is a plot showing % wound healing on the Y-axis; the x axis identifies the samples tested: control media, pre-menopausal human ASC (control); inhibitor at 48 hours, inhibitor for 72 hours, control post-human-ASCs; activator at 48 hours, and activator at 72 hours. FIG. 13B shows tissue treated (from top to bottom) with Control media (a). pre-hASC control (b); pre-hASC+inhibitor (c), post-hASC control (d); and post-hASC+activator. The white arrows indicate wound edges after initial wounding. The red arrowheads point at the epithelialized edges of the migrating fronts 4 days after wounding. Scale bar=200 μm.

FIG. 15A-FIG. 5F panels A, B, C, D, E, and F are pictures showing the effects of IPF and non-IPF lung fibroblast-derived EVs on representative ex vivo lung punches from an aging male mouse at 20× (panels A, B, C) and 40× (panels D, E, F). Panels A and D, media control; Panels B and E, IPF lung fibroblast-derived exosomes; Panels C and F, non-IPF lung fibroblast derived exosomes.

FIG. 16A: Ashcroft score; FIG. 16B hydroxyproline (collagen content) P<0.05.

FIG. 18A-FIG. 18C is a representative picture showing that EVs performed equally to whole cell MSCs in an ex vivo wound healing assay. FIG. 18A, whole cell MSC; FIG. 18B exoxomes; FIG. 18C control.

FIG. 19A shows representative pictures from BLM control (panel 1), BLM+hASC whole cell (panel 2), BLM+hASC exosomes (panel 3); BLM+mASC (panel 4); and BLM+mASC exosomes (panel 5). FIG. 19B is a graph comparing Ashcroft scores. FIG. 19C is a graph comparing collagen content.

Figure 21A:
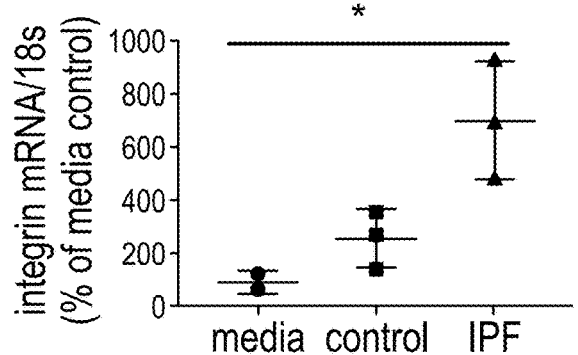
FIG. 21A-FIG. 21E shows the results of analysis of exosomes injected into punches from the urine from healthy subjects (control) and IPF patients for integrin mRNA expression (FIG. 21A), collagen type 1α1 mRNA expression (FIG. 21B), profibrotic c-Jun protein expression (FIG.
Figure 21B:
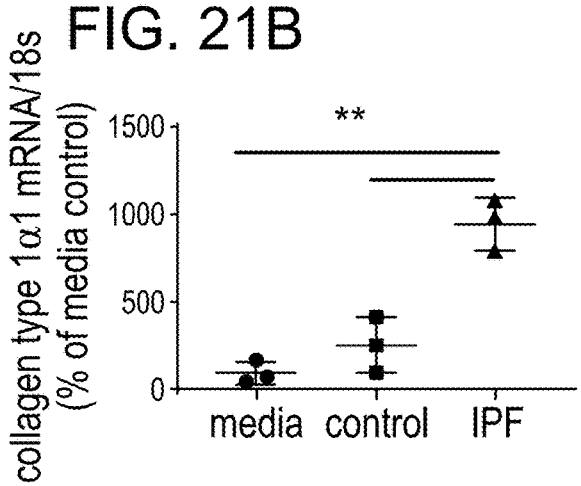
Figure 21C:
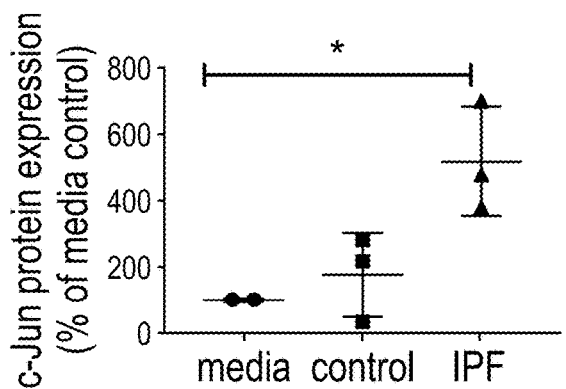
Figure 21D:
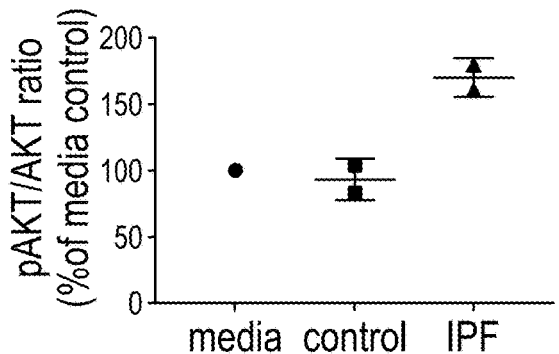
Figure 21E:
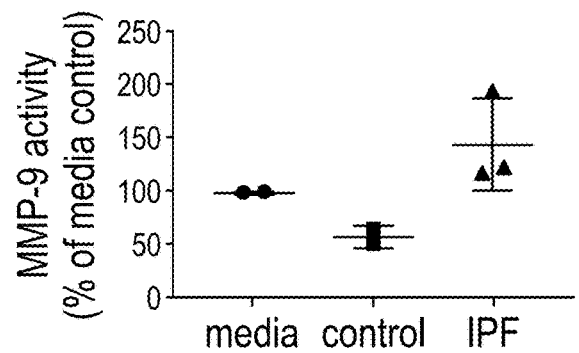

21C); pAK/pAKT ratio (FIG. 21D); and MMP-9 activity (FIG. 21E) compared to a media control The results show that IPF urine exosomes show increased integrin mRNA expression, collagen type 1α1 mRNA expression, c-Jun protein expression, pAKT/AKT protein expression, and MMP-9 activity compared to media and normal controls.

Figure 22:
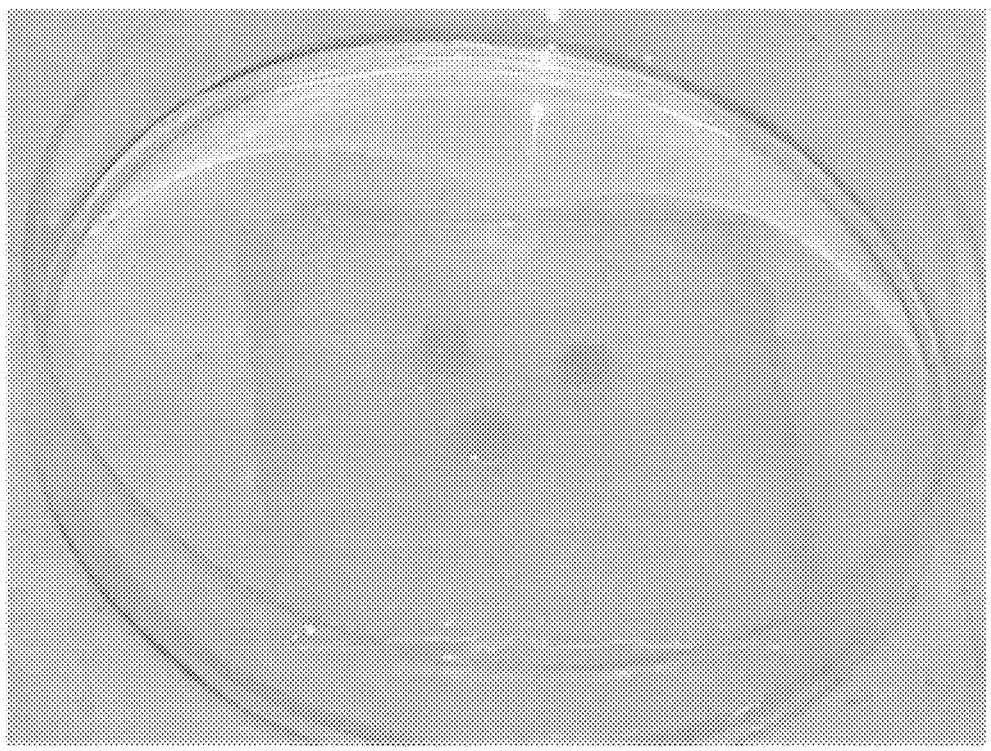

FIG. 22 shows photographs of ex vivo lung punches (4 mm) from the agarose-infused young and old mouse lungs that were injected with ASC derived exosomes and collected after 4 days.

FIG. 23A-FIG. 23H shows results obtained when exosomes derived from young ASCs were injected into lung punches isolated from day 10 post-BLM treated lung (right panels). Media control (left panels) received treatment with media only. Results show that punches treated with ASC exosomes (FIG. 23B) display reduced a smooth muscle actin expression compared to the control (FIG. 23A). The ASC exosomes treated punches also show an increase in anti-fibrotic CAV-1 (FIG. 23D) compared to the control (FIG. 23C); and a decrease in pro-fibrotic c-Jun (FIG. 23F) compared to the control (FIG. 23E). No modification in β actin was detected (FIG. 23H, FIG. 23G) This demonstrates that treatment of ex vivo lung punches with ASC exosomes modifies ex vivo lung punch tissue.

Figure 24A:
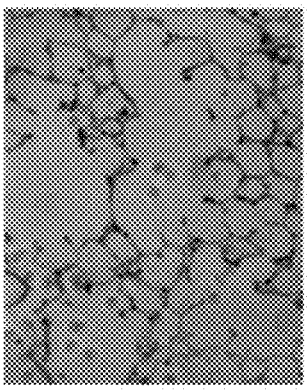
Figure 24B:
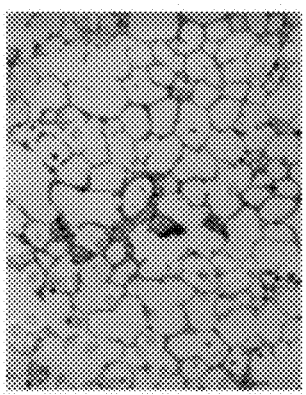
Figure 24D:
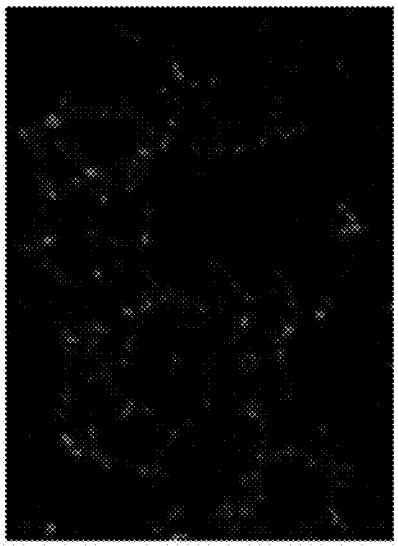
Figure 24C:
Figure 24F:
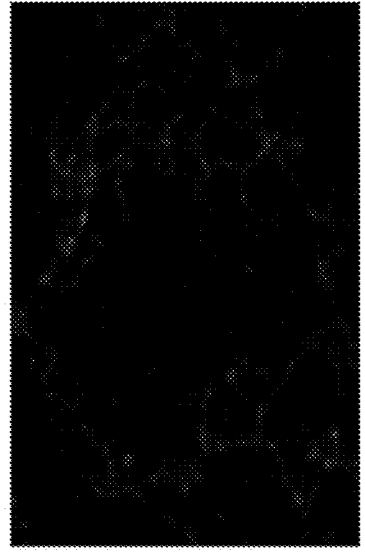
Figure 24E:
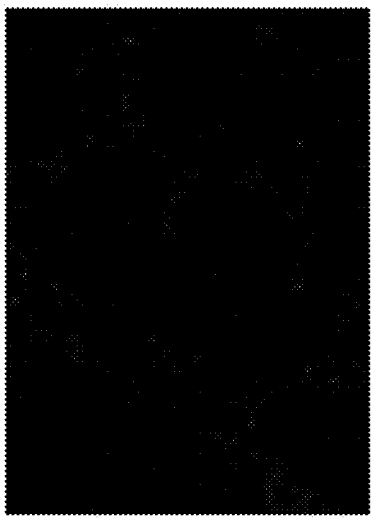

FIG. 24A-FIG. 24F left panels show ex vivo mouse punches injected with a media control; right panels show punches injected with ASC exosomes. FIG. 24A and FIG. 24B show trichrome histology of ex vivo mouse punches following contact with a media control (FIG. 24A) and ASC exosomes (FIG. 24B). FIG. 24C, 24D show results of immunofluorescent staining for surfactant protein C (SPC). Surfactant proteins are mainly expressed by distal lung epithelial cells. SPC is a pulmonary surfactant protein. SPC therefore was used as a marker for alveolar cell regeneration. FIG. 24E (control), and FIG. 24F show results of immunofluorescent staining for aquaporin 5 (AQP5). Aquaporin is a water channel protein, which plays a role in the generation of pulmonary secretions. Punches treated with ASC exosomes express increased Surfactant Protein C (SPC) and Aquaporin 5 (AQP5) compared to the control. The left panels show a few alveolar type 2 cells. The right panels show an increase in both alveoloar type 1 and type 2 cells, mostly type 2, with a little of type 1. This demonstrates that punch treatment with ASC exosomes increases expression of alveolar cell type 2 and type 1.

FIG. 25A-FIG. 25E shows results of experiments in which exosomes derived from either fibroblasts isolated from young male control lungs or myofibroblasts isolated from IPF lungs were injected into a naïve aging mouse lung punch and parameters associated with pulmonary fibrosis, namely integrin, miR-29, c-jun protein, ERα, and CAV-1 protein levels measured. FIG. 25 shows that expression of integrin mRNA, MIR-29a, Caveolin-1 protein; c-June protein; and estrogen receptor alpha, all of which are markers for IPF, were altered in the exosomes from patients with IPF compared to the normal control. More specifically, the level of integrin mRNA was increased (FIG. 25A), miR-29 decreased (FIG. 25B), antifibrotic CAV-1 protein decreased (FIG. 25C), profibrotic c-jun protein increased (FIG. 25D), ERα protein increased (FIG. 25E) compared to a media control and exosomes prepared from control lung fibroblasts. EVs from control lungs increased CAV-1 protein, an anti-fibrotic marker.

FIG. 26A-FIG. 26D shows results of experiments in which exosomes derived from the urine of subjects without lung disease (control) or from the urine of patients with IPF were injected into naïve aging mouse punches. The result show that EVs derived from the urine of patients with IPF likewise display an increase in integrin mRNA expression (FIG. 26A), an increase in collagen 1α1 mRNA expression (FIG. 26 B); an increase in profibrotic c-Jun protein expression (FIG. 26C) and an increase in the ratio of pAKT/AKT (FIG. 26D) compared to a urine control and a media control.

Figure 27A:
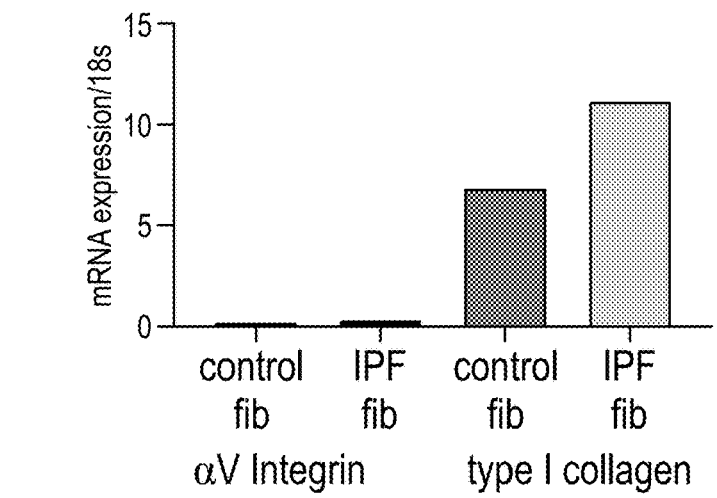
Figure 27B:
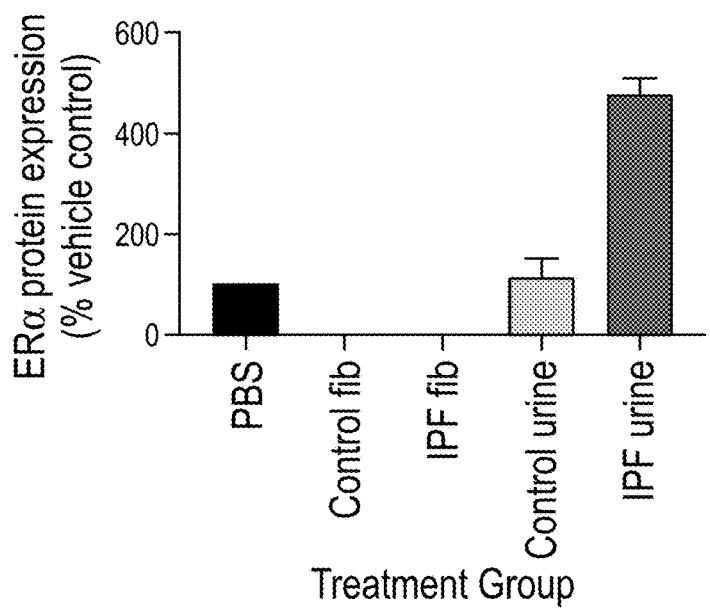
Figure 27C:
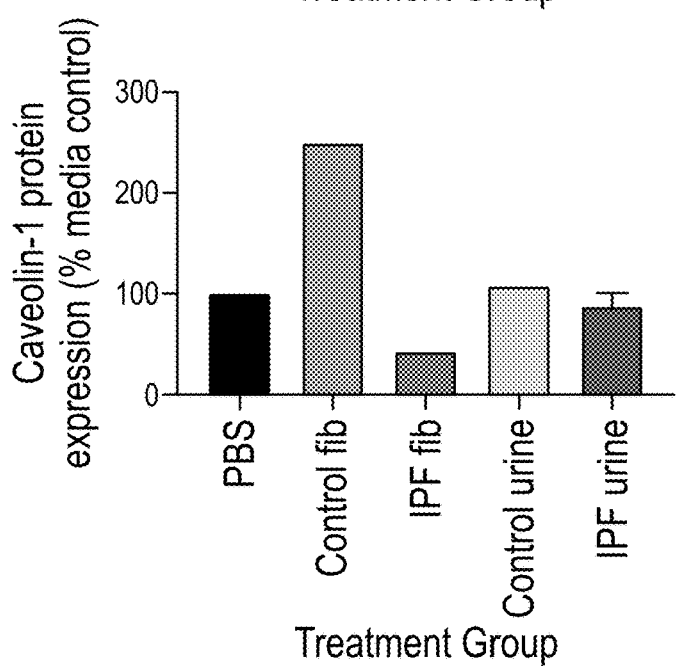

FIG. 27A-FIG. 27C shows results obtained when human lung punches were injected with exosomes derived from normal fibroblasts (control fib) and exosomes derived from IPF lung myofibroblasts (IPF fib) and collected 4 days later. Punches were processed for mRNA and protein expression. FIG. 27A shows that expression of αV integrin and of type I collagen in lungs injected with IPF fibroblast-derived exosomes is increased compared to the control. FIG. 27B shows that ERα protein expression in punches contacted with IPF urine was increased compared to controls. FIG. 27C shows that anti-fibrotic caveolin-1 protein expression was decreased in IPF urine and IPF fib samples compared to the controls.

Figures 28A, 28B, 28C, 28D, 28E:
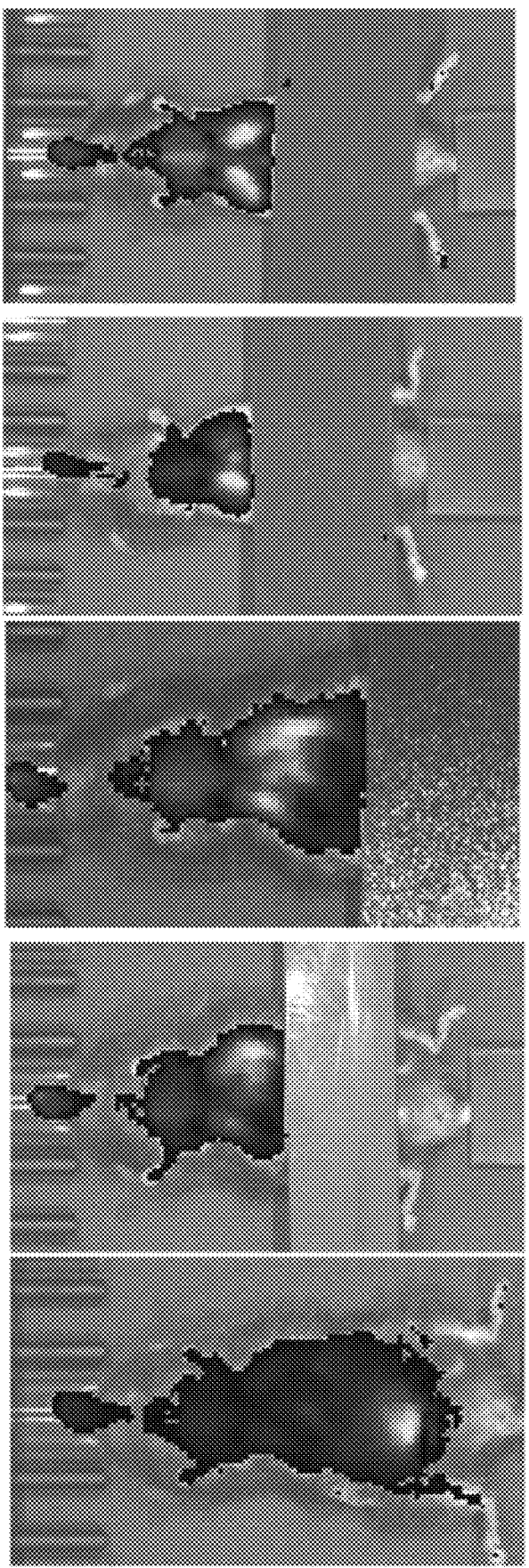

FIG. 28A -FIG. 28E, 28B, 28C, 28D, and 28E show time course of distribution of ExoGlowTM labeled exosomes injected via tail vein in a mouse 8 days after treatment with BLM. FIG. 28A, distribution after 5 minutes. As shown in FIG. 28B, after 30 minutes, the distribution of ExoGlow™ indicates migration of exosomes to the lungs. FIG. 28C shows the distribution at 2 hours. FIG. 28D shows distribution at 8 hours. FIG. 28E shows that at 20 hours, the distribution of ExoGlow indicates migration of exosomes to the kidneys.

FIG. 29A-FIG. 29D We studied two doses of ExGlow™ by transfusing 90 μg (FIG. 29 left hand side of each panel) and 40 μg (FIG. 29 right hand side of each panel) exosome dosages to mice and tracked the distribution of the labeled exosomes over a 24 hour period (panel A, 60 minutes; panel B, 90 minutes, panel C 6 hours; panel D 24 hours. The results show more vivid ExoGlow™ fluorescence at the 90 μg dosing.

Figure 30:
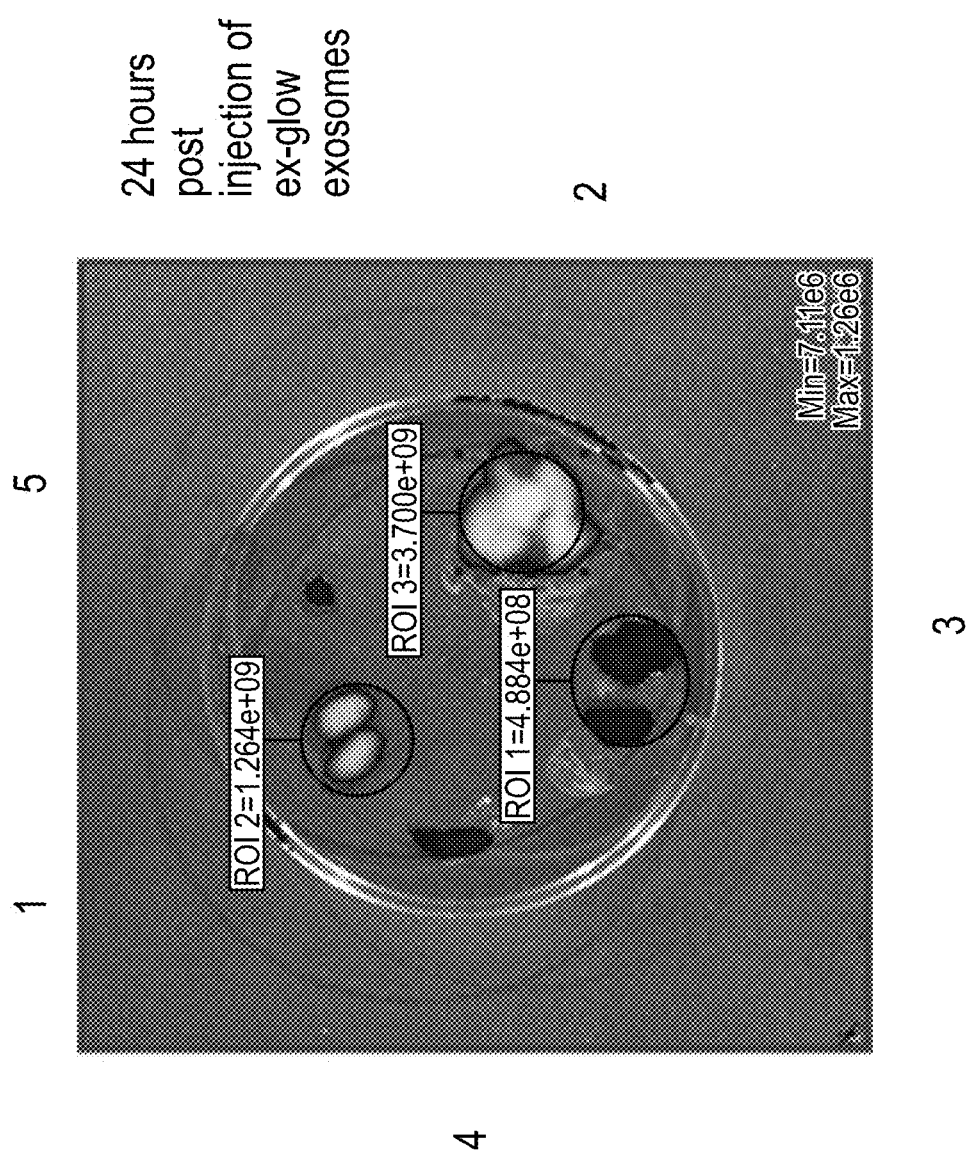

We sacrificed the ExoGlow™ mice, and studied ExoGlow™ fluorescence in the mouse lung after 24 hours. FIG. 30 shows the vivid Exo-Glow™ fluorescence 24 hours post-injection of Exo-Glow™ exosomes in kidney (1) and liver (2) at the 90 μg dosing. At 24 hour, exosomes cannot be detected in the lungs, spleen and heart ((3, 4, 5) at the 90 μg dosing.

Mouse lung punch was injected with exosomes containing nanoparticles and then examined by electron microscopy. Electron micrographs of Type II alveolar epithelial cells with exosomes containing nanoparticles are shown in FIG. 31A, FIG. 31B (higher magnification), FIG. 32A and FIG. 32B (higher magnification). FIG. 31A and FIG. 31B show the exosomes membrane opposed to the membrane of the type I alveolar epithelial cell, and the nanoparticles are seen within the alveolar epithelial cell. The arrows in FIG. 31A, FIG. 31B (higher magnification) show that the exosomes cell membrane is still intact. FIG. 32A and FIG. 32B show exosomes containing nanoparticles being engulfed.

DETAILED DESCRIPTION OF EMBODIMENTS

As used herein and in the appended claims, the singular forms "a", "an", and "the" include plural reference unless the context clearly dictates otherwise. Thus, for example, reference to a "peptide" is a reference to one or more peptides and equivalents thereof known to those skilled in the art, and so forth.

As used herein, the term "about" means plus or minus 20% of the numerical value of the number with which it is being used. Therefore, about 50% means in the range of 40%-60%.

The term "adipocyte" as used herein refers to the functional cell type of fat, or adipose tissue that is found throughout the body, particularly under the skin. Adipocytes store and synthesize fat for energy, thermal regulation and cushioning against mechanical shock. Although the lineage of adipocytes is still unclear, it appears that mesenchymal stem cells can differentiate into two types of lipoblasts, one that give rise to white adipocytes and the other to brown adipocytes. Both types of adipocytes store fat. Adipose tissue may be brown or white adipose tissue, derived from, for example, subcutaneous, omental/visceral, mammary, gonadal, periorgan or other adipose tissue site.

The term "adipose stem cell," "adipose-derived stem cell," or "ASC" as used herein refers to pluripotent stem cells, mesenchymal stem cells, and more committed adipose progenitors and stroma obtained from adipose tissue.

"Administering" when used in conjunction with a therapeutic means to give or apply a therapeutic directly into or onto a target organ, tissue or cell, or to administer a therapeutic to a subject, whereby the therapeutic positively impacts the organ, tissue, cell, or subject to which it is targeted. Thus, as used herein, the term "administering", when used in conjunction with EVs or compositions thereof, can include, but is not limited to, providing EVs into or onto the target organ, tissue or cell; or providing EVs systemically to a patient by, e.g., intravenous injection, whereby the therapeutic reaches the target organ, tissue or cell. "Administering" may be accomplished by parenteral, oral or topical administration, by inhalation, or by such methods in combination with other known techniques.

The term "allogeneic" as used herein refers to being genetically different although belonging to or obtained from the same species.

The term "alveolus" or "alveoli" as used herein refers to an anatomical structure that has the form of a hollow cavity. Found in the lung, the pulmonary alveoli are spherical outcroppings of the respiratory sites of gas exchange with the blood. The alveoli contain some collagen and elastic fibers. Elastic fibers allow the alveoli to stretch as they fill with air when breathing in. They then spring back during breathing out, in order to expel the carbon dioxide-rich air.

The term "amino acid" is used to refer to an organic molecule containing both an amino group and a carboxyl group; those that serve as the building blocks of naturally occurring proteins are alpha amino acids, in which both the amino and carboxyl groups are linked to the same carbon atom. The terms "amino acid residue" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The following represent groups of amino acids that are conservative substitutions for one another:
Alanine (A), Serine (S), Threonine (T);
Aspartic Acid (D), Glutamic Acid (E);
Asparagine (N), Glutamine (Q);
Arginine (R), Lysine (K);
Isoleucine (I), Leucine (L), Methionine (M), Valine (V); and
Phenylalanine (F), Tyrosine (Y), Tryptophan (W).

Amniotic membranes. Amniotic membranes develop from extra-embryonic tissue and consist of a fetal component (the chorionic plate) and a maternal component (the decidua, meaning the lining of the pregnant uterus), which are held together by the chorionic villi and connect the cytotrophoblastic shell of the chorionic sac to the decidua basalis. The fetal component, which includes the amniotic and chorionic fetal membranes, separates the fetus from the endometrium. The amniochorionic membrane forms the outer limits of the sac that encloses the fetus, while the innermost layer of the sac is the amniotic membrane.

From within outward, the amniotic membrane (AM) consists of (A) an epithelial monolayer, (B) a thick basement membrane, (C) a compact layer, (D) a fibroblast layer, and (E) a spongy layer. The amniotic epithelium, the innermost layer nearest to the fetus, and in contact with the amniotic fluid, consists of a single layer of cells uniformly arranged on the basement membrane. The epithelial layer can be removed while the basement membrane and stromal surfaces remain morphologically intact. The basement membrane is composed of a network of reticular fibers. The compact layer of stromal matrix adjacent to the basement membrane forms the main fibrous skeleton of the AM. The collagens of the compact layer are secreted by mesenchymal cells situated in the fibroblast layer. Interstitial collagens (types I and III) predominate and form parallel bundles that maintain the mechanical integrity of the AM. Collagens type V and VI form filamentous connections between interstitial collagens and the epithelial basement membrane. The fibroblast layer is composed of a loose fibroblast network embedded in a mass of reticulum. The spongy layer of the stromal matrix sits adjacent to the chorionic membrane, and represents the tissue of the extraembryonic coelom, which is compressed between the amnion and the chorion. It contains a nonfibrillar meshwork of mostly type III collagen. The spongy layer is loosely connected to the chorionic membrane; hence the AM is easily separated from the chorion by means of blunt dissection (Niknejad, H. et al, Eur. Cells and Materials (2008) 15: 88-99).

The term "amniotic stem cells" as used herein refers to pluripotent stem cells, multipotent stem cells, and progenitor cells derived from amniotic membrane, which can give rise to a limited number of cell types in vitro and/or in vivo under an appropriate condition, and expressly includes both amniotic epithelial cells and amniotic stromal cells.

The term "angiogenic factor" as used herein refers to any of a group of substances present in the circulation (most of which are polypeptides—e.g., angiogenin, fibroblast growth factor, transforming growth factors and some lipids), which play a role in blood vessel formation (angiogenesis). The expression levels of angiogenic factors, such as VEGF, IGF, PDGF, HGF, FGF, TGF, Angiopoeitin-1, and stem cell factor (SCF) have been found to differ amongst bone-derived-, cartilage-derived-, and adipose-derived MSCs (Peng et al., 2008, Stems Cells and Development, 17: 761-774).

The terms "animal," "patient," and "subject" as used herein include, but are not limited to, humans and non-human vertebrates such as wild, domestic and farm animals. According to some embodiments, the terms "animal," "patient," and "subject" may refer to humans. According to some embodiments, the terms "animal," "patient," and "subject" may refer to non-human mammals.

As used herein, the phrase "subject in need" of treatment for a particular condition is a subject having that condition, diagnosed as having that condition, or at risk of developing that condition. According to some embodiments, the phrase "subject in need" of such treatment also is used to refer to a patient who (i) will be administered a composition of the described invention; (ii) is receiving a composition of the described invention; or (iii) has received at least one a composition of the described invention, unless the context and usage of the phrase indicates otherwise.

The term "antibody" as used herein refers to a polypeptide or group of polypeptides comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. As used herein, a "targeted binding agent" is an antibody, or binding fragment thereof, that preferentially binds to a target site. According to some embodiments, the targeted binding agent is specific for only one target site. According to some embodiments, the targeted binding agent is specific for more than one target site. According to some embodiments, the targeted binding agent may be a monoclonal antibody and the target site may be an epitope. The term "epitope" as used herein refers to that portion of an antigen or other macromolecule capable of forming a binding interaction that interacts with the variable region binding pocket of an antibody. "Binding fragments" of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay). An antibody may be an oligoclonal antibody, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody, and an antibody that can be labeled in soluble or bound form, as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', single stranded antibody (svFC), dimeric variable region (Diabody) and di-sulphide stabilized variable region (dsFv). As discussed herein, minor variations in the amino acid sequences of antibodies or immunoglobulin molecules are contemplated as being encompassed by the described invention, providing that the variations in the amino acid sequence maintain at least about 75%, and in some embodiments, at least about 80%, about 90%, about 95%, and about 99% sequence identity to the antibodies or immunoglobulin molecules described herein. Conservative amino acid replacements are contemplated. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. According to some embodiments, amino- and carboxy-termini of fragments or analogs occur near boundaries of functional domains. Structural and functional domains can be identified by comparison of the nucleotide and/or amino acid sequence data to public or proprietary sequence databases. For example, computerized comparison methods can be used to identify sequence motifs or predicted protein conformation domains that occur in other proteins of known structure and/or function. Methods to identify protein sequences that fold into a known three-dimensional structure are known. See, for example, Bowie et al. Science 253:164 (1991), which is incorporated by reference in its entirety.

As used herein, the term "antigen" refers to a molecule, e.g., a peptide, polypeptide, protein, fragment, or other biological moiety, which elicits an antibody response in a subject, or is recognized and bound by an antibody.

The term "autocrine signaling" as used herein refers to a type of cell signaling in which a cell secretes signal molecules that act on itself or on other adjacent cells of the same type. The terms "autologous" or "autogeneic" as used interchangeably herein mean derived from the same organism.

The term "binding" and its other grammatical forms as used herein means a lasting attraction between chemical substances. Binding specificity involves both binding to a specific partner and not binding to other molecules. Functionally important binding may occur at a range of affinities from low to high, and design elements may suppress undesired cross-interactions. Post-translational modifications also can alter the chemistry and structure of interactions. "Promiscuous binding" may involve degrees of structural plasticity, which may result in different subsets of residues being important for binding to different partners. "Relative binding specificity" is a characteristic whereby in a biochemical system a molecule interacts with its targets or partners differentially, thereby impacting them distinctively depending on the identity of individual targets or partners.

The term "biomarker" (or "biosignature") as used herein refers to a peptide, a protein, a nucleic acid, an antibody, a gene, a metabolite, or any other substance used as an indicator of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

The term "caveollins (Cays)" as used herein refers to integrated plasma membrane proteins that are complex signaling regulators with numerous partners and whose activity is highly dependent on cellular context (Boscher, C, Nabi, I R. Adv. Exp. Med. Biol. (2012) 729: 29-50). Cays are both positive and negative regulators of cell signaling in and/or out of caveolae, invaginated lipid raft domains whose formation is caveolin expression dependent. Caveolins and rafts have been implicated in membrane compartmentalization; proteins and lipids accumulate in these membrane microdomains where they transmit fast, amplified and specific signaling cascades. The term "caveolin 1 (CAV1)", refers to a scaffolding protein that links integrin subunits to the tyrosine kinase FYN, an initiating step in coupling integrins to the Ras-ERK pathway and promoting cell cycle progression.

The term "CCC motif chemokine ligand 18 (CCL18)" as used herein refers to a small protein derived from alveolar macrophages that acts as a chemo-attractant. CCL18 is mainly secreted by antigen-presenting cells such as monocytes, macrophages and dendritic cells (Guiot, J. et al. Lung (2017) 195(3): 273-280, citing Hieshima K, et al. J Immunol. 1997; 159(3): 1140-49). In the setting of pulmonary fibrosis, alveolar macrophages are believed to be the main source of CCL18 in the lung and play a role in the pathogenesis of pulmonary fibrosis (Id., citing Prasse A, et al. Am J Respir Crit Care Med. 2006; 173(7): 781-92). Serum CCL18 is increased in IPF but is not specific of the disease (Id., citing Prasse A, et al. Am J Respir Crit Care Med. 2006; 173(7): 781-92; Prasse A, et al. Arthritis Rheum. 2007; 56(5): 1685-93; Luzina I G, et al. J Cell Physiol. 2006; 206(1): 221-8). In IPF, CCL18 is negatively correlated to pulmonary function tests (TLC and DLCO) (Id., citing Prasse A, et al. Arthritis Rheum. 2007; 56(5): 1685-93). In a prospective study, it has been shown that patients with serum levels of CCL18>150 ng/ml were independently associated with death in IPF (HR 1.98, 95% CI 2.49-25.51, p=0.005) (Id., citing Prasse A, et al. Am J Respir Crit Care Med. 2009; 179(8): 717-23). Moreover, pirfenidone, one of the specific anti-fibrotic therapies in IPF, significantly suppressed the expression of CCL18 on macrophages (Id., citing Saito Y, et al. Immunopharmacol Immunotoxicol. 2016; 38(6): 46471). Baseline concentration >150 ng/ml is associated with higher mortality (Id.).

The term "chorion" as used herein refers to the outer fetal membrane that surrounds the amnion, the embryo, and other membranes and entities in the womb. A spongy layer of loosely arranged collagen fibers separates the amniotic and chorionic mesoderm. The chorionic membrane consists of mesodermal and trophoblastic regions. Chorionic and amniotic mesoderm are similar in composition. A large and incomplete basal lamina separates the chorionic mesoderm from the extravillous trophoblast cells. The latter, similar to trophoblast cells present in the basal plate, are dispersed within the fibrinoid layer and express immunohistochemical markers of proliferation. The Langhans fibrinoid layer usually increases during pregnancy and is composed of two different types of fibrinoid: a matrix type on the inner side (more compact) and a fibrin type on the outer side (more reticulate). At the edge of the placenta and in the basal plate, the trophoblast interdigitates extensively with the decidua (Cunningham, F. et al., The placenta and fetal membranes, Williams Obstetrics, 20th ed. Appleton and Lange, 1997, 95-125; Benirschke, K. and Kaufmann, P. Pathology of the human placenta. New York, Springer-Verlag, 2000, 42-46, 116, 281-297). The chorion, which interfaces maternal tissues, consists of four layers. These are, from within outward: (F) the cellular layer, a thin layer consisting of an interlacing fibroblast network, which is frequently imperfect or completely absent; (G) a reticular layer, which consists of a reticular network, the fibers of which tend to be parallel, along with a few fibroblasts and many Hofbauer cells; (H) a pseudo-basement membrane, which is a layer of dense connective tissue firmly adherent to the reticular layer above, and which sends anchoring and branching fibers down into the trophoblast; and (I) a trophoblast layer, which is the deepest layer of the chorion consisting of from two to 10 layers of trophoblast cells in contact, on their deeper aspect, with maternal decidua. This layer contains the chorionic villi (Bourne, G L, Am. J. Obstet. & Gynec. (1960) 79 (6): 1070-73).

"Cluster of Differentiation" or "cluster of designation" (CD) molecules are utilized in cell sorting using various methods, including flow cytometry. Cell populations usually are defined using a "+" or a "−" symbol to indicate whether a certain cell fraction expresses or lacks a particular CD molecule.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences.

The term "condition" as used herein refers to disorders or diseases caused by any underlying mechanism or disorder, or injury.

The term "conditioned medium" (or plural, media), as used herein refers to spent culture medium harvested from cultured cells containing metabolites, growth factors, RNA and proteins released into the medium by the cultured cells.

The term "contact" and its various grammatical forms as used herein refers to a state or condition of touching or of immediate or local proximity.

The term "culture medium" (or plural, media), as used herein refers to a substance containing nutrients in which cells or tissues are cultivated for controlled growth.

The term "cytokine" as used herein refers to small soluble protein substances secreted by cells, which have a variety of effects on other cells. Cytokines mediate many important physiological functions, including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor (TNF)-related molecules, including TNFα and lymphotoxin; immunoglobulin super-family members, including interleukin 1 (IL-1); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

As used herein, the term "derived from" is meant to encompass any method for receiving, obtaining, or modifying something from a source of origin.

As used herein, the terms "detecting", "determining", and their other grammatical forms, are used to refer to methods performed for the identification or quantification of a biomarker, such as, for example, the presence or level of miRNA, or for the presence or absence of a condition in a biological sample. The amount of biomarker expression or activity detected in the sample can be none or below the level of detection of the assay or method.

The term "differentiation" as used herein refers to a process of development with an increase in the level of organization or complexity of a cell or tissue, accompanied by a more specialized function.

The terms "disease" or "disorder" as used herein refer to an impairment of health or a condition of abnormal functioning. The term "fibrotic disease" as used herein refers to a condition marked by an increase of interstitial fibrous tissue. The terms "lung tissue disease" or "lung disease" as used herein refers to a disease that affects the structure of the lung tissue, for example, without limitation, pulmonary interstitium. Scarring or inflammation of lung tissue makes the lungs unable to expand fully ("restrictive lung disease"). It also makes the lungs less capable of taking up oxygen (oxygenation) and releasing carbon dioxide. Examples of lung tissue diseases include, but are not limited to, idiopathic pulmonary fibrosis (IPF), acute lung injury (ALI), radiation-induced fibrosis in the lung, a fibrotic condition associated with lung transplantation, and sarcoidosis, a disease in which swelling (inflammation) occurs in the lymph nodes, lungs, liver, eyes, skin, or other tissues.

The term "endogenous" as used herein refers to that which is naturally occurring, incorporated within, housed within, adherent to, attached to, or resident in. The term "exogenous" as used herein refers to that which is non-naturally occurring, or that is originating or produced outside of a specific EV, cell, organism, or species.

As used herein, the term "enrich" is meant to refer to increasing the proportion of a desired substance, for example, to increase the relative frequency of a subtype of cell or cell component compared to its natural frequency in a cell population. Positive selection, negative selection, or both are generally considered necessary to any enrichment scheme. Selection methods include, without limitation, magnetic separation and fluorescence-activated cell sorting (FACS).

The term "exacerbation" as used herein refers to an increase in the severity of a disease or any of its signs or symptoms.

The term "expand" and its various grammatical forms as used herein refers to a process by which dispersed living cells propagate in vitro in a culture medium that results in an increase in the number or amount of viable cells.

As used herein, the term "expression" and its various grammatical forms refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. Expression may also refer to the post-translational modification of a polypeptide or protein.

The term "extracellular vesicles" or "EVs" as used herein includes exosomes and microvesicles that carry bioactive molecules, such as proteins, RNAs and microRNAs, that may be released into and influence the extracellular environment. Microvesicles are small membrane-enclosed sacs thought to be generated by the outward budding and fission of membrane vesicles from the cell surface. Exosomes originate predominantly from preformed multivesicular bodies that are released upon fusion with the plasma membrane.

The term "fibroblast" as used herein refers to a connective tissue cell that makes and secrets collagen protein. Fibroblasts, the most common cell type found in connective tissues, play an important role in healing wounds. Like other cells of connective tissue, fibroblasts are derived from primitive mesenchyme (a type of loose connective tissue derived from all three germ layers and located in the embryo). In certain situations, epithelial cells can give rise to fibroblasts, a process called epithelial-mesenchymal transition. The term "myofibroblasts" as used herein refers to fibroblasts in wound areas that have some characteristics of smooth muscle, such as contractile properties and fibers, and are believed to produce, temporarily, type III collagen.

The term "growth factor" as used herein refers to extracellular polypeptide molecules that bind to a cell-surface receptor triggering an intracellular signaling pathway, leading to proliferation, differentiation, or other cellular response. These pathways stimulate the accumulation of proteins and other macromolecules, e.g., by increasing their rate of synthesis, decreasing their rate of degradation, or both.

Fibroblast Growth Factor (FGF). The fibroblast growth factor (FGF) family currently has over a dozen structurally related members. FGF1 is also known as acidic FGF; FGF2 is sometimes called basic FGF (bFGF); and FGF7 sometimes goes by the name keratinocyte growth factor. Over a dozen distinct FGF genes are known in vertebrates; they can generate hundreds of protein isoforms by varying their RNA splicing or initiation codons in different tissues. FGFs can activate a set of receptor tyrosine kinases called the fibroblast growth factor receptors (FGFRs). Receptor tyrosine kinases are proteins that extend through the cell membrane. The portion of the protein that binds the paracrine factor is on the extracellular side, while a dormant tyrosine kinase (i.e., a protein that can phosphorylate another protein by splitting ATP) is on the intracellular side. When the FGF receptor binds an FGF (and only when it binds an FGF), the dormant kinase is activated, and phosphorylates certain proteins within the responding cell, activating those proteins.

FGFs are associated with several developmental functions, including angiogenesis (blood vessel formation), mesoderm formation, and axon extension. While FGFs often can substitute for one another, their expression patterns give them separate functions. For example, FGF2 is especially important in angiogenesis, whereas FGF8 is involved in the development of the midbrain and limbs.

Insulin-Like Growth Factor (IGF-1). IGF-1, a hormone similar in molecular structure to insulin, has growth-promoting effects on almost every cell in the body, especially skeletal muscle, cartilage, bone, liver, kidney, nerves, skin, hematopoietic cell, and lungs. It plays an important role in childhood growth and continues to have anabolic effects in adults. IGF-1 is produced primarily by the liver as an endocrine hormone as well as in target tissues in a paracrine/autocrine fashion. Production is stimulated by growth hormone (GH) and can be retarded by undernutrition, growth hormone insensitivity, lack of growth hormone receptors, or failures of the downstream signaling molecules, including tyrosine-protein phosphatase non-receptor type 11 (also known as SHP2, which is encoded by the PTPN11 gene in humans) and signal transducer and activator of transcription 5B (STAT5B), a member of the STAT family of transcription factors. Its primary action is mediated by binding to its specific receptor, the Insulin-like growth factor 1 receptor (IGF1R), present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Growth hormone is made in the pituitary gland, released into the blood stream, and then stimulates the liver to produce IGF-1. IGF-1 then stimulates systemic body growth. In addition to its insulin-like effects, IGF-1 also can regulate cell growth and development, especially in nerve cells, as well as cellular DNA synthesis.

IGF-1 was shown to increase the expression levels of the chemokine receptor CXCR4 (receptor for stromal cell-derived factor-1, SDF-1) and to markedly increase the migratory response of MSCs to SDF-1 (Li, Y, et al. 2007 Biochem. Biophys. Res. Communic. 356(3): 780-784). The IGF-1-induced increase in MSC migration in response to SDF-1 was attenuated by PI3 kinase inhibitor (LY294002 and wortmannin) but not by mitogen-activated protein/ERK kinase inhibitor PD98059. Without being limited by any particular theory, the data indicate that IGF-1 increases MSC migratory responses via CXCR4 chemokine receptor signaling which is PI3/Akt dependent.

Transforming Growth Factor Beta (TGF-β). There are over 30 structurally related members of the TGF-β superfamily, and they regulate some of the most important interactions in development. The proteins encoded by TGF-β superfamily genes are processed such that the carboxy-terminal region contains the mature peptide. These peptides are dimerized into homodimers (with themselves) or heterodimers (with other TGF-β peptides) and are secreted from the cell. The TGF-β superfamily includes the TGF-β family, the activing family, the bone morphogenetic proteins (BMPs), the Vg-1 family, and other proteins, including glial-derived Müllerian inhibitory factor, which is involved in mammalian sex determination. TGF-β family members TGF-β1, 2, 3, and 5 are important in regulating the formation of the extracellular matrix between cells and for regulating cell division (both positively and negatively). TGF-β1 increases the amount of extracellular matrix epithelial cells make both by stimulating collagen and fibronectin synthesis and by inhibiting matrix degradation. TGF-βs may be critical in controlling where and when epithelia can branch to form the ducts of kidneys, lungs, and salivary glands.

Vascular Endothelial Growth Factor (VEGF). VEGFs are growth factors that mediate numerous functions of endothelial cells including proliferation, migration, invasion, survival, and permeability. The VEGFs and their corresponding receptors are key regulators in a cascade of molecular and cellular events that ultimately lead to the development of the vascular system, either by vasculogenesis, angiogenesis, or in the formation of the lymphatic vascular system. VEGF is a critical regulator in physiological angiogenesis and also plays a significant role in skeletal growth and repair.

VEGF's normal function creates new blood vessels during embryonic development, after injury, and to bypass blocked vessels. In the mature established vasculature, the endothelium plays an important role in the maintenance of homeostasis of the surrounding tissue by providing the communicative network to neighboring tissues to respond to requirements as needed. Furthermore, the vasculature provides growth factors, hormones, cytokines, chemokines and metabolites, and the like, needed by the surrounding tissue and acts as a barrier to limit the movement of molecules and cells.

The term "healthy control' as used herein refers to a subject in a state of physical well-being without signs or symptoms of a fibrotic disease.

The term "hybridization" as used herein refers to the binding of two single stranded nucleic acid molecules to each other through base pairing. Nucleotides will bind to their complement under normal conditions, so two perfectly complementary strands will bind (or 'anneal') to each other readily. However, due to the different molecular geometries of the nucleotides, a single inconsistency between the two strands will make binding between them more energetically unfavorable. Measuring the effects of base incompatibility by quantifying the rate at which two strands anneal can provide information as to the similarity in base sequence between the two strands being annealed.

As used herein, the term "identical," "percent identity," "shared identity," and the like, in the context of two or more nucleic acid or amino acid sequences, refers to two or more sequences or subsequences that are the same, or that have a specified percentage of amino acid residues or nucleotides that are the same (e.g., at least about 60% or about 65% identity, or at least about 70-95% identity, or at least 95% identity), when compared and aligned for maximum correspondence over a window of comparison, or over a designated region as measured using a sequence comparison algorithm as known in the art, or by manual alignment and visual inspection. Sequences having, for example, at least about 60% to 95% or greater sequence identity are considered to be substantially identical. Such a definition also applies to the complement of a test sequence. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988), e.g., as implemented in the program PC/GENE (Intelligenetics, Mountain View, Calif., USA). For example, the described identity can exist over a region that is at least about 15 to 25 amino acids or nucleotides in length, or over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a word length (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands. The described invention also relates to nucleic acid molecules, the sequence of which is degenerate in comparison with the sequence of an above-described hybridizing molecule. When used in accordance with the present invention the term "being degenerate as a result of the genetic code" means that due to the redundancy of the genetic code, different nucleotide sequences code for the same amino acid. The described invention also relates to nucleic acid molecules which comprise one or more mutations or deletions, and to nucleic acid molecules which hybridize to one of the herein described nucleic acid molecules, which show (a) mutation(s) or (a) deletion(s).

The term "infuse" and its other grammatical forms as used herein refers to introduction of a fluid other than blood into a vein.

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least about 5%, at least about 10%, at least about 15%, at least about 20%, at least about 25%, at least about 30%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99%.

The term "inhibitor" as used herein refers to a molecule that reduces the amount or rate of a process, stops the process entirely, or that decreases, limits, or blocks the action or function thereof. Enzyme inhibitors are molecules that bind to enzymes thereby decreasing enzyme activity. Inhibitors may be evaluated by their specificity and potency.

The term "injury," as used herein, refers to damage or harm to a structure or function of the body caused by an outside agent or force, which may be physical or chemical The term "isolated" is used herein to refer to material, such as, but not limited to, a nucleic acid, peptide, polypeptide, or protein, which is: (1) substantially or essentially free from components that normally accompany or interact with it as found in its naturally occurring environment. The terms "substantially free" or "essentially free" are used herein to refer to considerably or significantly free of, or more than about 95%, 96%, 97%, 98%, 99% or 100% free. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state.

The term "Krebs von den Lungen-6 (KL-6)/MUC1" as used herein refers to a mucinous high-molecular-weight glycoprotein, classified as cluster 9 (MUC1) of lung tumor and differentiation antigens. KL-6 splits off at the cystine bond near the epithelial membrane surface and becomes distributed in pulmonary epithelial lining fluid. It is predominantly expressed on alveolar type II cells in the lung, with expression increasing in proliferating, regenerating or injured type II cells more than normal type II cells. Serum levels of KL-6 are elevated in a variety of interstitial lung diseases that are characterized by alveolar epithelial cell damage. Serum KL-6 concentrations are associated with alveolar epithelial barrier dysfunction, as they have been shown to correlate with indices of alveolar capillary permeability. Serum baseline level >1000 U/ml is associated with worse prognosis and >1300 U/ml with increased risk of acute exacerbation (Guiot, J. et al. Lung (2017) 195(3): 273-280).

The term "liposome" as used herein refers to a synthetic, spherical extracellular vesicle consisting of one or more phospholipid bilayers surrounding a hollow or aqueous core.

The terms "lung interstitium" or "pulmonary interstitium" are used interchangeably herein to refer to an area located between the airspace epithelium and pleural mesothelium in the lung. Fibers of the matrix proteins, collagen and elastin, are the major components of the pulmonary interstitium. The primary function of these fibers is to form a mechanical scaffold that maintains structural integrity during ventilation.

The term "mesenchymal stem cells" or "MSCs" as used herein refers to non-blood adult stem cells found in a variety of tissues. They are characterized by their spindle-shape morphologically, by the expression of specific markers on their cell surface, and by their ability, under appropriate conditions, to differentiate along a minimum of three lineages (osteogenic, chondrogenic, and adipogenic). When referring to bone or cartilage, MSCs commonly are known as osteochondrogenic, osteogenic, or chondrogenic, since a single MSC has shown the ability to differentiate into chondrocytes or osteoblasts, depending on the medium. MSCs secrete many biologically important molecules, including interleukins 6, 7, 8, 11, 12, 14, and 15, M-CSF, Flt-3 ligand, SCF, LIF, bFGF, VEGF, P1GF and MCP1 (Majumdar, et al., J. Cell Physiol. 176: 57-66 (1998); Kinnaird et al., Circulation 109: 1543-49 (2004)). There is general agreement that MSCs lack typical hematopoietic antigens, namely CD14, CD34, and CD45 (Pittenger et al., Science 284: 143-47 (1999)).

The term "mimic" as used herein means a compound or substance that chemically resembles a parent compound or substance and retains at least a degree of the desired function of the parent compound or substance.

The term "microRNA," "miRNA", or "miR" as used herein refers to a class of small, non-coding RNA molecules, usually from about 18 to about 28 nucleotides in length.

MicroRNAs are partially complementary to one or more messenger RNA (mRNA) molecules, and function in post-transcriptional regulation of gene expression and RNA silencing.

The term "matrix metalloproteinases" as used herein refers to a collection of zinc-dependent proteases involved in the breakdown and the remodeling of extracellular matrix components (Guiot, J. et al. Lung (2017) 195(3): 273-280, citing Oikonomidi et al. Curr Med Chem. 2009; 16(10): 1214-1228). MMP-1 and MMP-7 seem to be primarily overexpressed in plasma of IPF patients compared to hypersensitivity pneumonitis, sarcoidosis and COPD with a possible usefulness in differential diagnosis (Id., citing Rosas I O, et al. PLoS Med. 2008; 5(4): e93). They are also involved in inflammation and seem to take part to the pathophysiological process of pulmonary fibrosis (Id., citing Vij R, Noth I. Transl Res. 2012; 159(4): 218-27; Dancer R C A, et al. Eur Respir J. 2011; 38(6): 1461-67). The most studied is MMP-7, which is known as being significantly increased in epithelial cells both at the gene and protein levels and is considered to be active in hyperplastic epithelial cells and alveolar macrophages in IPF (Id., citing Fujishima S, et al. Arch Pathol Lab Med. 2010; 134(8): 1136-42). There is also a significant correlation between higher MMP-7 concentrations and disease severity assessed by forced vital capacity (FVC) and DLCO (% pred) (Id., citing Rosas I O, et al. PLoS Med. 2008; 5(4): e93). Higher levels associated to disease progression and worse survival (>4.3 ng/ml for MMP-7) (Id.). The MMP2 gene provides instructions for making matrix metallopeptidase 2. This enzyme is produced in cells throughout the body and becomes part of the extracellular matrix, which is an intricate lattice of proteins and other molecules that forms in the spaces between cells. One of the major known functions of MMP-2 is to cleave type IV collagen, which is a major structural component of basement membranes, the thin, sheet-like structures that separate and support cells as part of the extracellular matrix.

MMPs play a critical role in neuroinflammation through the cleavage of ECM proteins, cytokines and chemokines. (Ji. R-R et al, US Neurology, Touch Briefings (2008) 71-74). MMP-2 is constitutively expressed and normally present in brain and spinal cord tissues. In contrast, MMP-9 is normally expressed at low levels, but upregulated in many injury and disease states such as spinal cord injury and brain trauma (Id., citing Rosenberg, G A. Glia (2002) 39: 279-91); it is also induced in the crushed sciatic nerve and causes demyelination, a condition associated with neuropathic pain, by the cleavae of myelin basic protein. (Id., citing Chattopadhyay, S. et al. Brain Behav. Immun. (20007) 21: 561-8). Besides targeting matrix, because MMPs can process a variety of growth factors and other extracellular cytokines and signals, they may contribute to the neurovascular remodeling that accompanies chronic CNS injury. (Id., citing Zhao, B Q, et al. Nat. Med. (2006) 12: 441-45).

The term "modulate" as used herein means to regulate, alter, adapt, or adjust to a certain measure or proportion.

The term "neuropathic pain" as used herein refers to pain derived from injury to the peripheral nervous system (e.g., peripheral nerves) or the CNS, which may result from major surgeries, e.g., amputation and thoracotomy, diabetic neuropathy, viral infection, chemotherapy, spinal cord injury, stoke, etc. Neuropathic pain is often characterized by spontaneous pain, described as shooting, lancinating, or bringing pain, and also by evoked pain, such as hyperalgesia (increased responsiveness to noxious stimuli) to mechanical and thermal stimuli. Mechanical allodynia, meaning painful responses to normally innocuous tactile stimuli may be the most distinct symptom of neuropathic pain. There are at least two phases of neuropathic pain in animal models: an early phase (first several days) when neuropathic pain is developed, and late phase (from a week to months and even years) when neuropathic pain is maintained. Animal model experiments have shown that MMP-9 induces early-phase neuropathic pain by activating IL-1β and microglia in the early phase. (Ji. R-R et al, US Neurology, Touch Briefings (2008) 71-74). MMP-2 inhibition experiments showed that MMP-2 contributes to late-phase neuropathic pain development by activating IL-1β and astrocytes in the late phase. [Id.] Apart from their pathological roles, MMP-9 and MMP-2 also play a physiological roles in regulating development and regeneration; depending on whether functional or dysfunctional remodeling occurs, the result might be recovery or the induction of aberrant neuronal circuits. (Ji, R-R et al, Trends Pharmacol. Sci. (2009) 30 (7): 336-40). Using a rat adjuvant-induced arthritis model, it was shown that the Chinese medicine crocin may alleviate neuropathic pain in AIA rats by inhibiting the expression of pain-related molecules through the Wnt5a/β-catenin pathway. Wang, J-F et al. Neural Plasticity (2020) 4297483. Although it was long known that crocin can effectively alleviate pain sensitization in rat pain models, its mechanism was unknown. Crocin significantly increased the mechanical thresholds of adjuvant-induced arthritis in rats, suggesting that crocin can alleviate neuropathic pain. Crocin significantly decreased the levels of pain-related factors and glial activation. Foxy5, activator of Wnt5a, inhibited these effects of crocin in AIA rats. In addition, intrathecal injection of a Wnt5a inhibitor significantly decreased hyperalgesia in AIA rats.

The term "nerve" as used herein refers to a whitish fiber or bundle of fibers that transmits impulses of sensation to the brain or spinal cord, and impulses from the brain or spinal cord to the muscles and organs.

The term "nervous system" as used herein refers to the network of nerve cells and fibers which transmits nerve impulses between parts of the body. The central nervous system (CNS) is that part of the nervous system that consists of the brain and spinal cord. It is one of the two major divisions of the nervous system. The other is the peripheral nervous system (PNS) which is outside the brain and spinal cord. The peripheral nervous system (PNS) connects the central nervous system (CNS) to sensory organs (such as the eye and ear), other organs of the body, muscles, blood vessels and glands. The peripheral nerves include the 12 cranial nerves, the spinal nerves and roots, and the autonomic nerves of the autonomic nervous system (ANS), meaning the part of the nervous system responsible for control of the bodily functions not consciously directed, such as breathing, the heartbeat, and digestive processes.

The term "normal healthy subject" as used herein refers to a subject having no symptoms or other evidence of a fibrotic condition.

The term "nucleic acid" is used herein to refer to a deoxyribonucleotide or ribonucleotide polymer in either single- or double-stranded form, and, unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The term "organ" as used herein refers to a differentiated structure consisting of cells and tissues and performing some specific function in an organism.

As used herein, the term "paracrine signaling" refers to short range cell-cell communication via secreted signal molecules that act on adjacent cells.

The term "pharmaceutical composition" is used herein to refer to a composition that is employed to prevent, reduce in intensity, cure or otherwise treat a target condition or disease. The terms "formulation" and "composition" are used interchangeably herein to refer to a product of the described invention that comprises all active and inert ingredients.

The term "pharmaceutically acceptable," is used to refer to the carrier, diluent or excipient being compatible with the other ingredients of the formulation or composition and not deleterious to the recipient thereof. The carrier must be of sufficiently high purity and of sufficiently low toxicity to render it suitable for administration to the subject being treated. The carrier further should maintain the stability and bioavailability of an active agent. For example, the term "pharmaceutically acceptable" can mean approved by a regulatory agency of the Federal or a state government or listed in the U.S. Pharmacopeia or other generally recognized pharmacopeia for use in animals, and more particularly in humans.

The term "pluripotent" as used herein refers to the ability to develop into multiple cells types, including all three embryonic lineages, forming the body organs, nervous system, skin, muscle, and skeleton. A "pluripotent stem cell," "PSC," or "pluripotent cell" is a cell that has the ability under appropriate conditions of producing progeny of several different cell types that are derivatives of all of the three germinal layers (endoderm, mesoderm, and ectoderm). Examples of pluripotent stem cells are embryonic stem (ES) cells, embryonic germ stem (EG) cells, embryonic carcinoma (EC) cells, induced pluripotent stem (iPS) cells, and adult stem cells. PSCs may be derived from any organism of interest, including, e.g., primate, human, canine, feline, murine, equine, porcine, avian, camel, bovine, ovine, etc.

The term "precision medicine" as used herein refers to an approach for disease treatment and prevention that takes into account individual variability in genes, environment and lifestyle. A precision medicine approach allows for a more accurate prediction of which treatment and prevention strategies for a particular disease will work in which groups of patients. This is in contrast to a one-size-fits-all approach, in which disease treatment and prevention strategies are developed for the average person with less consideration for differences between individuals.

The term "primer" refers to a nucleic acid which, when hybridized to a strand of DNA, is capable of initiating the synthesis of an extension product in the presence of a suitable polymerization agent. The primer is sufficiently long to uniquely hybridize to a specific region of the DNA strand. A primer also may be used on RNA, for example, to synthesize the first strand of cDNA.

The term "progenitor cell" as used herein refers to an early descendant of a stem cell that can only differentiate, but can no longer renew itself. Progenitor cells mature into precursor cells that mature into mature phenotypes. Hematopoietic progenitor cells are referred to as colony-forming units (CFU) or colony-forming cells (CFC). The specific lineage of a progenitor cell is indicated by a suffix, such as, but not limited to, CFU-E (erythrocytic), CFU-F (fibroblastic), CFU-GM (granulocytic/macrophage), and CFU-GEMM (pluripotent hematopoietic progenitor).

The term "pulmonary compliance" as used herein refers to the change in lung volume per unit change in pressure. Dynamic compliance is the volume change divided by the peak inspiratory transthoracic pressure. Static compliance is the volume change divided by the plateau inspiratory pressure. Pulmonary compliance measurements reflect the elastic properties of the lungs and thorax and are influenced by factors such as degree of muscular tension, degree of interstitial lung water, degree of pulmonary fibrosis, degree of lung inflation, and alveolar surface tension (Doyle D J, O'Grady K F. Physics and Modeling of the Airway, D, in Benumof and Hagberg's Airway Management, 2013). Total respiratory system compliance is given by the following calculation:

$$C = \Delta V / \Delta P$$

where $\Delta V$=change in lung volume, and $\Delta P$=change in airway pressure This total compliance may be related to lung compliance and thoracic (chest wall) compliance by the following relation:

$$\frac{1}{C_T} = \frac{1}{C_L} + \frac{1}{C_{Th}}$$

where $C_T$=total compliance (e.g., 100 mL/cm $H_2O$)
$C_L$=lung compliance (e.g., 200 mL/cm $H_2O$)
$C_{Th}$=thoracic compliance (e.g., 200 mL/cm $H_2O$)
The values shown in parentheses are some typical normal adult values that can be used for modeling purposes (Id.).

The term "purification" and its various grammatical forms as used herein refers to the process of isolating or freeing from foreign, extraneous, or objectionable elements.

The term "reference sequence" refers to a sequence used as a basis for sequence comparison. A reference sequence may be a subset or the entirety of a specified sequence.

The term "repair" as used herein as a noun refers to any correction, reinforcement, reconditioning, remedy, making up for, making sound, renewal, mending, patching, or the like that restores function. When used as a verb, it means to correct, to reinforce, to recondition, to remedy, to make up for, to make sound, to renew, to mend, to patch or to otherwise restore function.

The term "stem cells" refers to undifferentiated cells having high proliferative potential with the ability to self-renew that can generate daughter cells that can undergo terminal differentiation into more than one distinct cell phenotype. The term "renewal" or "self renewal" as used herein, refers to the process by which a stem cell divides to generate one (asymmetric division) or two (symmetric division) daughter cells having development potential indistinguishable from the mother cell. Self renewal involves both proliferation and the maintenance of an undifferentiated state.

The term "adult (somatic) stem cells" as used herein refers to undifferentiated cells found among differentiated cells in a tissue or organ. Their primary role in vivo is to maintain and repair the tissue in which they are found. Adult stem cells, which have been identified in many organs and tissues, including brain, bone marrow, peripheral blood, blood vessels, skeletal muscles, skin, teeth, gastrointestinal tract, liver, ovarian epithelium, and testis, are thought to reside in a specific area of each tissue, known as a stem cell niche, where they may remain quiescent (non-dividing) for long periods of time until they are activated by a normal need for more cells to maintain tissue, or by disease or tissue injury. Mesenchymal stem cells are an example of adult stem cells.

The terms "surfactant protein A (SP-A)" and "surfactant protein D (SP-D)" refer to hydrophobic, collagen-containing calcium-dependent lectins, with a range of nonspecific immune functions at pulmonary and cardiopulmonary sites. SP-A and SP-D play crucial roles in the pulmonary immune response, and are secreted by type II pneumocytes, nonciliated bronchiolar cells, submucosal glands, and epithelial cells of other respiratory tissues, including the trachea and bronchi. SP-D is important in maintaining pulmonary surface tension, and is involved in the organization, stability, and metabolism of lung parenchyma (Wang K, et al. Medicine (2017) 96 (23): e7083). An increase of 49 ng/mL (1 SD) in baseline SP-A level was associated with a 3.3-fold increased risk of mortality in the first year after presentation. SP-A and SP-D are predictors of worse survival in a one year mortality regression model (Guiot, J. et al. Lung (2017) 195(3): 273-280).

The term "symptom" as used herein refers to a sign or an indication of disorder or disease, especially when experienced by an individual as a change from normal function, sensation, or appearance.

As used herein, the term "therapeutic agent" or "active agent" refers to refers to the ingredient, component or constituent of the compositions of the described invention responsible for the intended therapeutic effect.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50, which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest, reduction, or elimination of the progression of a disease manifestation.

As used herein, the term "tissue" refers to a collection of similar cells and the intercellular substances surrounding them. For example, adipose tissue is a connective tissue consisting chiefly of fat cells surrounded by reticular fibers and arranged in lobular groups or along the course of smaller blood vessels. Connective tissue is the supporting or framework tissue of the body formed of fibrous and ground substance with numerous cells of various kinds. It is derived from the mesenchyme, and this in turn from the mesoderm. The varieties of connective tissue include, without limitation, areolar or loose; adipose; sense, regular or irregular, white fibrous; elastic; mucous; lymphoid tissue; cartilage and bone.

The terms "treat," "treated," or "treating" as used herein refers to both therapeutic treatment and/or prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

As used herein, the terms "wild type," "naturally occurring," or grammatical equivalents thereof, are meant to refer to an amino acid sequence or a nucleotide sequence that is found in nature and includes allelic variations; that is, an amino acid sequence or a nucleotide sequence that usually has not been intentionally modified. Accordingly, the term "non-naturally occurring," "synthetic," "recombinant," or grammatical equivalents thereof, are used interchangeably to refer to an amino acid sequence or a nucleotide sequence that is not found in nature; that is, an amino acid sequence or a nucleotide sequence that usually has been intentionally modified. It is understood that once a recombinant nucleic acid is made and reintroduced into a host cell or organism, it will replicate non-recombinantly, i.e., using the in vivo cellular machinery of the host cell rather than in vitro manipulations, however, such nucleic acids, once produced recombinantly, although subsequently replicated non-recombinantly, are still considered recombinant for the purpose of the described invention.

EVs and EV Preparations

According to some embodiments, the described invention provides a composition comprising a population of isolated EVs. When included in a pharmaceutical composition, the pharmaceutical composition contains the composition comprising a population of isolated EVs and a pharmaceutically acceptable carrier. According to some embodiments, the EVs are membrane (i.e., lipid bilayer) vesicles derived from mesenchymal stem cells (MSCs). According to some embodiments, the MSCs are allogeneic to a subject for whom administration of the pharmaceutical composition is contemplated. According to some embodiments, the MSCs are autologous to a subject for whom administration of the pharmaceutical composition is contemplated.

According to some embodiments, the source of MSCs is a tissue autologous to the recipient subject. According to some embodiments, the source of the MSCs is a tissue allogeneic to the recipient subject. According to some embodiments, the tissue is mammalian. According to some embodiments, the tissue is human. According to some embodiments, the source of the MSCs is placental tissue obtained from one or more areas, including both material and fetal tissue, e.g., amniotic membrane, chorionic membrane, or umbilical cord. According to some embodiments, the source of MSCs is adipose tissue. According to some embodiments, the adipose tissue is subcutaneous white adipose tissue. According to some embodiments, the source of MSCs is bone marrow, umbilical cord tissue, dental pulp, lung tissue, or heart tissue. According to some embodiments, the source of the MSCs is a body fluid. According to some embodiments, the body fluid is peripheral blood, umbilical cord blood, or amniotic fluid.

Amniotic and Chorionic Tissue

Human amniotic mesenchymal cells (hAMSC) and human chorionic mesenchymal cells (hCMSC) are thought to be derived from extraembryonic mesoderm. hAMSC and hCMSC can be isolated from first-, second-, and third-trimester mesoderm of amnion and chorion, respectively.

For hAMSC, isolations are usually performed with term amnion dissected from the deflected part of the fetal membranes to minimize the presence of maternal cells. For example, homogenous hAMSC populations can be obtained by a two-step procedure, whereby: minced amnion tissue is treated with trypsin to remove hAEC and the remaining mesenchymal cells are then released by digestion (e.g., with collagenase or collagenase and DNase). The yield from term amnion is about 1 million hAMSC and 10-fold more hAEC per gram of tissue (Casey, M. and MacDonald P., Biol Reprod, 1996, 55: 1253-1260).

hCMSCs are isolated from both first- and third-trimester chorion after mechanical and enzymatic removal of the trophoblastic layer with dispase. Chorionic mesodermal tissue is then digested (e.g., with collagenase or collagenase plus DNase). Mesenchymal cells also have been isolated from chorionic fetal villi through explant culture, although maternal contamination is more likely (Zhang, X., et al., Biochem Biophys Res Commun, 2006, 340: 944-952; Soncini, M. et al., J Tissue Eng Regen Med, 2007, 1: 296-305; Zhang et al., Biochem Biophys Res Commun, 2006, 351: 853-859).

The surface marker profile of cultured hAMSC and hCMSC, and mesenchymal stromal cells (MSC) from adult bone marrow are similar. All express typical mesenchymal markers (CD90, CD73, CD105) but are negative for hematopoietic (CD34 and CD45) and monocytic markers (CD14). Surface expression of SSEA-3 and SSEA-4 and RNA for OCT-4 has been reported (Wei J. et al., Cell Transplant, 2003, 12: 545-552; Wolbank, S. et al., Tissue Eng, 2007, 13: 1173-1183; Alviano, F. et al., BMC Dev Biol, 2007, 7: 11; Zhao, P. et al, Transplantation, 2005, 79: 528-535).

Both first- and third trimester hAMSC and hCMSC express low levels of HLA-A, B, C but not HLA-DR, indicating an immunoprivileged status (Portmann-Lanz, C. et al, Am J Obstet Gynecol, 2006, 194: 664-673; Wolbank, S. et al., Tissue Eng, 2007, 13: 1173-1183).

Umbilical Cord Tissue

MSCs from the umbilical cord matrix (UC-MM) are obtained by different culture methods depending on the source of cells, e.g., MSCs from the connective matrix, from subendothelial cells from the umbilical vein or even from whole umbilical cord explant. They are generally well cultured in DMEM medium, supplemented with various nutritional and growth factors; in certain cases prior treatment of vessels with hyaluronic acid has proved beneficial (Baban, B. et al., J Reprod Immunol, 2004, 61: 67-77).

Bone Marrow

Human bone marrow can be obtained from the iliac crest of patients after having obtained their written consent. BM is collected aseptically into K2EDTA tubes. The buffy coat is isolated by centrifugation (450×g, 10 min), suspended in 1.5 mL PBS, and used for culture. The separated buffy coat is layered onto equal volume of Ficoll (GE Health Care, USA) and centrifuged (400×g, 20 min). Cells at the interface are removed, and washed twice in sterile PBS.

Human bone marrow progenitor cells are cultured on tissue treated culture plates in DMEM medium supplemented with 10% FBS and penicillin/streptomycin (50 U/mL and 50 mg/mL, respectively). The plates are maintained at 37° C. in a humidified atmosphere containing 5% $CO_2$ for 48 h. To exchange the medium, the plates are washed with PBS in order to remove non-adhered cells and the medium is replaced. The remaining cells have a heterogeneous fibroblastic-like appearance and exhibit colony formation. The cultures can be maintained for an additional week with one medium exchange.

Adipose Tissue

In comparison to BM-MSC, MSC from adipose tissue, the adipose-derived stromal/stem cells (ASCs), occur at a 100-1000-fold higher frequency within adipose tissue on a volume basis (Aust L, et al., Cytotherapy. 2004; 6(1): 7-14). Harvesting adipose tissue is also minimally invasive and less painful than bone marrow tissue. Conventional enzymatic methods, using enzymes such as collagenase, trypsin, or dispase, are widely used for MSC isolation from adipose tissue. Although the isolation techniques for adipose tissue-derived cells are rather diverse, they follow a certain standard procedure. Differences lie mainly in numbers of washing steps, enzyme concentrations, centrifugation parameters, erythrocyte lysis methods as well as in filtration, and eventually culture conditions (Oberbauer E, et al., Cell Regen (Lond). 2015; 4: 7, citing Zuk P A, et al., Mol Biol Cell. 2002; 13(12): 4279-95; Gimble J, Guilak F. Cytotherapy. 2003; 5(5): 362-9; Carvalho P P, et al., Tissue Eng Part C Meth. 2013; 19(6): 473-8).

An exemplary protocol for isolating MSCs from adipose tissue includes the steps of obtaining adipose tissue by surgical resection or lipoaspiration; washing the tissue 3-5 times for 5 minutes in PBS each wash, discarding the lower phase until clear; adding collagenase and incubating 1-4 hr at 37° C. on a shaker; adding 10% FBS to neutralize the collagenase; centrifuging the digested fat at 800×g for 10 min; aspirating floating adipocytes, lipids and liquid, leaving the stromal vascular fraction (SVF) pellet; resuspending the SVF pellet in 160 mM $NH_4Cl$ and incubating for 10 minutes at room temperature; centrifuging at 400×g for 10 min at room temperature; layering cells on Percoll or Histopaque gradient; centrifuging at 1000×g for 30 minutes at room temperature; washing cells twice with PBS and centrifuging at 400×g for 10 min between each wash; resuspending the cell pellet in PBS and filtering cells through a 100 μM nylon mesh; passing the cells through a 400 μM nylon mesh; centrifuging at 400×g for 10 minutes; resuspending the cell pellet in 40% FBS/DMEM culture medium and plating the cells. The plastic-adherent cell fraction, including ASCs, can be obtained after passaging or cryopreservation or further cultivated for expansion for a more homogeneous ASC population (Id.).

An exemplary protocol for expansion and subculture of human MSCs includes the following steps: Precoating a tissue culture vessel with 5 μg/mL of PRIME-XV MatrIS F or PRIME-XV Human Fibronectin for 3 hr at room temperature or overnight at 2-8° C.; prewarming PRIME-XV MSC Expansion SFM to 37° C. for no more than 30 min; removing spent media from T-75 flask culture and gently rinsing cells once with 10 mL of PBS for each T-75 flask; adding 3 mL of room temperature TrupLE™ Express to each T-75 flask, and tilting the flask in all directions to disperse the TrypLE™ Express evenly over the cells; incubating the cells at 37° C., 5% $CO_2$ to allow the cells to detach; adding 5 mL of PRIME-XV MSC expansion SFM to the flask and dispersing the cells by pipetting the media over the entire growing surface of the flask; transferring the contents to a 15 mL conical tube; centrifuging the cells at 400×g for 5 min and aspirating the supernatant; resuspending the cell pellet in a small amount of pre-warmed PRIME-XV MSC Expansion SFM and counting the cells; resuspending 4.5-5.0×$10^5$ cells into 20 mL of the pre-warmed PRIME-XV MSC Expansion SFM for each pre-coated T-75 flask; gently aspirating off PRIME-XV attachment substrate solution from the flask and slowly adding the cell suspension to a T-75 flask; and incubating the cells at 37° C., 5% $CO_2$. Spent media is removed and discarded and the cells fed with pre-warmed PRIME-XV MSC Expansion SFM every two days.

Dental Pulp

Similar to adipose tissue, generating stem cells from dental pulp is a relatively noninvasive and noncontroversial process. Deciduous teeth may be sterilized, and the dental pulp tissue separated from the pulp chamber and root canal, revealed by cutting around the cementoenamel junction using sterilized dental burs (Tsai A I, et al., Biomed Res Int. 2017: 2851906). After separation, the dental pulp may be isolated using, for example, a barbed broach or a sharp excavator (Id.). MSCs may be isolated enzymatically or non-enzymatically as described above for adipose tissue.

Lung or Heart Tissue

MSCs may be cultured from tissue biopsies or transplanted tissues. A study in heart transplant patients demonstrated that MSCs present in transplanted hearts were all of donor origin (Hoogduijn M J, et al., Am J Transplant. 2009 January; 9(1): 222-30). No MSCs of recipient origin were found, even not many years after transplantation. Similar data were found in lung transplant patients (Lama V N, et al., J Clin Invest. 2007 April; 117(4): 989-96). These data suggest that MSCs do not migrate between tissues, not even under inflammatory conditions as found in transplanted organs (Eggenholfer E, et al., Front Immunol. 2014; 5: 148).

For the isolation of lung or heart tissue-derived MSCs, tissues are minced into pieces and digested with a culture medium containing 0.2% collagenase (Wako) at 37° C. for 30 min. The collagenase is removed by washing twice with 1×PBS. The cell suspension is filtered through a cell strainer (40-μm) and collected in a 50-ml tube. Red blood cells are removed by incubating cells in 1×RBC lysis buffer (BioLegend) for 5 min at room temperature. Then, $2 \times 10^7$ cells are seeded onto a collagen I-coated, 10-cm dish using MesenCult medium containing 1× MesenPure and 10 nM of a Rock inhibitor. MSCs may be cultured for up to three passages to reduce any artefacts potentially introduced by long-term culture.

Blood

Umbilical cord blood MSCs are obtained from 40 mL of UCB with citrate phosphate dextrose (Sigma-Aldrich, St. Louis, Mo.) as anticoagulant, and centrifuged through Ficoll-Paque (1.077 g/cm3) according to the manufacturer's instructions. MSC fractions are washed with PBS, counted using trypan blue exclusion staining and plated onto fibronectin-coated tissue culture flasks (Becton Dickinson) in MSC expansion medium (Iscove modified Dulbecco medium (IMDM, Life Technologies) and 20% FBS supplemented with 10 ng/mL recombinant human bFGF (Pepro-tech, Rocky Hill N.J.), 100 U penicillin, 100 U streptomycin and 2 mM L-Glutamine (Life Technologies/Gibco). Cells are allowed to adhere overnight and nonadherent cells washed out with medium changes.

In an exemplary protocol for obtaining MSCs from whole blood, a diluted mixture of PBS and peripheral blood is layered in a 50 ml centrifuge tube on top of Ficoll-Paque, and centrifuged at 400×g for 30-40 minutes at 20° C. in a swinging-bucket rotor without break. The upperlayer is aspirated, leaving the mononuclear cell layer (lymphocytes, monocytes and thrombocytes) undisturbed at the interface. The mononuclear cell layer is carefully transferred into a new 50 ml centrifuge tube. Cells are washed with PBS (pH 7.2) containing 2 mM EDTA, centrifuged at 300×g for 10 min at room temperature and the supernatant discarded. For removal of platelets, the cell pellet is resuspended in 50 mL buffer and centrifuged at 200×g for 10-15 minutes at room temperature. The supernatant containing the platelets is removed. This step is repeated. The cell pellet is resuspended in DMEM, 20% FBS and 1% antibiotic-antimycotic. Cultures are maintained at 37° C. in a humidified atmosphere containing 5% $CO_2$. Suspended cells are discarded after 5-7 days of culture and adherent cells left to grow on the flask surface. Culture medium is changed every 3 days.

Amniotic Fluid

Amniotic fluid is formed at 2 weeks after fertilization in the amniotic cavity of early gestation (Kim E Y, et al., BMB Rep. 2014 March; 47(3): 135-140). Amniotic fluid keeps the fetus safe and supports organ development. The first progenitor cells derived from amniotic fluid was reported in 1993 by Torricelli et al. (Ital J Anat Embryol. 1993 April-June; 98(2): 119-26). Many studies have identified amniotic fluid (AF) as a source of MSCs. These AF-MSCs express the pluripotent marker Oct-4 in almost 90% of the active condition, and they also have multiple differentiation capacity like amniotic membrane MSCs (Tsai M S, et al., Hum Reprod. 2004 June; 19(6): 1450-6; De Coppi P, et al., Nature Biotechnol. 2007 January; 25(1): 100-6). AF is also routinely used to perform the standard evaluation of karyotyping, and genetic and molecular tested for diagnostic purposes. After prenatal diagnostic testing, AF cells can be used as a source of fetal progenitor cells or otherwise discarded (Prusa A R, et al., Med Sci Monit. 2002 November; 8(11): RA253-7). Use of these cells could minimize ethical objections, have a high renewal activity, and maintain genetic stability (Kim E Y, et al., BMB Rep. 2014 March; 47(3): 135-140). AF-MSCs are easily isolated and offer advantages of nontumorigenicity and low immunogenic activity. (Id.).

Amniotic fluid samples are obtained by amniocentesis performed between 16 and 20 weeks of gestation for fetal karyotyping. A two-stage culture protocol can be used for isolating MSCs from amniotic fluid (Tsai M S, et al., Hum Reprod. 2004 June; 19(6): 1450-6). For culturing amniocytes (first stage), primary in situ cultures are set up in tissue culture-grade dishes using Chang medium (Irvine Scientific, Santa Ana, Calif.). Metaphase selection and colony definition is based on the basic requirements for prenatal cytogenetic diagnosis in amniocytes (Moertel C A, et al., 1992; *Prenat Diagn* 12, 671-683). For culturing MSCs (second stage), non-adhering amniotic fluid cells in the supernatant medium are collected on the fifth day after the primary amniocytes culture and kept until completion of fetal chromosome analysis. The cells are then centrifuged and plated in 5 ml of α-modified minimum essential medium (α-MEM; Gibco-BRL) supplemented with 20% fetal bovine serum (FBS; Hyclone, Logan, Utah) and 4 ng/ml basic fibroblast growth factor (bFGF; R&D systems, Minneapolis, Minn.) in a 25 $cm^2$ flask and incubated at 37° C. with 5% humidified $CO_2$ for MSC culture. Similar to MSCs from umbilical cord blood and first-trimester fetal tissues, surface antigens such as SH3, SH4, CD29, CD44 and HLA-A,B,C (MHC class I) may be found, and CD10, CD11b, CD14, CD34, CD117, HLA-DR,DP,DQ (WIC class II) and EMA are absent (Tsai M S, et al., Hum Reprod. 2004 June; 19(6): 1450-6; Pittenger M F, et al., Science 284, 143-7; Colter D C, et al., Proc Natl Acad Sci USA 98, 78415; Young H Y, et al., Anat Rec 264, 51-62).

According to some embodiments, to characterize the adherent MSCs, osteoblastic differentiation is induced by culturing confluent human MSCs for 3 weeks in osteoblastic differentiation media (all from Sigma) and after three weeks, the cells are stained by Alizarin. To induce adipocyte differentiation, confluent MSCs are cultured 1 to 3 weeks in differentiation medium, and lipid droplet staining is carried out by S Red Oil (Sigma).

According to some embodiments, flow cytometry can be used to characterize cell markers expressed on the surface of the isolated MSCs. According to some embodiments, the phenotype of the adherent MSCs is CD73+, CD90+, CD105+, CD34−, CD45−.

According to some embodiments, the EVs contain microvesicles, exosomes, or both. According to some embodiments, the EVs have a diameter ranging from about 30 nm to 200 nm, i.e., at least 30 nm, at least 31 nm, at least 32 nm, at least 33 nm, at least 34 nm, at least 35 nm, at least 36 nm, at least 37 nm, at least 38 nm, at least 39 nm, at least 40 nm, at least 41 nm, at least 42 nm, at least 43 nm, at least 44 nm, at least 45 nm, at least 46 nm, at least 47 nm, at least 48 nm, at least 49 nm, at least 50 nm, at least 51 nm, at least 52 nm, at least 53 nm, at least 54 nm, at least 55 nm, at least 56 nm, at least 57 nm, at least 58 nm, at least 59 nm, at least 60 nm, at least 61 nm, at least 62 nm, at least 63 nm, at least 64 nm, at least 65 nm, at least 66 nm, at least 67 nm, at least 68 nm, at least 69 nm, at least 70 nm, at least 71 nm, at least 72 nm, at least 73 nm, at least 74 nm, at least 75 nm, at least 76 nm, at least 77 nm, at least 78 nm, at least 79 nm, at least 80 nm, at least 81 nm, at least 82 nm, at least 83 nm, at least 84 nm, at least 85 nm, at least 86 nm, at least 87 nm, at least 88 nm, at least 89 nm, at least 90 nm, at least 91 nm, at least 92 nm, at least 93 nm, at least 94 nm, at least 95 nm, at least 96 nm, at least 97 nm, at least 98 nm, at least 99 nm, at least 100 nm, at least 101 nm, at least 102 nm, at least 103 nm, at least 104 nm, at least 105 nm, at least 106 nm, at least 107 nm, at least 108 nm, at last 109 nm, at least 110 nm, at least 120 nm, at least 121 nm, at least 122 nm, at least 123 nm, at least 124 nm, at least 125 nm, at least 126 nm, at least 127 nm, at least 128 nm, at least 129 nm, at least 130 nm, at least 131 nm, at least 132 nm, at least 133 nm, at least 134 nm, at least 135 nm, at least 136 nm, at least 137 nm, at least 138 nm, at least 139 nm, at least 140 nm, at least 141 nm, at least 142 nm, at least 143 nm, at least 144 nm, at least 145 nm, at least 146 nm, at least 147 nm, at least 148 nm, at least 149 nm, at least 150 nm, at least 151 nm, at least 152 nm, at least 153 nm, at least 154 nm, at least 155 nm, at least 156 nm, at least 157 nm, at least 158 nm, at least 159 nm, at least 160 nm, at least 161 nm, at least 162 nm, at least 163 nm, at least 164 nm, at least 165 nm, at least 166 nm, at least 167 nm, at least 168 nm, at least 169 nm, at least 170 nm, at least 171 nm, at least 172 nm, at least 173 nm, at least 174 nm, at least 175 nm, at least 176 nm, at least 177 nm, at least 178 nm, at least 179 nm, at least 180 nm, at least 181 nm, at least 182 nm, at least 183 nm, at least 184 nm, at least 185 nm, at least 186 nm, at least 187 nm, at least 188 nm, at least 189 nm, at least 190 nm, at least 191 nm, at least 192 nm, at least 193 nm, at least 194 nm, at least 195 nm, at least 196 nm, at least 197 nm, at least 198 nm, at least 199 nm, or at least 200 nm. According to some embodiments, by electron microscopy, the EVs appear to have a cup-shaped morphology. According to some embodiments, they sediment at about 100,000×g and have a buoyant density in sucrose of about 1.10 to about 1.21 g/ml.

According to some embodiments, the EVs comprise proteins, nucleic acids, or both, including RNA species, such as miRNAs. According to some embodiments, the EVs are produced by transfection (meaning introduction of one or more foreign nucleic acid molecules into a eukaryotic cell usually followed by expression of those nucleic acid molecules in the cell) with an miRNA-29a mimic, an miRNA-199 inhibitor, or both.

According to some embodiments, the extracellular vesicles are isolated EVs. The term "an isolated population of EVs" as used herein refers to a population of EVs that is physically separated from its natural environment. According to some embodiments, isolated populations of EVs can be physically separated, in whole or in part, from tissue or cells with which the populations naturally exist. According to some embodiments, a composition comprising isolated EVs may be substantially free of cells or cell components, or it may be free or substantially free of conditioned media. According to some embodiments, the concentration of isolated EVs may be higher than the concentration EVs present in unmanipulated conditioned media. According to some embodiments, the population of EVs comprises an enriched subpopulation of EVs.

According to some embodiments, the EVs can be isolated from conditioned media harvested from cultured MSCs containing metabolites, growth factors, RNA and proteins released into the medium by the cultured MSCs.

According to some embodiments, a method for harvesting EVs from MSCs involves first culturing MSCs under standard conditions until they reach about 70% confluency, and then culturing the cells in a serum-free media for 24 hours. The conditioned media is then collected and subjected to differential centrifugation at 400×g for 10 minutes and 12000×g for 10 minutes in order to remove whole cells and cellular debris, producing a clarified conditioned media. The clarified conditioned media then is concentrated by ultrafiltration using a 100 kDa MWCO filter (Millipore), and then centrifuged again at 12000×g for 10 minutes. EVs then are isolated using size exclusion chromatography by loading the concentrated clarified conditioned media on a PBS-equilibrated Chroma S-200 column (Clontech), eluting with PBS, and collecting fractions of 350-550 microliters. Fractions containing EVs are identified and potentially pooled. Protein concentration is measured using a standard Bradford assay (Bio-Rad). Aliquots of the enriched extracellular vesicle preparations can be stored at −80° C.

According to some embodiments, EVs can be isolated from plasma. According to an exemplary method for isolating EVs from plasma, plasma is centrifuged at room temperature at 2000×g for 20 minutes. The supernatant is then transferred to a new microcentrifuge tube and centrifuged at 10,000×g 20 minutes. The supernatant is then transferred to a new microcentrifuge tube. 100 μL of PBS is added to the sample and then is mixed by vortexing. 60 μL of the Exosome Precipitation Reagent is added and was mixed thoroughly by vortexing. The samples are incubated at room temperature for 10 minutes and then are centrifuged at 10,000×g for 5 minutes at room temperature. The supernatant is discarded and the samples are centrifuged again at 10,000×g for 30 seconds. The residual supernatant is discarded and pellets are resuspended in 200 μL of PBS for RNA extraction and miRNA profiling.

According to some embodiments, EVs can be isolated from bronchoalveolar lavage fluid (BALF). According to an exemplary method for isolating EVs from BALF, BALF is diluted with an equal volume of PBS and transferred to 50-ml tubes. The tubes are centrifuged for 30 minutes at 2,000×g at 4° C. The supernatant is then transferred to ultracentrifuge tubes or bottles without pellet contamination and centrifuged for 45 min at 12,000×g 4° C. The supernatant is then transferred to ultracentrifuge tubes or bottles and centrifuged for 2 hours at 110,000×g 4° C. The pellets are then resuspended in 1 ml PBS and pooled in one of the tubes. The tube can be filled with PBS to dilute the resuspension in a large volume. The suspension is then filtered through a 0.22-μm filter, collected in a fresh ultracentrifuge tube or bottle, and centrifuged for 70 minutes at 110,000×g 4° C. The supernatant is poured off. The pellet is resuspended in 1 ml PBS, and then the tube filled with PBS and centrifuged for 70 min at 110,000×g 4° C. The supernatant is then discarded and the pellet resuspended in 30 to 100 μl sterile PBS and used or stored at −80° C.

According to some embodiments, EVs also can be purified by ultracentrifugation of the clarified conditioned media at 100,000×g. According to some embodiments, they also can be purified by ultracentrifugation into a sucrose cushion. GMP methods for extracellular vesicle purification from dendritic cells have been described in J Immunol Methods. 2002; 270: 211-226, which is incorporated by reference herein.

According to some embodiments, EVs can be purified by differential filtration through nylon membrane filters of defined pore size. For example, a first filtration though a large pore size will retain cellular fragments and debris; a subsequent filtration through a smaller pore size will retain EVs and purify them from smaller size contaminants.

According to some embodiments, the EV preparation can comprise synthetically engineered EVs. According to some embodiments, these synthetic EVs can be synthesized in vitro. According to some embodiments, the synthetic populations of EVs can be engineered to express an miRNA-29a mimic, an miRNA-199 inhibitor, or both. According to some embodiments, the miRNA-29a mimic, miRNA-199 inhibitor, or both, may or may not comprise nucleic acids that encode the parent miRNA-29a, miRNA-199, or both. According to some embodiments, the synthetic EVs comprise liposome membranes. Liposome synthesis is known in the art, and liposomes may be purchased from commercial sources.

The basic strategies involved in the preparation of liposomes include: steps for separation of lipids from organic solvent; steps for dispersion of lipids in an aqueous medium; purifying the resultant liposomes; and steps for analyzing the manufactured liposomes. Exemplary methods for dispersion of the lipids in the aqueous medium are outlined below.

Sonication is likely the most commonly used method for the dispersion of lipids, particularly for the manufacture of small unilamellar vesicles (SUVs). In this method, either a bath type sonicator or a probe sonicator is used to produce the liposomes passively. With bath sonication, the liposome dispersion is placed inside the sonicator, which allows for easy control of temperature, in comparison to the probe type. The probe sonication method requires a high input of energy to enhance the dispersion; because this creates heat, the vessel must be placed in a water or ice bath to control the temperature. The sonication method is limited by its low internal volume or ability to encapsulate large molecules. Additionally, the phospholipids and internal molecules may be subject to degradation, resulting in an unsuccessful encapsulation.

The French pressure cell method uses a process of extrusion and pushes multilamellar vesicles (MLVs) through a small orifice to disperse the lipids. The resulting liposomes tend to be larger than with the sonication method and it recalls encapsulated solutes longer than SUVs. However, the manufacturing process requires particularly high temperatures and there is a restricted working volume.

In the freeze-thaw method, the SUVs are frozen for a short period and then allowed to thaw over a long timeframe. This disperses the lipids and leads to the formation of large unilamellar vesicles (LUVs). The freeze-thaw method is limited by the concentration of phospholipids and ionic strength of the medium.

Other methods of dispersion include lipid film hydration, micro-emulsification, membrane extrusion and dried reconstituted vesicles. Factors to be considered include physicochemical characteristics of the material to be encapsulated, the medium in which lipid vesicle will be dispersed, concentration and potential toxicity of the encapsulated substance, the process of administration of the vesicles, size, polydispersity and shelf-life of vesicles, as well as reproducibility of safe and efficient products. According to some embodiments, the invention contemplates immediate use of EV preparations or short- and/or long-term storage of EV preparations, for example, in a cryopreserved state prior to use. Proteinase inhibitors are typically included in freezing media as they provide extracellular vesicle integrity during long-term storage. Freezing at −20° C. is not preferable since it is associated with increased loss of extracellular vesicle activity. According to some embodiments, the EV preparations are quick frozen at −80° C. to preserve activity. (See, for example, Kidney International (2006) 69, 1471-1476, incorporated herein by reference). Additives to the freezing media similar to those used for cryopreservation of intact cells, including, without limitation, DMSO, glycerol and polyethylene glycol, may be used in order to enhance preservation of extracellular vesicle biological activity.

Diagnosis and Methods of Treatment

According to some embodiments, a method for diagnosing a fibrotic disease in a subject comprises: (a) obtaining a urine sample from a subject and from a normal healthy control; (b) isolating EVs from the urine sample of the subject and the normal healthy control; (c) comparing miRNA composition of the urine sample from the subject to the miRNA composition of the urine sample from the normal healthy control; (d) detecting dysregulated miRNAs in the urine sample from the subject; and (e) diagnosing the subject with a fibrotic disease when the presence of one or more dysregulated miRNAs in the urine sample is detected. According to some embodiments, the fibrotic disease is one or more of a fibrotic lung disease, a fibrotic cardiac disease, a fibrotic renal disease, a fibrotic hepatic disease, a fibrotic skin disease, a fibrotic pancreatic disease, a fibrotic eye disease, a fibrotic joint disease, a fibrotic bone marrow disease, a fibrotic brain disease, a fibrotic intestinal disease, a fibrotic peritoneum disease, a fibrotic retroperitoneum disease, a fibrotic condition of the nerves or nervous system (e.g, CNS, PNS, ANS), a nerve compression, or an injury due to fibrosis. According to some embodiments, the dysregulated miRNAs comprise one or more of miR-134-5p, miR-196b-5p, miR-629-5p, miR-206, miR-192-5p, miR-320c, miR-125a-3p, miR-215-5p, miR-642a-3p, miR-5'76-3p, miR-3679-5p, miR-134-5p, miR-196b-5p, miR-629-5p, or miR-206. According to some embodiments, the one or more miRNAs is downregulated compared to the normal healthy control. According to some embodiments, the one or more miRNAs is upregulated compared to the normal healthy control.

According to some embodiments, an increased level of one or more of miR-192-5p, miR-320c, miR-125a-3p, miR-215-5p, miR-642a-3p, miR-576-3p, or miR-3679-5p compared to the control sample indicates that the subject has a fibrotic lung disease. According to some embodiments, a decreased level of one or more of miR-134-5p, miR-196b-5p, miR-629-5p, or miR-206 compared to the control sample indicates that the subject has a fibrotic disease. According to some embodiments, the fibrotic disease is a fibrotic lung disease. According to some embodiments, the method further comprises detecting the absence, presence, or level of expression of one or more biomarkers selected from KL-6/MUC1, SP-A, SP-D, CCL18, MMP-1, and MMP-7 in blood or serum from the subject. According to some embodiments, a level of expression of the one or more biomarkers is compared to the level of expression of the one or more biomarkers in a sample from a normal healthy control. According to some embodiments, the level of expression of the one or more biomarkers indicates a prognosis for the subject.

According to some embodiments, the subject is a human patient that has been diagnosed with or demonstrates symptoms of a lung injury. According to some embodiments, the subject is a human patient that has been diagnosed with or is at risk of a lung injury progressing to a fibrotic lung disease. According to some embodiments, the subject is a human patient that has been diagnosed with or demonstrates symptoms of pulmonary fibrosis. According to some embodiments, the subject is a human patient that has been diagnosed with or demonstrates symptoms of idiopathic pulmonary fibrosis. According to some embodiments, the subject is a human patient that has been diagnosed with or demonstrates symptoms of a bleomycin-induced lung injury.

According to some embodiments, the subject is a human patient that has been diagnosed with or demonstrates symptoms of a heart, kidney, nerve, or liver injury. According to some embodiments, the subject is a human patient that has been diagnosed with or is at risk of a heart, kidney, or liver injury progressing to a fibrotic disease. According to some embodiments, the subject is a human patient that has been diagnosed with or demonstrates symptoms of heart, kidney, or liver fibrosis.

According to some embodiments, a method of diagnosing and treating a fibrotic lung disease in a subject comprises diagnosing the subject with fibrotic lung disease according to steps (a), (b), (c), (d), and (e) above, and (f) administering a therapeutic amount of a pharmaceutical composition comprising either (i) a therapeutic amount of whole MSCs comprising synthetic EVs comprising an miR-29a mimic, an miR-199-3p inhibitor, or both to the diagnosed subject; or (ii) a therapeutic amount of a purified and enriched population of synthetic EVs comprising an miR-29a mimic, an miR-199-3p inhibitor, or both to the diagnosed patient, wherein the therapeutic amount is effective to upregulate expression of miR29a, downregulate expression of miR199-3p, or both, and to treat the fibrotic lung disease.

According to some embodiments, the pharmaceutical composition is effective to accomplish one or more of decreasing one or more symptoms of a fibrotic lung disease, increasing repair of a lung injury, reducing lung fibrosis, restoring lung function, reducing or eliminating the need for other active agents or therapeutics; and slowing progression of fibrotic lung disease.

According to some embodiments, a method of diagnosing and treating a fibrotic disease in a subject comprises diagnosing the subject with fibrotic disease according to steps (a), (b), (c), (d), and (e) above, and (f) administering a therapeutic amount of a pharmaceutical composition comprising either (i) a therapeutic amount of whole MSCs comprising synthetic EVs comprising an miR-29a mimic, an miR-199-3p inhibitor, or both to the diagnosed subject; or (ii) a therapeutic amount of a purified and enriched population of synthetic EVs comprising an miR-29a mimic, an miR-199-3p inhibitor, or both to the diagnosed patient, wherein the therapeutic amount is effective to upregulate expression of miR29a, downregulate expression of miR199-3p, or both, and to treat the fibrotic disease. According to some embodiments, a therapeutic effect of treating the fibrotic injury the pharmaceutical composition is effective to treat the fibrotic injury e.g., to lung or to nerves by accomplishing one or more of decreasing one or more symptoms of a fibrotic disease, increasing repair of an organ injury, reducing organ fibrosis, restoring organ function, reducing or eliminating the need for other active agents or therapeutics; or slowing progression of a fibrotic organ disease.

A "therapeutically effective amount," "therapeutic amount" or "effective amount" of a pharmaceutical composition comprising the EVs of the described invention is a predetermined amount calculated to achieve the desired biological effect. The activity contemplated by the described methods includes both medical therapeutic and/or prophylactic treatment, as appropriate. The specific dose of a composition administered according to the described invention to obtain a therapeutic and/or prophylactic therapeutic effect will, of course, be determined by the particular circumstances surrounding the case, including, for example, the composition administered, the route of administration, and the condition being treated. For example, a therapeutic dosage per day of the pharmaceutical composition described can be from about 1 mg/kg to about 1.6 mg/kg based on a 60 kg adult human subject. According to some embodiments, the therapeutically effective dose of the pharmaceutical composition containing EVs is about 1 mg/kg, about 1.1 mg/kg, about 1.2 mg/kg, about 1.3 mg/kg, about 1.4 mg/kg, about ⅕ mg/kg, or about 1.6 mg/kg. According to some embodiments, a standard effective dose of the pharmaceutical composition contains from about $1\times10^5$ to about $1\times10^9$ MSCs, i.e., $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$ whole MSCs. According to some embodiments, a standard effective dose of the pharmaceutical composition contains synthetic EVs comprising an miR-29a mimic, an miR199-3p inhibitor or both, derived from about $1\times10^5$ to about $10^9$ MSCs, i.e., $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, or $1\times10^9$ MSCs. However, it will be understood that the effective amount administered will be determined by the physician in the light of the relevant circumstances including the condition to be treated, the choice of composition to be administered, and the chosen route of administration, and therefore the above dosage ranges are not intended to limit the scope of the invention in any way. A therapeutically effective amount of composition of embodiments of this invention is typically an amount such that when it is administered in a physiologically tolerable excipient composition, it is sufficient to achieve an effective systemic concentration or local concentration in the tissue.

According to some embodiments, a method of treating a lung condition in a subject comprises administering to the subject a therapeutically effective amount of a pharmaceutical composition comprising a purified population of EVs comprising an miR-29a mimic, an miR-199-3p inhibitor, or both, and a pharmaceutically acceptable carrier.

According to some embodiments, the miR-29a mimic has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94% at least about 95%, at least about 96%, at least about 97%, at least about 98%, or at least about 99% sequence homology with SEQ ID NO: 1. According to some embodiments, the miR-199-3p inhibitor has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence homology with SEQ ID NO: 2.

According to some embodiments, the administering occurs nasally, intratracheally, orally, parenterally, intravenously, or intraperitoneally. The term "parenteral" as used herein refers to introduction into the body by means other than through the digestive tract, for example, without limitation, by way of an injection (i.e., administration by injection), including, for example, subcutaneously (i.e., an injection beneath the skin), intramuscularly (i.e., an injection into a muscle), intravenously (i.e., an injection into a vein), or infusion techniques.

According to some embodiments, a therapeutic effect of treating the fibrotic lung condition comprises one or more of: decreasing one or more symptoms of a lung condition, alleviating pain due to fibrosis, increasing repair of a lung injury, reducing lung fibrosis, restoring lung function, reducing or eliminating the need for other active agents or therapeutics, or slowing progression of fibrotic lung disease. According to some embodiments, lung function may be determined using one or more pulmonary function assays and measuring one or more pulmonary function values.

Pulmonary function assays or pulmonary function tests (PFTs) are well known in the art, and include spirometry, the most common PFT. Spirometry is the measurement of respiration, specifically the amount (volume) and/or speed (flow) of air that can be inhaled and exhaled. Lung function is physiologically divided into four volumes: expiratory reserve volume, inspiratory reserve volume, residual volume, and tidal volume (Barreiro T J, Perillo I. Am Fam Physician. 2004 Mar. 1; 69(5): 1107-14). Together, the four lung volumes equal the total lung capacity (TLC) (Id.). Lung volumes and their combinations measure various lung capacities such as functional residual capacity (FRC), inspiratory capacity, and vital capacity (VC) (Id.).

Pulmonary function values are the clinical outcome measurements of PFTs, and are well known in the art. Examples of pulmonary function values include, without limitation, FEV (forced expiratory volume), FVC (forced vital capacity), FEF (forced expiratory flow), Vmax (maximum flow), PEFR (peak expiratory flow rate), FRC (functional residual capacity), RV (residual volume), TLC (total lung capacity), DLCO (diffusion capacity of the lungs to carbon monoxide), and 6-MWT (6 minute walk test). Other pulmonary function values, or combinations thereof, are intended to be within the scope of the disclosure.

FEV measures the volume of air exhaled over a predetermined period of time by a forced expiration (exhalation) immediately after a full inspiration. For example, FEV1 is the volume that can be forcibly blown out in the first 1 second after full inspiration. FVC measures the total volume of air exhaled immediately after a full inspiration. Forced expiratory flow measures the volume of air exhaled during a FVC divided by the time in seconds. Vmax is the maximum flow measured during FVC. PEFR measures the maximum flow rate during a forced exhale starting from full inspiration. RV is the volume of air remaining in the lungs after a full expiration. TLC is the volume of air in the lungs at maximal inflation. Diffusing capacity (also known as transfer factor) is assessed using small volumes of carbon monoxide (CO) and measures the transfer of CO across the alveolar-capillary membrane (DLCO). The six-minute walk test (6MWT) measures the distance an individual is able to walk over a total of six minutes on a hard, flat surface. The goal is for the individual to walk as far as possible in six minutes. The individual is allowed to self-pace and rest as needed as they traverse back and forth along a marked walkway (Balke B. Rep Civ Aeromed Res Inst US. 1963 (53): 1-8).

Other lung function tests include pulse oximetry, wherein a small device placed on a subject's finger measures the oxygen saturation of the blood, and exercise stress tests on a treadmill or stationary bicycle to monitor active lung function. An arterial blood gas test is used to measure oxygen and carbon dioxide levels in a blood sample.

According to some embodiments, lung function may be determined using an imaging assay. A chest X-ray may be used to reveal scar tissue typical of pulmonary fibrosis, and it is useful for monitoring the course of the illness and treatment. Computerized tomography (CT) scanners use a computer to combine X-ray images taken from many different angles to produce cross-sectional images of internal structures in the body. HRCT (high-resolution computed tomography) is used to visualize the lung paranchyma and can be helpful in determining the extent of lung damage caused by pulmonary fibrosis.

According to some embodiments, lung function may be determined from a lung tissue sample (biopsy). The biopsy is then examined in a laboratory to diagnose pulmonary fibrosis or rule out other conditions. Biopsies may be obtained by any method known in the art. For example, in bronchoscopy, a small, flexible tube (bronchoscope) is passed through the mouth or nose into the lungs to obtain a small tissue sample. In bronchoalveolar lavage, salt water is injected through a bronchoscope into a section of lung, and then immediately suctioned out. The solution that is withdrawn contains cells from the air sacs. Although bronchoalveolar lavage samples a larger area of the lung than do other procedures, it may not provide enough information to diagnose pulmonary fibrosis. However, it might also be used to rule out other conditions.

Although a surgical biopsy is more invasive and has potential complications, it may be used to obtain a large enough tissue sample to make an accurate diagnosis. This procedure may be done as a minimally invasive surgery, called video-assisted thoracoscopic surgery (VATS), or as an open surgery (thoracotomy). During VATS, a small camera is inserted through two or three small incisions between the ribs. The camera allows the lungs to be viewed on a video monitor while removing tissue samples. During open surgery (thoracotomy), a lung sample is removed through an incision in the chest between the ribs.

Formulations

The phrase "pharmaceutically acceptable carrier" is art recognized. It is used to mean any substantially non-toxic carrier conventionally useable for administration of pharmaceuticals in which the isolated EVs of the present invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition. Exemplary carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in "Remington's Pharmaceutical Sciences" by E. W. Martin, which is incorporated herein by reference in its entirety. According to some embodiments, the pharmaceutically acceptable carrier is sterile and pyrogen-free water. According to some embodiments, the pharmaceutically acceptable carrier is Ringer's Lactate, sometimes known as lactated Ringer's solution.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, .alpha.-tocopherol, and the like; and metal chelating agents, such as citric acid, ethylenediamine tetraacetic acid (EDTA), sorbitol, tartaric acid, phosphoric acid, and the like.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

The local delivery of therapeutic amounts of a composition for the treatment of a lung injury or fibrotic lung disease can be by a variety of techniques that administer the compound at or near the targeted site. Examples of local delivery techniques are not intended to be limiting but to be illustrative of the techniques available. Examples include local delivery catheters, site specific carriers, implants, direct injection, or direct applications, such as topical application and, for the lungs, administration by inhalation.

Local delivery by an implant describes the surgical placement of a matrix that contains the pharmaceutical agent into the affected site. The implanted matrix releases the pharmaceutical agent by diffusion, chemical reaction, or solvent activators.

Specific modes of administration will depend on the indication. The selection of the specific route of administration and the dose regimen is to be adjusted or titrated by the clinician according to methods known to the clinician in order to obtain the optimal clinical response. The amount of active agent to be administered is that amount sufficient to provide the intended benefit of treatment. The dosage to be administered will depend on the characteristics of the subject being treated, e.g., the particular mammal or human treated, age, weight, health, types of concurrent treatment, if any, and frequency of treatments, and can be easily determined by one of skill in the art (e.g., by the clinician).

Pharmaceutical formulations containing the active agents of the described invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels, jellies, and foams; and parenteral dosage forms which include, but are not limited to, solutions, suspensions, emulsions, and dry powder; comprising an effective amount of a polymer or copolymer of the described invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics,* 6th Edition, MacMillan Publishing Co., New York (1980) can be consulted.

The pharmaceutical compositions of the described invention can be formulated for parenteral administration, for example, by injection, such as by bolus injection or continuous infusion. The pharmaceutical compositions can be administered by continuous infusion subcutaneously over a predetermined period of time. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents.

For oral administration, the pharmaceutical compositions can be formulated readily by combining the active agent(s) with pharmaceutically acceptable carriers well known in the art. Such carriers enable the actives of the disclosure to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, alter adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragecanth, methyl cellulose, hydroxypropylmethylcellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include, but are not limited to, push-fit capsules made of gelatin, as well as soft, scaled capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compositions for use according to the described invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In addition to the formulations described previously, the compositions of the described invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising any one or plurality of the active agents disclosed herein also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

For parenteral administration, a pharmaceutical composition can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

The described invention relates to all routes of administration including intramuscular, subcutaneous, sublingual, intravenous, intraperitoneal, intranasal, intratracheal, topical, intradermal, intramucosal, intracavernous, intrarectal, into a sinus, gastrointestinal, intraductal, intrathecal, intraventricular, intrapulmonary, into an abscess, intraarticular, subpericardial, into an axilla, into the pleural space, intradermal, intrabuccal, transmucosal, transdermal, via inhalation, via nebulizer, and via subcutaneous injection. Alternatively, the pharmaceutical composition may be introduced by various means into cells that are removed from the individual. Such means include, for example, microprojectile bombardment, via liposomes or via other nanoparticle device.

According to some embodiments, the pharmaceutical compositions of the claimed invention comprises one or more therapeutic agent other than the EVs as described. Examples of such additional active therapeutic agents include one or more immunomodulators, analgesics, anti-inflammatory agents, anti-fibrotic agents, proton pump inhibitors, or oxygen therapy.

Examples of immunomodulators include corticosteroids, for example, prednisone, azathioprine, mycophenolate, mycophenolate mofetil, colchicine, and interferon-gamma 1b.

Examples of analgesics include capsaisin, codeine, hydrocodone, lidocaine, oxycodone, methadone, resiniferatoxin, hydromorphone, morphine, and fentanyl.

Examples of anti-inflammatory agents include aspirin, celecoxib, diclofenac, diflunisal, etodolac, ibuprofen, indomethacin, ketoprofen, ketorolac nabumetone, naproxen, nintedanib, oxaprozin, pirfenidone, piroxicam, salsalate, sulindac, and tolmetin.

Examples of anti-fibrotic agents are nintedanib and pirfenidone.

Examples of proton pump inhibitors are omeprazole, lansoprazole, dexlansoprazole, esomeprazole, pantoprazole, rabeprazole, and ilaprazole.

According to the foregoing embodiments, the pharmaceutical composition may be administered once, for a limited period of time or as a maintenance therapy over an extended period of time, for example until the condition is ameliorated, cured or for the life of the subject. A limited period of time may be for 1 week, 2 weeks, 3 weeks, 4 weeks and up to one year, including any period of time between such values, including endpoints. According to some embodiments, the pharmaceutical composition may be administered for about 1 day, for about 3 days, for about 1 week, for about 10 days, for about 2 weeks, for about 18 days, for about 3 weeks, or for any range between any of these values, including endpoints. According to some embodiments, the pharmaceutical composition may be administered for more than one year, for about 2 years, for about 3 years, for about 4 years, or longer.

According to the foregoing embodiments, the composition or pharmaceutical composition may be administered once daily, twice daily, three times daily, four times daily or more.

All referenced journal articles, patents, and other publications are incorporated by reference herein in their entirety.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1: AETHER Clinical Trial

Introduction

Idiopathic pulmonary fibrosis (IPF) is a progressive and debilitating lung disease characterized by interstitial fibrosis with decreasing lung volumes and pulmonary insufficiency, eventually resulting in death.[1] Because of the insidious onset of symptoms, however, most patients receive a diagnosis at late stages of the disease after significant fibrosis has occurred. Diagnosis is established by the pathologic finding of usual interstitial pneumonia (UIP) and/or by high-resolution CT (HRCT).[2-4]

The natural history of this disease is characterized by inexorable progressive decline interspersed with "exacerbations" or periods of accelerated disease, which are often fatal.[1] Although two new drugs were recently approved by the Food and Drug Administration (FDA) for patients with IPF, neither is curative.[5-6]

In preclinical studies, mesenchymal stem cells (MSCs) have shown promise as a potential novel treatment for lung disease.[7-9] Studies of MSCs have shown that they contribute to tissue regeneration, home to sites of lung injury, contribute to tissue remodeling, decrease chronic airway inflammation, and restore alveolar fluid balance in acute lung injury.[10-15]

In addition to safety data from preclinical studies, human trials have also demonstrated the safety and tolerability of IV allogeneic mesenchymal stem cells (hMSCs).[16-23] A single-center, open-label phase Ib study assessed the safety and tolerability of multiple IV doses of adipose-derived stromal cell-stromal vascular fraction (n=14) for the treatment of IPF. Although short-term infusion toxicities and long-term ectopic tissue formation were reported, no adverse events related to the study treatment were observed.[21] In another single-center phase I study, patients with IPF received IV placenta-derived hMSCs (n=8). In this study, most adverse events were mild and self-limiting and no deaths were reported.[19]

Our study, the Allogeneic Human Cells in Patients With Idiopathic Pulmonary Fibrosis via Intravenous Delivery (AETHER) trial, was the first human trial designed to evaluate the safety of bone marrow-derived human allogeneic mesenchymal stem cells in patients with mild to moderate IPF.

Methods

AETHER was a single-center, nonrandomized, non-placebo-controlled phase I study of 9 patients with mild to moderate IPF. The study was conducted at the University of Miami Miller School of Medicine (Miami, Fla.). Eligible patients were between the ages of 40 and 90, had a diagnosis of IPF according to American Thoracic Society guidelines, an FVC of at least 50% predicted, and a diffusing capacity of the lungs for carbon monoxide (Dlco) of at least 30% predicted.[1] Patients received diagnoses by HRCT (lung biopsy was required in instances of inconclusive diagnosis). Patients with other infiltrative diseases, connective tissue disease, pulmonary hypertension, peripheral capillary oxygen saturation <93% at rest at sea level, life expectancy shorter than 1 year, and those actively listed for any organ transplant were excluded. Concomitant therapies, except oxygen supplementation and pulmonary rehabilitation, were prohibited.

Figure 1:
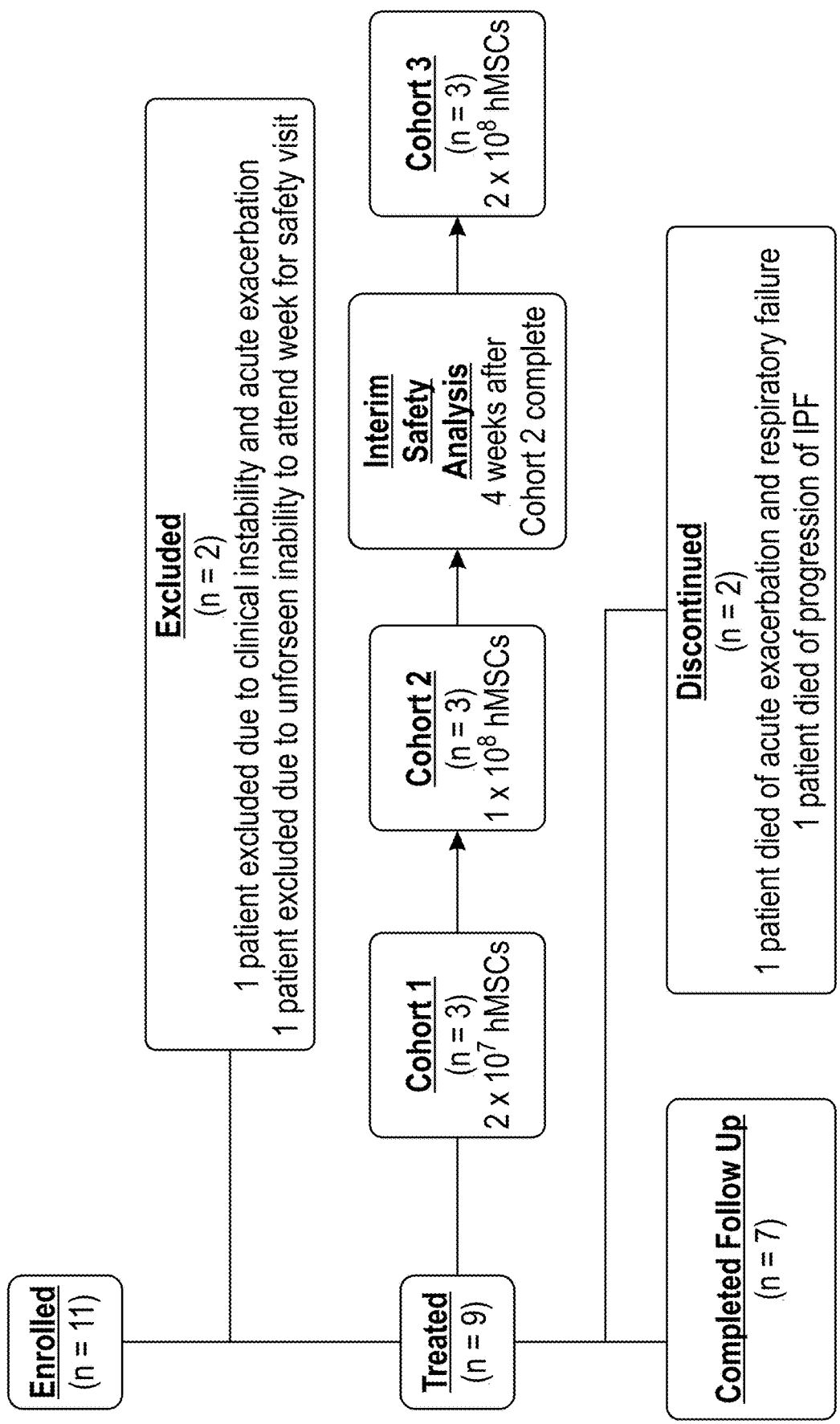
FIG. 1 is a flow chart of clinical trial participants in the Allogeneic Human Cells (hMSC) in patients with Idiopathic Pulmonary Fibrosis via Intravenous Delivery (AETHER) trial.
Figure 2A:
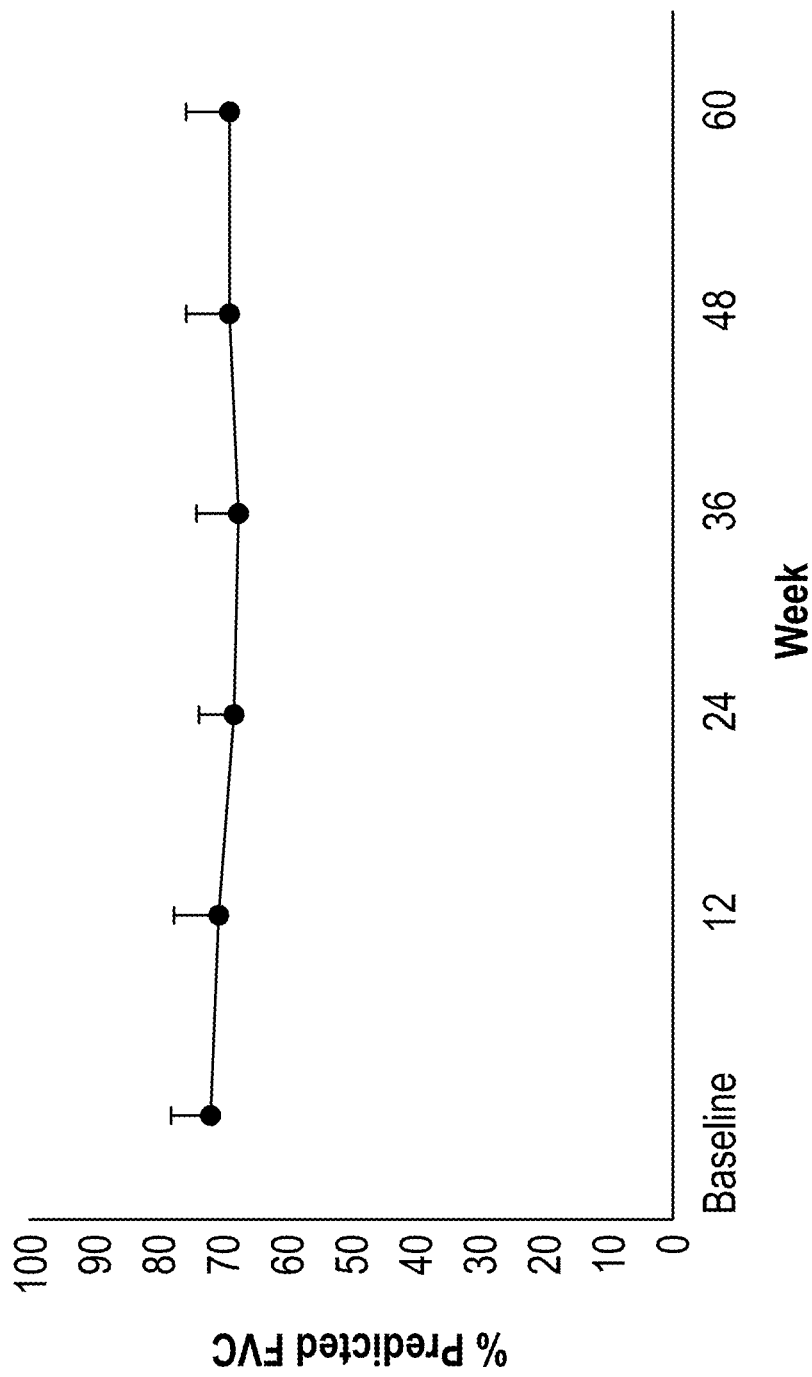
FIG. 2A-FIG. 2D are a series of graphs showing secondary efficacy outcomes during the 60-week study period.
Figure 2B:
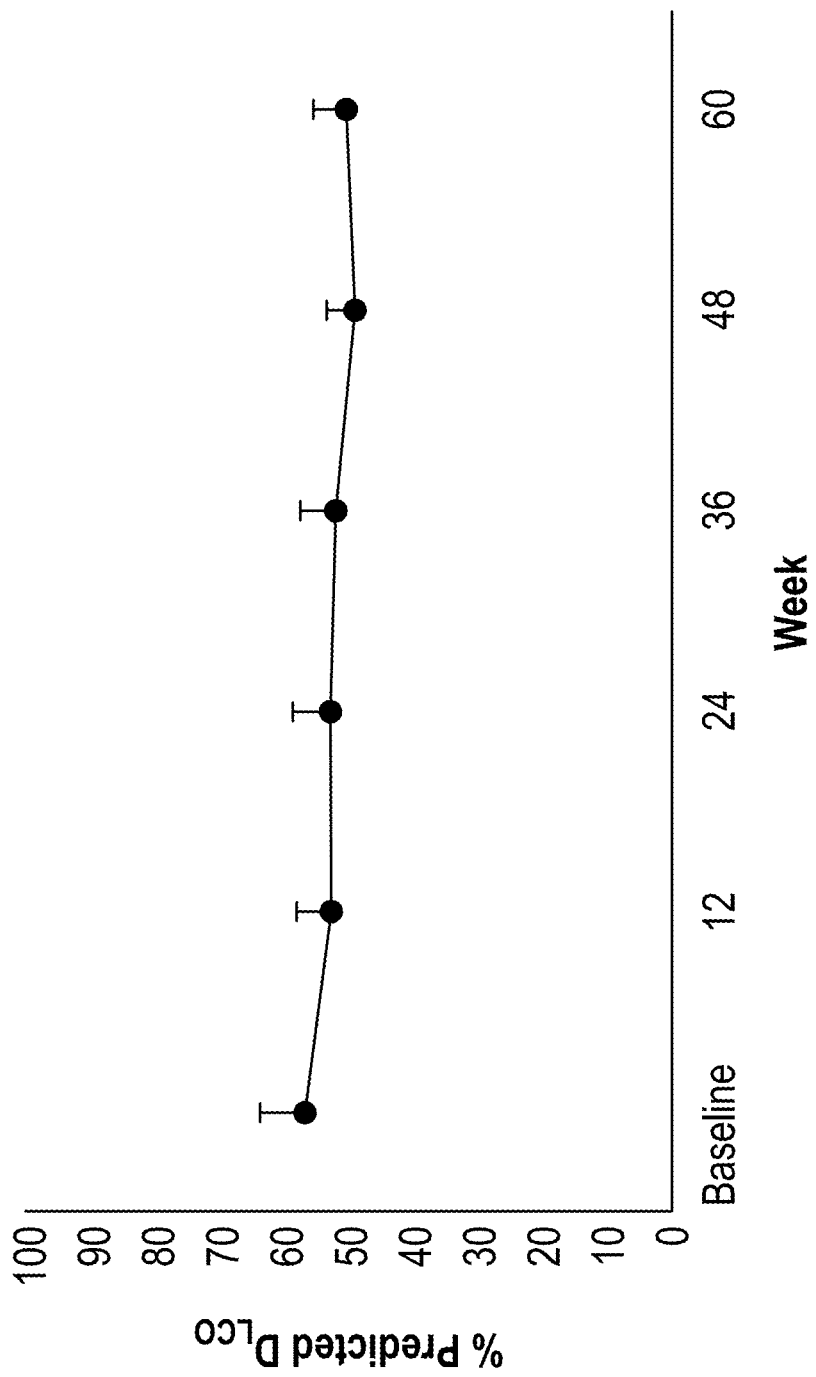
Figure 2C:
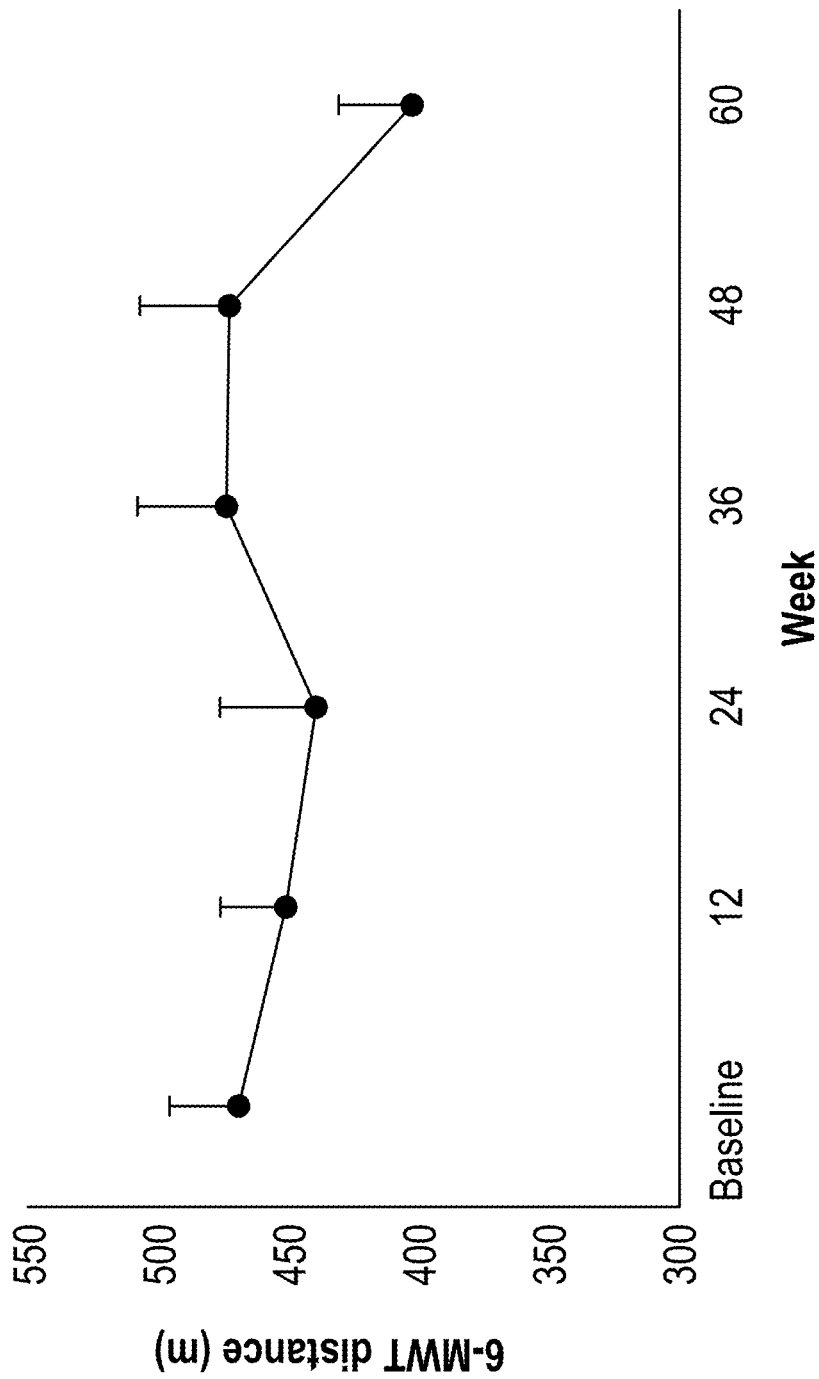
Figure 2D:
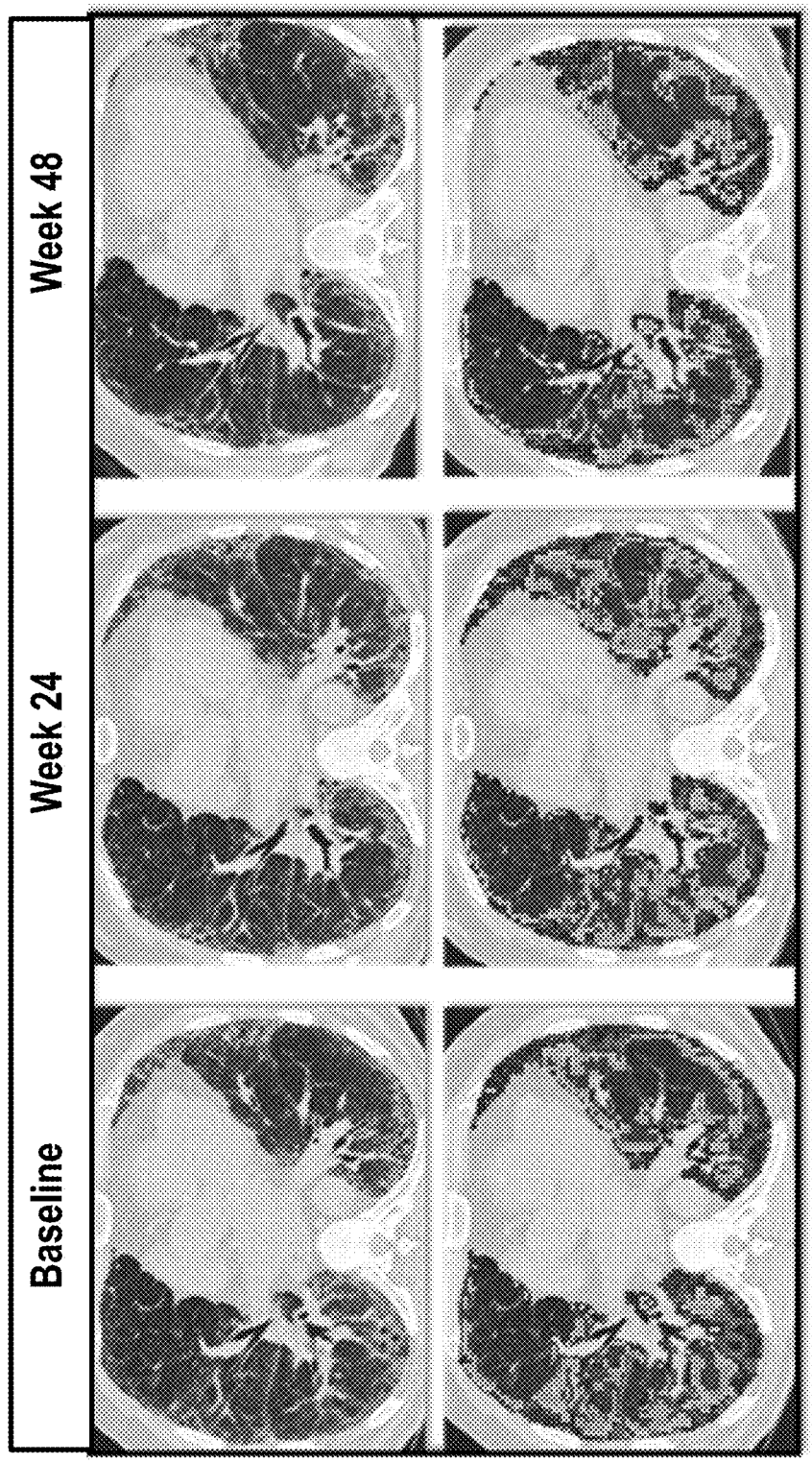

Eleven patients were enrolled between Oct. 30, 2013, and Sep. 9, 2014 (FIG. 1). Two participants withdrew before treatment (one from clinical instability and exacerbation of disease [patient 008] and another from an unforeseen inability to attend the week 4 safety visit [patient 009]). All patients provided written informed consent before enrollment and were treated according to the protocol approved by the University of Miami Institutional Review Board (protocol approval #20120924).

The primary end point was the incidence (at week 4 postinfusion) of any treatment emergent serious adverse events, defined as the composite of death, nonfatal pulmonary embolism, stroke, hospitalization for worsening dyspnea, and clinically significant laboratory test abnormalities. This definition of treatment-emergent adverse events was made on the basis of single-dose IV MSC clinical trials in cardiovascular disease and aging. These trials used 30-day treatment-emergent adverse events as a primary safety end point.[18, 24, 25] Secondary efficacy end points were exploratory and related to disease progression (rate of acute exacerbations as defined by consensus guidelines, and decline of lung function as measured by absolute FVC and Dlco).

Patients were assigned to 1 of 3 cohorts and received treatment between Nov. 21, 2013, and Oct. 13, 2014. Allocation ratio to cohorts was 1:1:1 (n=9), with enrolled patients sequentially assigned to the 3 cohorts. Dose escalation occurred between cohorts as shown in Table 1.

TABLE 1

Dosing Schedule of AETHER Participants

| Cohort | Subject ID | Dosing Date |
|---|---|---|
| Cohort 1 | 001 | Nov. 21, 2013 |
| $2 \times 10^7$ hMSCs/infusion | 002 | Jan. 22, 2014 |
| (20 million) | 003 | Feb. 26, 2014 |
| Cohort 2 | 004 | Apr. 17, 2014 |
| $1 \times 10^8$ hMSCs/infusion | 005 | May 9, 2014 |
| (100 million) | 006 | May 15, 2104 |
| Cohort 3 | 007 | Sep. 5, 2014 |
| $2 \times 10^8$ hMSCs/infusion | 010 | Oct. 8, 2014 |
| (200 million) | 011 | Oct. 13, 2014 |

AETHER = Allogeneic Human Mesenchymal Stem Cells in Patients With Idiopathic Pulmonary Fibrosis via Intravenous Delivery trial;
hMSCs = human mesenchymal stem cells Patients in the study received a standard dose of hMSCs rather than weight-based doses made on the basis of results from previous studies in patients with cardiovascular disease.[16] Detailed study procedures are listed in Table 2. At the initial screening visit, informed consent was obtained and medical history was reviewed. Baseline studies included physical examination, routine bloodwork, urinalysis, ECG, echocardiogram, high-resolution computed tomography (HRCT), spirometry, Dlco, lung volumes, 6-min walk test (6-MWT), and quality of life questionnaires. Treatment infusion was considered day 1. Adverse events were reviewed at day 1, week 1, and at all visits thereafter. The primary end point was assessed starting at week 4 until week 60 and additionally 28 days thereafter. Secondary efficacy end points were measured at baseline and every 12 weeks until week 60.

TABLE 2

AETHER schedule of assessments

| Visit | Screening ± 28 d | Baseline 2-4 wk | Day 1 Week 1 | Day 2 | Week 1 (Day 7) | Week 2 (Day 14) | Month 1 (Week 4) | Month 3 Week 12 (±3-5 d) | Month 6 Week 24 (±3-5 d) | Month 9 Week 36 (±3-5 d) | Month 12 Week 48 (±3-5 d) | Month 15 Week 60 (±3-5 d) |
|---|---|---|---|---|---|---|---|---|---|---|---|---|
| Informed consent | x | | | | | | | | | | | |
| Full medical history | x | | | | | | | | | | | |
| Physical examination | x | x | x | x | x | x | x | x | x | x | x | x |
| Chem7, LFTs, PT/INR | x | | | | | | x | x | x | x | x | x |
| Urinalysis, CBC, and metabolic profile | x | | x | x | x | x | x | x | x | | | |
| Spirometry | x | | | | | | | x | x | x | x | x |
| Dlco | x | | | | | | | x | x | x | x | x |
| Echo-cardiogram | x | | | | | | | | | | | x |
| ECG | x | x | x | x | x | x | x | x | x | x | x | x |
| Treatment | | | x | | | | | | | | | |
| Review adverse events | | | x | | x | x | x | x | x | x | x | x |
| HRCT | x | | | | | | | | x | | x | |
| 6-MWT | x | | | | | | | x | x | x | x | x |
| Lung volumes | x | | | | | | | x | x | x | x | x |
| QOL questionnaires | x | | | | | | x | x | x | x | x | x |

CBC = complete blood count; Chem7 = sodium, potassium, chloride, uric acid, glucose, blood urea nitrogen, creatinine; Dlco = diffusing capacity of the lungs for carbon monoxide; ECG = electrocardiogram; HRCT = high-resolution CT; LFTs = liver function tests (alanine transaminase, alkaline phosphatase, aspartate transaminase, bilirubin, albumin, total protein, gamma glutamyl transpeptidase); PT/INR = prothrombin time (PT) along with its derived measures of prothrombin ratio and international normalized ratio (INR); QOL = quality of life; 6-MWT = six minute walk test.

Isolation of hMSCs

Because of the potential for pregnancy-induced antibodies to men's antigens, hMSCs were obtained only from men. Two men aged 24 and 25 years underwent bone marrow aspiration. Donors were neither related nor human leukocyte antigen-matched to recipients. Screening of allogeneic donors followed standard transplant practices and all allogeneic donors met allogeneic donor eligibility criteria as outlined in 21 CFR Part 1271. Donor eligibility screening included testing for antibodies against HIV-1/2, human T-lymphocyte virus I/II, hepatitis C virus, hepatitis B core (IgG and IgM), and cytomegalovirus; nucleic acid testing for HIV-1, hepatitis C virus, and West Nile virus; and testing for the surface antigen of the hepatitis B virus, *Trypanosoma cruzi* enzyme-linked immunosorbent assay, and rapid plasma reagin.

For each donor, a total of 60 mL of bone marrow was aspirated from the posterior iliac crest. The mononuclear cell fraction was isolated using a density gradient with lymphocyte separation media (specific gravity, 1.077). Low-density cells were collected and washed with Plasma-Lyte A containing 1% human serum albumin. Washed cells were sampled and viable cell numbers determined. The bone marrow mononuclear cells were seeded into 225 cm$^2$ tissue culture flasks in alpha Minimal Essential Medium containing 20% fetal bovine serum. After 14 days of culture, passage zero (P0) cells were harvested by trypsin treatment and expanded into 60 individual flasks. These flasks were incubated for a further 7 to 10 days before harvesting of MSCs by trypsin treatment (P1 cells). All procedures used in the preparation of the investigational product followed protocols previously published.[26]

Safety and Monitoring

After administration of hMSCs, patients were observed overnight in the ICU for any clinically significant changes in respiratory or cardiovascular parameters. Vital signs were assessed 2 hours before infusion, at the start of the infusion, and every 15 minutes after infusion.

The incidence and nature of all serious adverse events were reviewed and independently evaluated by the data safety monitoring board to determine whether they could be related to MSC administration. The data safety monitoring board was responsible for reviewing data for each cohort before dose escalation and for making recommendations regarding the continuation of the trial on the basis of the interim safety analysis performed 4 weeks after treatment of the last patient in cohort 2.

A nonsafety-related temporary hold was placed on the study on Jun. 30, 2015, by the FDA. All 9 participants were dosed before the hold; therefore, the dosing schedule was not affected. Adverse events were graded according to the Medical Dictionary for Regulatory Activities (MedDRA) scale.

Statistical Analysis

No formal statistical justification was performed to determine sample size. Cohort size was determined on the basis of expected requirements for safety analyses and projected enrollment rates. A 2-tailed Student t test was used to evaluate differences in secondary end points from baseline. A P value <0.05 was considered statistically significant.

Results

Table 3 summarizes the baseline characteristics of the 9 patients receiving treatment. Mean age of patients was 71.6 (±6.13) years, and all patients were white men of Hispanic/Latino or Caucasian descent. Mean time from diagnosis was 22 months. On the basis of baseline total lung capacity, FVC, Dlco, 6-MWT results, and the use of supplemental oxygen, patients in cohort 3 appear to have had more advanced disease than patients in cohorts 1 and 2. Eight patients received a diagnosis by HRCT; 1 required a lung biopsy because of a lack of honeycombing on the baseline HRCT.

TABLE 3

| | Baseline Characteristics of Treated Patients | | | |
|---|---|---|---|---|
| Characteristic | Cohort 1 $2 \times 10^7$ hMSCs/Infusion | Cohort 2 $1 \times 10^8$ hMSCs/Infusion | Cohort 3 $2 \times 10^8$ hMSCs/Infusion | All Cohorts |
| Age, years, mean (SD) | 71.00 (7.21) | 73.33 (4.04) | 70.33 (8.62) | 71.6 (6.13) |
| Men, No. (%) | 3 (100) | 3 (100) | 3 (100) | 9 (100) |
| Race, white, No. (%) | 3 (100) | 3 (100) | 3 (100) | 9 (100) |
| Ethnicity, Caucasian, No. (%) | 1 (33.3) | 2 (66.7) | 3 (100) | 6 (67) |
| Ethnicity, Hispanic/Latino, No. (%) | 2 (66.7) | 1 (33.3) | 0 (0) | 3 (33) |
| Time from diagnosis ≤ 1 y, No. (%) | 2 (66.7) | 0 (0) | 1 (33.3) | 3 (33) |
| Time from diagnosis ≥ 1 y, No. (%) | 1 (33.3) | 3 (100) | 2 (66.7) | 6 (67) |
| HRCT diagnosis, No. (%) | 2 (66.7) | 3 (100) | 3 (100) | 8 (88.9) |
| HRCT + biopsy diagnosis, No. (%) | 1 (33.3) | 0 (0) | 0 (0) | 1 (11.1) |
| TLC, L, mean (SD) | 4.15 (0.59) | 4.39 (1.22) | 3.93 (0.21) | 4.16 (0.71) |
| FVC, % predicted, mean (SD) | 76.00 (18.73) | 69.67 (21.55) | 56.33 (8.39) | 67.33 (17.23) |

TABLE 3-continued

Baseline Characteristics of Treated Patients

| Characteristic | Cohort 1<br>$2 \times 10^7$<br>hMSCs/Infusion | Cohort 2<br>$1 \times 10^8$<br>hMSCs/Infusion | Cohort 3<br>$2 \times 10^8$<br>hMSCs/Infusion | All<br>Cohorts |
|---|---|---|---|---|
| FVC, mL, mean (SD) | 2.88 (0.45) | 2.77 (0.82) | 2.49 (0.23) | 2.75 (0.52) |
| DLCO, % predicted, mean (SD) | 69.67 (21.78) | 44.33 (4.62) | 45.33 (11.24) | 53.11 (17.60) |
| 6-MWT, meters, mean (SD) | 415 (58.66) | 493 (48.77) | 340 (186.35) | 416 (120.52) |
| Baseline supplemental $O_2$, No. (%) | 0 (0) | 1 (33.3) | 2 (66.7) | 3 (33.3) |

HRCT = high-resolution CT;
TLC = total lung capacity;
Dlco = diffusing capacity of the lungs for carbon monoxide;
6-MWT = 6 Minute Walk Test;
FVC = forced vital capacity;
SD = standard deviation.

Eleven patients were enrolled in the study, but 2 patients withdrew before treatment. A total of 9 patients (3 per cohort) received treatment, and 7 patients completed the study (FIG. 1). Two patients in cohort 3 died before study completion, 1 at 10 weeks and 3 days postinfusion and the other died at 29 weeks and 6 days postinfusion (Table 4). Reported results are made on the basis of the modified intention-to-treat set, which includes all 9 patients that received treatment.

TABLE 4

Modified Intention-to-Treat Set

| Subject Status | Cohort 1<br>$2 \times 10^7$ hMSCs/<br>Infusion | Cohort 2<br>$1 \times 10^8$ hMSCs/<br>Infusion | Cohort 3<br>$2 \times 10^8$ hMSCs/<br>Infusion | Total, No.<br>(%) |
|---|---|---|---|---|
| Started, No. (%) | 3 (100) | 3 (100) | 3 (100) | 9 (100) |
| Completed, No. (%) | 3 (100) | 3 (100) | 1 (33.3) | 7 (78) |
| Not completed, No. (%) | 0 (0) | 0 (0) | 2 (66.7) | 2 (22) |

Data are No. of participants (%).
Modified intention-to-treat set = participants treated with hMSCs, regardless of study completion.

Table 5 summarizes patients' respiratory and hemodynamic parameters at baseline, during treatment, and at 2 hours postinfusion. None of the participants experienced clinically significant changes in any of these parameters and all patients received the full treatment dose.

TABLE 5

Respiratory and Hemodynamic Parameters at Baseline and After hMSC Infusion

| Subject ID | 2 h Before Infusion (Baseline) | | | Start/During Infusion | | | 2 h After Infusion | | |
|---|---|---|---|---|---|---|---|---|---|
| | HR (beats/min) | MAP (mm Hg) | $SpO_2$ (%) | HR (beats/min) | MAP (mm Hg) | $SpO_2$ (%) | HR (beats/min) | MAP (mm Hg) | $SpO_2$ (%) |
| 001 | 69 | 120/73 | 95 | 76 | 121/70 | 96 | 79 | 115/74 | 96 |
| 002 | 67 | 116/71 | 97 | 75 | 108/63 | 95 | 74 | 115/60 | 97 |
| 003 | 65 | 158/68 | 99 | 63 | 150/49 | 99 | 68 | 134/55 | 98 |
| 004 | 54 | 132/61 | 98 | 56 | 120/68 | 100 | 62 | 129/72 | 99 |
| 005 | 54 | 153/83 | 97 | 58 | 162/77 | 98 | 56 | 154/76 | 94 |
| 006 | 70 | 152/72 | 99 | 65 | 148/82 | 100 | 67 | 130/80 | 99 |
| 007 | 61 | 127/63 | 94 | 58 | 137/58 | 94 | 58 | 140/55 | 95 |
| 010 | 61 | 158/76 | 97 | 60 | 165/74 | 98 | 66 | 155/74 | 96 |
| 011 | 56 | 139/78 | 98 | 57 | 126/71 | 98 | 61 | 97/49 | 95 |

HR = heart rate; MAP = mean arterial pressure; $SpO_2$ = peripheral capillary oxygen saturation.

A total of 21 adverse events occurred in 7 patients in the modified intention-to-treat set (Table 6). The most frequently recorded adverse events included bronchitis (3 patients) and common cold (2 patients). Of the 21 adverse events recorded, only 1 (generalized anxiety disorder in patient 007 that began at 8 weeks postinfusion) was classified as possibly related to the study intervention (grade 3; MedDRA). No probable (grade 4; MedDRA) or definite (grade 5; MedDRA) adverse events were reported.

TABLE 6

Adverse Events: Pooled Data From the AETHER Trial

| Adverse Events | Cohort 1 (n = 3) $2 \times 10^7$ hMSCs/ Infusion | Cohort 2 (n = 3) $1 \times 10^8$ hMSCs/ Infusion | Cohort 3 (n = 3) $2 \times 10^8$ hMSCs/ Infusion | Total, No. (%) |
|---|---|---|---|---|
| Treatment-emergent adverse events | 0 | 0 | 0 | 0 |
| Any adverse events | 3 | 1 | 3 | 7 (78) |
| Most frequent adverse events[a] | | | | |
| Bronchitis | 3 | 0 | 0 | 3 (33) |
| Common cold | 1 | 0 | 1 | 2 (22) |
| Less frequent adverse events | | | | |
| Sinusitis | 1 | 0 | 0 | 1 (11) |
| Squamous cell carcinoma | 1 | 0 | 0 | 1 (11) |
| Worsening hypoxia | 0 | 0 | 1 | 1 (11) |
| Dyspnea | 0 | 0 | 1 | 1 (11) |
| Increased cough | 0 | 0 | 1 | 1 (11) |
| Mild sore throat | 1 | 0 | 0 | 1 (11) |
| Rhinitis | 0 | 0 | 1 | 1 (11) |
| Body aches | 0 | 0 | 1 | 1 (11) |
| Leg swelling | 1 | 0 | 0 | 1 (11) |
| Prostatitis | 0 | 0 | 1 | 1 (11) |
| Generalized anxiety disorder[b] | 0 | 0 | 1 | 1 (11) |
| Serious adverse event(s) | | | | |
| Respiratory failure | 0 | 0 | 1 | 1 (11) |
| Progression of idiopathic pulmonary fibrosis[c] | 0 | 0 | 2 | 1 (22) |
| Fatal adverse event(s) | 0 | 0 | 2 | 2 (22) |

[a]Adverse events reported by more than one patient in the study.
[b]Adverse event possibly related to the study.
[c]Corresponds to MedDRA term "IPF," which includes disease worsening and exacerbations of IPF.

There were no instances of treatment-emergent adverse events. No events of worsened dyspnea or acute exacerbation were reported within 30 days of treatment. One patient experienced worsened dyspnea at 4 weeks and 5 days postinfusion (patient 007), and the same patient experienced an acute exacerbation at 7 weeks and 3 days postinfusion.

Three serious adverse events (2 instances of death [patients 007 and 010] and 1 instance of respiratory failure [patient 007]) occurred in cohort 3. Patient 007 experienced an acute exacerbation and subsequent respiratory failure resulting in death at 10 weeks and 3 days postinfusion. Patient 010 experienced progression of IPF (defined as disease worsening according to MedDRA), resulting in death at 29 weeks and 6 days postinfusion. None of these serious adverse events was determined to be treatment-related.

Table 7 shows the progression of lung function parameters over the course of the study. Data for participants 007 and 010 are not available beyond week 4. FIG. 2 shows progression of select respiratory parameters up to 60 weeks postinfusion. Data combined for all cohorts (n=7) demonstrated a mean absolute decline in % predicted FVC of 3.0% and a 5.4% decline in % predicted $D_{LCO}$. Overall, 6-MWT improved by 36 weeks postinfusion (+1% improvement from baseline), and declined to −4.4% from baseline by week 60 (FIG. 2). These data are considered exploratory because the study was not powered for efficacy analyses and lacked a placebo-control arm.

TABLE 7

Progression of Lung Function Parameters

| Subject ID | Baseline | Week 12 | Week 24 | Week 36 | Week 48 | Week 60 |
|---|---|---|---|---|---|---|
| TLC, L, Mean | | | | | | |
| 001 | 3.60 | 3.21 | 3.90 | 3.12 | 3.16 | 3.12 |
| 002 | 4.08 | 4.59 | 4.04 | 4.63 | 4.76 | 4.80 |
| 003 | 4.78 | 5.08 | 4.07 | 4.39 | 4.39 | 3.34 |
| 004 | 5.79 | 4.39 | 4.97 | 4.50 | 5.81 | 5.62 |
| 005 | 3.85 | 3.66 | 3.53 | 4.45 | 4.17 | 4.39 |
| 006 | 3.54 | 3.47 | 3.31 | 3.62 | 4.29 | 4.52 |
| 007 | 3.73 | N/A | N/A | N/A | N/A | N/A |
| 010 | 4.14 | N/A | N/A | N/A | N/A | N/A |
| 011 | 3.91 | 4.09 | 4.25 | 4.18 | 4.67 | 4.85 |
| FVC, L, Mean | | | | | | |
| 001 | 2.48 | 2.14 | 2.56 | 2.20 | 2.26 | 1.95 |
| 002 | 3.38 | 3.64 | 2.98 | 3.39 | 3.34 | 3.34 |
| 003 | 2.91 | 2.85 | 2.92 | 2.65 | 2.69 | 2.83 |
| 004 | 3.76 | 3.50 | 3.67 | 3.62 | 3.75 | 3.61 |
| 005 | 2.18 | 2.20 | 2.17 | 2.05 | 2.07 | 2.03 |

TABLE 7-continued

Progression of Lung Function Parameters

| Subject ID | Baseline | Week 12 | Week 24 | Week 36 | Week 48 | Week 60 |
|---|---|---|---|---|---|---|
| 006 | 2.58 | 2.62 | 2.4 | 2.54 | 2.42 | 2.48 |
| 007 | 2.25 | N/A | N/A | N/A | N/A | N/A |
| 010 | 2.51 | N/A | N/A | N/A | N/A | N/A |
| 011 | 2.70 | 2.76 | 2.50 | 2.47 | 2.75 | 2.94 |
| $D_{LCO}$, % Predicted, Mean | | | | | | |
| 001 | 63 | 50 | 50 | 52 | 46 | 45 |
| 002 | 52 | 50 | 44 | 46 | 40 | 43 |
| 003 | 94 | 79 | 84 | 80 | 72 | 79 |
| 004 | 47 | 42 | 49 | 50 | 47 | 46 |
| 005 | 47 | 44 | 51 | 44 | 39 | 45 |
| 006 | 39 | 41 | 33 | 33 | 41 | 43 |
| 007 | 48 | N/A | N/A | N/A | N/A | N/A |
| 010 | 33 | N/A | N/A | N/A | N/A | N/A |
| 011 | 55 | 63 | 58 | 58 | 58 | 51 |
| 6-MWT, meters, Mean | | | | | | |
| 001 | 471 | 460 | 417 | 540 | 450 | 360 |
| 002 | 420 | 402 | 270 | 315 | 381 | 300 |
| 003 | 354 | 393 | 405 | 465 | 420 | 366 |
| 004 | 531 | 423 | 495 | 540 | 560 | 486 |
| 005 | 510 | 540 | 540 | 525 | 432 | 393 |
| 006 | 438 | 396 | 405 | 390 | 432 | 405 |
| 007 | 225 | N/A | N/A | N/A | N/A | N/A |
| 010 | 240 | N/A | N/A | N/A | N/A | N/A |
| 011 | 555 | 540 | 540 | 537 | 630 | 510 |

TLC = total lung capacity;
FVC = forced vital capacity
6-MWT = 6 minute walk test; N/A = not applicable.

Discussion

AETHER was the first clinical trial conducted over 60 weeks to support the safety of a single IV infusion of bone marrow-derived hMSCs in patients with IPF. All study objectives followed the recommendations of the FDA and the American Thoracic Society.[1]

AETHER trial met its primary end point of safety, showing that the administration of hMSCs is safe in patients with IPF up to $2 \times 10^8$ cells/infusion. The intervention was well-tolerated in all patients and there were no treatment-emergent serious adverse events reported. A majority of patients (78%) experienced treatment unrelated adverse events including, but not limited to, bronchitis, common cold, and sinusitis (Table 7), which one might expect given the long duration of the study and the characteristics of the population being studied.

References for Example 1

1. Raghu G, et al. An official ATS/ERS/JRS/ALAT statement: idiopathic pulmonary fibrosis: evidence-based guidelines for diagnosis and management. Am J Resp Crit Care Med. 183(6):788-824.
2. Travis W D, et al. Idiopathic nonspecific interstitial pneumonia: report of an American Thoracic Society project. Am J Resp Crit Care Med. 2008; 177(12):1338-1347.
3. Nishimura K, et al. Usual interstitial pneumonia: histologic correlation with high-resolution CT. Radiology. 1992; 182(2):337-342.
4. Johkoh T, Muller N L, Cartier Y, et al. Idiopathic interstitial pneumonias: diagnostic accuracy of thin-section $C_T$ in 129 patients. Radiology. 1999; 211(2):555-560.
5. King T E Jr., Bradford W Z, Castro-Bernardini S, et al. A phase 3 trial of pirfenidone in patients with idiopathic pulmonary fibrosis. N Engl J Med. 2014; 370(22):2083-2092.
6. Richeldi L, et al. Nintedanib in patients with idiopathic pulmonary fibrosis: Combined evidence from the TOMORROW and INPULSIS® trials. Res Med. 2016; 113:74-79.
7. Moodley Y, et al. Human umbilical cord mesenchymal stem cells reduce fibrosis of bleomycin-induced lung injury. Am J Pathol. 2009; 175(1):303-313.
8. Rojas M, Xu J, Woods C R, et al. Bone marrow-derived mesenchymal stem cells in repair of the injured lung. Am J Resp Cell Mol Bio. 2005; 33(2):145-152.
9. Tashiro J, et al. Therapeutic benefits of young, but not old, adipose-derived mesenchymal stem cells in a chronic mouse model of bleomycin-induced pulmonary fibrosis. Transl Res. 2015; 166(6):554-567.
10. Ortiz L A, et al. Mesenchymal stem cell engraftment in lung is enhanced in response to bleomycin exposure and ameliorates its fibrotic effects. Proc Natl Acad Sci USA. 2003; 100(14): 8407-8411.
11. Ishizawa K, et al. Bone marrow-derived cells contribute to lung regeneration after elastase-induced pulmonary emphysema. FEBS Lett. 2004; 556(1-3):249-252.
12. Spees J L, et al. Engraftment of bone marrow progenitor cells in a rat model of asbestos-induced pulmonary fibrosis. Am J Resp Crit Care Med. 2007; 176(4):385-394.
13. Spees J L, et al. Bone marrow progenitor cells contribute to repair and remodeling of the lung and heart in a rat model of progressive pulmonary hypertension. FASEB J. 2008; 22(4): 1226-1236.
14. Bonfield T L, et al. Human mesenchymal stem cells suppress chronic airway inflammation in the murine ovalbumin asthma model. Am J Physiol. 2010; 299(6):L760-L770.
15. Lee J W, et al. Allogeneic human mesenchymal stem cells for treatment of E. coli endotoxin-induced acute lung injury in the ex vivo perfused human lung. Proc Natl Acad Sci USA. 2009; 106(38): 16357-16362.

16. Hare J M, Traverse J H, Henry T D, et al. A randomized, double-blind, placebo-controlled, dose-escalation study of intravenous adult human mesenchymal stem cells (prochymal) after acute myocardial infarction. J Am Coll Cardiol. 2009; 54(24):2277-2286.
17. Liang J, et al. Allogenic mesenchymal stem cells transplantation in refractory systemic lupus erythematosus: a pilot clinical study. Ann Rheum Dis. 2010; 69(8):1423-1429.
18. Hare J M, et al. Comparison of allogeneic vs autologous bone marrow-derived mesenchymal stem cells delivered by transendocardial injection in patients with ischemic cardiomyopathy: the POSEIDON randomized trial. JAMA. 2012; 308(22):2369-2379.
19. Chambers D C, et al. A phase 1b study of placenta-derived mesenchymal stromal cells in patients with idiopathic pulmonary fibrosis. Respirology. 2014; 19(7): 1013-1018.
20. Le Blanc K, et al. Mesenchymal stem cells for treatment of steroid-resistant, severe, acute graft-versus-host disease: a phase II study. Lancet. 2008; 371(9624):1579-1586.
21. Tzouvelekis A, et al. A prospective, non-randomized, no placebo-controlled, phase Ib clinical trial to study the safety of the adipose derived stromal cells-stromal vascular fraction in idiopathic pulmonary fibrosis. J Transl Med. 2013; 11:171.
22. Weiss D J, et al. A placebo-controlled, randomized trial of mesenchymal stem cells in COPD. Chest. 2013; 143 (6): 1590-1598.
23. Wilson J G, Liu K D, Zhuo H, et al. Mesenchymal stem (stromal) cells for treatment of ARDS: a phase 1 clinical trial. Lancet. 2015; 3(1):24-32.
24. Heldman A W, et al. Transendocardial mesenchymal stem cells and mononuclear bone marrow cells for ischemic cardiomyopathy: the TAC-HFT randomized trial. JAMA. 2014; 311(1):62-73.
25. Golpanian S, et al. Rationale and design of the allogeneic human mesenchymal stem cells (hMSC) in patients with aging frailty via intravenous delivery (CRATUS) study: a phase I/II, randomized, blinded and placebo controlled trial to evaluate the safety and potential efficacy of allogeneic human mesenchymal stem cell infusion in patients with aging frailty. Oncotarget. 2016; 7(11): 11899-11912.
26. Trachtenberg B, Velazquez D L, Williams A R, et al. Rationale and design of the Transendocardial Injection of Autologous Human Cells (bone marrow or mesenchymal) in Chronic Ischemic Left Ventricular Dysfunction and Heart Failure Secondary to Myocardial Infarction (TAC-HFT) trial: a randomized, double-blind, placebo-controlled study of safety and efficacy. Am Heart J. 2011; 161(3):487-493.
27. Ley B, et al. Unified baseline and longitudinal mortality prediction in idiopathic pulmonary fibrosis. Eur Resp J. 2015; 45(5): 1374-1381.
28. Lama V N, Phan S H. The extrapulmonary origin of fibroblasts: stem/progenitor cells and beyond. Proc Am Thorac Soc. 2006; 3(4):373-376.
29. Phillips R J, Burdick M D, Hong K, et al. Circulating fibrocytes traffic to the lungs in response to CXCL12 and mediate fibrosis. J Clin Invest. 2004; 114(3): 438-446.
30. Salazar K D, et al. Mesenchymal stem cells produce Wnt isoforms and TGF-beta1 that mediate proliferation and procollagen expression by lung fibroblasts. Am J Physiol. 2009; 297(5):L1002-L1011.
31. Hashimoto N, Jin H, Liu T, Chensue S W, Phan S H. Bone marrow-derived progenitor cells in pulmonary fibrosis. J Clin Invest. 2004; 113(2): 243-252.
32. Raghu G, et al. Idiopathic pulmonary fibrosis: clinically meaningful primary endpoints in phase 3 clinical trials. Am J Resp Crit Care Med. 2012; 185(10):1044-1048.

Example 2: ReCELL-IPF Repeated Dose Study

To expand our prior study (AETHER) and clarify the safety of MSCs in lung disease, this study proposes to test the safety of multi-dose bone marrow derived mesenchymal stem cells (MSCs).

The Allogeneic Human Mesenchymal Stem Cells (MSCs) in patients with IPF (AETHER) trial was the first study designed to evaluate the safety of a single intravenous infusion of bone marrow-derived MSCs in patients with IPF (NCT02013700). This Phase I Trial to Evaluate the Safety, Tolerability, and Potential Efficacy of Multi-dose Allogeneic Human Mesenchymal Stem Cell Infusions in Patients with Idiopathic Pulmonary Fibrosis (ReCELL-IPF) Trial uses the same intravenous delivery method as in our completed AETHER trial. ReCELL-IPF is the first multi-dose safety study with MSCs delivered intravenously and that will establish safety and explore efficacy of this treatment in patients with IPF. We have designed ReCELL-IPF to advance the safety findings of AETHER and establish safety and tolerability of a multi-dose regimen of infusion of MSCs. The first-in-man trial design will address whether safety of MSC therapy is dose-dependent and/or donor-dependent. This 52 week trial, randomized by donor, will be the first trial to use MSCs from multiple donors; whereby each subject receives the same donor MSCs for all three dosages. Our safety and tolerability measures ensure valuable data for a future later phase trial design, while exploratory data for efficacy measures will establish future power calculations as well as potential factors to be used in assessing efficacy. Coupled to these exploratory studies assessing biomarkers and transcriptomics, we will innovatively develop intermediary measures for determination of treatment efficacy in those studies, accelerating development.

The trial is focused on patients with mild to moderate IPF, ages 40-75. While the use of the approved "anti-fibrotic" drugs to treat IPF, pirfenidone and nintedanib, has been shown to slow the progression of the disease, (1, 2) both compounds have considerable side effects and neither is curative. Their efficacy also appears similar from "real-world" analyses (3). Morbidity and mortality from IPF remains high, adding to the urgency for alternative therapeutic options. The AETHER trial was a single dose safety study; safety needs to be assured with a multi-dose regimen in the same mild to moderate stage patients with IPF.

The basic study design consists of block randomization by donor of patients with mild to moderate IPF using a multi-dose intervention (MSCs infusion) for three dosages of allogeneic MSCs of $1\times10^8$ (100 million) MSCs/infusion delivered via peripheral intravenous infusion for a total of $3\times10^8$ (300 million) MSCs/patient every four months for one year. Subjects will be randomized by donor so that they receive all three dosages from the same donor in a proof of concept clinical investigation that has clinical equipoise. Differences in the rate of decline of FVC (percent predicted) and DLCO in patients with mild to moderate IPF at 52 week follow up, are expected to reflect results from AETHER showing that the mean decline in % predicted FVC and DLCO were below the thresholds for disease suggesting that MSC therapy could have efficacy in patients with IPF. Subjects in AETHER also had a dip in their walk distance and DLCO at 24 and 48 weeks raising the question of enhanced efficacy with a multi-dose regimen. We realize that only descriptive statistics will be associated with outcomes in this Aim (mean change in FVC, DLCO, and six-minute walk distance/oxygen saturation pre and post treatment at 52 weeks) for the three different treatment groups. Means at baseline and 52 week follow up for each outcome, as well as the change over time, will be provided for each group from this data, we will also attempt to obtain estimates of the efficacy based on the major outcomes, such as FVC (percent predicted), absolute decline of DLCO, and six-minute walk distance. Changes in % FVC are an established outcome of disease progression in patients with IPF as demonstrated in numerous studies. In fact, decreases in FVC as small as 5-10% at 24 weeks have been associated with more than twofold higher mortality risk in IPF patients (4).

We will enroll 18 mild to moderate IPF patients who meet all inclusion and exclusion criteria. The study will include a total of 17 visits (+screening) over the 52 week study, and four telephone follow-up calls, as listed below:

Screening Visit: Within 28 Days of Day 1 visit
Visit 1=Baseline: Within 14 days of Day 1 visit
Visit 2: Day 1 Treatment administration—first dose
Visit 3: Day 2
Visit 4: Week 1—Day 7 (±2 days)
Telephone follow-up: Day 14 (±2 days)
Visit 5: Week 4: Day 28 (±3 days)
Visit 6: Week 12 (±3 days)
Visit 7: Week 16 (±2 days) Treatment administration—second dose
Visit 8: 1 day after visit 7
Visit 9: Week 17 (±2 days)
Telephone follow-up: Week 18 (±2 days)
Visit 10: Week 20 (±3 days)
Visit 11: Week 28 (±3 days)
Visit 12: Week 32 (±2 days) Treatment administration—third dose
Visit 13: 1 day after visit 12
Visit 14: Week 33 (±2 days)
Telephone follow-up: Week 34 (±2 days)
Visit 15: Week 36 (±3 days)
Visit 16: Week 44 (±3 days)
Visit 17: Week 52 (±5 days)

Samples will be collected at baseline and before and after each infusion of MSCs for banking for exploratory studies on selected biomarkers and transcriptomics. Additional exploratory endpoints include difference in frequency of acute exacerbations of IPF; difference in subject reported dyspnea and quality of life (QOL) assessment using University of California San Diego Shortness of Breath Questionnaire (UCSD-SOBA) (5, 6), and St George's Respiratory Questionnaire (SGRQ) (7); all-cause mortality; quantitative changes in HRCT scans of chest; and difference in selected biomarkers and transcriptomics.

We have chosen to measure KL-6, surfactant proteins SP-A and D, and MMP-7 as exploratory biomarkers before and after each infusion (8-11). There is limited data to validate the role of clinically useful biomarkers that are able to diagnose disease, identify responses to therapy, or define prognosis at the time of diagnosis and none have been studied in the setting of cell-based therapy in IPF (12). The most recent ATS consensus guidelines referenced several notable clinical trials that identified biomarkers including KL-6/MUC1, SP-A and D, CCL18, MMP-1, and MMP-7 (12).

Many of these biomarkers relate to alterations in type II alveolar epithelial cell behavior including release of Krebs von den Lungen-6 antigen (KL-6) (13) and changes in surfactant protein (SP) levels in the bloodstream (10). Multiple studies of small groups of IPF patients have shown that serum levels of SP-A and SP-D are higher in patients with a UIP (usual interstitial pneumonia) pattern compared to healthy controls. However, both SP-A and SP-D levels are also elevated in other chronic interstitial lung diseases, and may therefore not be able to distinguish UIP from other interstitial pneumonias (NSIP, BOOP) or sarcoid (14). While studies have demonstrated higher serum SP-A and SP-D levels in IPF subjects compared to patients with sarcoidosis and berylliosis (15) patients with ILD secondary to systemic sclerosis have also shown similar levels of serum surfactant proteins to those seen in IPF subjects. In some models, high serum levels of surfactant appear to be associated with worse survival (15, 16). Kinder and colleagues found that serum SP-A, but not serum SP-D, was an independent predictor of mortality (17). The utility in using these serum levels to predict mortality is again variable. Greene, et al. noted that when SP-A and SP-D serum levels were used in a multivariate analysis they did not improve mortality prediction beyond clinical variables (15).

Peripheral blood levels of MMP-7 alone have been shown to be an independent predictor of mortality in IPF (18, 19). In a study of 118 South Korean IPF patients, an MMP-7 level >12.1 ng/mL was associated with a risk of death during follow-up more than twice that of patients with lower plasma levels. However, high levels of MMP-7 and SP-A in combination predicted shorter survival and greater lung function decline compared with those with high levels of one biomarker. Furthermore, high baseline levels of both MMP-7 and SP-A were associated with a risk of death during follow up 3.8 times that of patients with low levels of both biomarkers. Unfortunately, the addition of these two biomarkers to clinical parameters (age, % FVC, % DLCO, and change in FVC in 6 months) did not improve prognostication beyond clinical parameters alone (19).

The experimental approach consists of random assignment of patients with mild to moderate IPF to one of three donor MSCs. Subjects will be randomized by donor and receive all dosages from the same donor. Data will be collected at different time points. A total of 18 patients will be enrolled with the expectation that all patients will complete 52 week follow up. Because the current literature shows equivalent efficacy for either of the anti-fibrotic therapies, and allowing background therapy with pirfenidone or nintedanib will facilitate enrollment, either drug will be permitted (3, 20). Subjects who take pirfenidone or nintedanib for at least 2 months prior to enrollment will not be excluded from this study.

High resolution computed tomography of chest: Three HRCT of chests will be performed with 0.45 Rem total exposure. The protocol is the same as used for the AETHER study. HRCT (1 mm) will be run on a Siemens Definition 64 slice CT scanner (Siemens Healthineers, Malvern, Pa.). Scanning parameters are: supine position, full inspiration, kV 120, effective mAs 100, collimation 64×0.6 mm, axial reconstructed slice thickness 1 mm, reconstruction algorithm B45f. Coronal, sagittal, and MW images will also be reconstructed.

Echocardiograms: Four echocardiograms are conducted in the study at screening to confirm normal right ventricular function. The other three echocardiograms done in the study determine that there is no development of impaired right ventricular function and/or echocardiographic evidence of pulmonary hypertension defined as right ventricular systolic pressure greater than 40 mm Hg from the multi-dose MSC infusions.

Biological sample processing: Blood will be centrifuged at 500 g, serum removed for plasma studies, aliquoted into Eppendorf tubes, and stored at −80° C. until use. Analyses of biological samples will be batched to minimize freeze/thawing, which can influence measurements. The candidate biomarkers to be tested include MMP-7 (R&D systems), KL-6 (myBiosource), SFA and D (BioVendor ELISA). Blood will be sent for transgenomics.

Health-related quality of life questionnaires: The St. George's Respiratory Questionnaire (SGRQ) (12-month version) (7) is a self-administered health-related quality of life (HRQL) questionnaire used as an important outcome of treatment effect in patients with IPF. This instrument for asthma and COPD is applied to patients with IPF and contains 50 items divided into three components: Symptoms (8 items), Activity (16 items) and Impacts (26 items). Each item has an empirically derived weight, and scores ranging from 0 to 100 are calculated for each component, as well as a total score. Higher scores indicate greater impairment in HRQL. The University of California, San Diego shortness of Breath questionnaire (UCSD-SOBA) (5, 6) is another HRQL instrument that has 21 items that assess severity of shortness of breath during specific activities of daily living and is used as an important outcome of treatment effect in patients with IPF. If patients do not routinely perform the activity, they are asked to estimate the degree of shortness of breath anticipated. Three additional items ask about limitations due to: shortness of breath, fear of harm from over-exertion and fear of shortness of breath. Items are scored on a 6 point scale (0="not at all" to 5="maximal or unable to do because of breathlessness") with scores ranging from 0 to 120.

References for Example 2

1. King T E, Jr., et al. A phase 3 trial of pirfenidone in patients with idiopathic pulmonary fibrosis. *N Engl J Med* 2014; 370: 2083-2092.
2. Richeldi L, et al. Efficacy and safety of nintedanib in idiopathic pulmonary fibrosis. *N Engl J Med* 2014; 370: 2071-2082.
3. Hughes G, et al. Real World Experiences: Pirfenidone and Nintedanib are Effective and Well Tolerated Treatments for Idiopathic Pulmonary Fibrosis. *J Clin Med* 2016; 5.
4. du Bois R M, et al. Forced vital capacity in patients with idiopathic pulmonary fibrosis: test properties and minimal clinically important difference. Am J Respir Crit Care Med 2011; 184: 1382-1389.
5. Eakin E G, et al. Validation of a new dyspnea measure: the UCSD Shortness of Breath Questionnaire. University of California, San Diego. Chest 1998; 113: 619-624.
6. Kupferberg D H, et al. Minimal clinically important difference for the UCSD Shortness of Breath Questionnaire. J Cardiopulm Rehabil 2005; 25: 370-377.
7. Swigris J J, et al. The SF-36 and SGRQ: validity and first look at minimum important differences in IPF. Respir Med 2010; 104: 296-304.
8. Ishikawa N, Hattori N, Yokoyama A, Kohno N. Utility of KL-6/MUC1 in the clinical management of interstitial lung diseases. Respir Investig 2012; 50: 3-13.
9. Kennedy B, et al. Biomarkers to identify ILD and predict lung function decline in scleroderma lung disease or idiopathic pulmonary fibrosis. Sarcoidosis Vasc Diffuse Lung Dis 2015; 32: 228-236.
10. Hamai K, et al. Comparative Study of Circulating MMP-7, CCL18, KL-6, SP-A, and SP-D as Disease Markers of Idiopathic Pulmonary Fibrosis. Dis Markers 2016: 4759040.
11. Guiot J, Moermans C, et al. Blood Biomarkers in Idiopathic Pulmonary Fibrosis. Lung 2017; 195: 273-280.
12. Raghu G, et al, American Thoracic Society ERSJRS, Latin American Thoracic S. Diagnosis of Idiopathic Pulmonary Fibrosis. An Official ATS/ERS/JRS/ALAT Clinical Practice Guideline. Am J Respir Crit Care Med 2018; 198: e44-e68.
13. Zheng P, et al. Diagnostic value of KL-6 in idiopathic interstitial pneumonia. J Thorac Dis 2018; 10: 4724-4732.
14. Chiba H, Otsuka M, Takahashi H. Significance of molecular biomarkers in idiopathic pulmonary fibrosis: A mini review. Respir Investig 2018; 56: 384-391.
15. Greene K E, et al. Serum surfactant proteins-A and -D as biomarkers in idiopathic pulmonary fibrosis. Eur Respir J 2002; 19: 439-446.
16. Takahashi H, et al. Serum surfactant proteins A and D as prognostic factors in idiopathic pulmonary fibrosis and their relationship to disease extent. Am J Respir Crit Care Med 2000; 162: 1109-1114.
17. Kinder B W, et al. Serum surfactant protein-A is a strong predictor of early mortality in idiopathic pulmonary fibrosis. Chest 2009; 135: 1557-1563.
18. Bauer Y, et al. MMP-7 is a predictive biomarker of disease progression in patients with idiopathic pulmonary fibrosis. ERJ Open Res 2017; 3.
19. Song J W, et al. Blood biomarkers MMP-7 and SP-A: predictors of outcome in idiopathic pulmonary fibrosis. Chest 2013; 143: 1422-1429.
20. Zhang Y, et al. Histopathologic and Molecular Analysis of Idiopathic Pulmonary Fibrosis Lungs from Patients Treated with Pirfenidone or Nintedanib. Histopathology 2018.

Example 3: ASC Tempering of Established Fibrosis by Modulating the Myofibroblast Phenotype Through microRNAs 29a and 199-3p Introduction In this study, we investigated the hypothesis that allogeneic ASCs from young mouse donors (7) have the ability to reduce pulmonary fibrosis when administered 12 days post bleomycin (BLM) injury. This time point represents the fibrotic phase (days 10-21 after BLM, with a peak at approximately day 14) (6, 8, 16, 17).

Bleomycin Mouse Model of Pulmonary Fibrosis

Although a number of animal models exist and can be useful (e.g., the TGF-β adenovirus transduction model or the radiation-induced fibrosis model), the bleomycin model is well-documented and the best characterized murine model in use today to demonstrate efficacy of a particular drug or protein kinase inhibitor in the post-inflammatory/pre-fibrotic/fibro-preventive stages (Vittal, R. et al., J Pharmacol Exp Ther., 321(1): 35-44, 2007; Vittal, R. et al., Am J Pathol., 166(2): 367-75, 2005; Hecker L. et al., Nat. Med., 15(9): 1077-81, 2009).

The antibiotic bleomycin, which was originally isolated from *Streptomyces verticillatus* (Umezawa, H. et al., Cancer 20: 891-895, 1967), was subsequently found to be effective against squamous cell carcinomas and skin tumors (Umezawa, H., Fed Proc, 33: 2296-2302, 1974); however, its usefulness as an anti-neoplastic agent was limited by dose-dependent pulmonary toxicity resulting in fibrosis (Muggia, F. et al., Cancer Treat Rev, 10: 221-243, 1983).

The delivery of bleomycin via the intratracheal route (generally 1.25-4 U/kg, depending on the source) has the advantage that a single injection of the drug produces lung injury and resultant fibrosis in rodents (Phan, S. et al., Am Rev Respir Dis 121: 501-506, 1980; Snider, G. et al., Am Rev Respir Dis. 117: 289-297, 1978; Thrall, R. et al., Am J Pathol, 95: 117-130, 1979). Intratracheal delivery of the drug to rodents results in direct damage initially to alveolar epithelial cells. This event is followed by the development of neutrophilic and lymphocytic pan-alveolitis within the first week (Janick-Buckner, D. et al., Toxicol Appl Pharmacol., 100(3): 465-73, 1989). Subsequently, alveolar inflammatory cells are cleared, fibroblast proliferation is noted, and extra-cellular matrix is synthesized (Schrier D. et al., Am Rev Respir Dis., 127(1): 63-6, 1983). The development of fibrosis in this model can be seen biochemically and histologically by day 14 with maximal responses generally noted around days 21-28 (Izbicki G. et al., Int J Exp Pathol., 83(3): 111-9, 2002; Phan, S. et al., Chest., 83(5 Suppl): 44S-45S, 1983). Beyond 28 days, however, the response to bleomycin is more variable. Original reports suggest that bleomycin delivered intratracheally may induce fibrosis that progresses or persists for 60-90 days (Thrall R. et al., Am J Pathol., 95(1): 117-30, 1979; Goldstein R., et al., Am Rev Respir Dis., 120(1): 67-73, 1979; Starcher B. et al., Am Rev Respir Dis., 117(2): 299-305, 1978); however, other reports demonstrate a self-limiting response that begins to resolve after this period (Thrall R. et al., Am J Pathol., 95(1): 117-30, 1979; Phan, S. et al., Chest, 83(5 Suppl): 44S-45S, 1983; Lawson W. et al., Am J Pathol. 2005; 167(5): 1267-1277). While the resolving nature of this model does not mimic human disease, this aspect of the model offers an opportunity for studying fibrotic resolution at these later time points.

Materials and Methods

Animals. Male C57BL/6 mice were obtained from the Jackson Laboratories (Bar Harbor, Me.). 22-month old male mice were used for all experiments (n=6-8/group). 4-month old male C57BL/6 were used for isolation of ASCs. Animals were housed under pathogen-free conditions with food and water ad libitum. All experiments and procedures were approved by the Institutional Animal Care and Use Committee at University of Miami Miller School of Medicine (Miami, Fla.).

BM-induced lung injury. After induction of anesthesia with ketamine, bleomycin sulfate (Sigma-Aldrich Corp; St. Louis, Mo.) dissolved in 50 µl sterile saline was administered by direct intratracheal instillation (2.0 U/kg). Control mice received 50 µl of intratracheal sterile saline. Mice were weighed at baseline, day 7 post-BLM, and at sacrifice. Mice were sacrificed 21 days following BLM or saline administration.

ASC isolation from young mice. Donor ASCs were isolated from the subcutaneous adipose pads of 4-month-old male C57Bl/6 mice, as previously described (7). Mice were anesthetized with ketamine (200 mg/kg) and xylazine (10 mg/kg) injected intraperitoneally. Subcutaneous adipose tissue was excised, washed in phosphate buffer solution without $Ca^{2+}$ and $Mg^{2+}$ (PBS) containing 30% GIBCO® Pen/Strep (Life Technologies; Grand Island, N.Y.) and digested in media containing 0.75% type II collagenase (Sigma-Aldrich; St. Louis, Mo.). The suspension was centrifuged to separate floating adipocytes from the stromal vascular fraction. The resultant pellet was resuspended and cultured in ADSC™ Growth Medium (Lonza Group Ltd; Basel, Switzerland). Cells were expanded in plastic Thermo Scientific™ Nunc™ Cell Culture Treated Flasks with Filter Caps (Thermo Fisher Scientific, Inc., Waltham, Mass.). After a 24-hr incubation period, non-adherent cells were removed. When the adherent cells became confluent, they were trypsinized, expanded for 2-3 passages and cryopreserved in Recovery™ Cell Culture Freezing Medium (Life Technologies). Characterization of ASCs was performed as previously described (7). Briefly, ASCs were incubated with fluorescence-labeled antibodies and analyzed by flow-assisted cell sorting (FACS) Canto™ II (BD Biosciences; San Jose, Calif.). For mesenchymal differentiation potential, the Mouse Mesenchymal Stem Cell Functional Identification Kit (R&D Systems Inc.; Minneapolis, Minn.) was used according to the manufacturer's instructions and pluripotency assessed via osteogenic and adipogenic differentiation (9).

Briefly, for osteogenic differentiation, $4.2 \times 10^3$ MSCs/cm$^2$ were plated on a 24-well culture plate in StemXVivo® Osteogenic/Adipogenic Base Media. Cells were cultured to 50-70% confluency, and then the medium was replaced with Osteogenic Differentiation Media to induce osteogenesis. Every 3-4 days, media was replaced with fresh Differentiation Media. After 14-21 days, osteocytes were fixed and osteopontin was detected using immunocytochemistry for confirmation of differentiation. For adipogenic differentiation, $2.1 \times 10^4$ MSCs/cm$^2$ were plated on a 24-well culture plate in StemXVivo® Osteogenic/Adipogenic Base Media. Cells were cultured to 100% confluency, and then the medium was replaced with Adipogenic Differentiation Medium to induce osteogenesis. Every 3-4 days, media was replaced with fresh Differentiation Medium. After 10-14 days, adipocytes were fixed and FABP4 was detected using immunocytochemistry for confirmation of differentiation.

Lung micro-computed tomography. Mice underwent thoracic imaging by micro-computed tomography (µCT) (SkyScan microCT, Bruker, Belgium) at baseline and 7 days following BLM or saline administration. Scan parameters used were according to a previously validated protocol as follows (18). Mice were lightly anesthetized by intraperitoneal ketamine injection. Respiratory-gated µCT images were acquired with the following image parameters: 50 kVp X-ray source, 500 µA current and 193 millisecond exposure time per projection, with 0.7° increments, 0.5 mm aluminum filter. Total scan time was approximately 9 minutes per mouse. Images obtained were reconstructed using manufacturer's software (SkyScan NRecon, Bruker, Belgium) with the following settings: image smoothing 5, beam-hardening correction 31%, ring artifact reduction 6, and histogram dynamic range 0-0.03 attenuation values. Since aging mice are frail, they were unable to be anesthetized and scanned after day 7 post-BLM.

ASC administration. Young donor-derived ASCs (passage 2 or 3) were thawed in a 37° C. water bath and washed in PBS to remove the cell freezing solution prior to injection. ASCs were then passed through a 70 µm cell strainer to remove cell clumps. Cells were counted and resuspended in PBS immediately prior to injection. At 12 days post-BLM injury, mice were administered $5 \times 10^5$ ASCs in 200 µl of PBS by tail vein injection over 1 minute. Control mice received 200 µl of PBS by tail-vein injection.

Histological analysis and Ashcroft scoring. Right lung lobes were inflated with 10% neutral buffered formalin (NBF) under 25 cm $H_2O$ constant pressure. Lungs were fixed in 10% NBF for 24 hours and then transferred to PBS at 4° C. Samples were embedded in paraffin and 4 µm sections were taken for hematoxylin-eosin and Masson's Trichrome staining. Pulmonary fibrosis was assessed by a pathologist (S.S) blinded to the experimental groups using the numerical Ashcroft scale (19) on Masson's Trichrome-stained slides at 20× magnification. Individual fields were assessed by systematically moving over a 32-square grid; each field was assessed for severity of fibrosis and assigned a score of 0 (normal lung) to 8 (total fibrosis of the field). Mean±SEM values are reported.

Hydroxyproline assay. Collagen content is assessed by quantifying hydroxyproline, an amino acid present in appreciable quantities in collagen. Left lung lobes were harvested for tissue analyses. Lung hydroxyproline assay was performed according to the manufacturer's instructions (Hydroxyproline Assay Kit; Sigma-Aldrich, St. Louis, Mo.). Briefly, 2 mg lung fragments were weighed and homogenized in 100 µl of distilled water. An equal volume of 10 N HCl was added to the samples before drying at 49° C. for 3 hours. 50 µl of sample was loaded onto the plate and incubated overnight at 37° C. A hydroxyproline standard curve was prepared according to a standard solution (between 0 and 1 µg/well). Absorbance was measured at 557 nm, using the SoftMax Pro Software (Molecular Devices Corp; Sunnyvale, Calif.). Lung collagen content per mg of tissue was calculated from hydroxyproline measurement by dividing by a factor of 13.5%, as previously described (48).

Isolation of myofibroblasts from human and mouse lungs. After receiving signed informed consent, lung samples were obtained at the time of lung biopsy at the University of Miami from patients with IPF. This study was approved by the Institutional Review Board at the University of Miami Leonard M. Miller School of Medicine and was conducted in compliance with HIPAA regulations. Human lung and a portion of mouse left lung 21 days post-BLM injury, were cut into small pieces and plated in a 6 well plate (NUNC, Thermoscientific, Waltham, Mass.) for 30 minutes prior to adding media. Human and mouse cells were allowed to grow and transferred to a T25 flask when confluent. A portion of cells were placed on a chamber slide and myofibroblasts identified by positive staining for α-SMA (Abcam, Cambridge, Mass.) and vimentin (Abcam, Cambridge, Mass.). Cells were used for experiments between 2 and 4 passages.

Western analyses. Lung tissue and myofibroblasts were homogenized and lysates were collected for Western analyses as previously described (20). For AKT and pAKT, 10 and 25 µg of protein lysate, respectively, were loaded onto 10% polyacrylamide gels. Goat anti-AKT (1:1000) and rabbit anti-pAKT (1:1000) were used to detect protein expression, respectively (Santa Cruz Biotechnology, Dallas, Tex.). For CAV-1, 15 µs of protein was loaded. Immunoreactive bands were determined by exposing nitrocellulose blots to a chemiluminescence solution (Denville Scientific Inc.; Metuchen, N.J.) followed by exposure to Amersham Hyperfilm ECL (GE Healthcare Limited; Buckinghamshire, UK). Image J version 1.48v (National Institutes of Health; Bethesda, Md.) was used to determine relative density of bands. β-actin expression was determined using mouse anti-β-actin (1:10000). All values were corrected for corresponding β-actin band.

Isolation of RNA and real-time polymerase chain reaction. Total RNA was extracted from lung tissue and myofibroblast homogenates. Amplification and measurement of target RNA was performed on the Step 1 real time PCR system, as previously described (49). α$_v$-integrin, collagen al and tumor necrosis factor alpha (TNFα) mRNA expression were measured. TaqMan probes and primers for amplification of the specific transcripts were designed using the Primer Express 1.5 from Applied Biosystems (Foster City, Calif.). TaqMan ribosomal RNA control reagents (Life Technologies, Carlsbad, Calif.) designed to detect 18S ribosomal RNA, were used as an endogenous control to normalize for variations in the isolated RNA amount. For microRNA 29a and microRNA-199-3p analyses, cDNA was generated using qScript™ microDNA cDNA Synthesis Kit (Quanta Biosciences, Beverly, Mass.) according to manufacturer's instructions. Amplification of microRNA-29a and microRNA-199-3p was performed using specific primers (IDT, Coralville, Iowa) using Real-Time SYBR Green qRT-PCR Amplication kit (Quanta Biosciences, Beverly, Mass.). U6 expression was used as a control for microRNA analyses, and relative expression was calculated using the comparative C(T) method (50).

Double transfection of myofibroblasts. Myofibroblasts were isolated as previously described from lungs obtained at biopsy (21) from patients with IPF and mouse lungs 21 day post BLM. Myofibroblasts expressed positive staining for αSMA. Inhibitors and mimic plasmids were commercially synthesized (Exiqon, Germantown Md.). Cells were plated in 6 well plates 24 hours prior to transfection and transfected when 80% confluent in complete medium. Cells were co-transfected with plasmids containing miR-29a mimic AACCGATTTCAGATGGTGCT (SEQ ID NO: 1) (Exiqon, Germantown, Md.) and miR-199-3p inhibitor AAC-CAATGTGCAGACTACTG (SEQ ID NO: 2) (Exiqon, Germantown, Md.). The nucleotide sequence of a control plasmid with CMV promoter is shown in Table 8 below. Media was changed to 0.1% BSA and was collected at 24, 48 and 72 hours to perform a time course of miRNA expression. Mutated control reporter plasmids were used as controls. Protein was subsequently collected 48 hours post-transfection at the time of maximum response to measure MMP-2 activity and CAV-1 expression.

TABLE 8

SEQ ID NO: 3
AACAAAATATTAACGCTTACAATTTCCATTCGCCATTCAGGCTGCGCAACTGTTGGGAAGGGCGATCGGTGCGGGCCTCTTCGCTATTACG
CCAGCTGGCGAAAGGGGGATGTGCTGCAAGGCGATTAAGTTGGGTAACGCCAGGGTTTTCCCAGTCACGACGTTGTAAAACGACGGCCA
GTGCCAAGCTGATCTATACATTGAATCAATATTGGCAATTAGCCATATTAGTCATTGGTTATATAGCATAAATCAATATTGGCTATTGGCCA
TTGCATACGTTGTATCTATATCA
TAATATGTACATTTATATTGGCTCATGTCCAATATGACCGCCATGTTGACATTGATTATTGACTAGTTATTAATAGTAATCAATTACGGGTC
ATTAGTTCATAGCCCATATATGGAGTTCCGCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATGGGTGGAGTATTTACGGTAAACTGCCCACT
TGGCAGTACATCAAGTGTAT
CATATGCCAAGTCCGCCCCCTATTGACGTCAATGACGGTAAATGGCCCGCCTGGCATTATGCCCAGTACATGACCTTACGGGACTTTCCTAC
TTGGCAGTACATCTACGTATTAGTCATCGCTATTACCATGGTGATGCGGTTTTGGCAGTACACCAATGGGCGTGGATAGCGGTTTGACTCA
CGGGGATTTCCAAGTCTCCACCCCATTGACGTCAATGGGAGTTTGTTTTGGCACCAAAATCAACGGGACTTTCCAAATGTCGTAATAACC
CCGCCCCGTTGACGCAAATGG
GCGGTAGGCGTGTACGGTGGGAGGTCTATATAAGCAGAGCTCGTTTAGTGAACCGTCAGAATTTTGTAATACGACTCACTATAGGGCGGC
CGGGAATTCGTCGACTGGATCCAGTACCGAGGAGATCTGCGCCGCGATCGCCGGCGCGCCAGATCTCAAGCTTAACTAGCTAGCGGACCG
ACGCGTACGCGGCCGCTCGAGCAGAAACTCATCTCAGAAGAGGATCTGGCAGCAAATGATATCCTGGATTACAAGGATGACGACGATAA
GGTTTAAACGGCCGGCCGCGGTCATAGCTGTTTCCTGAACAGATCCCGGGTGGCATCCCTGTGACCCCTCCCCAGTGCCTCTCCTGGCCCT
GGAAGTTGCCACTCCAGTGCCCACCAGCCTTGTCCTAATAAAATTAAGTTGCATCATTTTGTCTGACTAGGTGTCCTTCTATAATATTATGG

TABLE 8 -continued

```
GGTGGAGGGGGTGGTATGGAGCAAGGGGCAAGTTGGGAAGACAACCTGTAGGGCCTGCGGGGTCTATTGGGAACCAAGCTGGAGTG
CAGTGGCACAATCTTGGCTCACTGCAATCTCCGCCTCCTGGGTTCAAGCGA
TTCTCCTGCCTCAGCCTCCCGAGTTGTTGGGATTCCAGGCATGCATGACCAGGCTCAGCTAATTTTTGTTTTTTTGGTAGAGACGGGGTTTC
ACCATATTGGCCAGGCTGGTCTCCAACTCCTAATCTCAGGTGATCTACCCACCTTGGCCTCCCAAATTGCTGGGATTACAGGCGTGAACCAC
TGCTCCCTTCCCTGTCCTTCTGATTTTAAAATAACTATACCAGCAGGAGGACGTCCAGACACAGCATAGGCTACCTGGCCATGCCCAACCGG
TGGGACATTTGAGTTGCTT
GCTTGGCACTGTCCTCTCATGCGTTGGGTCCACTCAGTAGATGCCTGTTGAATTGGGTACGCGGCCAGCGGCGAGCGGTATCAGCTCACTC
AAAGGCGGTAATACGGTTATCCACAGAATCAGGGGATAACGCAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTGCGCTCTCCTGTTCCGACCCTGCCGCTTACCGGATACCTGTC
CGCCTTTCTCCCTTCGGGAAGCGTGGCGCTTTCTCATAGCTCACGCTGTAGGTATCTCAGTTCGGTGTAGGTCGTTCGCTCCAAGCTGGGCT
GTGTGCACGAACCCCCGTTCAGCCCGACCGCTGCGCCTTATCCGGTAACTATCGTCTTGAGTCCAACCCGGTAAGACACGACTTATCGCC
ACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGAACAGTATTTGGTATCTGCGCTCTGCTGAAGCCAGTT
ACCTTCGGAAAAAGAGTTGGTAGCTCTTGATCCGGCAAACAAACCACCGCTGGTAGCGGTGGTTTTTTTGTTTGCAAGCAGCAGATTACGC
GCAGAAAAAAAGGATCTCAAGAAGATCCTTTGATCTTTTCTACGGGGTCTGACGCTCAGTGGAACGAAAACTCACGTTAAGGGATTTTGG
TCATGAGATTATCAAAAGGATCT
TCACCTAGATCCTTTTAAATTAAAAATGAAGTTTTAAATCAATCTAAAGTATATATGAGTAACCTGAGGCTATGGCAGGGCCTGCCGCCCCG
ACGTTGGCTGCGAGCCCTGGGCCTTCACCCGAACTTGGGGGGTGGGGTGGGGAAAAGGAAGAAACGCGGGCGTATTGGCCCCAATGGG
GTCTCGGTGGGGTATCGACAGAGTGCCAGCCCTGGGACCGAACCCCGCGTTTATGAACAAACGACCCAACACCGTGCGTTTTATTCTGTCT
TTTTATTGCCGTCATAGCGCGGGT
TCCTTCCGGTATTGTCTCCTTCCGTGTTTCAGTTAGCCTCCCCCTAGGGTGGGCGAAGAACTCCAGCATGAGATCCCCGCGCTGGAGGATC
ATCCAGCCGGCGTCCCGGAAAACGATTCCGAAGCCCAACCTTTCATAGAAGGCGGCGGTGGAATCGAAATCTCGTGATGGCAGGTTGGG
CGTCGCTTGGTCGGTCATTTTCTTCGAATTATTCTTCACCGGCATCTGCATCCGGGGTCTTGAAGGCGTGCTGGTACTCCACGATGCCCAGC
TCGGTGTTGCTGTGATCCTCCTC
CACGCGGCGGAAGGCGAACATGGGGCCCCGTTCTGCAGGATGCTGGGGTGGATGGCGCTCTTGAAGTGCATGTGGCTGTCCACCACGG
AGCTGTAGTAGCCGCCGTCGCGCAGGCTGAAGGTGCGGGTGAAGCTGCCATCCAGATCGTTATCGCCCATGGGGTGCAGGTGCTCCACG
GTGGCGTTGCTGCGGATGATCTTGTCGGTGAAGATCACGCGTGTCCTCGGGGAAGCCGGTGCCCATCACCTTGAAGTCGCCGATCACGCGG
CCGGCCTCGTAGCGGTAGCTGAAGCTC
ACGTGCAGCACGCCGCCGTCCTCGTACTTCTCGATGCGGTGTTGGTGTAGCCGCCGTTGTTGATGGCGTGCAGGAAGGGGTTCTCGTAG
CCGCTGGGGTAGGTGCCGAAGTGGTAGAAGCCGTAGCCCATCACGTGGCTCAGCAGGTAGGGCTGAAGGTCAGGGCGCCTTTGGTGCT
CTTCATCTTGTTGGTCATGCGGCCCTGCTCGGGGGTGCCCTCTCCGCCGCCCACCAGCTCGAACTCCACGCCGTTCAGGGTGCCGGTGATG
CGGCACTCGATCTCCATGGCGGGCA
GGCCGCTCTCGTCGCTCTCCATGGTTGTGGCCATATTATCATCGTGTTTTTCAAAGGAAAACCACGTCCCGTGGTTCGGGGGGCCTAGAC
GTTTTTTTAACCTCGACTAAACACATGTAAAGCATGTGCACCGAGGCCCCAGATCAGATCCCATACAATGGGGTACCTTCTGGGCATCCTTC
AGCCCCTTGTTGAATACGCTTGAGGAGAGCCATTTGACTCTTTCCACAACTATCCAACTCACAACGTGGCACTGGGGTTGTGCCGCCTTTGC
AGGTGTATCTTATACACGTG
GCTTTTGGCCGCAGAGGCACCTGTCGCCAGGTGGGGGGTTCCGCTGCCTGCAAAGGGTCGCTACAGACGTTGTTTGTCTTCAAGAAGCTT
CCAGAGGAACTGCTTCCTTCACGACATTCAACAGACCTTGCATTCCTTTGGCGAGAGGGGAAAGACCCCTAGGAATGCTCGTCAAGAAGA
CAGGGCCAGGTTTCCGGGCCCTCACATTGCCAAAAGACGGCAATATGGTGGAAAATAACATATAGACAAACGCACACCGGCCTTATTCCA
AGCGGCTTCGGCCAGTAACGTTAGG
GGGGGGGGCGGAATTCGAACCCCAGAGTCCCGCTCAGAAGAACTCGTCAAGAAGGCGATAGAAGGCGATGCGCTGCGAATCGGGAGCG
GCGATACCGTAAAGCACGAGGAAGCGGTCAGCCCATTCGCCGCCAAGCTCTTCAGCAATATCACGGGTAGCCAACGCTATGTCCTGATAG
CGATCCGCCACACCCAGCCGGCCACAGTCGATGAATCCAGAAAAGCGGCCATTTTCCACCATGATATTCGGCAAGCAGGCATCGCCATGG
GTCACGACGAGATCCTCGCCGTCGGGCATGCTCGCCTTGAGCCTGGCGAACAGTTCGGCTGGCGCGAGCCCCTGATGCTCTTCGTCAGA
TCATCCTGATCGACAAGACCGGCTTCCATCCGAGTACGTGCTCGCTCGATGTTTCGCTTGGTGGTCGAATGGGCAGGTAGCCGGA
TCAAGCGTATGCAGCCGCCGCATTGCATCAGCCATGATGGATACTTTCTCGGCAGGAGCAAGGTGAGATGACAGGAGATCCTGCCCCGGC
ACTTCGCCCAATAGCAGCCAGTCCCTTCCCGCTTCAGTGACAACGTCGAGCA
CAGCTGCGCAAGGAACGCCCGTCGTGGCCAGCCACGATAGCCGCGCTGCCTCGTCTTGCAGTTCATTCAGGGCACCGGACAGGTCGGTCT
TGACAAAAAGAACCGGGCGCCCCTGCGCTGACAGCCGGAACACGGCGGCATCAGAGCAGCCGATTGTCTGTTGTGCCCAGTCATAGCCG
AATAGCCTCTCCACCCAAGCGGCCGGAGAACCTGCGTGCAATCCATCTTGTTCAATCATGCGAAACGATCCTCATCCTGTCTCTTGATCGAT
CTTTGCAAAAGCCTAGGCCTCCAA
AAAAGCCTCCTCACTACTTCTGGAATAGCTCAGAGGCCGAGGCGGCCTCGGCCTCTGCATAAATAAAAAAAATTAGTCAGCCATGGGGCG
GAGAATGGGCGGAACTGGGCGGAGTTAGGGGCGGGATGGGCGGAGTTAGGGGCGGGACTATGGTTGCTGACTAATTGAGATGCATGC
TTTGCATACTTCTGCCTGCTGGGGAGCCTGGGGACTTTCCACACCTGGTTGCTGACTAATTGAGATGCATGCTTTGCATACTTCTGCCTGCT
GGGGAGCCTGGGGACTTTCCACACCC
TAACTGACACACATTCCACAGCTGGTTCTTTCCGCCTCAGGACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCACATTTCCCCGAAAAGTGCCACCTGACGCGCCCTGTAG
CGGCGCATTAAGCGCGGCGGGTGTGGTGGTTACGCGCAGCGTGACCGCTACACTTGCCAGCGCCCTAGCGCCCGCTCCTTTCGCTTTCTTC
CCTTCCTTTCTCGCCACGT
TCGCCGGCTTTCCCCGTCAAGCTCTAAATCGGGGCTCCCTTTAGGGTTCCGATTTAGTGCTTTACGGCACCTCGACCCCAAAAACTTGAT
TAGGGTGATGGTTCACGTAGTGGGCCATCGCCCTGATAGACGGTTTTTCGCCCTTTGACGTTGGAGTCCACGTTCTTTAATAGTGGACTCTT
GTTCCAAACTGGAACAACACTCAACCCTATCTCGGTCTATTCTTTTGATTTATAAGGGATTTTGCCGATTTCGGCCTATTGGTTAAAAAATGA
GCTGATTTAACAAAAATT
TAACGCGAATTTTAACAAAATATT
```

Zymography for matrix metalloproteinase activity-2. Matrix metalloproteinase-2 (MMP-2) activity was measured in lung tissue and myofibroblasts homogenates, as previously described (7). Briefly, samples and standards (Chemicon) were loaded onto 10% zymogram gels (Novex—Life Technologies). Following electrophoresis, gels were incubated for 24 hours at 37° C. in a gelatinase solution to allow for determination of MMP-2 proteolytic activity without interference from associated tissue inhibitors. Relative MMP-2 activity was measured by densitometry using Image J version v1.48 (National Institutes of Health, Bethesda, Md.). Data were analyzed using GraphPad Prism 6.0 (San Diego, Calif.). All values are expressed as mean±SEM. Overall significance of differences within experimental groups was determined using unpaired Student's t-tests, using Welch's correction as appropriate. P values less than 0.05 were considered statistically significant.

Results

BLM-Induced Pulmonary Fibrosis.

BLM-induced lung injury was confirmed prior to ASC administration in the aged mouse model by interval weight change and in vivo lung imaging with μCT 7 days following BLM administration. Mice treated with intratracheal BLM lost significantly more weight than saline controls (Table 9). There was no difference in interval weight loss in response to BLM between mice ultimately in the BLM only or BLM+ASC day 12 group (Table 9). However, at 21-day sacrifice, mice treated with BLM+ASC at day 12 weighed more than the BLM only group (Table 9, p<0.05). Saline controls lost minimal weight by day of sacrifice compared to both BLM-only and BLM+ASCs day 12 groups (Table 9).

TABLE 9

Weight changes

| Group (n = 4-5/group) | Interval weight change at day 7 (mean ± SEM) | Overall weight change at day 21 (mean ± SEM) |
| --- | --- | --- |
| Saline | −2.2 ± 0.68% | −6.5 ± 1.3% |
| BLM only | −14.2 ± 1.7%[a] | −27.3 ± 3.7%[aa] |
| BLM + ASCs at day 12 | −11.2 ± 2.4%[a] | −15.0 ± 2.6%[a,b] |

[a]p < 0.05 vs. saline;
[aa]p < 0.01 vs. saline;
[b]p < 0.05 vs. BLM only

Figure 3A:
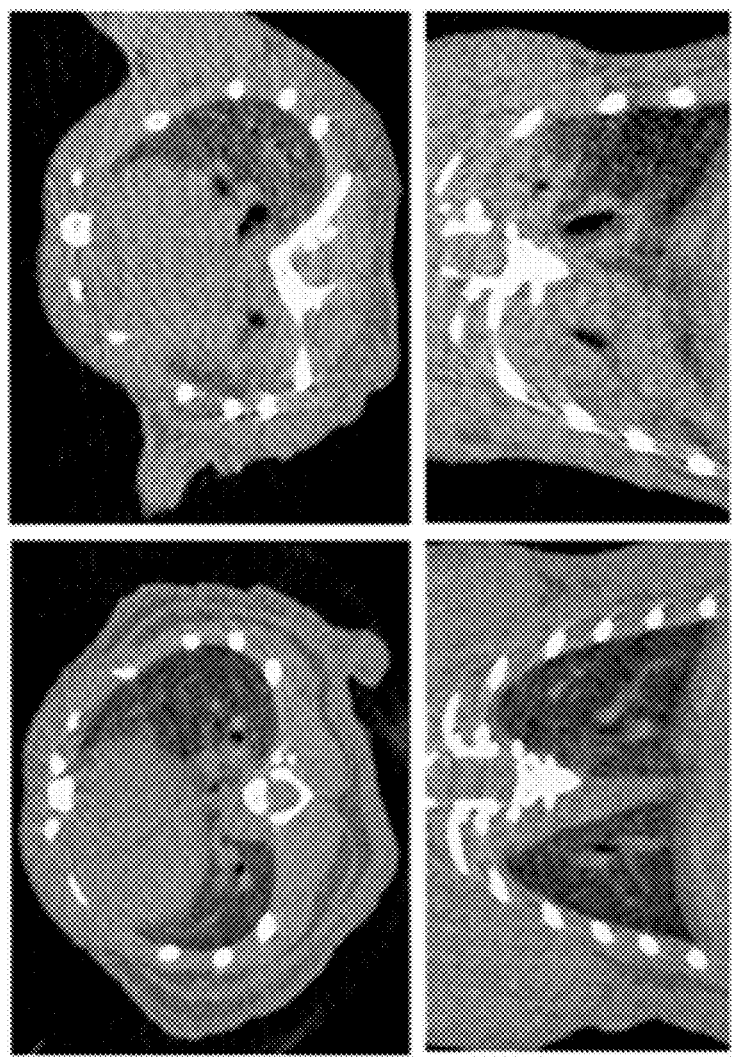
FIG. 3A-FIG. 3B show bleomycin-induced lung injury evidenced by micro computed tomography (μCT) 7 days post-instillation.
Figure 3B:

Baseline chest μCT prior to BLM administration demonstrated well-aerated lungs without evidence of pulmonary edema or increased tissue density (FIG. 3A, left). By day 7 post-BLM, chest μCT demonstrated increased attenuation over the lung fields and loss of aeration indicating lung injury in mice given intra-tracheal BLM (FIG. 3A, right). Control mice treated with intra-tracheal saline showed no significant changes or evidence of lung injury compared to their baseline chest μCT (FIG. 3B).

ASCs Administered 12 Days after BLM-Injury Decrease Lung Fibrosis in Aged Mice.

Figure 4D:
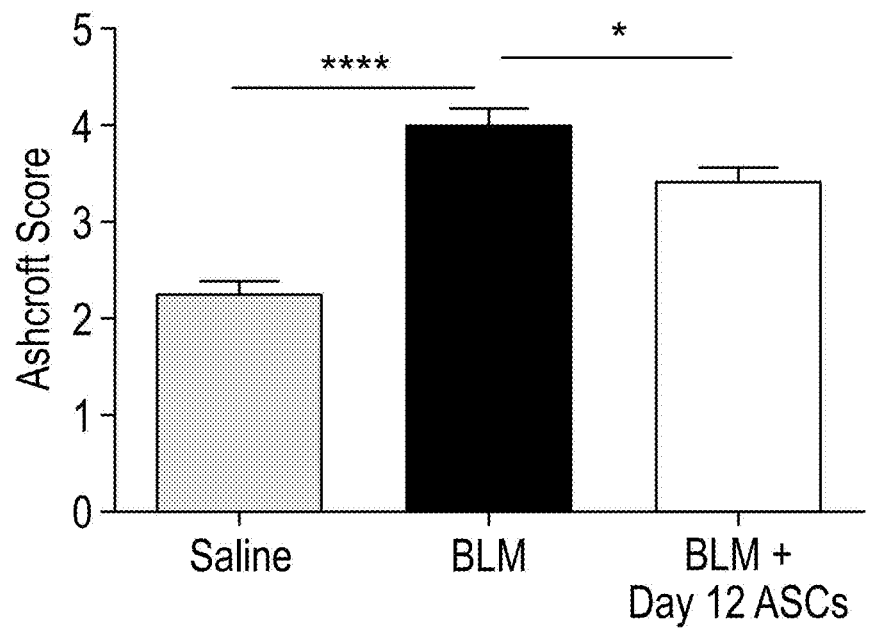

At 21-day sacrifice, lungs were harvested for histologic analysis of lung fibrosis and collagen content. Lungs from BLM-treated mice exhibited interstitial fibrosis with increased collagen deposition, alveolar wall thickening, and distortion of alveolar architecture (FIG. 4B). Saline controls did not demonstrate evidence of pulmonary fibrosis (FIG. 4A). Compared to BLM controls, mice treated with ASCs on day 12 post-BLM (FIG. 4C) had less severe lung fibrosis on histological sections as measured by Ashcroft scoring (FIG. 4D, p<0.05).

Figure 4E:
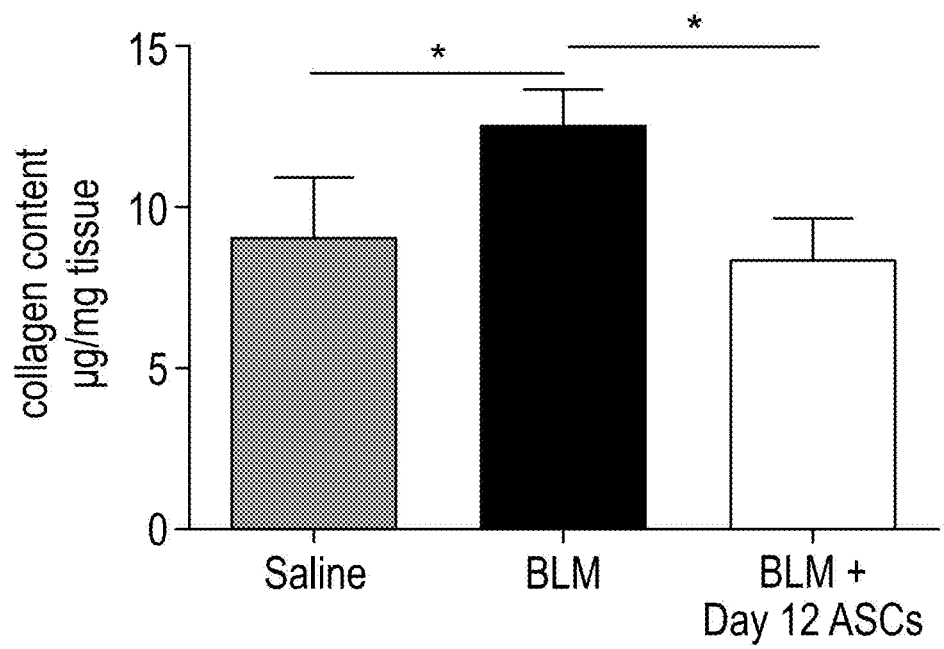

Lung collagen content, another indirect quantification of pulmonary fibrosis, was increased in BLM-only group compared to saline controls (FIG. 4E). Treatment with ASCs 12 days after BLM injury resulted in a significant decrease in lung collagen content compared to BLM-only group (FIG. 4E).

ASCs Decrease mRNA Expression of Established Molecular Markers of Fibrosis and Inflammation.

Delayed administration of ASCs (day 12 post-BLM) resulted in a significant decrease in markers associated with BLM-induced pulmonary injury. TNF-α, a marker of inflammation, was increased in BLM-treated mice compared to saline controls (Table 10; p<0.05). ASC treatment at day 12 decreased BLM-induced mRNA expression of TNF-α by sacrifice on day 21 (Table 10; p<0.05). Expression of $\alpha_v$-integrin mRNA, a transmembrane cell adhesion molecule that modulates tissue fibrosis (22) and collagen type 1, were also increased in BLM-treated mice compared to saline controls (Table 10; p<0.05). Treatment with ASCs on day 12 resulted in decreased mRNA expression of $\alpha_v$-integrin and collagen (Table 10; p<0.05).

TABLE 10

Effect of ASC treatment on markers of fibrosis and inflammation after bleomycin-induced lung injury

| Group (n = 4-5/group) | $\alpha_v$ integrin mRNA/18S | Collagen type 1α1 mRNA/18s | TNF-α mRNA/18S |
| --- | --- | --- | --- |
| Saline | 0.45 ± 0.095 | 31 ± 13 | 0.24 ± 0.009 |
| BLM only | 1.09 ± 0.14[a] | 213 ± 63 | 0.80 ± 0.180[a] |
| BLM + ASCs at day 12 | 0.35 ± 0.19[b] | 54 ± 25 [b] | 0.02 ± 0.009[b] |

[a]p < 0.05 vs. saline;
[b]p < 0.05 vs. BLM only
BLM, bleomycin;
ASCs, adipose-derived mesenchymal stem cells.

ASCs Administered on Day 12 Decrease BLM-Induced Lung AKT Activation.

Protein kinase B (PKB, or Akt) plays a role in cell metabolism, growth, proliferation, and survival. Its activation is controlled by a multi-step process that involves phosphoinositide-3-kinase (PI3K). (See Hemmings, B A, and Restuccia, D F, Cold Spring Harb. Perspect. Biol. (2012) 4Z(9): a011189, corrected by Cold Spring Harb. Perspect. Biol. (1015) 7(4): a026609). The PI3K-PKB/Akt pathway is highly conserved, and its activation is tightly controlled via a multistep process. Activated receptors directly stimulate class 1A PI3Ks bound via their regulatory subunit or adapter molecules such as the insulin receptor substrate (IRS) proteins. This triggers activation of PI3K and conversion by its catalytic domain of phosphatidylinositol (4,5)-bisphosphate (PIP2) lipids to phosphatidylinositol (3,4,5)-trisphosphate (PIP3). PKB/Akt binds to PIP3 at the plasma membrane, allowing PDK1 to access and phosphorylate T308 in the "activation loop," leading to partial PKB/Akt activation (Id., citing Alessi, D R et al., "Characterization of a 3-phosphoinositide-dependent protein kinase which phosphorylates and activates protein kinase Bα," Curr Biol (1997) 7: 261-269). This PKB/Akt modification is sufficient to activate mTORC1 by directly phosphorylating and inactivating proline-rich Akt substrate of 40 kDa (PRAS40) and tuberous sclerosis protein 2 (TSC2) (Id., citing Vander Haar, E et al., "Insulin signalling to mTOR mediated by the Akt/PKB substrate PRAS40," Nat Cell Biol (2007) 9: 316-323). mTORC1 substrates include the eukaryotic translation initiation factor 4E binding protein 1 (4EBP1), and ribosomal protein S6 kinase, 70 kDa, polypeptide 1 (S6K1), which, in turn, phosphorylates the ribosomal protein S6 (S6/RPS6), promoting protein synthesis and cellular proliferation. Phosphorylation of Akt at S473 in the carboxy-terminal hydrophobic motif, either by mTOR (Id., citing Sarbassov, D D et al., "Phosphorylation and regulation of Akt/PKB by the rictor-mTOR complex," (2005) Science 307: 1098-1101) or by DNA-PK (Id., citing Feng, J et al., "Identification of a PKB/Akt hydrophobic motif Ser-473 kinase as DNA-dependent protein kinase," J Biol Chem (2004) 279: 41189-41196), stimulates full Akt activity. Full activation of Akt leads to additional substrate-specific phosphorylation events in both the cytoplasm and nucleus, including inhibitory phosphorylation of the pro-apoptotic FOXO proteins (Id., citing Guertin D A et al., "Ablation in mice of the mTORC components raptor, rictor, or mLST8 reveals that mTORC2 is required for signaling to Akt-FOXO and PKCα, but not S6K1," Dev Cell (2006) 11: 859-871). Fully active PKB/Akt mediates numerous cellular functions including angiogenesis, metabolism, growth, proliferation, survival, protein synthesis, transcription, and apoptosis. Dephosphorylation of T308 by PP2A (Id., citing Andjelković, M et al., "Activation and phosphorylation of a pleckstrin homology domain containing protein kinase (RAC-PK/PKB) promoted by serum and protein phosphatase inhibitors," Proc Natl Acad Sci (1996) 93: 5699-5704), and S473 by PHLPP1/2 (Id., citing Brognard, J et al., "PHLPP and a second isoform, PHLPP2, differentially attenuate the amplitude of Akt signaling by regulating distinct Akt isoforms," Mol Cell (2007) 25: 917-931), and the conversion of PIP3 to PIP2 by PTEN (Stambolic, V et al., "Negative regulation of PKB/Akt-dependent cell survival by the tumor suppressor PTEN," Cell (1998) 95: 29-39) antagonize Akt signaling.

Figure 5:
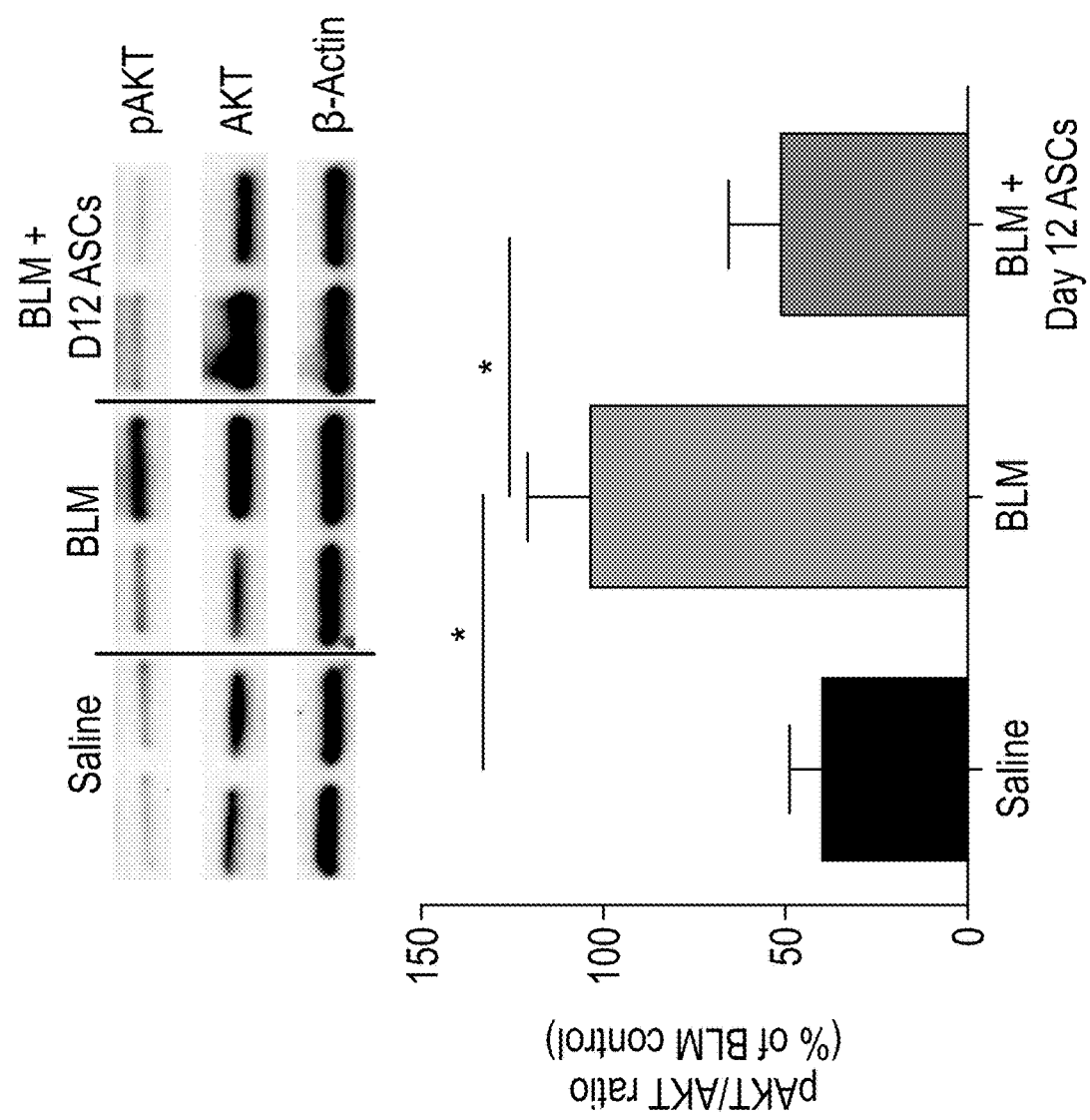
FIG. 5 shows that bleomycin (BLM)-induced AKT activation is inhibited by treatment with allogeneic adipose-derived mesenchymal stem cells (ASCs). Ratio of phosphorylated AKT to AKT protein expression in lung tissue of subjects was quantified by western analysis at 21-day sacrifice (bottom). Aged C57Bl/6 mice treated with intratracheal BLM demonstrated increased pAKT/AKT protein expression compared to saline-treated controls. Lungs from mice treated with intravenous infusion of allogeneic ASCs 12 days following BLM administration demonstrated decreased expression of pAKT/AKT compared to BLM only group. Inset (top) shows a representative western blot of 2 mice per treatment group and β-actin loading control. Data are graphed as mean±standard error of the mean (n=6-8/group). *$P<0.05$; $P<0.01$; *$P<0.001$; ****$P<0.0001$.

The AKT pathway is an active component in the development of lung fibrosis (23). Saline controls had significantly less phosphorylated AKT (pAKT) to AKT protein expression ratio compared to mice that were treated with intratracheal BLM (FIG. 5, p<0.05). Treatment with ASCs on day 12 post-BLM resulted in decreased activation of AKT (pAKT/AKT) compared to BLM controls (FIG. 5, p<0.05).

ASCs Increase Expression of Anti-Fibrotic miR-29a and Decrease Expression of Profibrotic miR-199-3p Following BLM-Administration In Vivo.

MiR-29a, a well-characterized anti-fibrotic mediator in several diseases including lung fibrosis (24), was significantly decreased in the lungs of BLM-treated mice compared to saline control lungs (FIG. 6; p<0.01). Mice treated with ASCs 12 days following BLM-injury demonstrated increased expression of miR-29a compared to BLM only controls (FIG. 6A; p<0.05). In contrast, miR-199-3p expression, reported to be upregulated in lung, kidney, and liver fibrosis (25), increased in BLM-treated lungs. ASC treatment downregulated miR-199-3p expression. (FIG. 6B; p=0.05).

Downstream Targets of miR-29a and -199-3p (MMP-2 and CAV-1) are Regulated In Vivo by ASC Infusion.

Figure 6A:
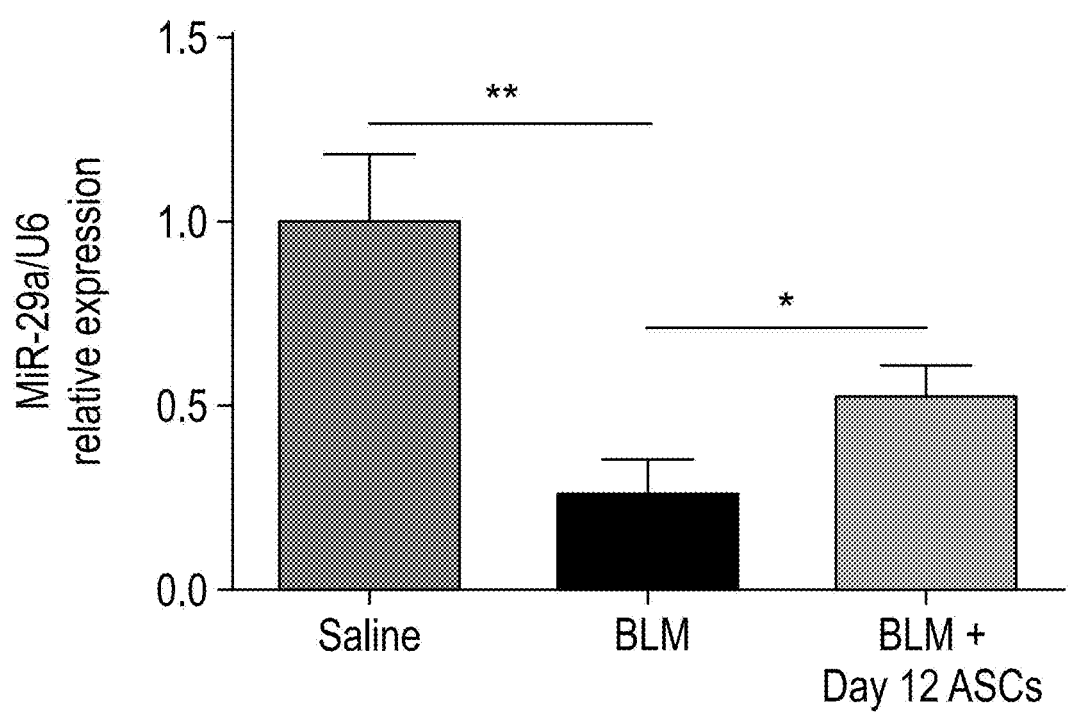
FIG. 6A-FIG. 6D show that lung miR-29a expression is increased and miR-199-3p expression is decreased by infusion of allogeneic adipose-derived mesenchymal stem cells (ASCs) following bleomycin (BLM)-induced downregulation. Downstream targets of miR-29a, metalloproteinase-2 (MMP-2) activity is decreased and miR-199-3p, caveolin 1 (CAV-1) expression is increased in vivo following administration of adipose-derived mesenchymal stem cells (ASCs) on day 12 post-injury. Aged C57Bl/6 mouse lung expression of miR-29a is decreased by 21-day sacrifice in response to bleomycin (BLM) lung injury compared to saline controls. Treatment with allogeneic ASCs on day 12 post-BLM infusion resulted in higher expression of miR-29a versus BLM-only controls. miR-29a (FIG. 6A) and miR-199-3p (FIG. 6B) expression were measured by reverse transcriptase polymerase chain reaction from total lung RNA. U6 expression was used as a control. Data are graphed as mean±standard error of the mean (n=6-8/group). *$P<0.05$, **$P<0.01$.
Figure 6B:
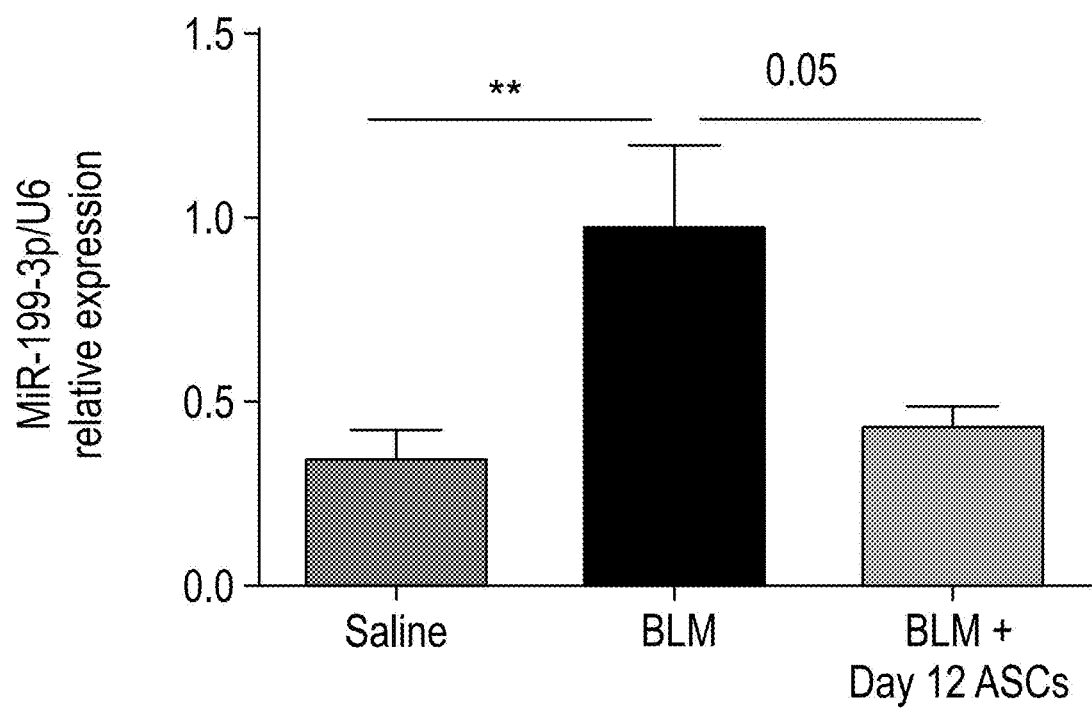
Figure 6C:
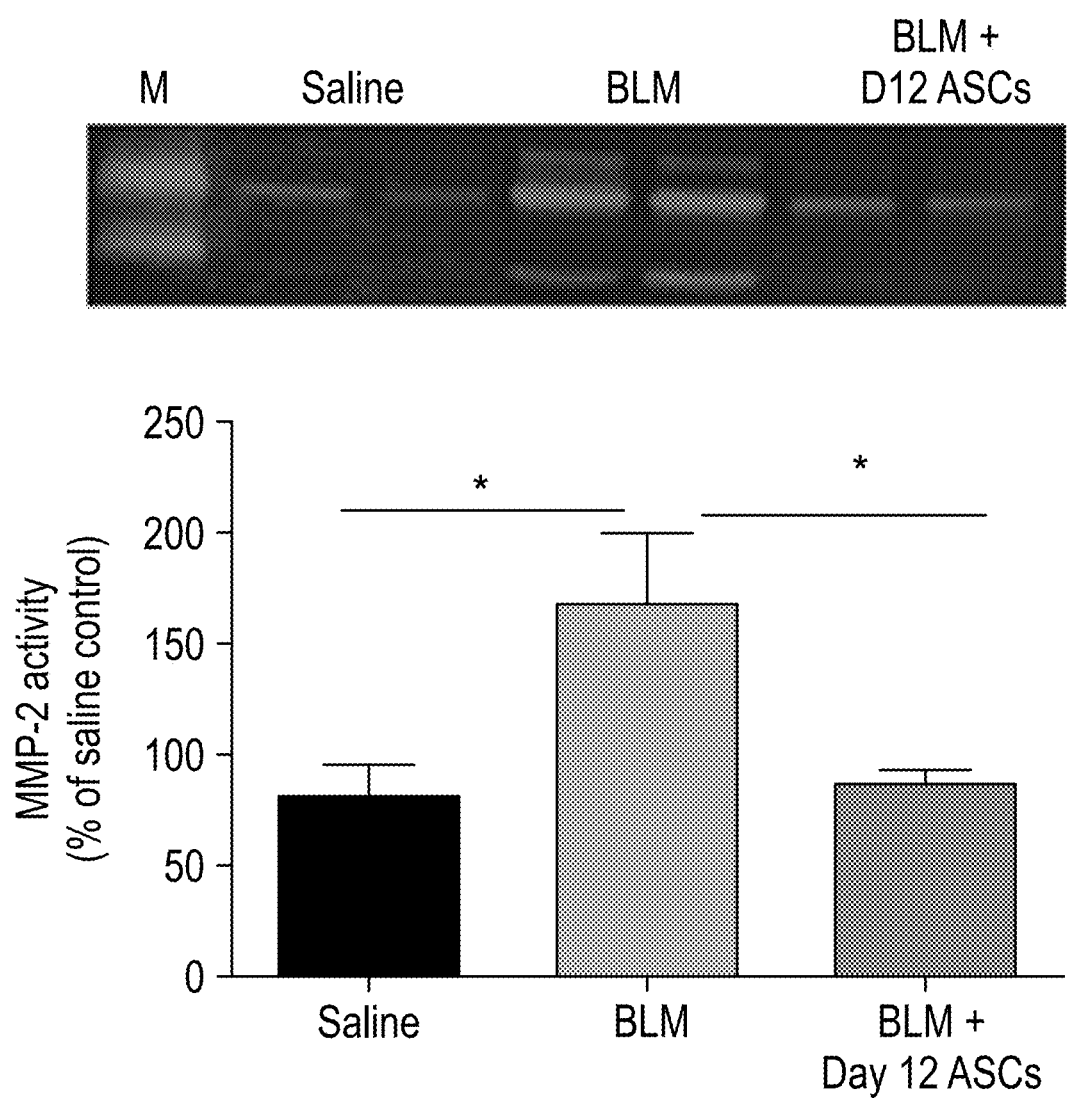
Figure 6D:
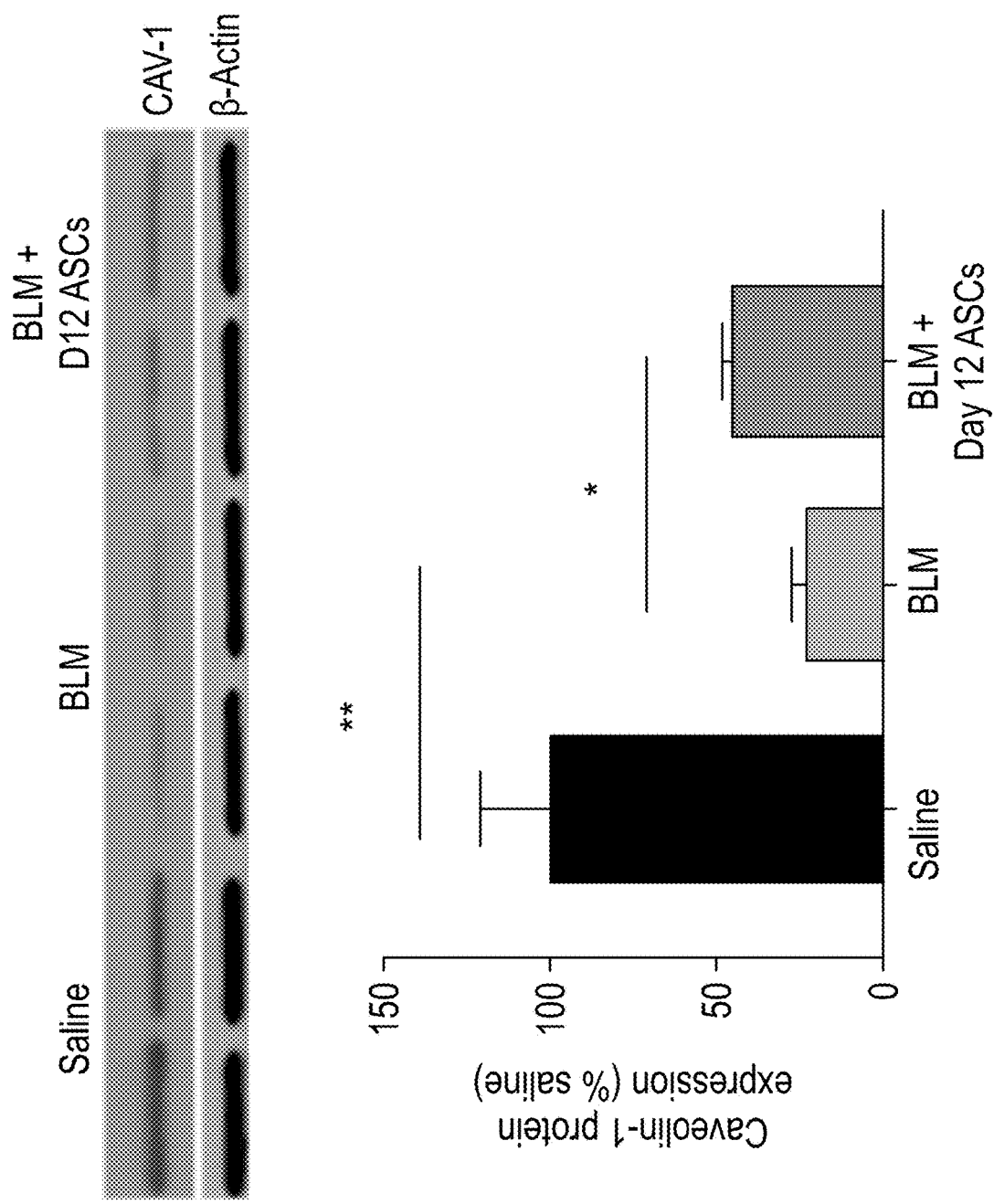

As previously shown (7), MMP-2 activity, a downstream target of miR-29a, was increased in the lungs of mice that received BLM compared to saline controls (FIG. 6C, p<0.05). Infusion of ASCs 12 days after BLM injury resulted in a decrease in MMP-2 activity compared to the BLM-only group (FIG. 6C, *p=0.05). CAV-1, known to be regulated by miR-199-3p, is an important structural molecule that is downregulated in fibrotic lung disease (25). Western analysis showed that ASC treatment at day 12 resulted in an increase of CAV-1 (FIG. 6D; p<0.05).

In Vitro Double Transfection with miR-29a Mimic and miR-199-3p Inhibitor Directly Regulates Relevant Downstream Targets, MMP-2 and CAV-1.

Figure 7:
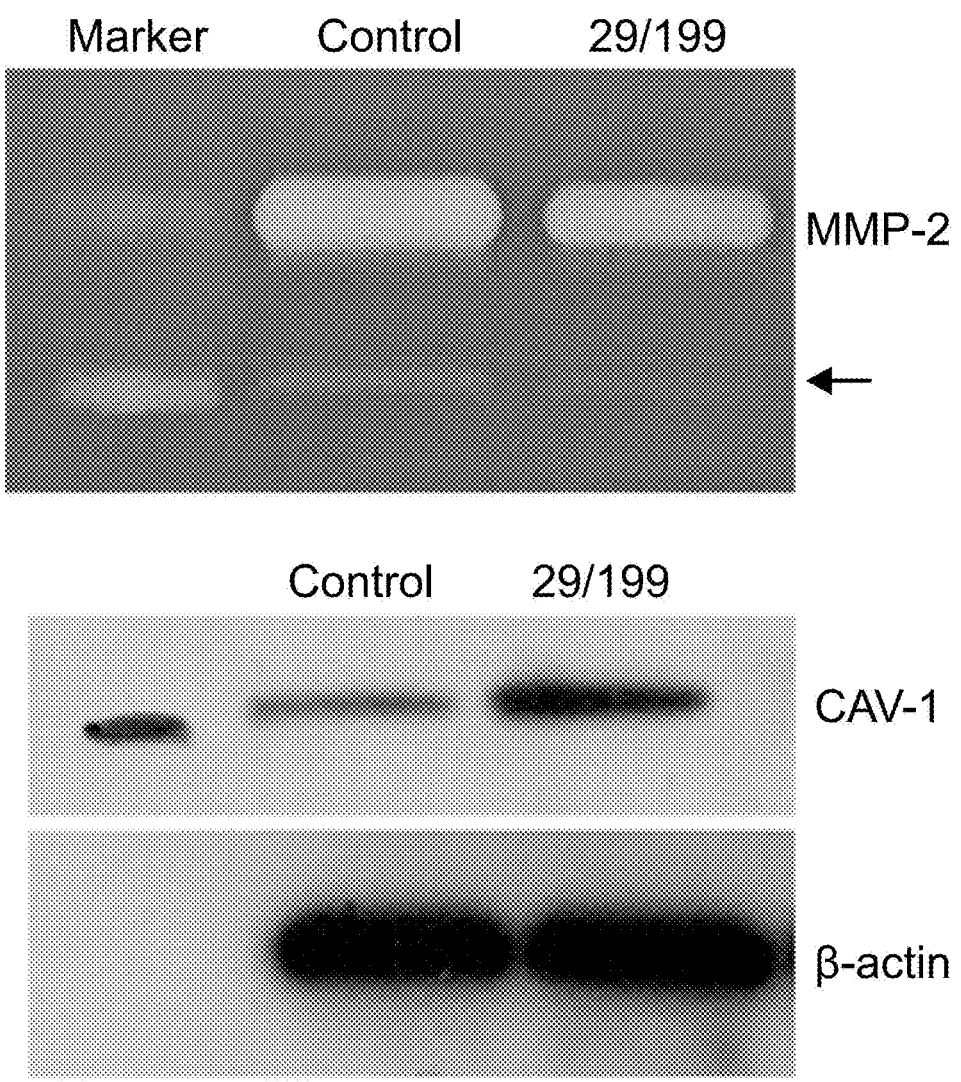
FIG. 7 shows that in vitro transfection of miR-29a mimic (SEQ ID NO: 1) and miR-199-3p inhibitor (SEQ ID NO: 2) regulates downstream targets MMP-2 and CAV-1 in human myofibroblasts. In vitro double transfection of miR-29a mimic and miR-199-3p inhibitor to myofibroblasts isolated from lungs of patients with IPF recapitulates the effects of in vivo ASC infusion. Myofibroblasts were transfected with scrambled controls (Control) or miR-29a and -199-3p (29/199). Upper panel is a representative zymogram for MMP-2 activity (as indicated by arrow) and lower panel is a western blot for CAV-1 expression and β-actin loading control. (n=2 experiments, shown is representative).

Given the observed downregulation of miR-29a and upregulation of miR-199-3p lung expression following BLM injury, we next sought to confirm that ASC-induced changes in downstream targets MMP-2 and CAV-1 expression were a direct effect of miRNA changes. We transfected myofibroblasts isolated from human lung tissue of patients with IPF and from BLM-treated mouse lungs with a mimic of miR-29a and an inhibitor of miR-199-3p. Upregulation of miR-29a (increased >5000 fold) and downregulation of lung miR-199-3p expression (decreased at least 100 fold) confirmed by RT-PCR, correlated with decreased MMP-2 activity (FIG. 7, top, arrow) and increased CAV-1 expression (FIG. 7, bottom) in both human and mouse isolates (data not shown). These in vitro data confirmed the relevance of ASC induced miR changes in vivo.

Discussion

Our previously published study demonstrated a preventive effect of infusing ASCs 24 hours after bleomycin instillation (26). In human disease, however, clinicians cannot discern when the insult(s) leading to eventual pulmonary fibrosis occurs, as most patients present to pulmonologists with moderate- or advanced-stage disease. Thus, to achieve closer clinical relevance in modeling human disease, we assessed the benefits of MSC therapy in aged mice with established fibrosis (16, 17).

We found that injection of ASCs 12 days following BLM instillation, after radiographic confirmation of lung injury at day 7, reduced severity of pulmonary fibrosis and diminished weight loss. In addition, treatment with ASCs on day 12 simultaneously reversed the BLM-induced downregulation of miR-29a, (24, 27, 28) and the BLM-induced upregulation of miR-199-3p (25), known anti-fibrotic and profibrotic mediators.

In our study, we used aged male mice since they develop more severe pulmonary fibrosis in response to BLM instillation compared to young mice (29). More importantly, BLM-induced pulmonary fibrosis in aged mice does not spontaneously recover as is seen with young male mice (15, 30). We also used young-donor derived ASCs, which we have previously shown to have benefits in this model, unlike ASCs derived from aged mice (7).

We performed chest μCT 7 days following BLM instillation in order to establish the presence of lung injury prior to ASC infusion on day 12 (16). Intratracheal BLM-treatment resulted in changes in lung images of BLM-treated mice by 7 days post-instillation, similar to the study by De Langhe et al (31). Changes in lungs seen on μCT have been correlated with histological changes following BLM administration (31, 32). While μCT scanning is not sensitive enough to accurately distinguish between pulmonary inflammation and fibrosis at this early stage (31, 32), it does provide a non-invasive test to confirm lung injury in response to BLM. Non-invasive lung imaging is increasingly used in pre-clinical studies to longitudinally evaluate lung pathology without need for terminal procedures (18, 32, 33). Although a μCT time course would be ideal, the older age of the mice renders them more susceptible to anesthesia-related death. Therefore we confirmed BLM-injury prior to treatment by interval weight loss at the time of μCT on day 7 and day 12.

To our knowledge this is the first study to demonstrate that a single-dose of ASCs can attenuate (meaning to dilute, thin, reduce, weaken, diminish) lung fibrosis when administered in the second week of BLM-induced pulmonary injury.

Multiple pathways leading to lung fibrosis appear to be targeted by MSCs. Activation of the AKT signaling pathway has been linked to dysregulation of ECM turnover resulting in lung fibrosis in lung tissue from patients with IPF (23) as well as BLM rodent models (38). PI3K/AKT signaling pathway is a potential therapeutic target in IPF (23) and the target of a current clinical trial in patients with IPF (NCT 01725139). More recently this pathway has been shown to be activated by the transcription factor c-Jun in multiple fibrotic diseases including IPF (39). Infusion of ASCs at day 12 post-BLM resulted in decreased activation of AKT in the lungs of treated mice compared to BLM controls, similar to our reported results of ASC infusion one day after BLM injury (7).

Dysregulation of miRNAs has been implicated in epigenetic changes in gene expression that are associated with the development of lung fibrotic diseases, including IPF (24, 28, 40). Studies have shown differential expression of approximately 10% of miRNAs in IPF versus control patients (41). Upregulation of profibrotic miRNAs and downregulation of anti-fibrotic miRNAs appear to contribute to the proliferation of fibroblasts and myofibroblasts leading to the aberrant response to epithelial injury and ECM collagen deposition (24, 27, 40, 42). These miRNAs regulate multiple pathways involved in fibrosis, such as TGF-β, TNF-α, AKT, and MAPK, which are modulated by MSCs (7, 8, 40). Furthermore, there is increasing evidence that MSCs may attenuate tissue fibrosis by delivering miRNAs to target organs such as kidneys (43), skin (44), and lungs (45). Thus, MSCs may act as a "factory" of miRNAs to modulate multiple target networks through co-operative action.

In this study, we evaluated in vivo changes of miR-29a expression, a well-established anti-fibrotic ECM mediator dysregulated in several fibrotic conditions, including IPF and BLM-lung injury (2, 24). Downregulation of miR-29a participates in upregulation of profibrotic target ECM genes including collagen 1 al and MMP-2 (46), and its overexpression reduces tissue fibrosis in several organs, including lungs (27). Montgomery and colleagues showed that administration of a pharmacological miR-29 mimic attenuated BLM-induced pulmonary fibrosis in C57Bl/6 mice, even when administered 10-17 days post-BLM. Similarly, we found that miR-29a expression decreased significantly in the lungs of the aged BLM model and was increased in the lungs of mice receiving ASCs on day 12 post-BLM. This correlated with decreased lung expression of known miR-29a targets MMP-2 and Col 1 al in ASC-treated mice. In fact, increased miR-29a has also been implicated in dampening TGFβ-induced AKT activation (47) which we also found to be the case in ASC-treated mice. Therefore, the effects of MSCs in pulmonary fibrosis may be carried out in part via gene expression regulation by miRNAs, such as miR-29a.

In parallel we also determined that miR-199-3p expression was downregulated in the lungs of BLM-injured mice receiving ASCs compared to BLM-injury alone. This occurred even though ASCs were administered at day 12 post-BLM. To complement and validate our studies we performed in vitro double transfection studies on myofibroblasts isolated from the lungs of patients with IPF or isolated from the lungs of mice treated with BLM for 21 days. We were able to simultaneously upregulate miR-29a and downregulate miR-199-3p expression in human and mouse myofibroblasts. Manipulation of these miRs downregulated MMP-2 activity and upregulated CAV-1 expression, downstream targets. These data confirmed the results we obtained in vivo after ASC treatment.

In summary, the current study evaluates the effect of administering young-donor allogeneic ASCs in the early fibrotic phase of BLM-induced pulmonary fibrosis in an aged mouse model. Our results suggest that ASCs administered in established fibrosis have the ability to attenuate lung fibrosis. At least one of the mechanisms appears to be via regulation of miRNA.

References for Example 3

1. Raghu G, et al. Idiopathic pulmonary fibrosis in US Medicare beneficiaries aged 65 years and older: incidence, prevalence, and survival, 2001-11. *Lancet Respir Med* 2014; 2: 566-572.
2. Collard H R, et al. A new era in idiopathic pulmonary fibrosis: considerations for future clinical trials. *Eur Respir J* 2015.
3. Hunninghake G M. A new hope for idiopathic pulmonary fibrosis. *N Engl J Med* 2014; 370: 2142-2143.
4. Toonkel R L, et al. Mesenchymal stem cells and idiopathic pulmonary fibrosis. Potential for clinical testing. *Am J Respir Crit Care Med* 2013; 188: 133-140.
5. Redente E F, et al. Age and sex dimorphisms contribute to the severity of bleomycin-induced lung injury and fibrosis. *Am J Physiol Lung Cell Mol Physiol* 2011; 301: L510-518.
6. Peng R, et al. Bleomycin induces molecular changes directly relevant to idiopathic pulmonary fibrosis: a model for "active" disease. *PLoS One* 2013; 8: e59348.
7. Tashiro J, et al. Therapeutic benefits of young, but not old, adipose-derived mesenchymal stem cells in a chronic mouse model of bleomycin-induced pulmonary fibrosis. *Transl Res* 2015; 166: 554-567.
8. Srour N, Thebaud B. Mesenchymal Stromal Cells in Animal Bleomycin Pulmonary Fibrosis Models: A Systematic Review. *Stem Cells Transl Med* 2015.
9. Aguilar S, et al. Bone marrow stem cells expressing keratinocyte growth factor via an inducible lentivirus protects against bleomycin-induced pulmonary fibrosis. *PLoS One* 2009; 4: e8013.
10. Garcia O, et al. Amniotic fluid stem cells inhibit the progression of bleomycin-induced pulmonary fibrosis via CCL2 modulation in bronchoalveolar lavage. *PLoS One* 2013; 8: e71679.
11. Lee S H, et al. The effect of adipose stem cell therapy on pulmonary fibrosis induced by repetitive intratracheal bleomycin in mice. *Exp Lung Res* 2014; 40: 117-125.
12. Moodley Y, et al. Human umbilical cord mesenchymal stem cells reduce fibrosis of bleomycin-induced lung injury. *Am J Pathol* 2009; 175: 303-313.
13. Glassberg M K, et al. Allogeneic Human Mesenchymal Stem Cells in Patients With Idiopathic Pulmonary Fibrosis via Intravenous Delivery (AETHER): A Phase I Safety Clinical Trial. *Chest* 2017; 151: 971-981.
14. Squillaro T, Peluso G, Galderisi U. Clinical Trials With Mesenchymal Stem Cells: An Update. *Cell Transplant* 2016; 25: 829-848.
15. Rubio G A, Elliot S J, Glassberg M K. What Should Be Chronic: The Animal, the Model, or Both? *Stem Cells Transl Med* 2016; 5: 703.
16. Bauer Y, et al. A novel genomic signature with translational significance for human idiopathic pulmonary fibrosis. *Am J Respir Cell Mol Biol* 2015; 52: 217-231.
17. Izbicki G, et al. Time course of bleomycin-induced lung fibrosis. *Int J Exp Pathol* 2002; 83: 111-119.
18. Vande Velde G, et al. Longitudinal micro-CT provides biomarkers of lung disease that can be used to assess the effect of therapy in preclinical mouse models, and reveal compensatory changes in lung volume. *Dis Model Mech* 2016; 9: 91-98.
19. Ashcroft T, Simpson J M, Timbrell V. Simple method of estimating severity of pulmonary fibrosis on a numerical scale. *J Clin Pathol* 1988; 41: 467-470.
20. Glassberg M K, et al. 17beta-estradiol replacement reverses age-related lung disease in estrogen-deficient C57BL/6J mice. *Endocrinology* 2014; 155: 441-448.
21. Glassberg M K, et al. Activation of the estrogen receptor contributes to the progression of pulmonary lymphangioleiomyomatosis via matrix metalloproteinase-induced cell invasiveness. *J Clin Endocrinol Metab* 2008; 93: 1625-1633.
22. Conroy K P, et al. alphav integrins: key regulators of tissue fibrosis. *Cell Tissue Res* 2016.
23. Mercer P F, et al. Exploration of a potent PI3 kinase/mTOR inhibitor as a novel anti-fibrotic agent in IPF. *Thorax* 2016.
24. Pandit K V, Milosevic J. MicroRNA regulatory networks in idiopathic pulmonary fibrosis. *Biochem Cell Biol* 2015; 93: 129-137.

25. Lino Cardenas C L, et al. miR-199a-5p Is upregulated during fibrogenic response to tissue injury and mediates TGFbeta-induced lung fibroblast activation by targeting caveolin-1. *PLoS Genet* 2013; 9: e1003291.
26. Tashiro J, et al. Therapeutic benefits of young, but not old, adipose-derived mesenchymal stem cells in a chronic mouse model of bleomycin-induced pulmonary fibrosis. *Translation Research* 2015.
27. Montgomery R L, et al. MicroRNA mimicry blocks pulmonary fibrosis. *EMBO Mol Med* 2014; 6: 1347-1356.
28. Lino Cardenas $C_L$, Kaminski N, Kass D J. Micromanaging microRNAs: using murine models to study microRNAs in lung fibrosis. *Drug Discov Today Dis Models* 2013; 10: e145-e151.
29. Sueblinvong V, et al. Predisposition for disrepair in the aged lung. *Am J Med Sci* 2012; 344: 41-51.
30. Redente E F, et al. Tumor necrosis factor-alpha accelerates the resolution of established pulmonary fibrosis in mice by targeting profibrotic lung macrophages. *Am J Respir Cell Mol Biol* 2014; 50: 825-837.
31. De Langhe E, et al. Quantification of lung fibrosis and emphysema in mice using automated micro-computed tomography. *PLoS One* 2012; 7: e43123.
32. Cavanaugh D, et al. Quantification of bleomycin-induced murine lung damage in vivo with micro-computed tomography. *Acad Radiol* 2006; 13: 1505-1512.
33. Marenzana M, Vande Velde G. Refine, reduce, replace: Imaging of fibrosis and arthritis in animal models. *Best Pract Res Clin Rheumatol* 2015; 29: 715-740.
34. Ortiz L A, et al. Mesenchymal stem cell engraftment in lung is enhanced in response to bleomycin exposure and ameliorates its fibrotic effects. *Proc Natl Acad Sci USA* 2003; 100: 8407-8411.
35. Moodley Y, et al. Anti-inflammatory effects of adult stem cells in sustained lung injury: a comparative study. *PLoS One* 2013; 8: e69299.
36. Huleihel L, et al. Modified mesenchymal stem cells using miRNA transduction alter lung injury in a bleomycin model. *Am J Physiol Lung Cell Mol Physiol* 2017: ajplung 00323 02016.
37. Hecker L, et al. Reversal of persistent fibrosis in aging by targeting Nox4-Nrf2 redox imbalance. *Sci Transl Med* 2014; 6: 231ra247.
38. Russo R C, et al. Phosphoinositide 3-kinase gamma plays a critical role in bleomycin-induced pulmonary inflammation and fibrosis in mice. *J Leukoc Biol* 2011; 89: 269-282.
39. Wernig G, et al. Unifying mechanism for different fibrotic diseases. *Proc Natl Acad Sci U S A* 2017; 114: 4757-4762.
40. Yang G, et al. Discovery and validation of extracellular/circulating microRNAs during idiopathic pulmonary fibrosis disease progression. *Gene* 2015; 562: 138-144.
41. Pandit K V, Milosevic J, Kaminski N. MicroRNAs in idiopathic pulmonary fibrosis. *Transl Res* 2011; 157: 191-199.
42. Kapetanaki M G, Mora A L, Rojas M. Influence of age on wound healing and fibrosis. *J Pathol* 2013; 229: 310-322.
43. Wang B, et al. Mesenchymal Stem Cells Deliver Exogenous MicroRNA-let7c via Exosomes to Attenuate Renal Fibrosis. *Mol Ther* 2016.
44. Fang S, et al. Umbilical Cord-Derived Mesenchymal Stem Cell-Derived Exosomal MicroRNAs Suppress Myofibroblast Differentiation by Inhibiting the Transforming Growth Factor-beta/SMAD2 Pathway During Wound Healing. *Stem Cells Transl Med* 2016.
45. Tang G N, et al. MicroRNAs Involved in Asthma After Mesenchymal Stem Cells Treatment. *Stem Cells Dev* 2016; 25: 883-896.
46. Cushing L, et al. miR-29 is a major regulator of genes associated with pulmonary fibrosis. *Am J Respir Cell Mol Biol* 2011; 45: 287-294.
47. Yang T, et al. miR-29 mediates TGFbeta1-induced extracellular matrix synthesis through activation of PI3K-AKT pathway in human lung fibroblasts. *J Cell Biochem* 2013; 114: 1336-1342.
48. Kliment C R, et al A novel method for accurate collagen and biochemical assessment of pulmonary tissue utilizing one animal. *Int J Clin Exp Pathol* 2011; 4: 349-355.
49. Karl M, et al. Differential effects of continuous and intermittent 17beta-estradiol replacement and tamoxifen therapy on the prevention of glomerulosclerosis: modulation of the mesangial cell phenotype in vivo. *The American journal of pathology* 2006; 169: 351-361.
50. Schmittgen T D, Livak K J. Analyzing real-time PCR data by the comparative C(T) method. *Nat Protoc* 2008; 3: 1101-1108.

Example 4: Estrogen Receptor Expression in ASCs Isolated from Old and Young Adipose Tissue Gonadal hormone production/activation declines during reproductive aging and has been linked to multiple age-associated diseases including cardiovascular disease (22, 23), diabetic kidney disease (16, 17, 19, 24), prostate cancer (25), lung cancer (26), and other lung disease (6, 7). Underlying differences between males and females may become more apparent with age-associated changes of gonadal hormones and their signaling due to either loss of protection and/or gain of harmful effects, or by the emergence of sex chromosome effects that may be suppressed by gonadal hormones. Our prior studies support a protective effect of estrogen in the lungs of aged female mice (6, 7); E2 replacement partially restored the destruction of interalveolar septa in the lungs of the aged mice. To date, to our knowledge there are no comparable studies in aged male mice. Recent population-based studies continue to suggest a protective effect of estrogens as menopause is associated with accelerated lung function decline (27). Changes of gonadal hormones in aging men are not as predictable as in women making comparable population studies in males more challenging (28).

Gonadal Hormones and the Human Lung.

The human lung is a gonadal hormone target tissue (34). Gonadal hormones regulate normal lung development, physiology, and are implicated in several lung diseases including asthma, pulmonary fibrosis, and pulmonary hypertension in males and females (2, 34). Although expression of androgen receptor (AR) and estrogen receptor (ER) have been documented in the lung (35), their signaling remains poorly understood.

Gonadal Hormones and the Rodent Lung.

Young male mice display a greater decline in static lung compliance compared with young female mice following BLM instillation (36). Markova et al (37) showed that young male C57BL/6 mice had ~25% more lung hydroxyproline, a measure of collagen content compared to the lungs of age-matched females. The increased level of lung collagen was not present in male mice deficient in the AR, indicating a contribution of the AR pathway to the observed male-female differences in lung collagen levels (37).

Summary: Taken together, these findings suggest that both estrogens and androgens may impact the pattern of lung inflammation and fibrosis.

In young mice, estrogens may be protective against fibrotic lung disease, while androgens may be harmful (36, 38, 39). These data have not been collected in aged BLM-treated mice. In preliminary data, we found no abnormalities in gonadal hormone concentrations in patients with IPF (unpublished data). However, increased gonadal sensitivity and responsiveness, which partly depends on the level of functional gonadal hormone receptors (40), could potentially account for the development of a gonadal hormone-driven disease and could also be responsible for the accelerated rate of its progression. In lung tissue obtained from male patients with IPF, we found a 30-fold increase in AR mRNA (Table 11) accompanied by an increase in AR receptor protein, which is reflected in increased transcriptionally active receptors at a dose of 5α-dihydroxytestosterone (DHT) that is physiologically relevant in older males (41). In support of the BLM model, there was a six-fold increase of AR mRNA in the lungs of BLM-treated male mice (Table 11). AR mediated pathways including protein kinase B (AKT) phosphorylation and transforming growth factor (TFG)β are known fibrotic pathways (42, 43).

TABLE 11

|  | IPF (n = 6) | Control (n = 5) |
|---|---|---|
| AR mRNA expression/18s | 337 ± 101 | 11.41 ± 3.2* |
|  | BLM (n = 15) | Saline (n = 16) |
| AR mRNA expression/18s | 2.0 ± 0.5 | 0.3 ± 0.2* |

*$p < 0.05$

IPF is predominately a male disease, although women are diagnosed with the disease (53). Our preliminary data suggest that AR expression and transcriptional activation is increased in lung tissue isolated from male patients with IPF (data not shown).

Figures 8A, 8B:
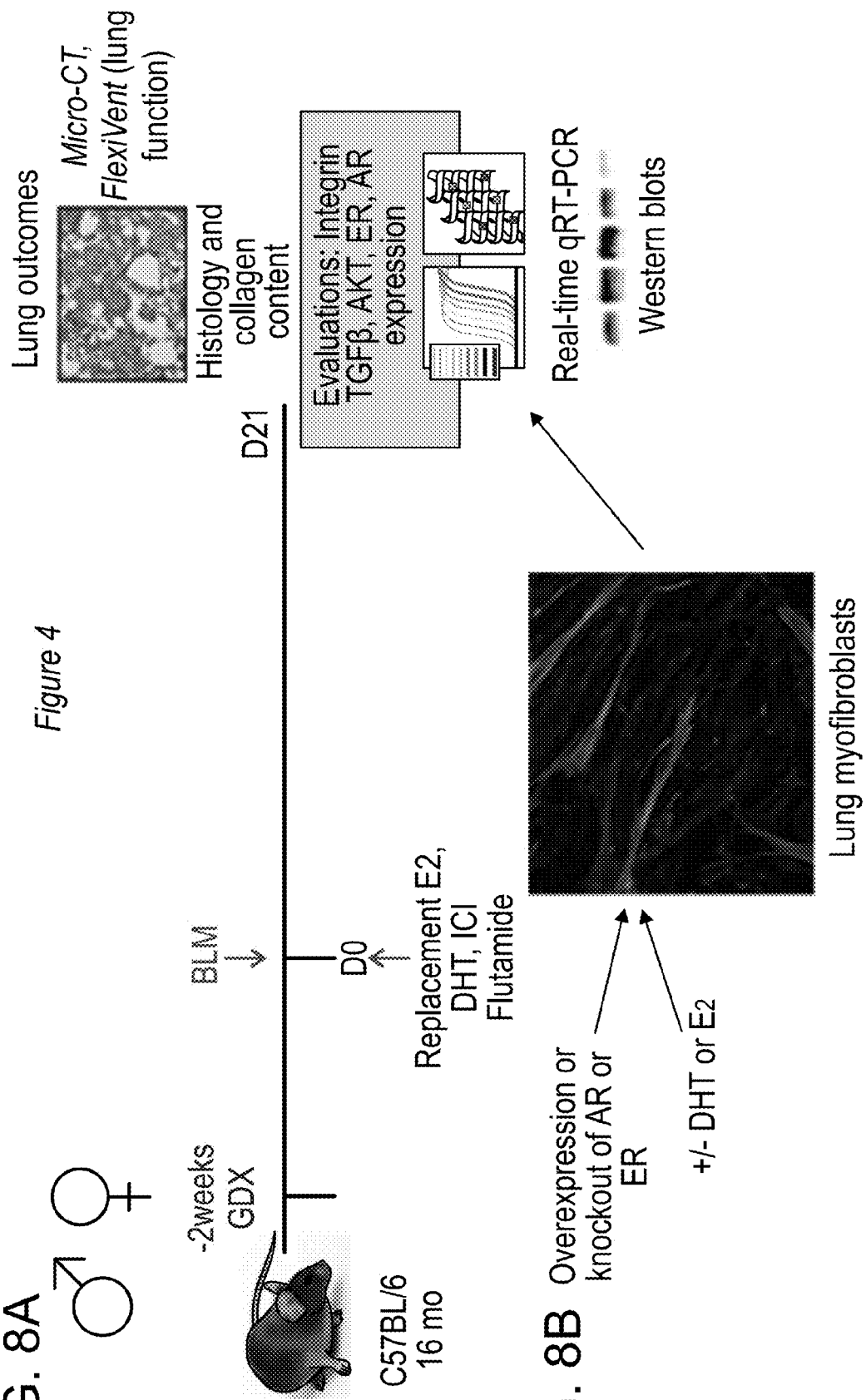
FIG. 8A schematically shows an in vivo experimental protocol whereby GDX is followed by bleomycin (BLM) intratrachial instillation, and replacement with 17B-estradiol (E2), dihydrotestosterone (DHT), ICI or flutamide with determination of results after D21 as measured by lung outcomes, evaluation of histology, collgen content, integrin, transforming growth factor (TGF)β, AKT activation, estrogen receptor (ER) and androgen receptor (AR) expression measured by real-time PCR and western analysis. These experiments compare GDX aging male and female BLM-treated mice and determine (1) if E2 is protective and androgens detrimental to fibrosis development, (2) if DHT is protective and estrogens are detrimental to fibrosis development.
FIG. 8B schematically shows an in vitro experimental protocol to determine the contribution of AR and ER expression in the development of lung fibrosis using myofibroblasts isolated from lungs of male and female patients with IPF. Myofibroblasts will be transfected to overexpress or knockout of AR or ER+/−DHT or E2 with determination of results by evaluation of integrin, TGFβ, AKT, ER, and AR, expression by real-time PCR and western analysis.

FIG. 8A schematically shows an in vivo experimental protocol whereby GDX is followed by bleomycin (BLM) intratrachial instillation, and replacement with 17B-estradiol (E2), dihydrotestosterone (DHT), ICI or flutamide with determination of results after D21 as measured by lung outcomes, evaluation of histology, collgen content, integrin, transforming growth factor (TGF)β, AKT activation, estrogen receptor (ER) and androgen receptor (AR) expression measured by real-time PCR and western analysis. These experiments compare GDX aging male and female BLM-treated mice and determine (1) if E2 is protective and androgens detrimental to fibrosis development, (2) if DHT is protective and estrogens are detrimental to fibrosis development. FIG. 8B schematically shows an in vitro experimental protocol to determine the contribution of AR and ER expression in the development of lung fibrosis using myofibroblasts isolated from lungs of male and female patients with IPF. Myofibroblasts will be transfected to overexpress or knockout of AR or ER+/−DHT or E2 with determination of results by evaluation of integrin, TGFβ, AKT, ER, and AR, expression by real-time PCR and western analysis.

TABLE 12

| Table 12: All mice will be GDX four weeks prior to BLM administration | Male | Female |
|---|---|---|
| Placebo | 8 | 8 |
| DHT | 8 | 8 |
| E2 | 8 | 8 |
| DHT + Flutamide OR E2 + ICI | 8 | 8 |

LM-induced lung fibrosis is worse in male mice compared to female mice (8), mimicking the sex difference in patients with IPF. We hypothesize that aging male patients with IPF have more severe disease than females of the same age due to androgens in males since we also hypothesize that estrogens are protective.

We will gonadectomize (GDX) mice to see if sex differences are removed and determine the effects of E2 and DHT replacement on mice in the setting of lung fibrosis. To avoid the potential confound of T being converted to E2, we use DHT. Finally we will assess whether gonadal hormones stimulate or prevent AKT phosphorylation and TFGβ activation, fibrotic pathways shown to be important in IPF (44).

Experimental design: We will use 16 month old C57BL6 male and female mice (equivalent to 65 year old males and females) (Table 11). We will perform gonadectomy (GDX) four weeks prior to BLM administration to ensure the absence of confounding hormones between individual mice. BLM (2.0 Ukg/BW in 50 µl saline) or 50 µl of sterile saline (controls) will be administered by direct intratracheal instillation via intubation. At the time of BLM administration, mice will receive placebo, E2 (0.05 mg/pellet) (45), or DHT (5.0 mg/pellet) (46). We will replace mice with a dose of DHT that will replicate concentrations found in serum of adult C57Bl/6 mice (~0.25 ng/ml) (47). E2 infusions will maintain E2 blood levels similar to E2 levels reported to be in the range of 10-30 pg/ml in 4-7 month old female C57BL6 mice depending on the stage of the estrous cycle (48). Mice will be sacrificed at 21 days following BLM administration and lung tissue collected. Uterine weight will be measured in female mice as a measure of efficacy of E2 replacement.

Lung Assessments: At sacrifice, lungs will be inflated, perfused (49), and studied as follows: 1) We will measure ER subtype and AR mRNA and protein expression; 2) In parallel we will measure metrics of fibrosis including histologic and quantitative measures (Ashcroft, collagen types I and III expression, hydroxyproline) (49), as well as associated molecular markers and downstream pathways of fibrosis (e.g. αvintegrin, matrix metalloproteinases (MMP), AKT phosphorylation) and TFGβ. Lung function will be measured using FlexiVent system (Scireq, Montreal Canada) as described by De Vleeschauwer et al. (50).

Measurement of serum hormone levels: At the time of sacrifice, blood will be collected for measurement of E2 DHT, and testosterone concentrations by competitive enzyme immunoassay kits (Ligand Assay and Analysis Core at University of Virginia, Charlottesville Va.).

References for Example 4

1. Sathish V; Prakash Y. Sex differences in pulmonary anatomy and physiology: Implications for health and disease. Sex differences in physiology; 2016. p. 89-106.

2. Glassberg M K, Catanuto P, Shahzeidi S, Aliniazee M, Lilo S, Rubio G A, Elliot S J. Estrogen deficiency promotes cigarette smoke-induced changes in the extracellular matrix in the lungs of aging female mice. Transl Res 2016; 178: 107-117.
3. Glassberg M K, Choi R, Manzoli V, Shahzeidi S, Rauschkolb P, Voswinckel R, Aliniazee M, Xia X, Elliot S J. 17beta-estradiol replacement reverses age-related lung disease in estrogen-deficient C57BL/6J mice. Endocrinology 2014; 155: 441-448.
4. Elliot S J, Karl M, Berho M, Potier M, Zheng F, Leclercq B, Striker G E, Striker L J. Estrogen deficiency accelerates progression of glomerulosclerosis in susceptible mice. The American journal of pathology 2003; 162: 1441-1448.
5. Elliot S J, Karl M, Berho M, Xia X, Pereria-Simon S, Espinosa-Heidmann D, Striker G E. Smoking induces glomerulosclerosis in aging estrogen-deficient mice through cross-talk between TGF-beta1 and IGF-I signaling pathways. J Am Soc Nephrol 2006; 17: 3315-3324.
6. Karl M, Berho M, Pignac-Kobinger J, Striker G E, Elliot S J. Differential effects of continuous and intermittent 17beta-estradiol replacement and tamoxifen therapy on the prevention of glomerulosclerosis: modulation of the mesangial cell phenotype in vivo. The American Journal of Pathology 2006; 169: 351-361.
7. Doublier S, Lupia E, Catanuto P, Elliot S J. Estrogens and progression of diabetic kidney damage. Curr Diabetes Rev 2011; 7: 28-34.
8. Nelson A W, Tilley W D, Neal D E, Carroll J S. Estrogen receptor beta in prostate cancer: friend or foe? Endocrine-related cancer 2014; 21: T219-234.
9. Siegfried J M, Stabile L P. Estrongenic steroid hormones in lung cancer. Seminars in oncology 2014; 41: 5-16.
10. Triebner K, Matulonga B, Johannessen A, Suske S, Benediktsdottir B, Demoly P, Dharmage S C, Franklin K A, Garcia-Aymerich J, Gullon Blanco J A, Heinrich J, Holm M, Jarvis D, Jogi R, Lindberg E, Moratalla Rovira J M, Muniozguren Agirre N, Pin I, Probst-Hensch N, Puggini L, Raherison C, Sanchez-Ramos J L, Schlunssen V, Sunyer J, Svanes C, Hustad S, Leynaert B, Gomez Real F. Menopause Is Associated with Accelerated Lung Function Decline. Am J Respir Crit Care Med 2017; 195: 1058-1065.
11. Vermeulen A, Kaufman J M, Goemaere S, van Pottelberg I. Estradiol in elderly men. Aging Male 2002; 5: 98-102.
12. Sathish V, Martin Y N, Prakash Y S. Sex steroid signaling: implications for lung diseases. Pharmacol Ther 2015; 150: 94-108.
13. Taylor A H, Al-Azzawi F. Immunolocalisation of oestrogen receptor beta in human tissues. J Mol Endocrinol 2000; 24: 145-155.
14. Voltz J W, Card J W, Carey M A, Degraff L M, Ferguson C D, Flake G P, Bonner J C, Korach K S, Zeldin D C. Male sex hormones exacerbate lung function impairment after bleomycin-induced pulmonary fibrosis. Am J Respir Cell Mol Biol 2008; 39: 45-52.
15. Markova M S, Zeskand J, McEntee B, Rothstein J, Jimenez S A, Siracusa L D. A role for the androgen receptor in collagen content of the skin. J Invest Dermatol 2004; 123: 1052-1056.
16. Carey M A, Card J W, Voltz J W, Germolec D R, Korach K S, Zeldin D C. The impact of sex and sex hormones on lung physiology and disease: lessons from animal studies. American journal of physiology Lung cellular and molecular physiology 2007; 293: L272-278.
17. McGee S P, Zhang H, Karmaus W, Sabo-Attwood T. Influence of sex and disease severity on gene expression profiles in individuals with idiopathic pulmonary fibrosis. Int J Mol Epidemiol Genet 2014; 5: 71-86.
18. Webb P, Lopez G N, Greene G L, Baxter J D, Kushner P J. The limits of the cellular capacity to mediate an estrogen response. Mol Endocrinol 1992; 6: 157-167.
19. Li Y, Kishimoto I, Saito Y, Harada M, Kuwahara K, Izumi T, Hamanaka I, Takahashi N, Kawakami R, Tanimoto K, Nakagawa Y, Nakanishi M, Adachi Y, Garbers D L, Fukamizu A, Nakao K. Androgen contributes to gender-related cardiac hypertrophy and fibrosis in mice lacking the gene encoding guanylyl cyclase-A. Endocrinology 2004; 145: 951-958.
20. Kono M, Fujii T, Lim B, Karuturi M S, Tripathy D, Ueno N T. Androgen Receptor Function and Androgen Receptor-Targeted Therapies in Breast Cancer: A Review. JAMA Oncol 2017; 3: 1266-1273.
21. Friedman S L, Sheppard D, Duffield J S, Violette S. Therapy for fibrotic diseases: nearing the starting line. Sci Transl Med 2013; 5: 167sr161.
22. Doublier S, Lupia E, Catanuto P, Periera-Simon S, Xia X, Korach K, Berho M, Elliot S J, Karl M. Testosterone and 17beta-estradiol have opposite effects on podocyte apoptosis that precedes glomerulosclerosis in female estrogen receptor knockout mice. Kidney Int 2011; 79: 404-413.
23. Oshida K, Waxman D J, Corton J C. Chemical and Hormonal Effects on STAT5b-Dependent Sexual Dimorphism of the Liver Transcriptome. PLoS One 2016; 11: e0150284.
24. Brouillette J, Rivard K, Lizotte E, Fiset C. Sex and strain differences in adult mouse cardiac repolarization: importance of androgens. Cardiovasc Res 2005; 65: 148-157.
25. Nelson J F, Felicio L S, Osterburg H H, Finch C E. Altered profiles of estradiol and progesterone associated with prolonged estrous cycles and persistent vaginal cornification in aging C57BL/6J mice. Biol Reprod 1981; 24: 784-794.
26. Tashiro J, Elliot S J, Gerth D J, Xia X, Pereira-Simon S, Choi R, Catanuto P, Shahzeidi S, Toonkel R L, Shah R H, El Salem F, Glassberg M K. Therapeutic benefits of young, but not old, adipose-derived mesenchymal stem cells in a chronic mouse model of bleomycin-induced pulmonary fibrosis. Transl Res 2015; 166: 554-567.
27. De Vleeschauwer S I, Rinaldi M, De Vooght V, Vanoirbeek J A, Vanaudenaerde B M, Verbeken E K, Decramer M, Gayan-Ramirez G N, Verleden G M, Janssens W. Repeated invasive lung function measurements in intubated mice: an approach for longitudinal lung research. Lab Anim 2011; 45: 81-89.
28. Raghu G, Chen S Y, Hou Q, Yeh W S, Collard H R. Incidence and prevalence of idiopathic pulmonary fibrosis in US adults 18-64 years old. Eur Respir J 2016; 48: 179-186.

Example 5. Estrogen Receptor Expression in Premenopausal and Post-Menopausal ASCS Estrogen receptor-α (ERα) (Id., citing Eckert, R. L., Mullick, A., Rorke, E. A., and Katzenellenbogen, B. S. (1984) Endocrinology 114, 629-637), a member of the nuclear receptor family, is a ligand-dependent transcription factor that mediates physiological responses to its cognate ligand, 17β-estradiol (E2), in estrogen target tissues such as the breast, uterus, and bone (Id., citing Barkhem, T., Nilsson, S., and Gustafsson, J. A. (2004) Am. J. Pharmacogenomics 4, 19-28). Because ERα is a short-lived protein (half-life of 4-5 h), its cellular levels are strictly regulated (Id., citing Eckert, R. L., Mullick, A., Rorke, E. A., and Katzenellenbogen, B. S. (1984) Endocrinology 114, 629-637). Although ERα turnover is a continuous process (Id., citing Eckert, R. L., Mullick, A., Rorke, E. A., and Katzenellenbogen, B. S. (1984) Endocrinology 114, 629-637 Eckert, R. L., Mullick, A., Rorke, E. A., and Katzenellenbogen, B. S. (1984) Endocrinology 114, 629-637), dynamic fluctuations in receptor levels, mediated primarily by the ubiquitin-proteasome pathway (Id., citing Alarid, E. T., Bakopoulos, N., and Solodin, N. (1999) Mol. Endocrinol. 13, 1522-1534; El Khissiin, A., and Leclercq, G. (1999) FEBS Lett. 448, 160-166, Nawaz, Z., Lonard, D. M., Dennis, A. P., Smith, C. L., and O'Malley, B. W. (1999) Proc. Natl. Acad. Sci. U.S.A 96, 1858-1862; Lonard, D. M., Nawaz, Z., Smith, C. L., and O'Malley, B. W. (2000) Mol. Cell 5, 939-948), occur in response to changing cellular conditions (Id., citing Reid, G., Denger, S., Kos, M., and Gannon, F. (2002) Cell. Mol. Life Sci. 59, 821-831; Fan, M., Bigsby, R. M., and Nephew, K. P. (2003) Mol. Endocrinol. 17, 356-365; Fan, M., Nakshatri, H., and Nephew, K. P. (2004) Mol. Endocrinol. 18, 2603-2615). In addition, differing ligands have been demonstrated to exert differential effects on steady-state levels of ERα (ID., citing Wijayaratne, A. L., and McDonnell, D. P. (2001) J. Biol. Chem. 276, 35684-35692, Preisler-Mashek, M. T., Solodin, N., Stark, B. L., Tyriver, M. K., and Alarid, E. T. (2002) Am. J. Physiol. Endocrinol. Metab. 282, 891-898). For example, E2 and the "pure" ERα antagonists (i.e. ICI 164,384, ICI 182,780, RU 58,668, and ZK-703) (12, 13) induce receptor turnover, whereas the "partial" agonist/antagonist 4-hydroxytamoxifen (4-OHT) stabilizes ERα (Id., citing Wijayaratne, A. L., Nagel, S. C., Paige, L. A., Christensen, D. J., Norris, J. D., Fowlkes, D. M., and McDonnell, D. P. (1999) Endocrinology 140, 5828-5840, Fan, M., Park, A., and Nephew, K. P. (2005) Mol. Endocrinol. 19, 2901-2914). E2-mediated ERα degradation is dependent on transcription, coactivator recruitment, and new protein synthesis, whereas ICI-induced degradation of ERα is independent of these processes (Id., citing Reid, G., Hubner, M. R., Metivier, R., Brand, H., Denger, S., Manu, D., Beaudouin, J., Ellenberg, J., and Gannon, F. (2003) Mol. Cell 11, 695-707; Nardulli, A. M., and Katzenellenbogen, B. S. (1986) Endocrinology 119, 2038-2046; Seo, H. S., Larsimont, D., Querton, G., El Khissiin, A., Laios, I., Legros, N., and Leclercq, G. (1998) Int. J. Cancer 78, 760-765.

The antiestrogen fulvestrant (ICI 182,780) causes immobilization of estrogen receptor-α (ERα) in the nuclear matrix accompanied by rapid degradation by the ubiquitin-proteasome pathway. (Long, X and Nephew, K P), J. Biological Chem. (2006) 281: 9607-15).

Mitochondrial reactive oxygen species (ROS) are implicated in the pathogenesis of aging and lung diseases, some of which include idiopathic pulmonary fibrosis (IPF), asbestosis, chronic obstructive lung disease (COPD), and lung cancer (Kim, S-J et al., "Mitochondrial catalase overexpressed transgenic mice are protected against lung fibrosis in part via preventing alveolar epithelial cell mitochondrial DNA damage," (2016) Free Radic. Biol. Med. 101: 482-90), citing Schumacker P T, Gillespie M N, Nakahira K, Choi A M K, Crouser E D, Piantadosi C A, Bhattacharya J. Mitochondria in lung biology and pathology: more than just a powerhouse. Am J Physiology—Lung Cell Mol Physiol. 2014; 306(11):L962-L974; Agrawal A, Mabalirajan U. Rejuvenating cellular respiration for optimizing respiratory function: targeting mitochondria. Am J Physiol—Lung Cell Mol Physiol. 2016; 310(2):L103-L113; Mossman B T, Lippmann M, Hesterberg T W, Kelsey K T, Barchowsky A, Bonner J C. Pulmonary endpoints (lung carcinomas and asbestosis) following inhalation exposure to asbestos. J Toxicol Environ Health Part B Crit Rev. 2011; 14(1-4):76-12; Cheresh P, Kim S J, Tulasiram S, Kamp D W. Oxidative stress and pulmonary fibrosis. Biochim Biophys Acta. 2013; 1832(7):1028-104; Kim S J, Cheresh P, Jablonski R P, Williams D B, Kamp D W. The role of mitochondrial DNA in mediating alveolar epithelial cell apoptosis and pulmonary fibrosis. Int J Mol Sci. 2015; 16(9):21486-21519). ROS, including H2O2, oxidize multiple cellular targets (i.e. DNA, proteins, and lipids) which activate a wide range of biological processes, such as mitochondrial dysfunction, DNA damage-response (i.e. p53 activation), apoptosis, altered cell growth, and signal transduction that can result in tissue injury, aberrant wound healing, and fibrosis [Id., citing Schumacker P T, Gillespie M N, Nakahira K, Choi A M K, Crouser E D, Piantadosi C A, Bhattacharya J. Mitochondria in lung biology and pathology: more than just a powerhouse. Am J Physiology—Lung Cell Mol Physiol. 2014; 306(11): L962-L974; Agrawal A, Mabalirajan U. Rejuvenating cellular respiration for optimizing respiratory function: targeting mitochondria. Am J Physiol—Lung Cell Mol Physiol. 2016; 310(2):L103-L113; Mossman B T, Lippmann M, Hesterberg T W, Kelsey K T, Barchowsky A, Bonner J C. Pulmonary endpoints (lung carcinomas and asbestosis) following inhalation exposure to asbestos. J Toxicol Environ Health Part B Crit Rev. 2011; 14(1-4):76-12; Cheresh P, Kim S J, Tulasiram S, Kamp D W. Oxidative stress and pulmonary fibrosis. Biochim Biophys Acta. 2013; 1832(7):1028-104; Kim S J, Cheresh P, Jablonski R P, Williams D B, Kamp D W. The role of mitochondrial DNA in mediating alveolar epithelial cell apoptosis and pulmonary fibrosis. Int J Mol Sci. 2015; 16(9):21486-21519]. Alveolar epithelial cell (AEC) injury from 'exaggerated' lung aging and mitochondrial dysfunction is prominently involved in the pathogenesis of pulmonary fibrosis [Id., citing Cheresh P, Kim S J, Tulasiram S, Kamp D W. Oxidative stress and pulmonary fibrosis. Biochim Biophys Acta. 2013; 1832(7):1028-1040; Kim S J, Cheresh P, Jablonski R P, Williams D B, Kamp D W. The role of mitochondrial DNA in mediating alveolar epithelial cell apoptosis and pulmonary fibrosis. Int J Mol Sci. 2015; 16(9):21486-21519; Selman M, Pardo A. Revealing the pathogenic and aging-related mechanisms of the enigmatic idiopathic pulmonary fibrosis. an integral model. Am J Respir Crit Care Med. 2014; 189(10):1161-1172; Thannickal V J, Murthy M, Balch W E, Chandel N S, Meiners S, Eickelberg O, Selman M, Pardo A, White E S, Levy B D, Busse P J, Tuder R M, Antony V B, Sznajder J I, Budinger G R. Blue journal conference. Aging and susceptibility to lung disease. Am J Respir Crit Care Med. 2015; 191(3):261-269; Bueno M, Lai Y C, Romero Y, Brands J, St Croix C M, Kamga C, Corey C, Herazo-Maya J D, Sembrat J, Lee J S, Duncan S R, Rojas M, Shiva S, Chu C T, Mora A L. PINK1 deficiency impairs mitochondrial homeostasis and promotes lung fibrosis. J Clin Investig. 2015; 125(2): 521-538; Patel A S, Song J W, Chu S G, Mizumura K, Osorio J C, Shi Y, El-Chemaly S, Lee C G, Rosas I O, Elias J A, Choi A M, Morse D. Epithelial cell mitochondrial dysfunction and PINK1 are induced by transforming growth factor-beta1 in pulmonary fibrosis. PLoS One. 2015; 10(3): e0121246].

There appears to be a link between oxidant-induced AEC mtDNA damage and apoptosis in the pathophysiology of pulmonary fibrosis. Transgenic mitochondria-targeted human catalase enforced expression (MCAT) mice have a prolonged lifespan associated with reduced mitochondrial H2O2 production, mtDNA damage, and preserved mitochondrial function [Id., citing Schriner S E, Linford N J, Martin G M, Treuting P, Ogburn C E, Emond M, Coskun P E, Ladiges W, Wolf N, Van Remmen H, Wallace D C, Rabinovitch P S. Extension of murine life span by overexpression of catalase targeted to mitochondria. Science. 2005; 308(5730):1909-1911]. Compared to wild-type (WT), MCAT mice are less susceptible to/are protected against degenerative diseases involving the brain, cardiac fibrosis, pulmonary hypertension, and lung cancer [Id., citing Schriner S E, Linford N J, Martin G M, Treuting P, Ogburn C E, Emond M, Coskun P E, Ladiges W, Wolf N, Van Remmen H, Wallace D C, Rabinovitch P S. Extension of murine life span by overexpression of catalase targeted to mitochondria. Science. 2005; 308(5730):1909-1911; Lee H Y, Choi C S, Birkenfeld A L, Alves T C, Jornayvaz F R, Jurczak M J, Zhang D, Woo D K, Shadel G S, Ladiges W, Rabinovitch P S, Santos J H, Petersen K F, Samuel V T, Shulman G I. Targeted expression of catalase to mitochondria prevents age-associated reductions in mitochondrial function and insulin resistance. Cell Metab. 2010; 12(6):668-674; Adesina S E, Kang B Y, Bijli K M, Ma J, Cheng J, Murphy T C, Hart C Michael, Sutliff R L. Targeting mitochondrial reactive oxygen species to modulate hypoxia-induced pulmonary hypertension. Free Radic Biol Med. 2015; 87:36-47]. AEC mitochondrial catalase therefore may play a role in limiting mtDNA damage and apoptosis following exposure to fibrogenic agents such as asbestos or bleomycin.

We studied wounds, wound healing and how to repair an oxidant injury using adipose derived cells from young and old models.

Model: An ex vivo human skin wound model (Pastar I, Stojadinovic O, Sawaya A P, Stone R C, Lindley L E, Ojeh N, Vukelic S, Samuels H H, Tomic-Canic M. Skin Metabolite, Farnesyl Pyrophosphate, Regulates Epidermal Response to Inflammation, Oxidative Stress, and Migration. J Cell Physiol 2016; 231: 2452-2463; Stojadinovic O, Tomic-Canic M. Human ex vivo wound healing model. Methods Mol Biol 2013; 1037: 255-264) was utilized to evaluate functional effect of ASCs on wound repair. Human skin samples were obtained from healthy women following panniculectomy (abdominal skin; median age 44). Informed consent was obtained per the requirements of the Institutional Review Board at the University of Miami protocol #20070922). Under sterile conditions, subcutaneous fat was trimmed from skin prior to generating wounds. A 3 mm punch (Acuderm) was used to make wounds in the epidermis through the reticular dermis and 3 mm discs of epidermis were excised. Skin discs (8 mm), with the 3 mm epidermal wound in the middle, were excised using a 6 mm biopsy punch (Acuderm). Wounded skin specimens were immediately transferred to air-liquid interface with DMEM medium (BioWhittaker) supplemented with antibiotics-antimycotics and 10% fetal bovine serum (Gemimi Bio-Products). The skin samples were incubated at 37° C. in a humidified atmosphere of 5% $CO_2$ for 4 days. Tissues were fixed in 10% formalin (Sigma-Aldrich), processed for paraffin embedding and stained with hematoxylin and eosin to follow the rate of healing. One-way analysis of variance was used to analyse rate of epithelialization among treatment groups; $p<0.05$ was considered significant.

Luciferase is part of the plasmid containing the gene being transfected-used as a reporter. Luciferase is then measured as a function of the transfection. β-galactosidase gene pRSV-βgal is co-transfected at the same time to control for transfection efficiency. To Assay, cells were washed two times in PBS and lysed with 100 μl of reporter lysis buffer (Promega) at room temperature for 15 min. Wells were scraped and the lysate transferred to a Microfuge tube, vortexed, and microcentrifuged for 2 min at 4 C. The supernatant was collected and frozen at −70 C until assayed.

ER expression and regulation decline in aging post-hASCs. Estrogen responsiveness is largely determined by the ER levels in target tissues (Webb P, Lopez G N, Greene G L, Baxter J D, Kushner P J. The limits of the cellular capacity to mediate an estrogen response. Molecular endocrinology 1992; 6: 157-167). Therefore we hypothesized that the decline in female ASC function could be in part related to declining ER expression.

FIG. 9 shows that ASCs isolated from post-menopausal (old female) adipose have decreased estrogen receptor expression and response to estrogen compared to ASCs isolated from pre-menopausal (young female) adipose. FIG. 9A compares ERα protein expression for pre-menopausal and post-menopausal tissue. FIG. 9B compares ERβ protein expression for pre-menopausal and post-menopausal female tissue. FIG. 9C (premenopausal) and FIG. 9D (post-menopausal) show the ratio of luciferase/B-gal for samples V, 0.1, 1, 1, 10, ICI (ICI 182,780 stands for fulvestrant, an estrogen receptor antagonist), E2 is estradiol; 1ICI/E2(1) and ICI/E2 (10) in nM concentration.

Figure 9A:
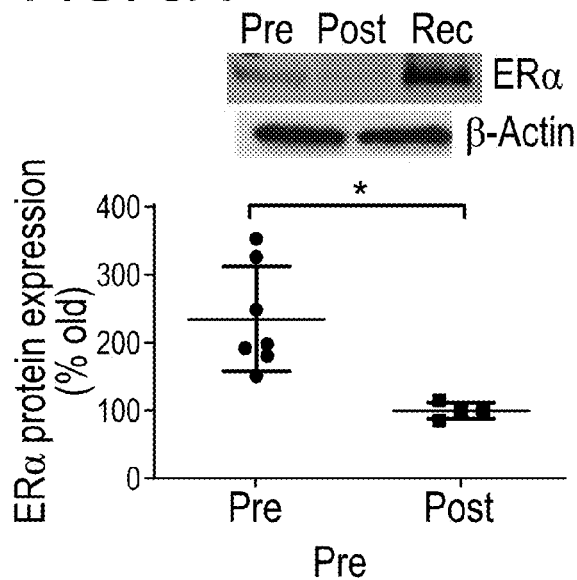
FIG. 9A-FIG. 9D shows that ASCs isolated from post-menopausal (old) adipose have decreased estrogen receptor expression and response to estrogen compared to ASCs isolated from pre-menopausal (young) adipose.
Figure 9B:
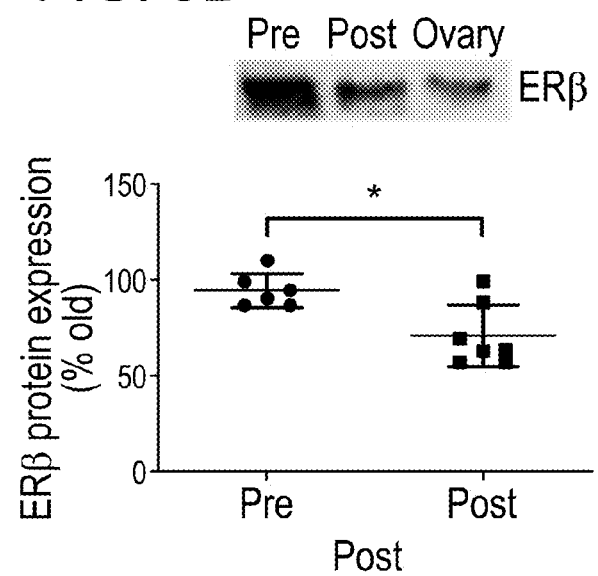
Figure 9C:
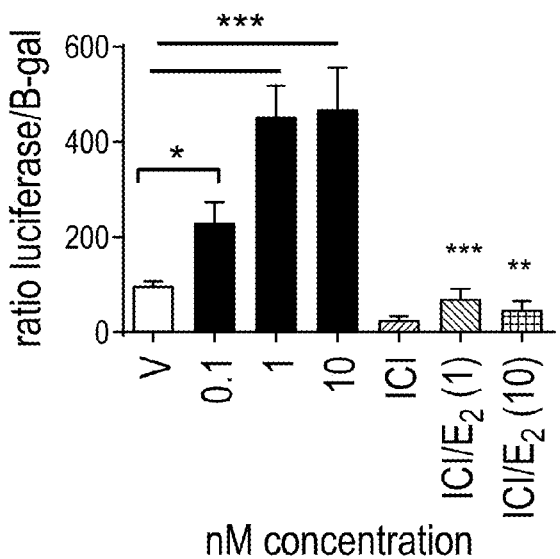
Figure 9D:
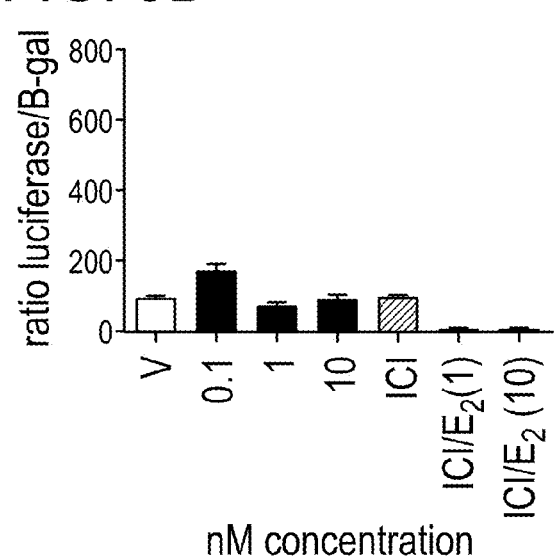

We found a 2-fold decrease of baseline ERα protein and mRNA expression in hASCs isolated from pre (<45 years old) relative to that of hASCs isolated from post-menopausal (>55 years old) women (FIG. 9A). ERβ expression decreased in the post-hASC group, although to a much lesser degree than ERα (FIG. 9B), leading to an alteration of the ER subtype ratio. We also tested whether ER transcriptional activation paralleled changes in ER expression levels. hASCs transfected with a luciferase-based reporter construct containing four estrogen response elements (ERE) were stimulated with physiologic concentrations of E2 (0.1 and 1 nm). Increased transcriptional activation up to greater than five-fold was noted in premenopausal cells (FIG. 9C) while pharmacologic levels (10 nM) increased activation greater than sixfold). In contrast, there was less than a two-fold change in ER transcriptional activation in hASCs from post-menopausal women (FIG. 9D). As expected ICI 182, 780, the complete ER antagonist, was able to block activation by E2 suggesting that these effects were ER-mediated. These results confirmed that the loss of ERα protein expression leads to repressed transcriptional activity in hASCs isolated from post-menopausal women.

Figure 10:
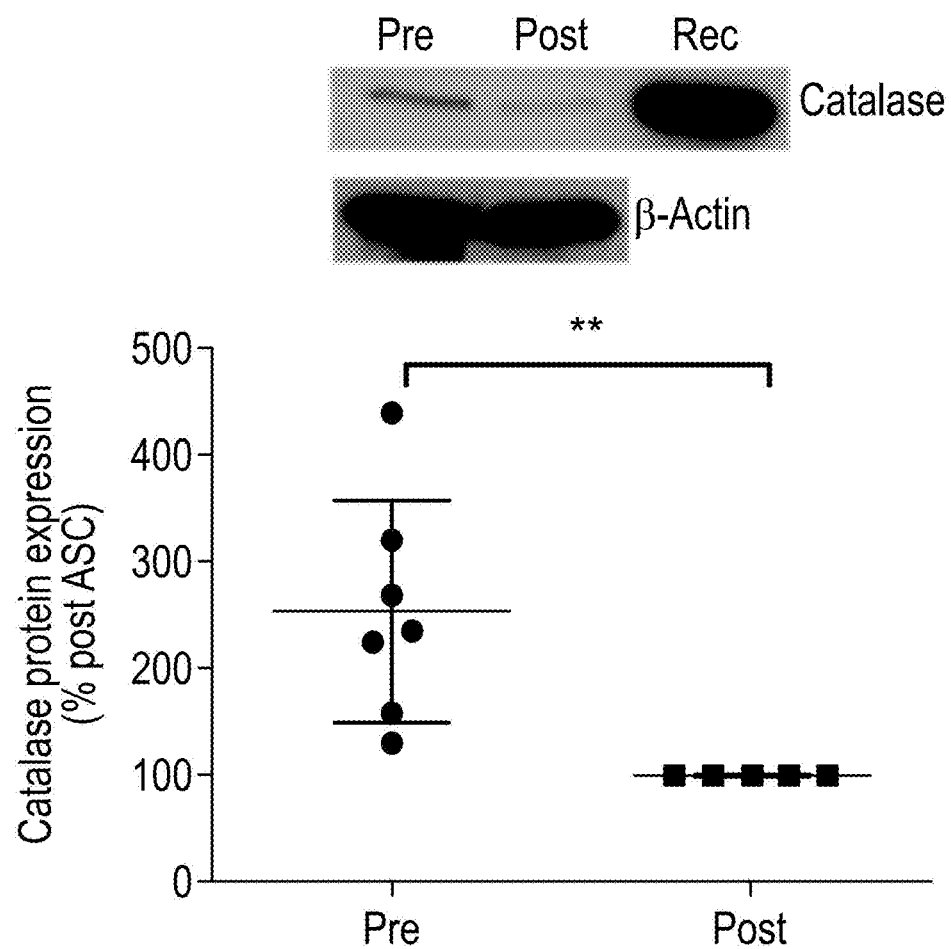
FIG. 10 shows that ASCs isolated from post-menopausal (old) adipose have decreased catalase expression compared to ASCs isolated from pre-menopausal (young) adipose.

FIG. 10 shows that ASCs isolated from post-menopausal (old) adipose have decreased catalase expression compared to ASCs isolated from pre-menopausal (young) adipose. Pre-hASCs express three fold more catalase compared to post-hASCs. Upper panel is a representative western blot showing catalase expression, lower panel shows β-actin loading control expression, Rec=recombinant. Data are graphed as mean±SEM % of post-hASCs (n=3 unique cell lines, **$p<0.01$).

Pre and post-hASCs were plated in 6 well plates until they reached 80% confluence. 24 hours prior to transfections, cells were exposed to antibiotic free-media. Transfections were performed using UltraCruz transfection reagent (Santa Cruz Biotechnology, Inc. Dallas, Tex.) according to manufacturers' directions. A time course was performed with Catalase CRISPR Activation plasmid (human, cat #sc-400353-ACT) or Catalase CRISPR/Cas9 inhibitor plasmid (human, cat #sc-400353) to determine optimum transfection efficiency. Relevant 20 nt non-coding scrambled control CRISPR plasmids were transfected in parallel (cat #sc-437275 for activation, and sc-418922 for inhibitor plasmid).

Figure 11:
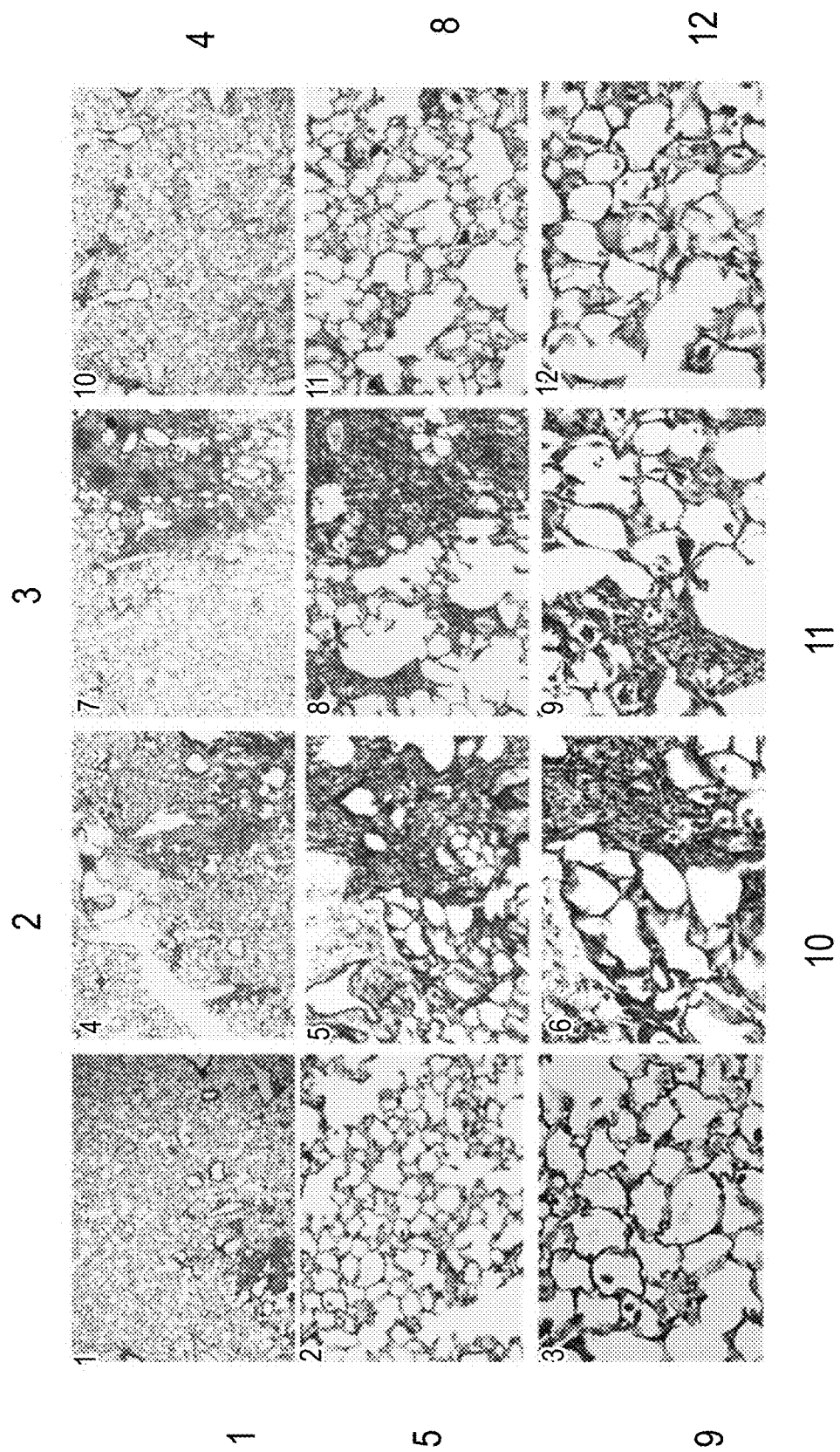
FIG. 11 shows lung histology 21 days post-BLM treatment and infusion of pre-menopausal ASCs ("pre-ASCs") or post-menopausal ASCs ("post-ASCs"").

To establish a mechanism related to the repair capacity of young hASCs, we infused pre and post hASCs (transfected with inhibitor or activator of catalase) into the BLM lung injury mouse model (Tashiro J, Elliot S J, Gerth D J, Xia X, Pereira-Simon S, Choi R, Catanuto P, Shahzeidi S, Toonkel R L, Shah R H, El Salem F, Glassberg M K. Therapeutic benefits of young, but not old, adipose-derived mesenchymal stem cells in a chronic mouse model of bleomycin-induced pulmonary fibrosis. Transl Res 2015; 166: 554-567). Infusion of pre-hASC transfected with inhibitor (hASCs+inh, FIG. 11 panels 6-8) did not reduce severity of fibrosis in the lung compared to post-hASCs transfected with catalase activator (hASCs+activator, FIG. 11, panels 10-12).

Figure 12A:
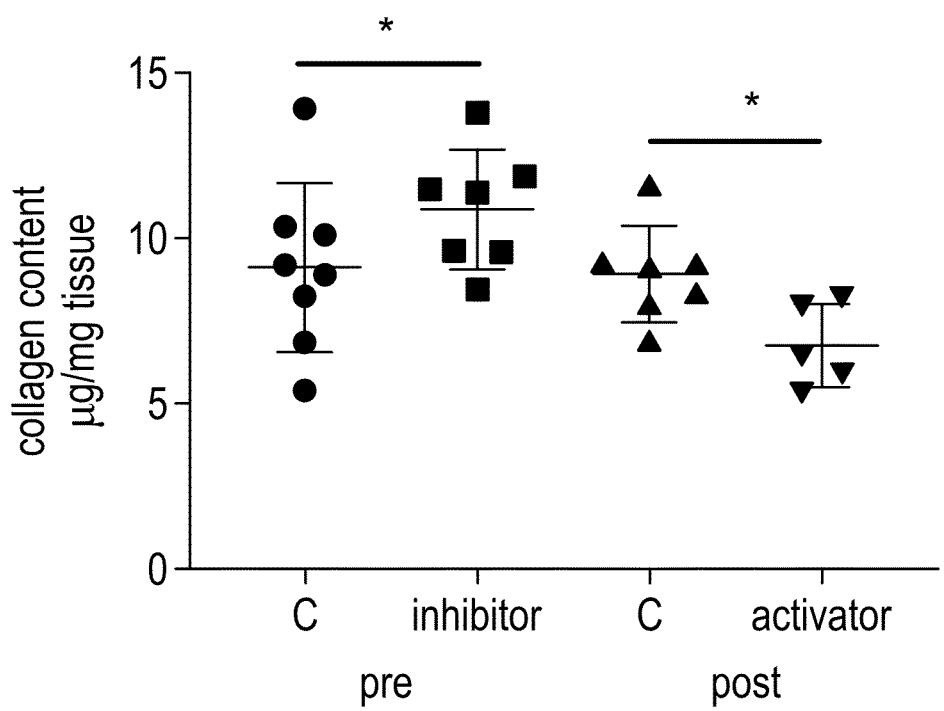
FIG. 12A and FIG. 12B shows that pre-menstrual hASCs transfected with catalase inhibitor increased lung hydroxyproline (collagen accumulation, FIG. 12A), and TNFα mRNA expression (FIG. 12B, relevant endpoints in the lung fibrosis model. C=pre-menopausal ASC control; inhibitor=pre-menopausal ASC transfected with catalase inhibitor; C'=post-menopausal ASC control; activator=post-menopausal ASC transfected with catalase activator.
Figure 12B:
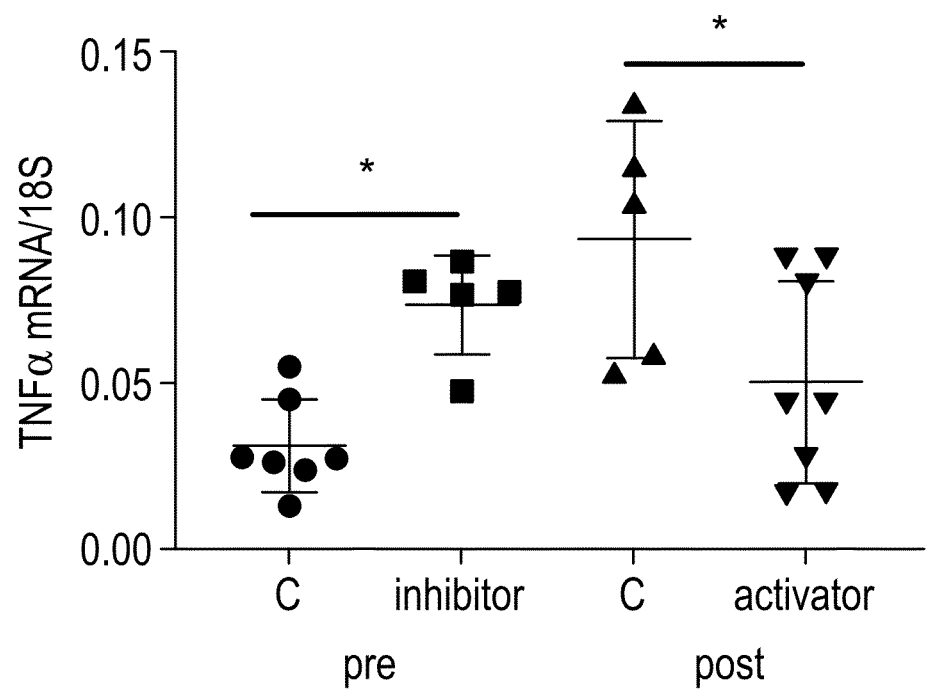

FIG. 12 shows parameters of fibrosis in lungs 21 days post BLM-treatment and infusion of pre or post-menopausal ASCs. Pre hASCs+inh increased lung hydroxyproline (collagen accumulation, FIG. 12A) and TNFα mRNA expression (FIG. 12B), relevant endpoints in the lung fibrosis model (34).

Figure 13B:
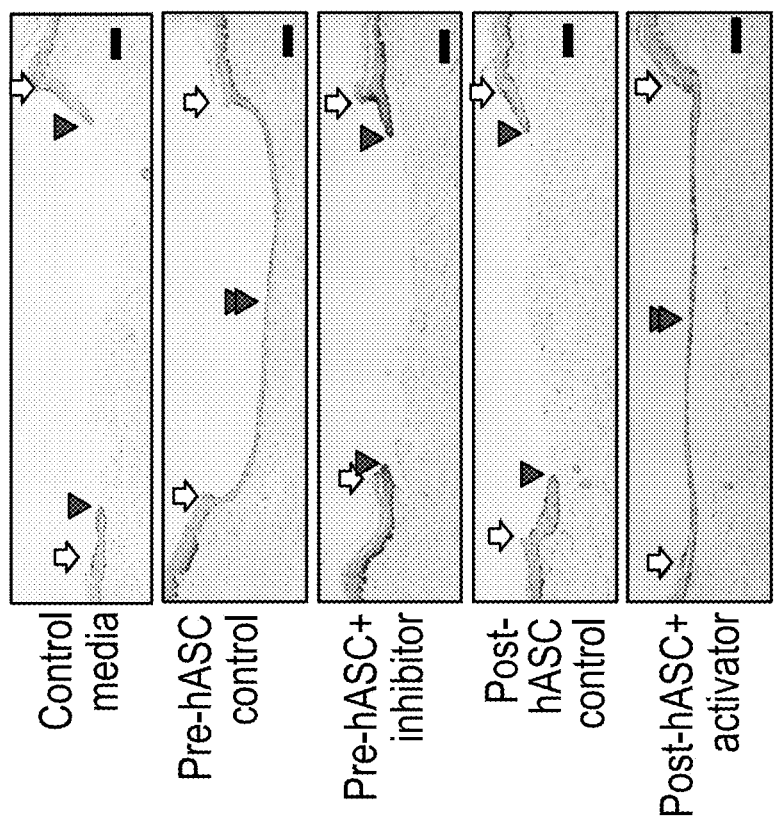
FIG. 13A and FIG. 13B show that wound healing is enhanced in post-menopausal ASCs after transfection with catalase activator.
Figure 13A:
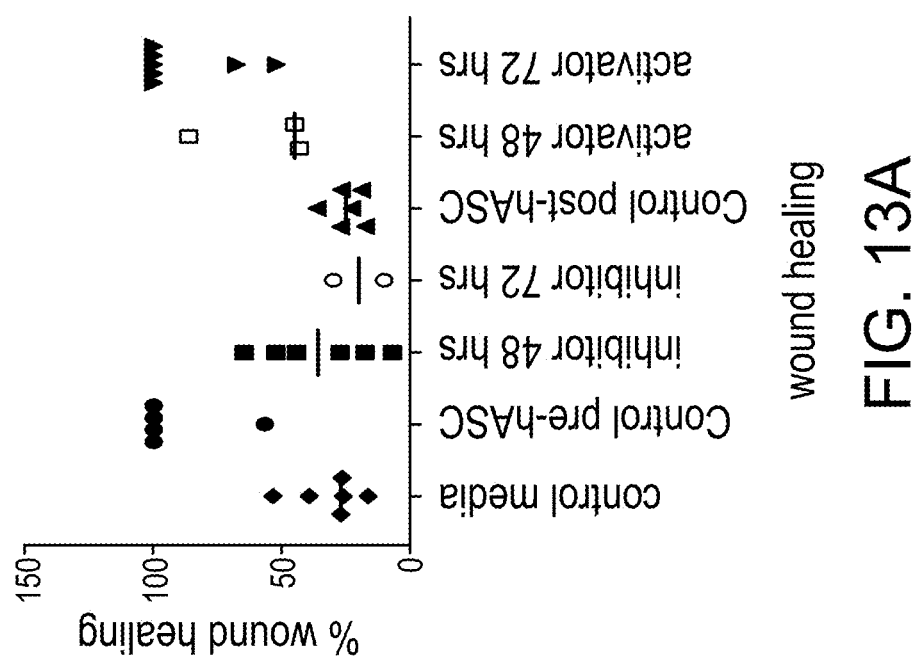

Taken together, decreasing ER and catalase expression in pre-hASCs similar to that noted in post-hASCs, reverse the effectiveness of the pre hASCs in wound repair and BLM-induced lung injury FIG. 13A and FIG. 13B show that wound healing is enhanced in post-menopausal ASCs after transfection with catalase activator. FIG. 13A is a plot showing % wound healing on the Y-axis; the x axis identifies the samples tested: control media, pre-menopausal human ASC (control); inhibitor at 48 hours, inhibitor for 72 hours, control post-human-ASCs; activator at 48 hours, and activator at 72 hours. FIG. 13B shows tissue treated (from top to bottom) with Control media (a). pre-hASC control (b); pre-hASC+inhibitor (c), post-hASC control (d); and post-hASC+activator. White arrows indicate wound edges after initial wounding, whereas red arrowheads point at the epithelialized edges of the migrating fronts 4 days after wounding; scale bar=200

Example 6: ASC Extracellular Vesicles Derived from Human Adipose and Lung Myofibroblasts Introduction In this study, we investigated the hypothesis that EVs derived from young ASCs could replicate the effects of whole cell MSCs in preventing or reversing BLM-induced pulmonary fibrosis in aged mice, while those derived from old ASCs would be ineffective or detrimental.

Our second objective was to determine whether EVs derived from myofibroblasts of patients with IPF could confer disease to normal lung tissue in contrast to EVs isolated from healthy lung fibroblasts of age matched controls. We compared the miRNA and protein profiles of lung tissue after in vivo exposure to young and old extracellular vesicle preparations to determine potential pathway alterations leading to lack of efficacy/promotion of damage/aging in the old. We investigated in parallel miRNA and protein differences in response between IPF and control EV preparations on ex vivo lung punches to determine pathways that promoted the disease phenotype and if any of the pathways were similar between IPF and old ASC derived EV preparations.

Methods

Cell culture. ASCs isolated from young and old male C57B L/6 mice were propagated and characterized (Tashiro J, Elliot S J, Gerth D J, Xia X, Pereira-Simon S, Choi R, Catanuto P, Shahzeidi S, Toonkel R L, Shah R H, El Salem F, Glassberg M K. Therapeutic benefits of young, but not old, adipose-derived mesenchymal stem cells in a chronic mouse model of bleomycin-induced pulmonary fibrosis. Transl Res 2015; 166: 554-567). ASCs (passage 2 or 3) were grown until 80% confluence in T175 flasks. Media was removed and each flask was washed 3 times with PBS to remove serum and serum proteins. Serum free media was added back to each flask. After 48 hours, media was collected and exosomes isolated and characterized (Zen Bio, NC).

Fibroblasts and myofibroblasts Lung samples were obtained at the time of lung biopsy at the University of Miami from patients with IPF. (Informed consent was obtained per the requirements of the Institutional Review Board at the University of Miami protocol #20060249). Human lung was cut into small pieces and plated in a 6 well plate (NUNC, Thermoscientific, Waltham, Mass.) for 30 minutes prior to adding media. Human cells were allowed to grow and transferred to a T25 flask when confluent. A portion of cells were placed on a chamber slide and myofibroblasts identified by positive staining for α-SMA (Abcam, Cambridge, Mass.) and vimentin (Abcam, Cambridge, Mass.). Cells were used for experiments between 2 and 4 passages.

Animal model. 22 month old male C57BL/6 mice were obtained from Jackson Laboratories. Animals were housed under specific pathogen-free conditions with food and water ad libitum. All experiments and procedures were approved by the Institutional Animal Care and Use Committee at the Leonard M. Miller School of Medicine at the University of Miami (Miami, Fla.), a facility accredited by the American Association for the Accreditation of Laboratory Animal Care.

BLM administration. After the administration of anesthesia, bleomycin sulfate (Sigma-Aldrich Corp; St. Louis, Mo.) dissolved in 50 µl sterile saline at 2.5 U per kg of bodyweight was administered by direct intratracheal instillation via intubation. Control mice received 50 µl of sterile saline using the same method. Mice were sacrificed at 21 days following BLM administration.

EV injections and time course. An ASC- or fibroblast-derived EV preparation, prepared as described above, was thawed immediately prior to injection in a 37° C. water bath and washed in PBS to remove the cell freezing solution. Twenty-four hours or ten days following BLM administration, each animal received 100 µl either PBS (control) or 40 µg of an EV preparation in 100 µl of PBS by tail vein injection over a 1 minute period. [30, 31] Control mice given intratracheal saline also received injections of a donor EV preparation, as described above. An initial group of mice received 20 and 40 µg of EVs. This was calculated based on the amount of the EV preparation derived from $10^5$ cells (number of cells utilized in whole cell experiments, equivalent to 20 µg).

Lung tissue analysis/immunohistochemistry. Left lung lobes were harvested for protein, MMP, and mRNA analysis. For morphometry and histology studies, right lung lobes were inflated with 10% neutral buffered formalin (NBF) under 25 cm $H_2O$ pressure. The lungs were postfixed by immersion in 10% NBF for 24 hours and then transferred to PBS at 4° C. Samples were paraffin-embedded and 4 µm sections were obtained for hematoxylin-eosin and Masson's Trichrome staining, Ashcroft scoring. Pulmonary fibrosis was assessed by a pathologist blinded to the experimental groups using the semi-quantitative Ashcroft method [32] on Masson's Trichrome-stained slides at 20× magnification. Individual fields were assessed by systematically moving over a 32-square grid; each field was assessed for fibrosis severity and assigned a score on a scale of 0 (normal lung) to 8 (total fibrosis of the field) and an average was obtained for each slide.

Collagen content assessment by Hydroxyproline content. Hydroxyproline content was determined according to the manufacturer's instructions (Hydroxyproline Assay Kit; Sigma-Aldrich, St. Louis, Mo.). Briefly, 2 mg lung fragments were weighed and homogenized in 100 µl of distilled water. An equal volume of 10 N HCl was added to the samples before drying at 49° C. for 3 hours. 50 µl of sample was loaded in the plate and incubated overnight at 37° C. A hydroxyproline standard curve was prepared according to a standard solution (between 0 and 1 ug/well). Hydroxyproline content was read at 557 nm, using the SoftMax Pro Software (Molecular Devices Corp; Sunnyvale, Calif.).

Real-Time PCR. Amplification and measurement of target RNA was performed on the Step 1 real time PCR system as previously described. [33] Transforming growth factor β (TGFβ), $α_v$-integrin, tumor necrosis factor alpha (TNFα), vascular endothelial growth factor (VEGF) and Nrf2 expression was measured using RNA extracted from lung tissues. In addition, MMP-2 and insulin-like growth factor (IGF) receptor mRNA expression was assessed in yASCs and oASCs. The TaqMan rRNA control reagents kit (Life Technologies) was used to detect 18S rRNA gene, an endogenous control, and samples were normalized to the 18S transcript content as previously described. [34]

Western Blot. Lung tissue was homogenized and western analysis was performed as previously described [35]. For pAKT, AKT, and β-actin, 5 to 25 µg of protein lysate was fractionated on 10% polyacrylamide gels. For TGFβ analysis, 60 µg of protein lysate was fractioned on a 12.5% gel. Immunoreactive bands were determined by exposing nitrocellulose blots to a chemiluminescence solution (Denville Scientific Inc.; Metuchen, N.J.) followed by exposure to Amersham Hyperfilm ECL (GE Healthcare Limited; Buckinghamshire, UK) (data not shown). To determine the relative amounts of protein densitometry Image J version 1.48v (National Institutes of Health; Bethesda, Md.) was utilized. All values from western blots were initially standardized to the corresponding β-actin band prior to comparative analyses.

MMP Activity. MMP-2 activity was assessed in lung tissue supernatants using a previously described method. [35] Briefly, Novex® 10% zymogram gels (Life Technologies) were incubated for 24 hours in a gelatinase solution, which allows the determination of total proteolytic MMP activities without interference from associated tissue inhibitors. Relative MMP activity was determined by densitometry using Image J (NIH).

Ex vivo human wound healing model. An ex vivo human skin wound model (14, 15) was utilized to evaluate functional effect of ASCs on wound repair. Human skin samples were obtained from healthy women following panniculectomy (abdominal skin; median age 44 (young)). Informed consent was obtained per the requirements of the Institutional Review Board at the University of Miami protocol #20070922). Under sterile conditions, subcutaneous fat was trimmed from skin prior to generating wounds. A 3 mm punch (Acuderm) was used to make wounds in the epidermis through the reticular dermis and 3 mm discs of epidermis were excised. Skin discs (8 mm), with the 3 mm epidermal wound in the middle, were excised using a 6 mm biopsy punch (Acuderm). Wounded skin specimens were immediately transferred to air-liquid interface with DMEM medium (BioWhittaker) supplemented with antibiotics-antimycotics and 10% fetal bovine serum (Gemimi Bio-Products). The skin samples were incubated at 37° C. in a humidified atmosphere of 5% CO2 for 4 days. Tissues were fixed in 10% formalin (Sigma-Aldrich), processed for paraffin embedding and stained with hematoxylin and eosin to follow the rate of healing.

Figure 14A:
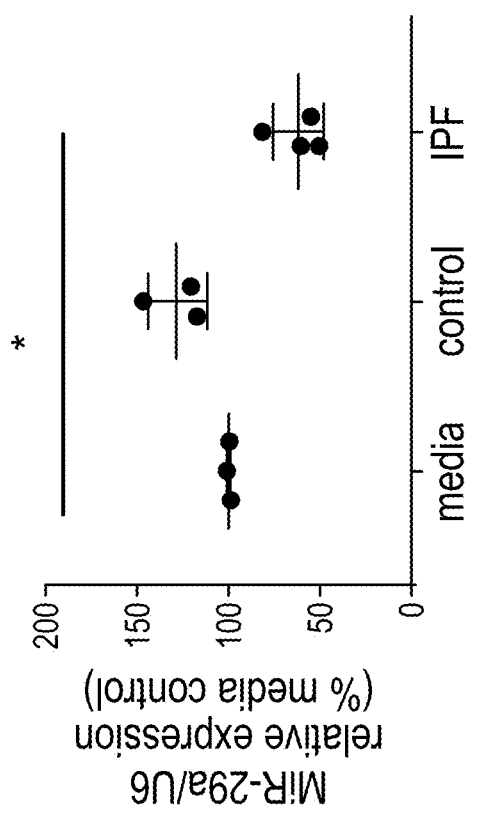
FIG. 14A-FIG. 14C is a series of graphs showing that IPF myofibroblast-derived EVs decrease the expression of anti-fibrotic markers caveolin-1 (FIG. 14A), microRNA 29a (miR-29) (FIG. 14B), and miR-let 7D (FIG. 14C) in 3-D punches.
Figure 14B:
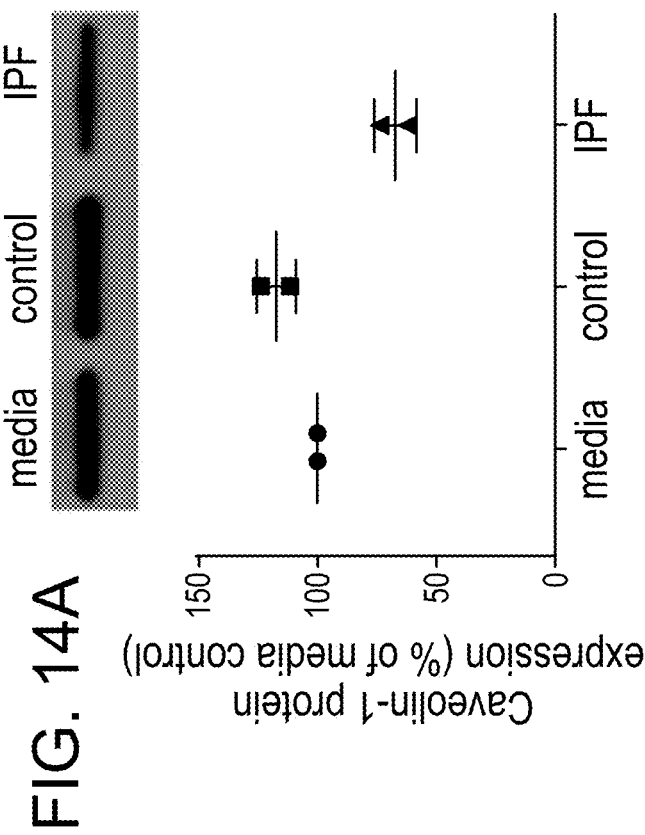
Figure 14C:
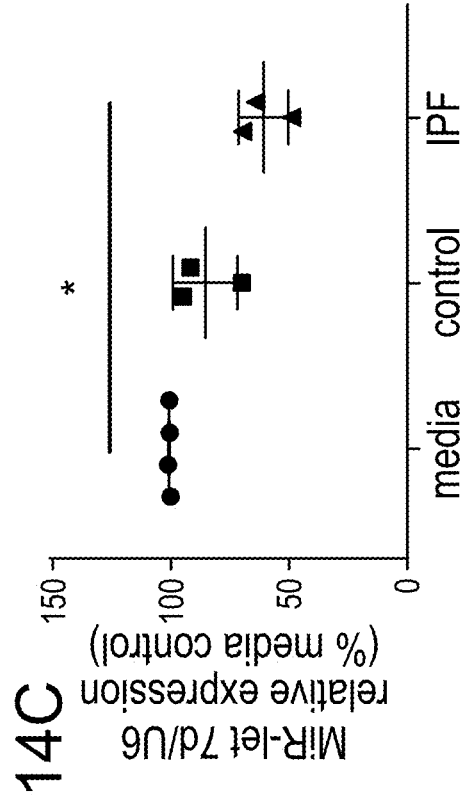

Ex Vivo lung punches. FIG. 14 is a series of graphs showing that IPF myofibroblast-derived EVs decrease the expression of anti-fibrotic markers caveolin-1 (FIG. 14C), microRNA 29a (miR-29) (FIG. 14D), and miR-let 7D (FIB. 14E) in 3-D punches.

Figures 15A, 15B, 15C, 15D, 15E, 15F:
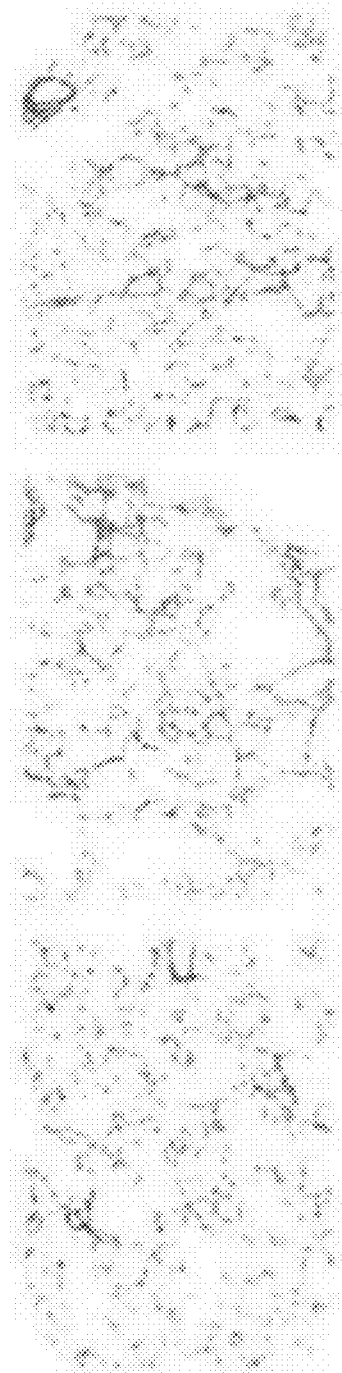

FIG. 15 is a series of pictures showing the effects of IPF and non-IPF lung fibroblast-derived EVs on representative ex vivo lung punches from an aging male mouse.

Statistics. One-way analysis of variance was used to analyze the rate of epithelialization among treatment groups; p<0.05 was considered significant.

Results

Given the inherent issues with separation of EVs into MVs and exosomes, we utilized size and protein content as characterization methods. Our EV preparation comprised vesicles at the upper limit of exosome size running an average of 140-150 nm in size, the higher end of exosome sizing.

Figure 16A:
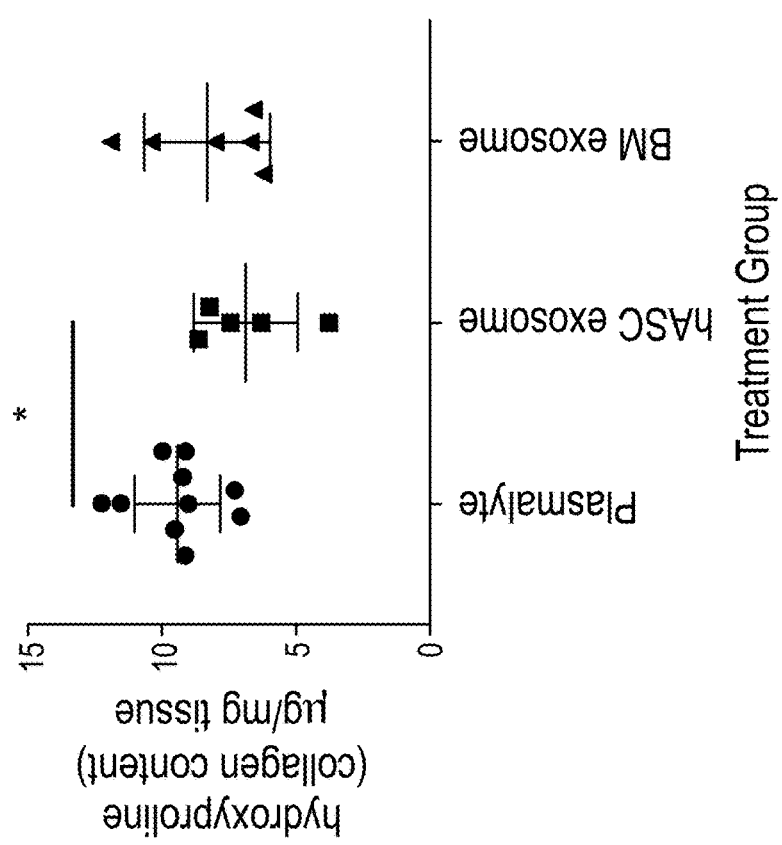
FIG. 16A and FIG. 16B shows graphs showing that mesenchymal stem cell-derived EVs reduced fibrosis in an established model of pulmonary fibrosis whether the EVs are derived from bone marrow or ASCs.
Figure 16B:
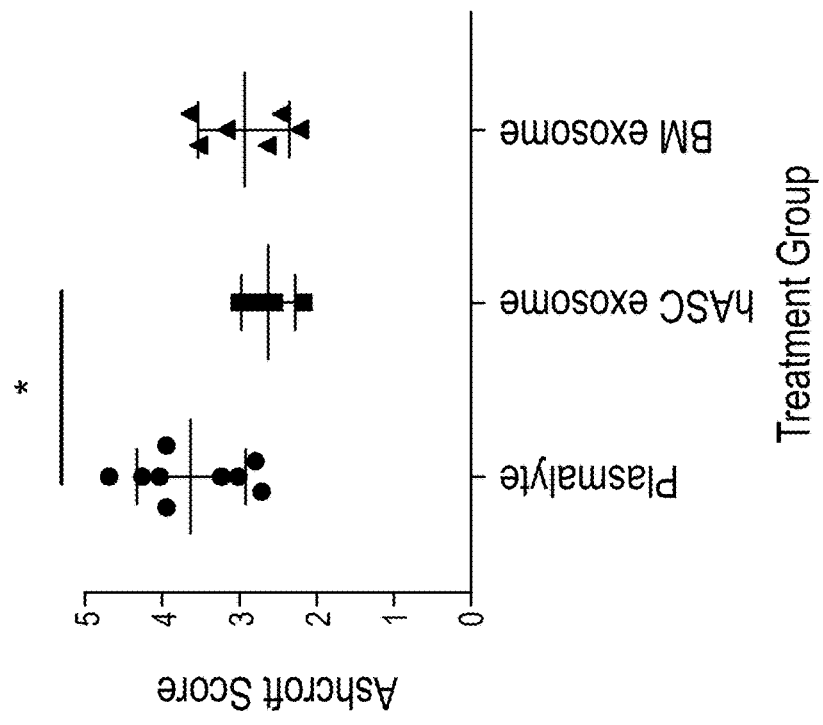

Similar to our previous study, infusion of a young EV preparation prevented BLM-induced fibrosis while infusion of an old EV preparation did not. We therefore infused the EV preparation after established fibrosis at day 10. We found that the young EV preparation was able to reverse the effects of BLM (mice gained weight or stopped losing weight). FIG. 16A-FIG. 16B are graphs showing that mesenchymal stem cell-derived EVs, whether the EVs are derived from bone marrow or ASCs, reduced fibrosis in an established model of pulmonary fibrosis. FIG. 16A: Ashcroft score; and FIG. 16B: hydroxyproline (collagen content) P<0.05

Figure 17:
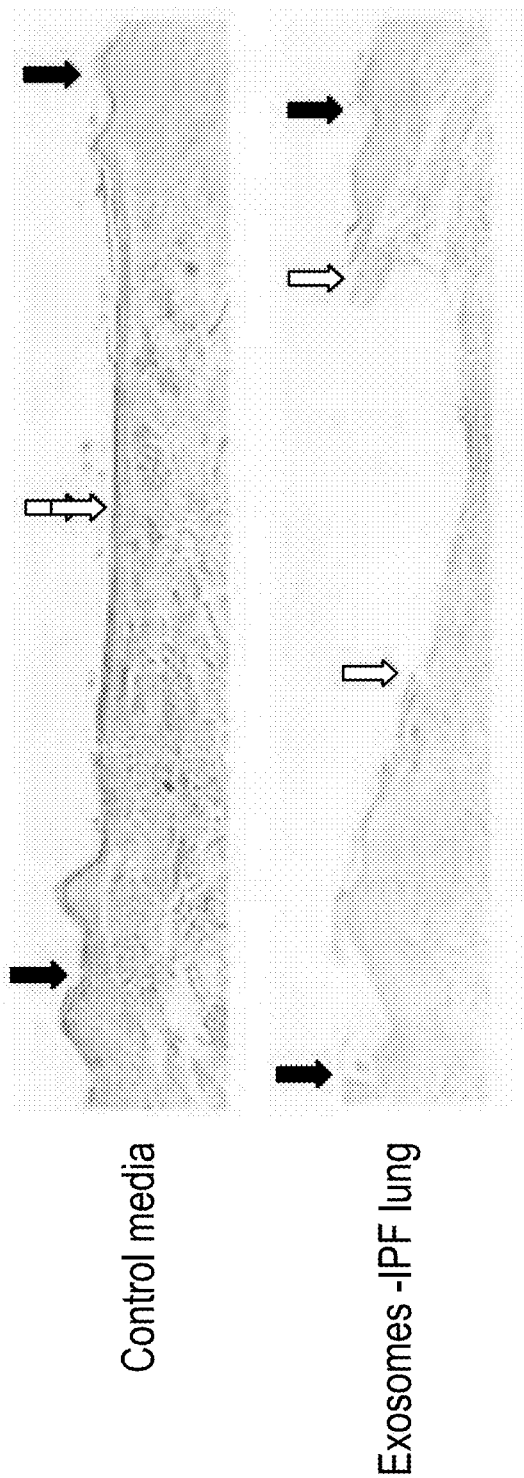
FIG. 17 is a picture showing that EVs derived from IPF lung fibroblasts prevent ex vivo wound healing.

We used an ex vivo wound healing model to assess efficacy of whole cell human ASCs and the EV preparations since fibrosis has been equated to a non-healing wound. We found that healing rate of a young EV preparation was higher than media alone and similar to whole cell therapy. FIG. 17 is a picture showing that EVs derived from IPF lung fibroblasts prevent ex vivo wound healing. FIG. 18 is a representative picture showing that EVs performed equally to whole cell MSCs in an ex vivo wound healing assay.

We performed micro arrays on the EV preparations and whole cells from young and old ASCs. Comparisons showed several miRs reported to be involved or associated with aging and reported as biomarkers of age-associated diseases including cardiovascular and chronic kidney disease.

Discussion

Figure 19A:
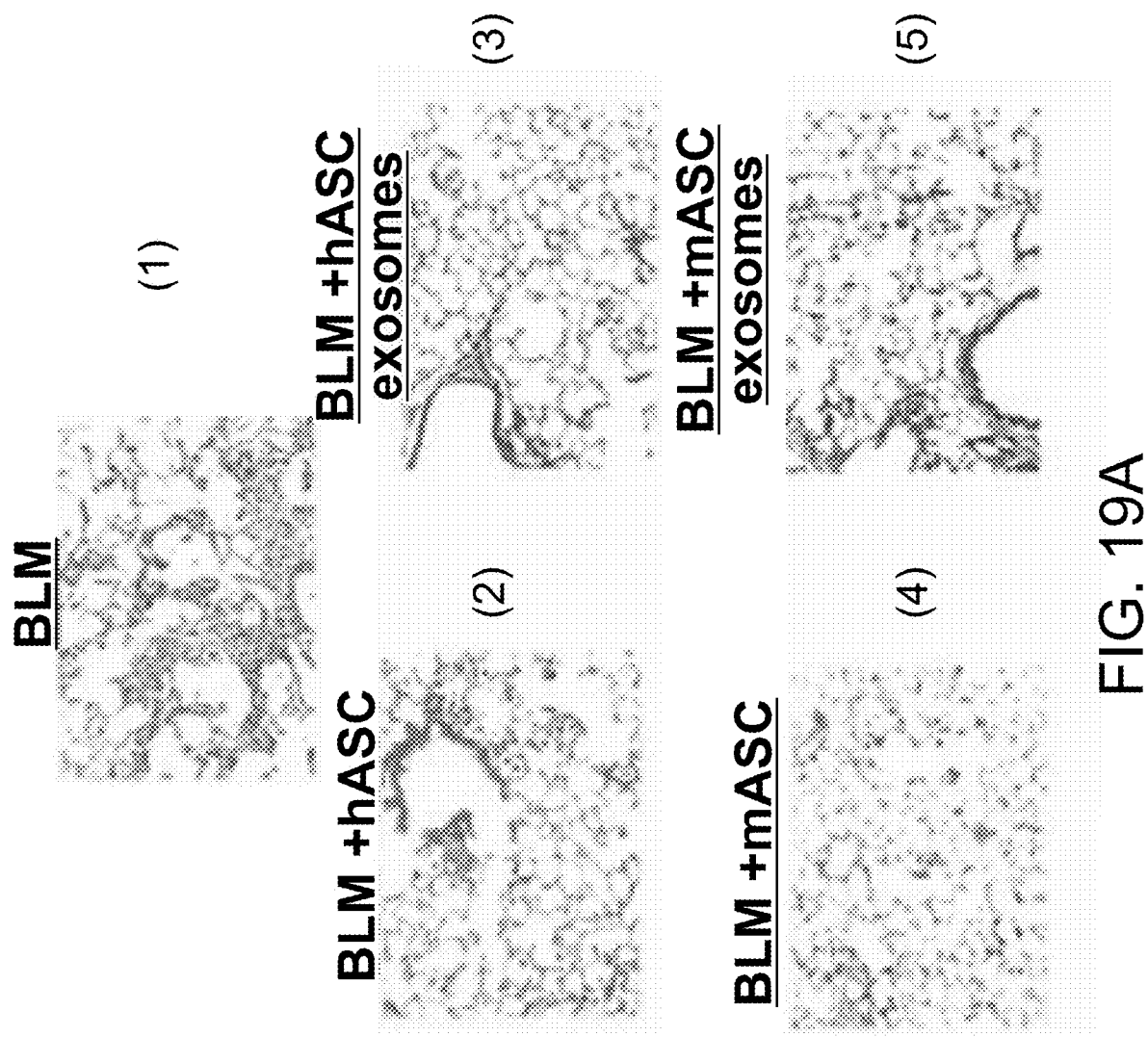
FIG. 19A, FIG. 19B, FIG. 19C show that mesenchymal stem cell-derived EVs are equally efficacious as whole cells in preventing pulmonary fibrosis.
Figures 19B, 19C:
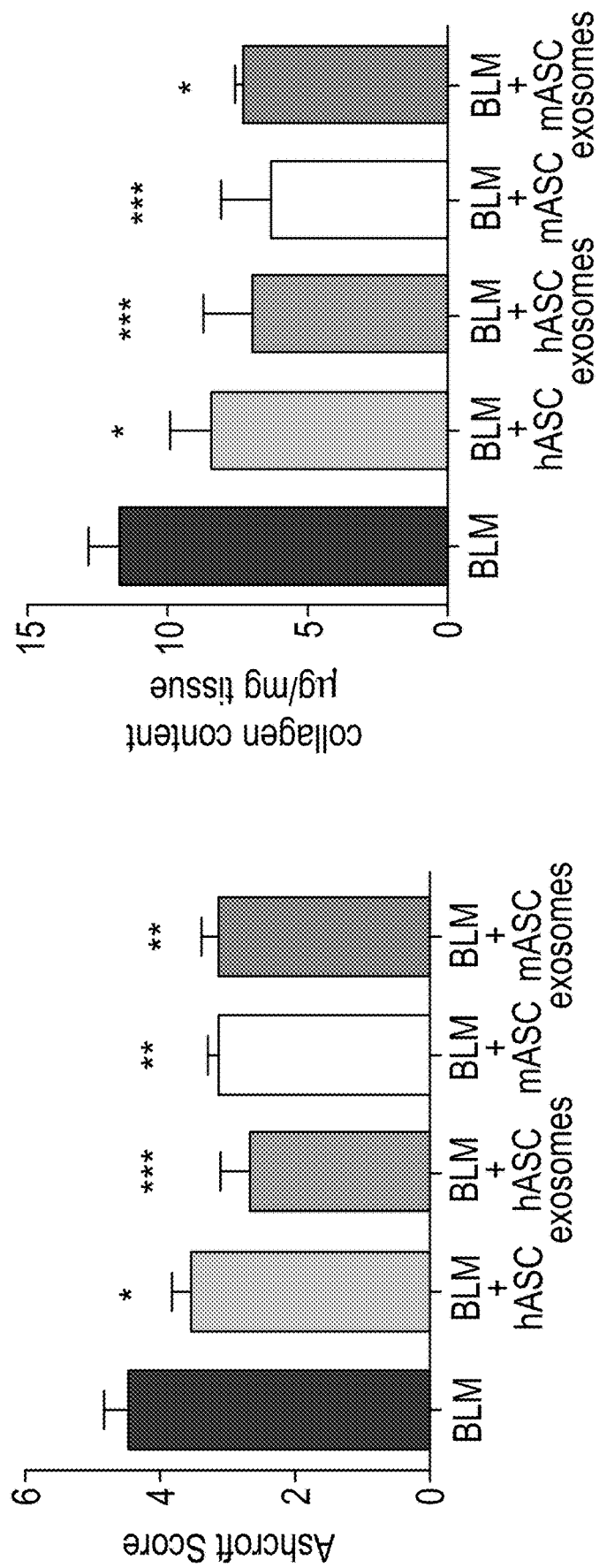

We have previously shown that young MSCs are effective in preventing BLM-induced fibrosis in an aging mouse model. This study extends those data to show that young EV preparations derived from mouse ASCs (mASCs) and human ASCs (hASCs) are equally efficacious as whole cell therapy in preventing the development of fibrosis or reversing established fibrosis. FIG. 19A, FIG. 19B, and FIG. 19C show that mesenchymal stem cell-derived EVs are equally efficacious as whole cells in preventing pulmonary fibrosis. FIG. 19A shows representative pictures from BLM control (panel 1)), whole human ASC (panel 2), human ASC exosomes (panel 3), whole mouse ASC (panel 4), and mouse ASC exosomes (panel 5). FIG. 19B is a graph comparing Ashcroft scores. FIG. 19C is a graph comparing collagen content.

Figure 20B:
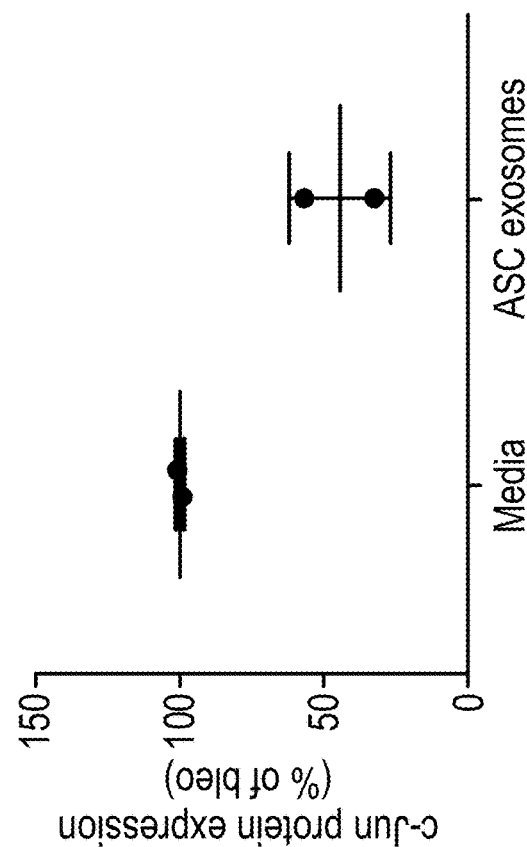
FIG. 20A and FIG. 20B shows two graphs depicting changes in expression of anti-fibrotic marker caveolin-1 (FIG. 20A) and profibrotic marker c-jun (FIG. 20B) after injection of ASC-derived EVs. EVs or media were injected into a lung punch from an aging mouse treated for 10 days with bleomycin. Punches were collected after 4 days and analyzed.
Figure 20A:
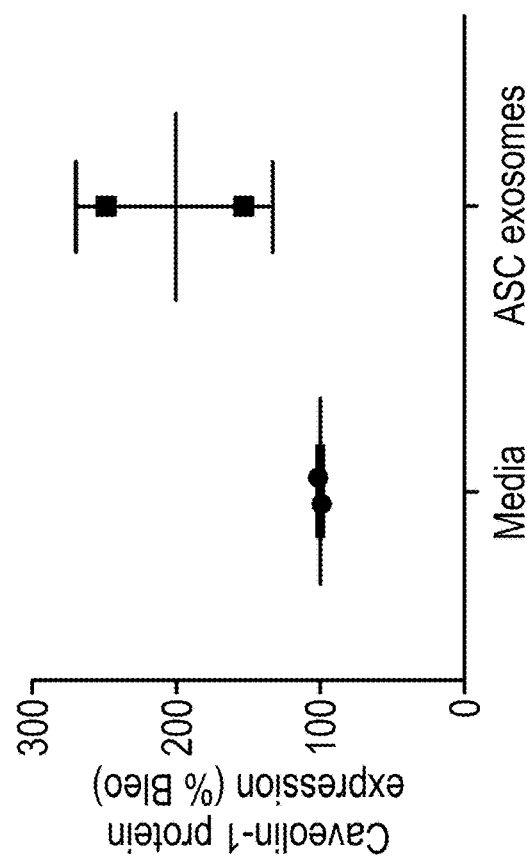

FIG. 20 is a graph showing changes in expression of anti-fibrotic marker caveolin-1 (FIG. 20A) and profibrotic marker c-jun (FIG. 20B) after injection of ASC-derived EVs. EVs or media were injected into a lung punch from an aging mouse treated for 10 days with bleomycin. Punches were collected after 4 days and analyzed.

To illustrate the effectiveness of the EV preparations we also performed functional assays on ex vivo skin wounds and obtained parallel results to that found in the lung. We reasoned that aging cells/EVs could lack efficacy due to their miRNA profile. Others have shown that a bidirectional exchange of miRNAs between injured cells and MSCs could reprogram the phenotype of MSCs, to acquire features of the injured tissues. To test this hypothesis, we performed preliminary arrays on lungs and ex vivo lung punches isolated from mice with established fibrosis treated with young and old EV preparations. We found that MSC-derived young EV preparations could activate regenerative programs, while aged EV preparations may send senescent signals. Wang et al. [78] investigated the role of MSC-EVs in the transmission of senescence signals limiting the tissue ability to repair kidney damage. The analysis of miRNAs differential expression in bone marrow MSC-EVs between young or old rats, and the study of their influence on epithelial-mesenchymal transition (EMT), showed that miR-133b-3p and miR-294 were downregulated in EVs from old rats and inhibited TGF-β1-mediated EMT. This suggested that these vesicular miRNAs could actually play a role in aged renal tissue fibrosis.

We have shown that MSCs derived from the adipose tissue of young mice prevent the progression of bleomycin (BLM)-induced lung fibrosis, while those derived from old mice do not (2). Cell-based therapy, particularly EVs derived from MSCs, may offer reprogramming of the fibrotic pathway, not only in the lung but also in other organs such as the skin allowing one systemic therapy to provide potentially multiple treatment effects.

References for Example 6

1. Gimble J M, Bunnell B A, and Guilak F. Human adipose-derived cells: an update on the transition to clinical translation. *RegenMed.* 2012; 7(2):225-35.
2. Liang X, Ding Y, Zhang Y, Tse H F, and Lian Q. Paracrine mechanisms of Mesenchymal Stem cell-based therapy: Current status and perspectives. *Cell transplantation.* 2013.
3. Ranganath S H, et al. Harnessing the Mesenchymal Stem Cell Secretome for the Treatment of Cardiovascular Disease. *Cell Stem Cell.* 2012; 10(3): 244-58.
4. Tolar J, Le Blanc K, Keating A, and Blazar B R. Concise Review: Hitting the Right Spot with Mesenchymal Stromal Cells. *Stem Cells.* 2010; 28(8):1446-55.
5. Beach A, et al. Exosomes: an overview of biogenesis, composition and role in ovarian cancer. *Journal of ovarian research.* 2014; 7(1): 14.
6. Thery C, Zitvogel L, and Amigorena S. Exosomes: composition, biogenesis and function. *Nat Rev Immunol.* 2002; 2(8):569-79.
7. Williams A E. Functional aspects of animal microRNAs. *Cellular and molecular life sciences: CMLS.* 2008; 65(4): 545-62.
8. Bruno S, et al. Mesenchymal stem cell-derived microvesicles protect against acute tubular injury. *J of the Am Society of Nephrology: JASN.* 2009; 20(5):1053-67.
9. Buyanovskaya O A, et al. Spontaneous aneuploidy and clone formation in adipose tissue stem cells during different periods of culturing. *Bulletin of experimental biology and medicine.* 2009; 148(1): 109-12.
10. Farsad K. Exosomes: novel organelles implicated in immunomodulation and apoptosis. *The Yale journal of biology and medicine.* 2002; 75(2): 95-101.
11. Neven K Y, et al. Extracellular Vesicles: How the External and Internal Environment Can Shape Cell-To-Cell Communication. *Curr Environ Health Rep.* 2017.
12. Tashiro J, et al. Therapeutic benefits of young, but not old, adipose-derived mesenchymal stem cells in a chronic mouse model of bleomycin-induced pulmonary fibrosis. *Transl Res.* 2015; 166(6):554-67.
13. Tomé M, et al. miR-335 orchestrates cell proliferation, migration and differentiation in human mesenchymal stem cells. *Cell Death and Differentiation.* 2011; 18(6): 985-95.
14. Pastar I, et al. Skin Metabolite, Farnesyl Pyrophosphate, Regulates Epidermal Response to Inflammation, Oxidative Stress, and Migration. *J Cell Physiol.* 2016; 231(11): 2452-63.
15. Stojadinovic O, and Tomic-Canic M. Human ex vivo wound healing model. *Methods Mol Biol.* 2013; 1037 (255-64.
16. Tan J L, et al. Amnion Epithelial Cell-Derived Exosomes Restrict Lung Injury and Enhance Endogenous Lung Repair. *Stem Cells Transl Med.* 2018; 7(2):180-96.

Example 7: Detection of Dysregulated miRNAs and Diagnosis of IPF

Dysregulation of miRNAs participate in the progression of fibrosis including idiopathic pulmonary fibrosis (IPF). Supporting this concept, molecular analysis of lung biopsies from patients with IPF reveal a unique mRNA transcriptome compared with the mRNA transcriptome found from non-fibrotic lung biopsy samples. Similarly, a recent study reported 47 differentially expressed serum miRNAs found in IPF patients compared to controls. In fact, miRNAs have emerged as diagnostic biomarkers for multiple diseases. Since EVs incorporate miRNAs and other cell-specific components that can be transferred to target cells, the focus has been on EVs that may carry a signature useful as a diagnostic biomarker for IPF. Since urine is a valuable diagnostic medium and has been shown to carry extracellular vesicle-containing miRNAs, we collected urine from 15 male subjects with IPF or fibrosis or interstitial lung disease (ILD) without IPF and compared their EV preparation-derived miRNA signatures to age-matched controls. Patients were screened to rule out kidney disease. We found 73 miRNAs that were dysregulated in IPF urine compared to patients with ILD (non-IPF). Of these at least 43 were identified as miRNAs previously shown to be dysregulated in either lung or serum from patients with IPF. These data suggest that urinary EVs could function as a non-invasive screening tool for IPF and potentially other lung diseases.

Methods

Urine collection: Random urine samples were collected from either control subjects or patients seen in clinic for pulmonary fibrosis. Urine was spun at 3000×g for 15 minutes to remove sediment and supernatant was aliquoted at 10 ml/tube. Tubes were frozen at −80° C. until exosome isolation.

EV Isolation (conditioned tissue culture medium, urine) and characterization: Cold (4° C.) sample was centrifuged at 3,000×g for 20 minutes at room temperature in a swinging bucket rotor to remove large cells and debris. The clarified supernatant was collected and then ultracentrifuged at 100, 000×g for 2 hours, fixed angle rotor, 4° C., to pellet EVs. The EV pellet was then resuspended in minimum volume of DPBS (approximately 120 µL/ultracentrifugation tube).

EVs were then characterized using a Thermo NanoDrop spectrophotometer for protein determination and approximate RNA concentration by direct absorbance; EVs were not lysed, stained, or RNA extracted prior to taking these measurements.

Particle diameter and concentration was assessed by tunable resistive pulse sensing (TRPS; (qNano, Izon Science Ltd) using a NP150 nanopore membrane at a 47 mm stretch. The concentration of particles was standardized using multi-pressure calibration with carboxylated polystyrene beads of a defined size (nm diameter) and at a defined concentration (particles/mL).

RNA Sequencing: RNA (including miRNA) from each sample (approx. 100 µg) was isolated using a commercial kit (Preserved Blood RNA Purification Kit I; Norgen; Cat #43400), which enables purification of total RNA, including RNA from approximately 18 nucleotides (nt) upwards. RNA was quantitated using a NanoDrop Spectrophotometer. RNA (50-200 ng) was used for sequencing.
a. Sequencing Service Provided: Small RNA-Seq
b. Sequencing Platform Illumina: MiSeq
c. Sequencing Platform Reagent: MiSeq Reagent Kit v3
d. Product Used for Library Preparation: Norgen Biotek Small RNA Library Prep Kit.
e. Small RNA-Seq Data Analysis Workflow Used: excerpt small RNA-seq Pipeline (v4.3.3) (http://genboree.org/the-Commons/projects/exrnatools-may2014/wiki/Small RNA-seq Pipeline)

Real-Time PCR: Amplification and measurement of target RNA was performed on the Step 1 real time PCR system. Transforming growth factor β (TGFβ), $α_v$-integrin, and tumor necrosis factor alpha (TNFα) was measured using RNA extracted from lung tissues. The TaqMan rRNA control reagents kit (Life Technologies) was used to detect 18S rRNA gene, an endogenous control, and samples were normalized to the 18Stranscript content. For microRNA 29a and microRNA-199-3p analyses, cDNA was generated using gScript™ microDNA cDNA Synthesis Kit (Quanta Biosciences, Beverly, Mass.) according to manufacturer's instructions. Amplification of microRNA-29a and microRNA-199-3p was performed (IDT, Coralville, Iowa) using Real-Time SYBR Green qRT-PCR Amplication kit (Quanta Biosciences, Beverly, Mass.). U6 expression was used as a control for microRNA analyses, and relative expression was calculated using the comparative C(T) method (8).

miRNA profiling and bioinformatics: In some experiments, the Nanostring nCounter® platform was used to screen for expression level of 800 miRNAs. A volume of three microliters (3 µL) for each sample was prepared and analyzed according to the manufacturer's protocol (NanoString Technologies, Seattle, Wash.). Briefly, a thermally controlled multiplexed ligation reaction was used to add specific DNA tag sequences on mature miRNAs. Following ligation, the excess tags were removed by affinity and the purified material was hybridized overnight at 65° C. with the nCounter® Human (V2) miRNA Expression Assay CodeSet. The nCounter® Prep Station was used to purify the hybridized probes and to attach the purified biotinylated complexes on the streptavidin-coated slides. miRNA counts were measured in two batches by the nCounter® Digital Analyzer. All samples were analyzed at NanoString's laboratory (NanoString Technologies, Seattle, Wash.). The nSolver software (http://www.nanostring.com/products/nSolver) was used to analyze and normalize the raw data using the top 100 most abundant miRNAs in all samples, according to the manufacturer's instructions. Positive controls were included to normalize for any differences in preparation, hybridization, and processing efficiency. Data were further tested for batch effects, normalized to the starting median volume and corrected for background noise using negative controls.

The following eleven miRs were found to be dysregulated in urinary EVs from patients with IPF, shown below in Table 13.

TABLE 13

| miRNA | Comparison to control | P Value |
| --- | --- | --- |
| miR-134-5p | Downregulated | 0.004811 |
| miR-196b-5p | Downregulated | 0.011259 |
| miR-629-5p | Downregulated | 0.003832 |
| miR-206 | Downregulated | 0.00472 |
| miR-192-5p | Upregulated | 0.005371 |
| miR-320c | Upregulated | 0.021017 |
| miR-125a-3p | Upregulated | 0.049727 |
| miR-215-5p | Upregulated | 0.000206 |
| miR-642a-3p | Upregulated | 0.025611 |
| miR-576-3p | Upregulated | 0.022969 |
| miR-3679-5p | Upregulated | 0.017913 |

Results

We found 73 miRNAs that were dysregulated in IPF urine compared to patients with ILD (non-IPF). Of these at least 43 were identified as miRNAs previously shown to be dysregulated in either lung or serum from patients with IPF.

FIG. 21 shows the results of analysis of exosomes injected into punches from the urine from healthy subjects (control) and IPF patients for integrin mRNA expression (FIG. 21A), collagen type 1α1 mRNA expression (FIG. 21B), profibrotic c-Jun protein expression (FIG. 21 C); pAK/pAKT ratio (FIG. 21D); and MMP-9 activity (FIG. 21E) compared to a media control The results show that IPF urine exosomes show increased integrin mRNA expression, collagen type 1α1 mRNA expression, c-Jun protein expression, pAKT/ AKT protein expression, and MMP-9 activity compared to media and normal controls.

These data suggest that urinary exosomes could function as a non-invasive screening tool for IPF and potentially other fibrotic diseases.

Example 8: 3D Lung Model-Ex Vivo Lung Punch

Agarose infused young and old mouse lungs were punched with a 4 mm punch, injected with MSC derived exosomes and collected after 4 days. Lung punches model the cellular and molecular interplay in the lung and make possible live cell imaging and genetic modifications.

FIG. 22 shows photographs of ex vivo lung punches (4 mm) from the agarose-infused young and old mouse lungs that were injected with ASC derived exosomes and collected after 4 days.

Exosomes derived from young ASCs were injected into punches isolated from day 10 post BLM-treated lung. The control did not receive treatment with the ASCs. FIG. 23 shows punches isolated from day 10 post-BLM treated lung injected with exosomes derived from young ASCs (right panels). Media control (left panels) received treatment with media only. Results show that punches treated with ASC exosomes (FIG. 23B) display reduced a smooth muscle actin expression compared to the control (FIG. 23A). The ASC exosomes treated punches also show an increase in antifibrotic CAV-1 (FIG. 23D) compared to the control (FIG. 23C); and a decrease in pro-fibrotic c-Jun (FIG. 23F) compared to the control (FIG. 23E). No modification in β actin was detected (FIG. 23H, FIG. 23G). This demonstrates that treatment of ex vivo lung punches with ASC exosomes modifies ex vivo lung punch tissue.

FIG. 24 left panels show ex vivo mouse punches injected with a media control; right panels show punches injected with ASC exosomes. FIGS. 24A and 24B show trichrome histology of ex vivo mouse punches following contact with a media control (FIG. 24A) and ASC exosomes (FIG. 24B). FIG. 24C, 24D show results of immunofluorescent staining for surfactant protein C (SPC). Surfactant proteins are mainly expressed by distal lung epithelial cells. SPC is a pulmonary surfactant protein. SPC therefore was used as a marker for aleveolar cell regeneration. FIG. 24E (control), and FIG. 24F show results of immunofluorescent staining for aquaporin 5 (AQP5). Aquaporin is a water channel protein, which plays a role in the generation of pulmonary secretions. Punches treated with ASC exosomes express increased Surfactant Protein C (SPC) and Aquaporin 5 (AQP5) compared to the control. The left panels show a few alveoloar type 2 cells. The right panels show an increase in both alveoloar type 1 and type 2 cells, mostly type 2, with a little of type 1. This demonstrates that punch treatment with ASC exosomes increases expression of alveolar cell type 2 and type 1.

Exosomes derived from either fibroblasts isolated from young male control lungs or myofibroblasts isolated from IPF lungs (purchased from Lonza or developed in our lab IRB number #20060249) were injected into a naïve aging mouse lung punch and parameters associated with pulmonary fibrosis, namely integrin, miR-29, c-jun protein, ERα, and CAV-1 protein levels measured. FIG. 25 shows that expression of integrin mRNA, MIR-29a, Caveolin-1 protein; c-June protein; and estrogen receptor alpha, all of which are markers for IPF, were altered in the exosomes from patients with IPF compared to the normal control. More specifically, the level of integrin mRNA was increased (FIG. 25A), miR-29 decreased [FIG. 25B], CAV-1 protein decreased (FIG. 25C), c-jun protein increased (FIG. 25D), ERα protein increased (FIG. 25E) compared to a media control and exosomes prepared from control lung fibroblasts. EVs from control lungs increased CAV-1 protein, an antifibrotic marker.

FIG. 26 shows results of experiments in which exosomes derived from the urine of subjects without lung disease (control) or from the urine of patients with IPF were injected into naïve aging mouse punches. The result show that EVs derived from the urine of patients with IPF likewise display an increase in integrin mRNA (FIG. 26A), an increase in collagen 1α1 mRNA (FIG. 26 B); an increase in profibrotic c-Jun protein expression (FIG. 26C) and an increase in the ratio of pAKT/AKT (FIG. 26D) compared to a urine control and a media control.

Human lung punches were injected with exosomes derived from normal fibroblasts (control fib), exosomes derived from IPF lung myofibroblasts (IPF fib), exosomes derived from urine from an IPF patient (IPF urine) and controls and collected 4 days later. Punches were processed for mRNA and protein expression.

FIG. 27A shows that expression of αV integrin and of type I collagen in lungs injected with IPF fibroblast-derived exosomes is increased compared to the control. FIG. 27B shows that ERα protein expression in punches contacted with IPF urine was increased compared to controls. FIG. 27C shows that anti-fibrotic caveolin-1 protein expression was decreased in IPF urine and IPF fib samples compared to the controls.

Discussion

We have shown that exosomes derived from young ASCs and injected into punches isolated from day 10 post-BLM treatment can modify tissue.

We have also shown that exosomes injected into ex vivo mouse punches can result in the increase of mainly type 2 epithelial cells, and some type 1 epithelial cells, which are indicators of wound healing progression.

We have shown that exosomes derived from myofibroblasts isolated from lungs of IPF patients injected into lung punches confer IPF. For example, we have shown that lung punches injected with exosomes derived from myofibroblasts isolated from lungs of patients with IPF showed an increase in markers for IPF, i.e., integrin mRNA increased, miR-29 decreased, profibrotic c-jun protein increased, ERα protein increased, and antifibrotic caveolin-1 decreased, compared to controls.

We have shown that exosomes derived from the urine of IPF patients when injected into naïve aging mouse lung punch showed the same changes, i.e., integrin mRNA increased, Collagen type 1 mRNA increased, profibrotic c-jun protein increased, and pAKT activation increased.

Example 9. ExoGlow-Labeled Exosomes In Vivo

ExoGlow™ (Systemsbio.com) specifically labels EV membranes with a proprietary fluorescent dye that delivers very low levels of background signal. ExoGlow™-membrane properties include excitation at 465 nm, emission at 635 nm, and laser line: 488 nm.

ExoGlow™ labeled exosomes were injected via tail vein in a mouse 8 days after treatment with BLM and the time course of their distribution determined. FIG. 28A, shows distribution after 5 minutes. As shown in FIG. 28B, after 30 minutes, the distribution of ExoGlow™ indicates migration of exosomes to the lungs. FIG. 28C shows the distribution at 2 hours. FIG. 28D shows distribution at 8 hours. FIG. 28E shows that at 20 hours, the distribution of ExoGlow indicates migration of exosomes to the kidneys.

Figure 29A:
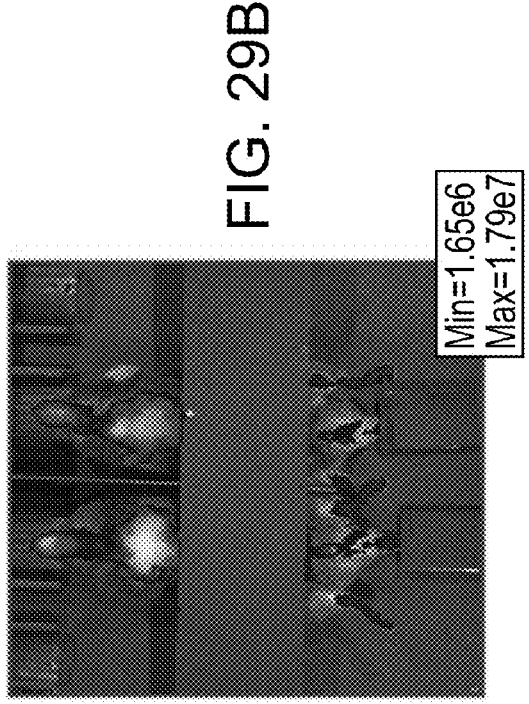
Figure 29B:
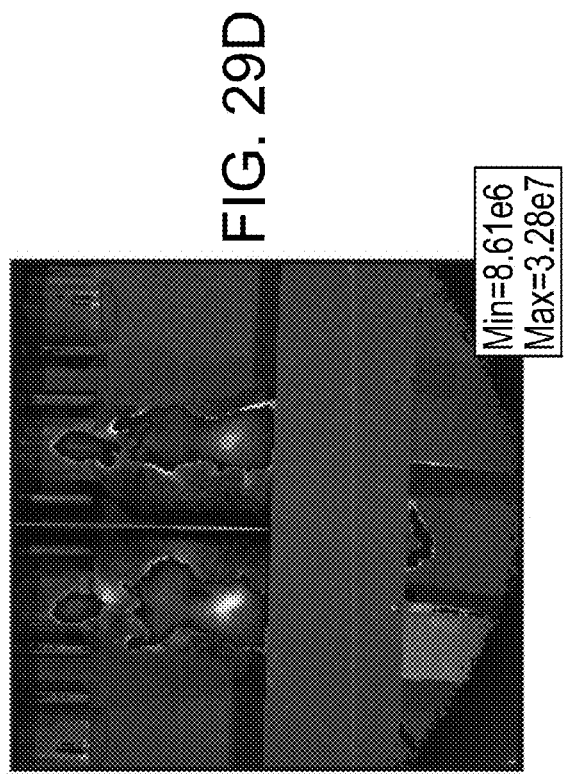
Figure 29C:
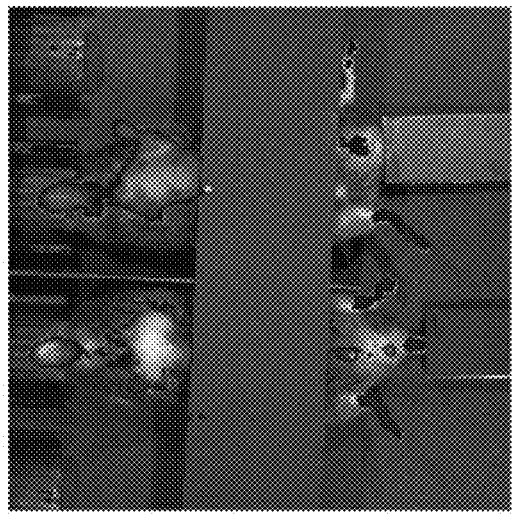
Figure 29D:
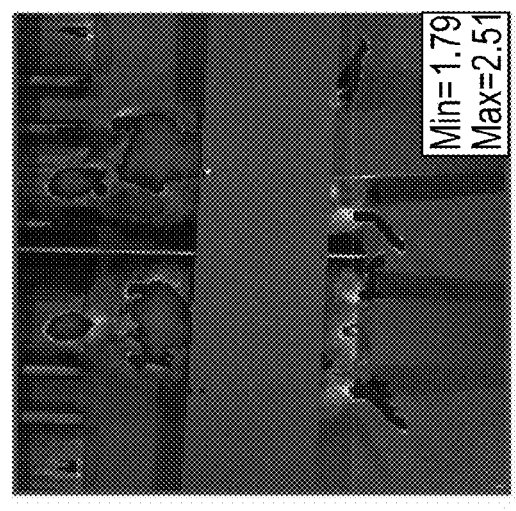

We studied two doses of ExGlow™ by transfusing 90 μg (FIG. 29 left hand side of each panel) and 40 μg (FIG. 29 right hand side of each panel) exosome dosages to mice and tracked the distribution of the labeled exosomes over a 24 hour period (FIG. 29A, 60 mins; FIG. 29B 90 mins; FIG. 29C 6 hrs; FIG. 29D 24 hrs). The results show more vivid ExoGlow™ fluorescence at the 90 μg dosing.

We sacrificed the ExoGlow™ mice from FIG. 29, and studied ExoGlow™ fluorescence in the mouse lung after 24 hours. FIG. 30 shows the vivid Exo-Glow™ fluorescence 24 hours post-injection of Exo-Glow™ exosomes in kidney (top left) and liver (right) at the 90 μg dosing. At 24 hours, exosomes cannot be detected in the lungs (3), spleen (4) and heart (5).

Mouse lung punch was injected with exosomes containing nanoparticles and then examined by electron microscopy. 0.001 mg of gold nanoparticles (nanospheres) modified with branched polyethylenimine (BPEI) of 10 nm size were mixed with $10^8$ exosomes. The mixture was vortexed and then placed in a thermomixer (Eppendorf ThermoMixer F1.5) @ 37° C. and speed of 300 rpm. After 3 hours, the mixture was vortexed, allowed to stand about 15 minutes at room temperature, and then placed @ 4° C. until used in the punches. Electron micrographs of Type II alveolar epithelial cells with exosomes containing nanoparticles are shown in FIG. 31A, FIG. 31B (higher magnification), FIG. 32A and FIG. 32B (higher magnification). FIG. 31A and FIG. 31B show the exosomes membrane apposed to the membrane of the type I alveolar epithelial cell, and the nanoparticles are seen within the alveolar epithelial cell. The arrows in FIG. 31A, FIG. 31B (higher magnification) show that the exosomes cell membrane is still intact. FIG. 32A and FIG. 32B show exosomes containing nanoparticles being engulfed.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of diagnosing and treating a fibrotic disease in a subject in need thereof comprising
    (a) obtaining a urine sample from the subject and from a healthy control;
    (b) isolating EVs from the urine sample obtained from the subject and healthy control;
    (c) detecting a level of expression of miRNAs in the EVs from the urine sample from the subject and in the EVs from the urine sample from the healthy control;
    (d) determining that expression of one or more of the miRNAs in the EVs from the subject is dysregulated compared to the healthy control; and
    (e) identifying the subject as one that can benefit therapeutically from being treated for a fibrotic disease:
        (i) when the presence of one or more dysregulated miRNAs in the EVs from the urine sample obtained from the subject is detected;
        (ii) when an increase in levels of one or more WNT proteins in the EVs from the urine sample from the subject compared to the healthy control is detected; or
        (iii) when the presence of one or more dysregulated miRNAs and an increase in levels of one or more WNT proteins in the EVs from the urine sample from the subject compared to the healthy control is detected; and
    (f) administering a therapeutic amount of a pharmaceutical composition comprising either:
        (i) at least about $1 \times 10^8$ whole MSCs comprising synthetic exosomes comprising a therapeutic amount of an miR-29a mimic, an miR-199-3p inhibitor, or both to the diagnosed subject; or
        (ii) a therapeutic amount of a purified and enriched population of synthetic exosomes comprising an miR-29a mimic, an miR-199-3p inhibitor, or both to the diagnosed subject;
            wherein the therapeutic amount is effective to upregulate expression of miR-29a, to downregulate expression of miR-199-3p, or both, and to effectively treat the fibrotic disease.

2. The method according to claim 1, wherein the sequence of the miR-29a mimic is at least about 70% homologous with SEQ ID NO: 1.

3. The method according to claim 1, wherein the sequence of the miR-199-3p inhibitor is at least about 70% homologous with SEQ ID NO: 2.

4. The method according to claim 1, wherein the upregulated expression of miR-29a is effective to decrease expression of MMP-2.

5. The method according to claim 1, wherein the downregulated expression of miR-199-3p is effective to upregulate CAV-1 expression.

6. The method according to claim 1, wherein the fibrotic disease is selected from one or more of a fibrotic lung disease, a fibrotic cardiac disease, a fibrotic renal disease, a fibrotic hepatic disease, a fibrotic skin disease, a fibrotic pancreatic disease, a fibrotic eye disease, a fibrotic joint disease, a fibrotic bone marrow disease, a fibrotic brain disease, a fibrotic intestinal disease, a fibrotic peritoneum disease, a fibrotic retroperitoneum disease, a fibrotic condition of a nerve, a nervous system, nerve compression, or injury due to fibrosis.

7. The method according to claim 6, wherein the fibrotic disease is fibrotic lung disease.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: miR-29a mimic

<400> SEQUENCE: 1
aaccgatttc agatggtgct                                              20

<210> SEQ ID NO 2
<211> LENGTH: 20
<212> TYPE: DNA
<213> ORGANISM: Artificial Sequence
<220> FEATURE:
<223> OTHER INFORMATION: miR-199-3p inhibitor

<400> SEQUENCE: 2
aaccaatgtg cagactactg                                              20

<210> SEQ ID NO 3
<211> LENGTH: 6219
<212> TYPE: DNA
<213> ORGANISM: Artificial Sequence
<220> FEATURE:
<223> OTHER INFORMATION: Plasmid

<400> SEQUENCE: 3
aacaaaatat taacgcttac aatttccatt cgccattcag gctgcgcaac tgttgggaag      60
ggcgatcggt gcgggcctct tcgctattac gccagctggc gaaaggggga tgtgctgcaa     120
ggcgattaag ttgggtaacg ccagggtttt cccagtcacg acgttgtaaa acgacggcca     180
gtgccaagct gatctataca ttgaatcaat attggcaatt agccatatta gtcattggtt     240
atatagcata aatcaatatt ggctattggc cattgcatac gttgtatcta tatcataata     300
tgtacattta tattggctca tgtccaatat gaccgccatg ttgacattga ttattgacta     360
gttattaata gtaatcaatt acgggtcat tagttcatag cccatatatg gagttccgcg      420
ttacataact tacggtaaat ggcccgcctg gctgaccgcc caacgacccc cgcccattga     480
cgtcaataat gacgtatgtt cccatagtaa cgccaatagg gactttccat tgacgtcaat     540
gggtggagta tttacggtaa actgcccact tggcagtaca tcaagtgtat catatgccaa     600
gtccgccccc tattgacgtc aatgacggta aatggcccgc ctggcattat gcccagtaca     660
tgaccttacg gactttcct acttggcagt acatctacgt attagtcatc gctattacca      720
tggtgatgcg gttttggcag tacaccaatg ggcgtggata gcggtttgac tcacggggat     780
ttccaagtct ccaccccatt gacgtcaatg ggagtttgtt ttggcaccaa aatcaacggg     840
actttccaaa atgtcgtaat aaccccgccc cgttgacgca aatgggcggt aggcgtgtac     900
```

```
ggtgggaggt ctatataagc agagctcgtt tagtgaaccg tcagaatttt gtaatacgac    960
tcactatagg gcggccggga attcgtcgac tggatccagt accgaggaga tctgcgccgc   1020
gatcgccggc gcgccagatc tcaagcttaa ctagctagcg gaccgacgcg tacgcggccg   1080
ctcgagcaga aactcatctc agaagaggat ctggcagcaa atgatatcct ggattacaag   1140
gatgacgacg ataaggttta acggccggc cgcggtcata gctgtttcct gaacagatcc    1200
cgggtggcat ccctgtgacc cctccccagt gcctctcctg gcctggaag ttgccactcc    1260
agtgcccacc agccttgtcc taataaaatt aagttgcatc attttgtctg actaggtgtc   1320
cttctataat attatgggt ggaggggggt ggtatggagc aagggcaag ttgggaagac     1380
aacctgtagg gcctgcgggg tctattggga accaagctgg agtgcagtgg cacaatcttg   1440
gctcactgca atctccgcct cctgggttca gcgattctc ctgcctcagc ctcccgagtt    1500
gttgggattc caggcatgca tgaccaggct cagctaattt ttgttttttt ggtagagacg   1560
gggtttcacc atattggcca ggctggtctc caactcctaa tctcaggtga tctacccacc   1620
ttggcctccc aaattgctgg gattacaggc gtgaaccact gctcccttcc ctgtccttct   1680
gattttaaaa taactatacc agcaggagga cgtccagaca cagcataggc tacctggcca   1740
tgcccaaccg gtgggacatt tgagttgctt gcttggcact gtcctctcat gcgttgggtc   1800
cactcagtag atgcctgttg aattgggtac gcggccagcg gcgagcggta tcagctcact   1860
caaaggcggt aatacggtta tccacagaat caggggataa cgcaggaaag aacatgtgag   1920
caaaaggcca gcaaaaggcc aggaaccgta aaaaggccgc gttgctggcg ttttttccata  1980
ggctccgccc ccctgacgag catcacaaaa atcgacgctc aagtcagagg tggcgaaacc   2040
cgacaggact ataaagatac caggcgtttc ccctggaag ctccctcgtg cgctctcctg    2100
ttccgaccct gccgcttacc ggatacctgt ccgcctttct cccttcggga agcgtggcgc   2160
tttctcatag ctcacgctgt aggtatctca gttcggtgta ggtcgttcgc tccaagctgg   2220
gctgtgtgca cgaaccccc gttcagcccg accgctgcgc cttatccggt aactatcgtc    2280
ttgagtccaa cccggtaaga cacgacttat cgccactggc agcagccact ggtaacagga   2340
ttagcagagc gaggtatgta ggcggtgcta cagagttctt gaagtggtgg cctaactacg   2400
gctacactag aagaacagta tttggtatct gcgctctgct gaagccagtt accttcggaa   2460
aaagagttgg tagctcttga tccggcaaac aaaccaccgc tggtagcggt ggtttttttg   2520
tttgcaagca gcagattacg cgcagaaaaa aaggatctca agaagatcct tgatcttttt   2580
ctacggggtc tgacgctcag tggaacgaaa actcacgtta agggattttg gtcatgagat   2640
tatcaaaaag gatcttcacc tagatccttt taaattaaaa atgaagtttt aaatcaatct   2700
aaagtatata tgagtaacct gaggctatgg caggcctgc cgccccgacg ttggctgcga    2760
gccctgggcc ttcacccgaa cttggggggt ggggtgggga aaaggaagaa acgcgggcgt   2820
attgccccca atgggtctc ggtgggtat cgacagagtg ccagccctgg gaccgaaccc     2880
cgcgtttatg aacaaacgac ccaacaccgt gcgttttatt ctgtcttttt attgccgtca   2940
tagcgcgggt tccttccggt attgtctcct tccgtgtttc agttagcctc ccctagggt    3000
gggcgaagaa ctccagcatg agatcccgc gctggaggat catccagccg gcgtcccgga    3060
aaacgattcc gaagcccaac ctttcataga aggcggcggt ggaatcgaaa tctcgtgatg   3120
gcaggttggg cgtcgcttgg tcggtcattt tcttcgaatt attcttcacc ggcatctgca   3180
tccggggtct tgaaggcgtg ctggtactcc acgatgccca gctcggtgtt gctgtgatcc   3240
tcctccacgc ggcggaaggc gaacatgggg ccccgttct gcaggatgct ggggtggatg    3300
```

```
gcgctcttga agtgcatgtg gctgtccacc acggagctgt agtagccgcc gtcgcgcagg    3360
ctgaaggtgc gggtgaagct gccatccaga tcgttatcgc ccatggggtg caggtgctcc    3420
acggtggcgt tgctgcggat gatcttgtcg gtgaagatca cgctgtcctc ggggaagccg    3480
gtgcccatca ccttgaagtc gccgatcacg cggccggcct cgtagcggta gctgaagctc    3540
acgtgcagca cgccgccgtc ctcgtacttc tcgatgcggg tgttggtgta gccgccgttg    3600
ttgatggcgt gcaggaaggg gttctcgtag ccgctgtggg aggtgccgaa gtggtagaag    3660
ccgtagccca tcacgtggct cagcaggtag gggctgaagg tcagggcgcc tttggtgctc    3720
ttcatcttgt tggtcatgcg gccctgctcg ggggtgccct ctccgccgcc caccagctcg    3780
aactccacgc cgttcagggt gccggtgatg cggcactcga tctccatggc gggcaggccg    3840
ctctcgtcgc tctccatggt tgtggccata ttatcatcgt gtttttcaaa ggaaaaccac    3900
gtccccgtgg ttcgggggc ctagacgttt ttttaacctc gactaaacac atgtaaagca    3960
tgtgcaccga ggccccagat cagatcccat acaatgggt accttctggg catccttcag    4020
ccccttgttg aatacgcttg aggagagcca tttgactctt ccacaacta tccaactcac    4080
aacgtggcac tggggttgtg ccgcctttgc aggtgtatct tatacacgtg gcttttggcc    4140
gcagaggcac ctgtcgccag gtgggggtt ccgctgcctg caaagggtcg ctacagacgt    4200
tgttgtctt caagaagctt ccagaggaac tgcttccttc acgacattca acagaccttg    4260
cattcctttg gcgagagggg aaagacccct aggaatgctc gtcaagaaga cagggccagg    4320
tttccgggcc ctcacattgc caaaagacgg caatatggtg gaaaataaca tatagacaaa    4380
cgcacaccgg ccttattcca agcggcttcg gccagtaacg ttagggggg gggcggaatt    4440
cgaaccccag agtcccgctc agaagaactc gtcaagaagg cgatagaagg cgatgcgctg    4500
cgaatcggga gcggcgatac cgtaaagcac gaggaagcgg tcagcccatt cgccgccaag    4560
ctcttcagca atatcacggg tagccaacgc tatgtcctga tagcgatccg ccacacccag    4620
ccggccacag tcgatgaatc cagaaaagcg gccatttcc accatgatat tcggcaagca    4680
ggcatcgcca tgggtcacga cgagatcctc gccgtcgggc atgctcgcct tgagcctggc    4740
gaacagttcg gctggcgcga gcccctgatg ctcttcgtcc agatcatcct gatcgacaag    4800
accggcttcc atccgagtac gtgctcgctc gatgcgatgt ttcgcttggt ggtcgaatgg    4860
gcaggtagcc ggatcaagcg tatgcagccg ccgcattgca tcagccatga tggatacttt    4920
ctcggcagga gcaaggtgag atgacaggag atcctgcccc ggcacttcgc ccaatagcag    4980
ccagtccctt cccgcttcag tgacaacgtc gagcacagct gcgcaaggaa cgcccgtcgt    5040
ggccagccac gatagccgcg ctgcctcgtc ttgcagttca ttcagggcac cggacaggtc    5100
ggtcttgaca aaaagaaccg ggcgcccctg cgctgacagc cggaacacgg cggcatcaga    5160
gcagccgatt gtctgttgtg cccagtcata gccgaatagc ctctccaccc aagcggccgg    5220
agaacctgcg tgcaatccat cttgttcaat catgcgaaac gatcctcatc ctgtctcttg    5280
atcgatcttt gcaaaagcct aggcctccaa aaaagcctcc tcactacttc tggaatagct    5340
cagaggccga gcggcctcg gcctctgcat aaataaaaaa aattagtcag ccatggggcg    5400
gagaatgggc ggaactgggc ggagttaggg gcggatgggc ggagttaggg gcgggacta    5460
tggttgctga ctaattgaga tgcatgcttt gcatacttct gcctgctggg gagcctgggg    5520
actttccaca cctggttgct gactaattga gatgcatgct ttgcatactt ctgcctgctg    5580
gggagcctgg ggactttcca caccctaact gacacacatt ccacagctgg ttctttccgc    5640
```

-continued

```
ctcaggactc ttccttttc aatattattg aagcatttat cagggttatt gtctcatgag      5700
cggatacata tttgaatgta tttagaaaaa taaacaaata ggggttccgc gcacatttcc      5760
ccgaaaagtg ccacctgacg cgccctgtag cggcgcatta agcgcggcgg gtgtggtggt      5820
tacgcgcagc gtgaccgcta cacttgccag cgccctagcg cccgctcctt tcgctttctt      5880
cccttccttt ctcgccacgt tcgccggctt tccccgtcaa gctctaaatc ggggctccc      5940 tttagggttc cgatttagtg ctttacggca cctcgacccc aaaaaacttg attagggtga      6000
tggttcacgt agtgggccat cgccctgata gacggttttt cgcccctttga cgttggagtc      6060 cacgttcttt aatagtggac tcttgttcca aactggaaca acactcaacc ctatctcggt      6120 ctattcttt gatttataag ggattttgcc gatttcggcc tattggttaa aaaatgagct       6180
gatttaacaa aaatttaacg cgaattttaa caaaatatt                             6219
```